(12) United States Patent
Russell et al.

(10) Patent No.: US 12,398,377 B2
(45) Date of Patent: Aug. 26, 2025

(54) PSEUDOTYPED VIRAL PARTICLES, COMPOSITIONS COMPRISING THE SAME, AND USES THEREOF

(71) Applicant: Interius BioTherapeutics, Inc., Philadelphia, PA (US)

(72) Inventors: Ronnie M. Russell, Philadelphia, PA (US); Philip R. Johnson, Sarasota, FL (US); Bruce Schnepp, Philadelphia, PA (US)

(73) Assignee: Interius Biotherapeutics, Inc., Philadelphia, PA (US)

( * ) Notice: Subject to any disclaimer, the term of this patent is extended or adjusted under 35 U.S.C. 154(b) by 0 days.

(21) Appl. No.: 19/043,304

(22) Filed: Jan. 31, 2025

(65) Prior Publication Data

US 2025/0171746 A1 May 29, 2025

Related U.S. Application Data

(63) Continuation of application No. 18/647,283, filed on Apr. 26, 2024, which is a continuation of application No. 18/157,421, filed on Jan. 20, 2023, now Pat. No. 12,104,177, which is a continuation of application No. 18/066,420, filed on Dec. 15, 2022, now Pat. No. 11,767,366.

(60) Provisional application No. 63/267,039, filed on Jan. 21, 2022, provisional application No. 63/266,044, filed on Dec. 27, 2021, provisional application No. 63/289,977, filed on Dec. 15, 2021, provisional application No. 63/289,888, filed on Dec. 15, 2021.

(51) Int. Cl.
*C12N 15/86* (2006.01)
*C07K 14/005* (2006.01)
*C07K 16/28* (2006.01)
*C12N 7/00* (2006.01)
*C12N 15/113* (2010.01)

(52) U.S. Cl.
CPC ............ *C12N 7/00* (2013.01); *C07K 14/005* (2013.01); *C07K 16/2896* (2013.01); *C12N 15/113* (2013.01); *C12N 15/86* (2013.01); *C12N 2740/15023* (2013.01); *C12N 2740/15043* (2013.01); *C12N 2760/20222* (2013.01)

(58) Field of Classification Search
None
See application file for complete search history.

(56) References Cited

U.S. PATENT DOCUMENTS

| | | |
|---|---|---|
| 4,439,196 A | 3/1984 | Higuchi |
| 4,447,224 A | 5/1984 | DeCant, Jr. et al. |
| 4,447,233 A | 5/1984 | Mayfield |
| 4,487,603 A | 12/1984 | Harris |
| 4,596,556 A | 6/1986 | Morrow et al. |
| 4,790,824 A | 12/1988 | Morrow et al. |
| 4,816,567 A | 3/1989 | Cabilly et al. |
| 4,941,880 A | 7/1990 | Burns |
| 4,946,778 A | 8/1990 | Ladner et al. |
| 5,064,413 A | 11/1991 | McKinnon et al. |
| 5,260,203 A | 11/1993 | Ladner et al. |
| 5,312,335 A | 5/1994 | McKinnon et al. |
| 5,383,851 A | 1/1995 | McKinnon, Jr. et al. |
| 5,399,163 A | 3/1995 | Peterson et al. |
| 6,005,079 A | 12/1999 | Casterman et al. |
| 6,096,002 A | 8/2000 | Landau |
| 6,620,135 B1 | 9/2003 | Weston et al. |
| 11,767,366 B1 | 9/2023 | Russell et al. |
| 2008/0227736 A1 | 9/2008 | Chen et al. |
| 2018/0036429 A1 | 2/2018 | Acharjee |
| 2018/0371064 A1 | 12/2018 | Fusil et al. |
| 2019/0055568 A1 | 2/2019 | Pulé et al. |
| 2020/0216502 A1 | 7/2020 | Albertini et al. |
| 2020/0371088 A1 | 11/2020 | Birnbaum et al. |
| 2021/0106632 A1 | 4/2021 | Kim et al. |
| 2023/0279363 A1 | 9/2023 | Russell et al. |

FOREIGN PATENT DOCUMENTS

| | | |
|---|---|---|
| EP | 0404097 A2 | 12/1990 |
| WO | WO-1988001649 A1 | 3/1988 |
| WO | WO-1993011161 A1 | 6/1993 |
| WO | WO-1994004678 A1 | 3/1994 |
| WO | WO-1994025591 A1 | 11/1994 |
| WO | WO-1997009433 A1 | 3/1997 |
| WO | WO-2004041862 A2 | 5/2004 |
| WO | WO-2016065323 A2 | 4/2016 |
| WO | WO-2020223240 A1 | 11/2020 |
| WO | WO-2022183072 A1 | 9/2022 |
| WO | WO-2023107593 A2 | 6/2023 |
| WO | WO-2023114884 A2 | 6/2023 |
| WO | WO-2023170681 A1 | 9/2023 |
| WO | 2024/067870 A1 | 4/2024 |

(Continued)

OTHER PUBLICATIONS

Andorko, J. et al., Blood, 2023, vol. 142: pp. 763-764.*
Zeller, S. et al., Mol. Ther., May 2012, vol. 20 Supplement 1: p. S135.*
U.S. Appl. No. 63/154,639, filed Feb. 26, 2021, ViraLogic Therapeutics, Inc.
5OYL Albertini, A.A. et al., "5OYL, VSV G CR2", RCSB PDB, Mar. 21, 2018, last revised Apr. 18, 2018, available at https://www.rcsb.org/structure/5OYL (last accessed Jan. 3, 2024), 6 pages.
5OY9—Albertini, A.A. et al., "5OY9, VSV G CR3", RCSB PDB, Mar. 21, 2018, last revised Apr. 18, 2018, available at https://www.rcsb.org/structure/5OY9 (last accessed Jan. 3, 2024), 6 pages.
Albertini et al., "Molecular and Cellular Aspects of Rhabdovirus Entry," Viruses (2012) 4:117-129.

(Continued)

*Primary Examiner* — Michael D Burkhart
(74) *Attorney, Agent, or Firm* — Goodwin Procter LLP

(57) ABSTRACT

Provided for herein are mutant VSV-G polypeptides, compositions comprising the same, and methods of using the same. Also provided for herein are polypeptides and compositions that bind to CD7 and uses thereof. Also provided for herein are polypeptides and compositions that bind to CD8 and uses thereof.

20 Claims, 26 Drawing Sheets

Specification includes a Sequence Listing.

(56) References Cited

FOREIGN PATENT DOCUMENTS

| WO | 2024/213019 A1 | 10/2024 |
|----|----------------|---------|
| WO | 2024/213153 A1 | 10/2024 |

OTHER PUBLICATIONS

Baert et al., "Influence of Immunogenicity on the Long-Term Efficacy of Infliximab in Crohn's Disease," (2003) New Engl. J. Med. 348:601-608.

Beniaminovitz et al., "Prevention of Rejection in Cardiac Transplantation by Blockade of the Interleukin-2 Receptor with a Monoclonal Antibody," (2000) New Engl. J. Med. 342(9):613-619.

C. Dunbar et al, "Gene therapy comes of age", 359 Science 1 (2018).

Chothia et al., "Canonical Structures for the Hypervariable Regions of Immunoglobulins," (1987) J. Mol. Biol. 196:901-917.

Chothia et al., "Conformations of Immunoglobulin Hypervariable Regions," (1989) Nature 342: 877-883.

Clackson et al., "Making Antibody Fragments Using Phage Display Libraries," (1991) Nature 352:624-628. (Abstract Only).

Donald J. Voet et al, "Fundamentals of biochemistry" (2008), chapters 3 and 4, 39-82.

Duverge and M. Negroni, "Pseudotyping lentiviral vectors: when the clothes make the virus", 12 Viruses 1311 (2020).

E. Pettersen et al., "UCSF Chimera—A visualization system for exploratory research and analysis", 25 J. Comp. Chem. 1605 (2004).

F. Amirache et al, "Mystery solved: VSV-G-LVs do not allow efficient gene transfer into unstimulated T cells, B cells, and HSCs cause they lack the LDL receptor", 123 Blood 1422 (2014).

Finkelshtein et al., "LDL Receptor and its Family Members Serve as the Cellular Receptors for Vesicular Stomatitis Virus," PNAS (2013) 110(18): 7306-7311.

Ghosh et al., "Natalizumab for Active Crohn's Disease," (2003) New Engl. J. Med. 348:24-32.

Herold et al., "Anti-CD3 Monoclonal Antibody in New-Onset Type 1 Diabetes Mellitus," (2002) New Engl. J. Med. 346(22):1692-1698.

Holliger et al., "Diabodies: Small Bivalent and Bispecific Antibody Fragments," (1993) Proc. Natl. Acad. Sci. USA 90: 6444-6448.

Holliger et al., "Engineered Antibody Fragments and the Rise of Single Domains," (2005) Nat. Biotechnol. 23(9): 1126-1136.

Hwang et al., "Engineering a Serum-Resistant and Thermostable Vesicular Stomatitis Virus G Glycoprotein for Pseudotyping Retroviral and Lentiviral Vectors," Gene Ther. (Aug. 2013) 20(8):807-815.

International Search Report and Written Opinion for PCT/US2022/081616, dated Jun. 15, 2023, 14 pages.

J. Rose and C. Gallione, "Nucleotide Sequences of the mRNAs Encoding the Vesicular Stomatitis Virus G and M Proteins Determined from cDNA Clones Containing the Complete Coding Regions", 39 J. Virology 519 (1981).

Kabat et al., "Unusual Distributions of Amino Acids in Complementarity-Determining (Hypervariable) Segments of Heavy and Light Chains of Immunoglobulins and Their Possible Roles in Specificity of Antibody-Combining Sites," (1977) J. Biol. Chem. 252(19):6609-6616.

Kabat, "The Structural Basis for Antibody Complementary," Adv. Prot. Chem. (1978) 32:1-75. (Abstract Only).

L. Naldini et al, "In vivo gene delivery and stable transduction of nondividing cells by a lentiviral vector", 272 Science 263 (1996).

Lathe, "Synthetic Oligonucleotide Probes Deduced from Amino Acid Sequence Data," J. Molec. Biol. (1985) 183:1-12.

Lee et al., "ASTCT Consensus Grading for Cytokine Release Syndrome and Neurologic Toxicity Associated with Immune Effector Cells," Biol. Blood Marrow Transplant (2019) 25:625-638.

Lipsky et al., "Infliximab and Methotrexate in the Treatment of Rheumatoid Arthritis," (2000) New Engl. J. Med. 343(22):1594-1602.

Liu et al., "Chimeric Mouse-Human IgG1 Antibody that can Mediate Lysis of Cancer Cells," Proc Natl. Acad. Sci., USA (1987) 84:3439-3443.

Liu et al., "Production of a Mouse-Human Chimeric Monoclonal Antibody to CD20 with Potent Fc-Dependent Biologic Activity," J. Immunology (1987) 139(10):3521-3526.

Liu et al., "Randomised, Double Blind, Placebo Controlled Study of Interferon Beta-1a in Relapsing-Remitting Multiple Sclerosis Analysed by Area under Disability/Time Curves," J. Neurol. Neurosurg. Psych. (1999) 67:451-456.

Marks et al., "By-Passing Immunization," J. Mol. Biol. (1991) 222: 581-597.

Michaels et al., "Preclinical proof of concept for VivoVec, a lentiviral-based platform for in vivo CAR T-cell engineering", J Immunother Cancer 2023;11:e006292. doi:10.1136/jitc-2022-006292, 40 pages.

Milgrom et al., "Treatment of Allergic Asthma with Monoclonal Anti-IgE Antibody," New Engl. J. Med. (1999) 341:1966-1973.

Muller, "[43] Determination of Affinity and Specificity of Anti-Hapten Antibodies by Competitive Radioimmunoassay," Meth. Enzymol. (1983) 92:589-601. (Abstract Only).

Muyldermans et al., "Recognition of Antigens by Single-Domain Antibody Fragments: the Superfluous Luxury of Paired Domains," (2001) Trends Biochem. Sci. 26(4):230-235.

N. Depolo et al., "VSV-G Pseudotyped lentiviral vector produced in human cells are inactivated by human serum", 2 Molecular therapy 218 (2000).

Neelapu et al., "Chimeric Antigen Receptor T-Cell Therapy—Assessment and Management of Toxicities," Nat. Rev. Clin. Oncology (Jan. 2018) 15(1):47-62.

Nikolic et al., "Structural Basis for the Recognition of LDL-Receptor Family Members by VSV Glycoprotein," Nature Comm. (2018) 9(1029): 1-12.

Notice of Allowance for U.S. Appl. No. 18/066,420 dated Jul. 26, 2023.

Notice of Allowance for U.S. Appl. No. 18/157,421 dated Aug. 25, 2023.

Pluckthun, "Antibodies from *Escherichia coli*," Nature (Oct. 4, 1990) vol. 347, No. 6292, pp. 497-498.

Portielji et al., "IL-12: A Promising Adjuvant for Cancer Vaccination," Cancer Immunol. Immunother. (2003) 52:133-144.

Presta, "Selection, Design, and Engineering of Therapeutic Antibodies," J. Allergy Clin. Immunol. (2005) 116(4):731-736.

R. Florkiewicz and J. Rose, "A Cell Line Expressing Vesicular Stomatitis Virus Glycoprotein fuses at low ph", 225 Science 721 (1984).

Reichmann et al., "Reshaping Human Antibodies for Therapy," Nature (1988) 332(6162):323-327.

Roche et al., "Crystal Structure of the Low-pH Form of the Vesicular Stomatitis Virus Glycoprotein G," Science (Jul. 14, 2006) 313:187-191.

Roche et al., "Structure of the Prefusion Form of the Vesicular Stomatitis Virus Glycoprotein G," Science (Feb. 9, 2007) 315:843-848.

S. P. J. Whelan, "Vesicular stomatis Virus", Encyclopedia of virology 291 (Elsevier ltd) (2008).

S. Roche et al, "Structures of vesicular stomatitis virus glycoprotein: membrane fusion revisited", 65 Cell Mol. Life Sci. 1716 (2008).

Slamon et al., "Use of Chemotherapy Plus a Monoclonal Antibody against HER2 for Metastatic Breast Cancer that Overexpresses HER2," (2001) New Engl. J. Med. 344(11):783-792.

Teachey et al., "Identification of Predictive Biomarkers for Cytokine Release Syndrome after Chimeric Antigen Receptor T-cell Therapy for Acute Lymphoblastic Leukemia," Cancer Discov. (Jun. 2016) 6(6):664-679.

Tsurushita et al., "Humanization of a Chicken Anti-IL-12 Monoclonal Antibody," J. Immuno. Methods (2004) vol. 295, pp. 9-19.

Yang et al., "A Randomized Trial of Bevacizumab, an Anti-Vascular Endothelial Growth Factor Antibody, for Metastatic Renal Cancer," (2003) New Engl. J. Med. 349(5):427-434.

Zardecki et al, "RCSB Protein Data Bank: A Resource for Chemical, Biochemical, and Structural Explorations of large and small biomolecules", 93 J. Chem. Educ. 569(2016).

(56) References Cited

OTHER PUBLICATIONS

INH-014USCI—USPTO Before the Patent Trial and Appeal Board *Kelonia Therapeutics Inc* v *InteriusBiotherapeutics Inc* PRG2024-00008 U.S. Pat. No. 11,767,366B1 Denying Institution of Post Grant Review dated May 17, 2024.

INH-014USCI—SPTO Before the Patent Trial and Appeal Board *Kelonia Therapeutics Inc* v *InteriusBiotherapeutics Inc* PRG2024-00008 U.S. Pat. No. 11,767,366B1 Petitioner's Request for Rehearing dated Jun. 17, 2024.

Ammayappan, et al "Characteristics of Oncolytic Vesicular Stomatitis Virus Displaying Tumor-Targeting Ligands", Journal of Virology, vol. 87, No. 24, Dec. 2013, pp. 13543-13555.

Petition for Post-Grant Review of U.S. Pat. No. 11,767,366, Before the Patent Trial and Appeal Board, *Kelonia Therapeutics, Inc.*, Petitioner V. *Interius Biotherapeutics, Inc.*, Patent Owner, 98 pages.

Declaration of Professor John K. Rose, PHD, in Support of Petition for Post-Grant Review of U.S. Pat. No. 11,767,366, Before the Patent Trial and Appeal Board, *Kelonia Therapeutics, Inc.*, Petitioner V. *Interius Biotherapeutics, Inc.*, Patent Owner, Exhibit 1002, 156 pages.

*Kelonia Therapeutics, Inc.* Petitioner v. *Interius Biotherapeutics, Inc.* Patent Owner U.S. Pat. No. 11,767,366 Case No. PGR2024-00008, Patent Owner's Opposition to Petitioner's Request for Rehearing, Jul. 26, 2024.

U.S. Appl. No. 63/154,639, filed Feb. 26, 2021, Applicant ViraLogic Therapeutics, Inc.

5OY9—Albertini, A.A. et al., "5OY9, VSV G CR3", RCSB PDB, Mar. 21, 2018, last revised Apr. 18, 2018, available at https://www.rcsb.org/structure/5OY9 (last accessed Jan. 3, 2024), 6 pages.

INH-014USCI—USPTO Before the Patent Trial and Appeal Board *Kelonia Therapeutics Inc* v *InteriusBiotherapeutics Inc* PRG2024-00008 U.S. Pat. No. 11,767,366B1 Petitioner's Request for Rehearing dated Jun. 17, 2024.

Notice of Allowance for U.S. Appl. No. 18/157,421 dated Jul. 26, 2023.

\* cited by examiner

```
SEQ_ID_NO_2   KFTIVPPHKQKGNWKNVPSNYHYCPSSSDLNWHNDLIGTALQVKMPKSHKAIQADGWMCH    60
SEQ_ID_NO_11  KISIVFPQKTSDWKKVPHEYNYCPTSAQEBHGTQTSIPVELTMPKGLTTBQVGPHCH      60
SEQ_ID_NO_13  KFTIVPPRHQKGNWKNVPSYYKYCPSSSQHWHNDLTSVSLHVKIPKSHKAIQAKGWMCH    60
SEQ_ID_NO_15  KITISPPQSLKGDWRFVPEGYNYCPTSAKEHJGOLIDIGLKLPARKSPKGISAIKGWMCR   60
SEQ_ID_NO_17  KPTIVPPQSQKGDWKQVPPNYRYCPSSAQKHWHGDLLGVNIRAPKMCKVHKAIKADGWMCH  60
SEQ_ID_NO_19  KPSIVPPQSKQWKNVFSSYHYCFSSSDYHYCSSSDHWHSDLLGITPNKVKMPKTHKAIQADGWMCH  60
SEQ_ID_NO_21  KPTIVPHNQKGSWNVSARIQYCPSTSDINWHRSLIGTSLQVKMPRSHKAIKADGWSCH     60
                 :  *  **:  :: : ** .:* **.*:*   :  *  **.:* * *   :.::.** :****

SEQ_ID_NO_2   ASFWVTTCDPRWYGPEYITHSIRSSTPSVEQCKESIEQTKQSFPWLNPGPSPQSCGYATVT   120
SEQ_ID_NO_11  SALWNTTCDFPWYGFKYITTBSIHHBBPTYYQCLEAIKAYKDGVSFNSGFPPQSCCIGTVF  120
SEQ_ID_NO_13  AAKWVTTCOFRWYGFKYITBSIHBBASTLEQCNTSIEQTDKQGVWINSGFPPQSCCIATVT  120
SEQ_ID_NO_15  AARWITTPCOFRWYGFKYITRSIHSFPRSNIQCCKEAIPLTNECNKINPCFPPQSCCIASVT 120
SEQ_ID_NO_17  AAKWVTTCDYRWYGPQVITESIHSFIPTKAQCEESIKQTWEGVWINPGFFTPTNCGYASVS  120
SEQ_ID_NO_19  AAKWIPTCDFRWYGPKYITHSIRSIQPTSEQCRESIKQTKQGFPWMSPGPSSFQHCGYATVT 120
SEQ_ID_NO_21  AAKWVTTCDFWYGPKYVTHEIRSMIPTVDQCKEBIAQTKQSFWLGPHSFPQSSDYASVT   120
                :: * :***:*** ::  * .  :* .    *: **** :**.::**

SEQ_ID_NO_2   DEAVIVQVTSKHVLVDEYTGBWYCGQFINGKCHNYICPTVBNSTYBBDYKVESLCGSH    180
SEQ_ID_NO_11  DAEAHKVFVTPHSYKVDEYPGKWIDPRFIGGSROKGGTOEBVHNSTNWPTSSDGSSVOSGL    180
SEQ_ID_NO_13  DAEVVVQATPHRVLVDEYTPGEWIDSQLVGSHCSKEVQPTVHNSTVWGRDYRITGLCBSN   180
SEQ_ID_NO_15  DSESVVVTVTKHQVLVDEYSGGSNIDSQFPGGSCTSPIDPVHNSTLWRADBYLDCICDQE   180
SEQ_ID_NO_17  DAESIIVQATAHSVMIDEYSGDMLESQFPTGPCTGSTCEFTHNSTLWYADYQVTGLCDSA   180
SEQ_ID_NO_19  DSVAVVQNPPRHVLVDEYTGHWIDSQFPNGKTETESCETVHNSTVYNSDYKVTGLCDAT   180
SEQ_ID_NO_21  DEEAVIVKAPSRQVLVDEYTGBWYCGQFPTGKHKDICPTVBNSTYBDYKVTSLCDAR    180
                :   .  *   :*.  .: *    *.       .  :* **.:   ..   : * .

SEQ_ID_NO_2   LISMDITPFSEQCELSSLGKESTGFRBNSAYETSSKACKBQYCKHWGVRLPSGVWFEMA   240
SEQ_ID_NO_11  STLVGGTFFSDYSEEITSMGLPETGIRSNYFPYVSTEGICKMPFCRKFCGYKLKNDLWFQIT   240
SEQ_ID_NO_13  LASVDITFFSEINSQKTSLSNSMTGFRSNHFAYESCEHACMQVVCQWCFKLPSCVWFELV   240
SEQ_ID_NO_15  SVAMDAVLFSTESSGKFEHPGKFSNCGIRSNYFPYESLKDVCQMPFCNRKCFKLPSGVWFEIR   240
SEQ_ID_NO_17  LVSTEVFSYKEDGLMTHSIGRQNTGYPSNYFPYEKGAAACRMKYCTHEGEIRLPSGVWFEMV   240
SEQ_ID_NO_19  LVDTFEITFFSSEDGKKESIGKPNTGYPSNYFAYEKGDKVCKPNYCKHAGVRLPSGVWFEFV   240
SEQ_ID_NO_21  LISMDITPFSEQCKLTSLGKESTGFRBNSAYEFSDKACPBQYCKHWGVRLPSGVWFEMA   240
                :   : :.:  .  :   .:      : *  *  .*     .* :*  * :.:::**

SEQ_ID_NO_2   DKDLSA------AARFPEGFEGSSIAPSQTSVQVSLIQOVEPILCYSLCQETWSFIRAGLP   296
SEQ_ID_NO_11  DPFDLDKTYRGLPRIKDCPLSSSIVTPGSNATDISLINDVESILDYALCQNTWSKIEBGSP   300
SEQ_ID_NO_13  DKDLFQ----AANLFSCPRGSSIHAPSQTSVDVSLIQDVERILDNSLCCQATWSKIPAKLE  296
SEQ_ID_NO_15  DAESHBKAQVELLIKKCPBGAVISAPNQSBADINLIMDVERILDNKKLGEATVIEBRAKEAQKV  300
SEQ_ID_NO_17  QKELLE----SVQMPSCPAGLTISAPTQTSVDVSLIDDVERMLDYSLCQETWSKVHSGLP   296
SEQ_ID_NO_19  DQDVYA-----AAKLPECFVGRTISAPTQTSVQVSLIDVERILDYSLCQETWSKIRSSQP   296
SEQ_ID_NO_21  DKDIYN------DAKFPDCFSKHSIAAPSQTSVQVSLIQOVEPILCYSLCQETWSKIRAHLP   296
                :           : :    .    :.:.::.*       .:  .:    *.:

SEQ_ID_NO_2   ISPVOLSTLAPKNPGTGFAFTIINGTLKVFSTRKIRVOIAAPILSHNV9MIKGTTPSEEL   356
SEQ_ID_NO_11  ITPVDLSYLGPKNSGAGPVSTIIBGSLHYPNSKYLFVELESPVIPRMEGKVAGTRIVRQL   360
SEQ_ID_NO_13  VSPVDLSYLAPKNPGSGPAFTIIBBGTLKYPETRYIRVDISNPIIPHMVGTNSGTTFPREL   356
SEQ_ID_NO_15  LTPDIXSYLGPKNPGCPAFTIIBBGTLKAYPNTRYIRVDIACGPVTPBITGFVSGTSFPVL   360
SEQ_ID_NO_17  ISPVDLGYIAPHPBGAGPAFTIINGTLKYFDTPYLRIDIEGPVLFPNMTGKVSGTPTKFEL   356
SEQ_ID_NO_19  VSPVDLSYLAPKNPGTGSPAFTINGTLKYFSTRYIRSDINPISVWGKISGSGPAEFEL   356
SEQ_ID_NO_21  ISPVDLSTLSEKNPGTGFAFTIINGTLKVFSTKXIRYQIASPIIPQWPSVIKGTTPSFEL   356
                :.* *:. :.:.  .** .  ::** : :   *: *:*.*  :: :   ::*.:  **

SEQ_ID_NO_2   WDDWAPYHDVEIGPRSVLKTSSYKFPLNMIGHGWLQSPLHLSSKAQVESHPHIQDAASQ   416
SEQ_ID_NO_11  WQQWPFBGESVKISPNCGVLTKQGYRPSLHIISTQSEVPMDIKKMERIVKMREHPHIEAAQTS   420
SEQ_ID_NO_13  WNOWIPYSOVEISGNGVLNTFGPFPSLYSISNGMLSDSDLRKKSQAQVPEBHPPAKDAASQ   416
SEQ_ID_NO_15  WQQNFPYGEHSIGPNGLLMFASGPYSLFSNVGTGVLDADIRKLGBATVIEBHHAKEAQKV   420
SEQ_ID_NO_17  WTENFYPDVEIGPNCSVLFTPBGYFPLYMIGHGMLLDSPLQKFSQAEFPVHHPPTAKEAVQK   416
SEQ_ID_NO_19  RTEWFFYEGVEIGPNSILKTPGEGYKFPLEMIGHGMLDSQEHKTSQAEVPEHPHLABAPKQ   416
SEQ_ID_NO_21  NTDWYPYEHDVEIGPRSVLKTAPSYKFPLNMIGHGNLDSPLHISSKAQVFBRHPHIQDAASQ   416
                     :.     :.   ::      : **:.  *.:: .    :.::.   *

SEQ_ID_NO_2   LP---QHSSLFFGTGSLSKNPIBKVEGNFSSWKESIASFPFIGLIXGLFLVLPVGIHLC    473
SEQ_ID_NO_11  IKKDTRSSVLITSGDTGVEKNSVELVEGWFSGWRSSINGVLAVIIGFYILIFLISLGIVLS    480
SEQ_ID_NO_13  LS----DDRTLPPGDTGLSFNSVELVEGWFGSSNKSTLASPPLIIGLSVALIPIIRLIVAIR   473
SEQ_ID_NO_15  VQ----DSEVIFPSDIGVEKNSVEVVBGWFSGMNRSLMSIFGILLIVCLVLVRILLXAX   477
SEQ_ID_NO_17  LS----DDETLPFGDTGIFKNPVEKVIGWFSWRSSVMAIVPSALLLVITVLMVRLCVAFR   473
SEQ_ID_NO_19  LP---SEETLFPGTGISKNPVELIEGWFSSWKRSTVVTPFFAIGVFTILYVVRAIVIAVR   473
SEQ_ID_NO_21  LP---GPEILFSCHGFTGLSKNPIEKVMKWNESSGWKTIASPFPIIGLVISLYFKLRIGLALC   473
                          .    .  .  ::  ****.: :.     : .  :  : :   :

SEQ_ID_NO_2   IKLFRTK-KFQIYTDIEMNRLGK---    495
SEQ_ID_NO_11  -SLFPQKRKFIYKSDVEMAHFR---   501
SEQ_ID_NO_13  YKYKG--RNTQRIYNQVERNSALGNK---   496
SEQ_ID_NO_15  YCCVRHFPRTIYEBDLEMKGPISRRA    502
SEQ_ID_NO_17  H---FCCQKFRKIYNDLENNQLFR---   494
SEQ_ID_NO_19  IPYQSSN-QFRIYNDIEHSRFRK---  495
SEQ_ID_NO_21  IKCPVQEKRPEIYTDIEMNRLDR---  495
                      *:**  :.
```

FIG. 3

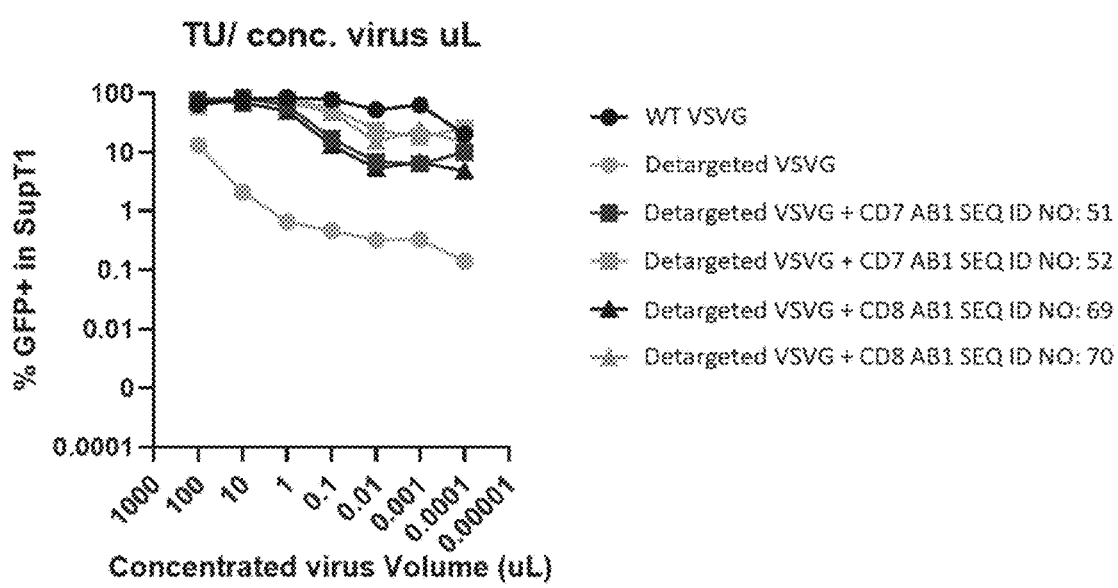
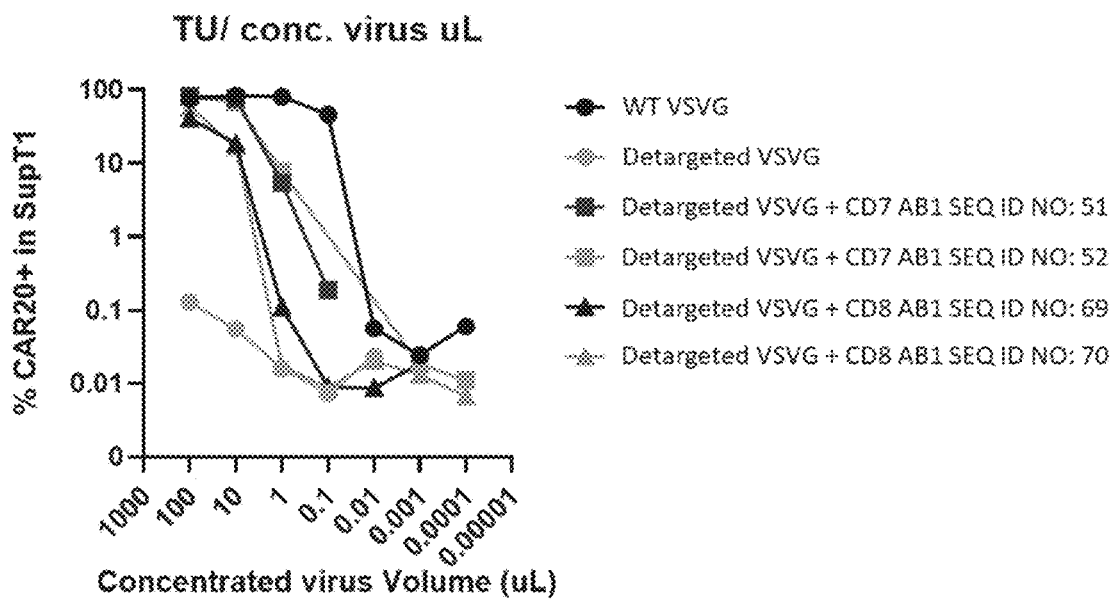
FIG. 9

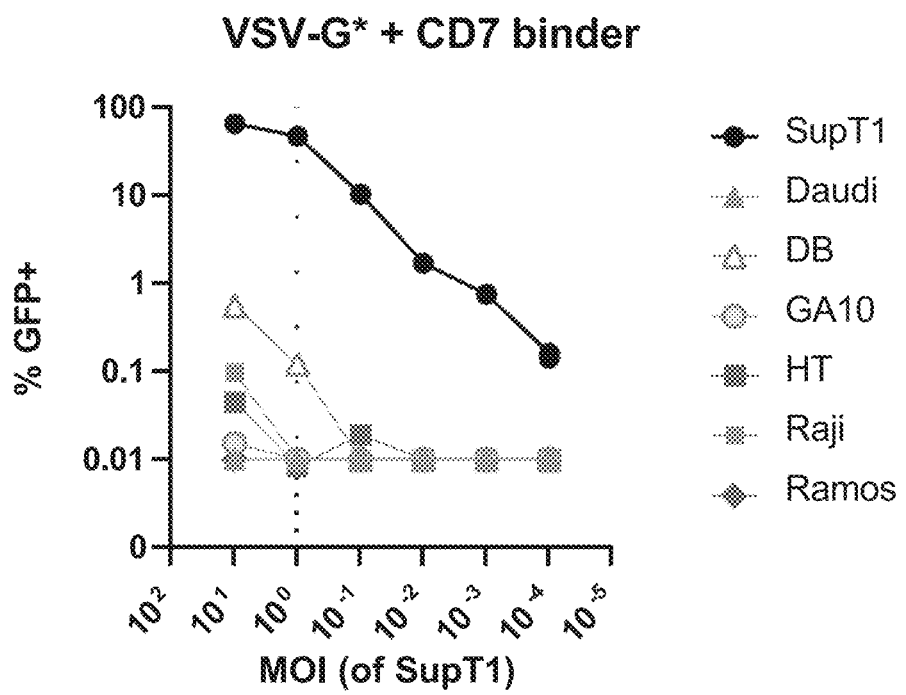
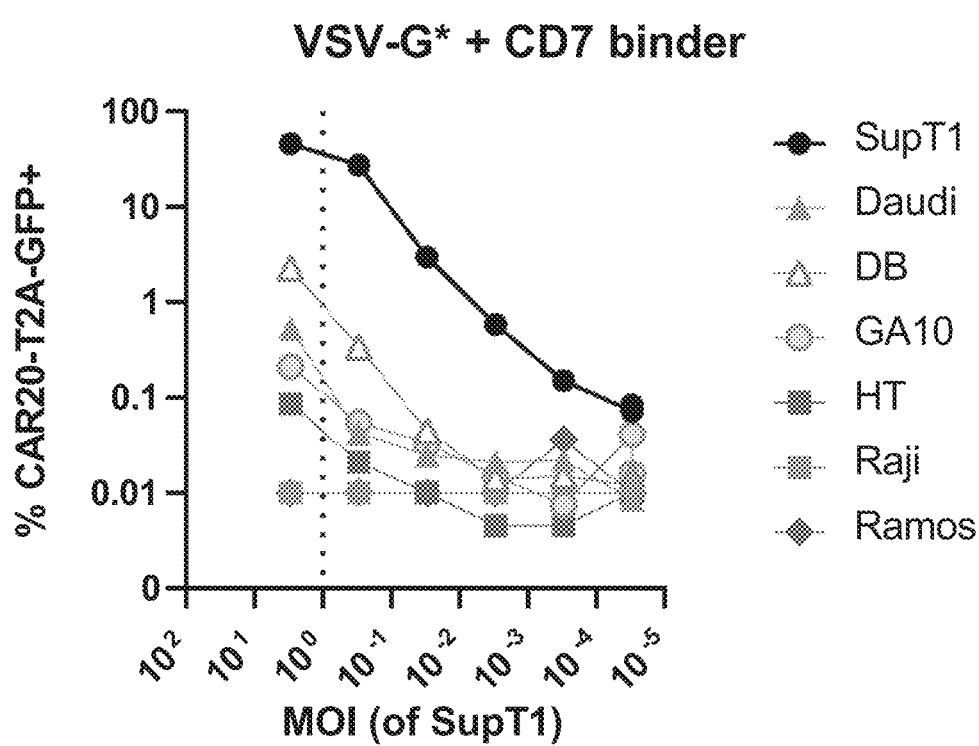
FIG. 11

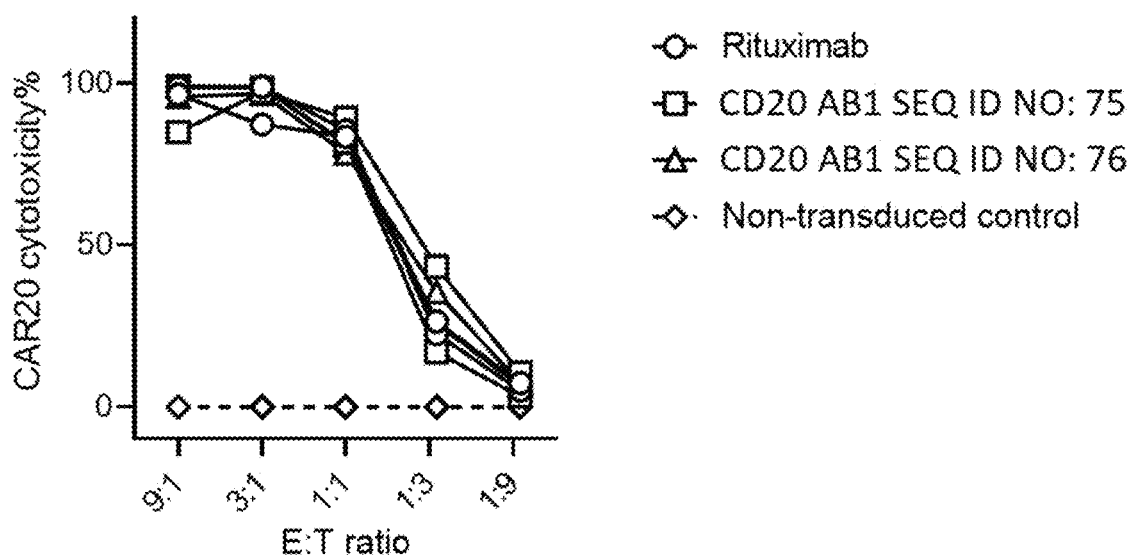
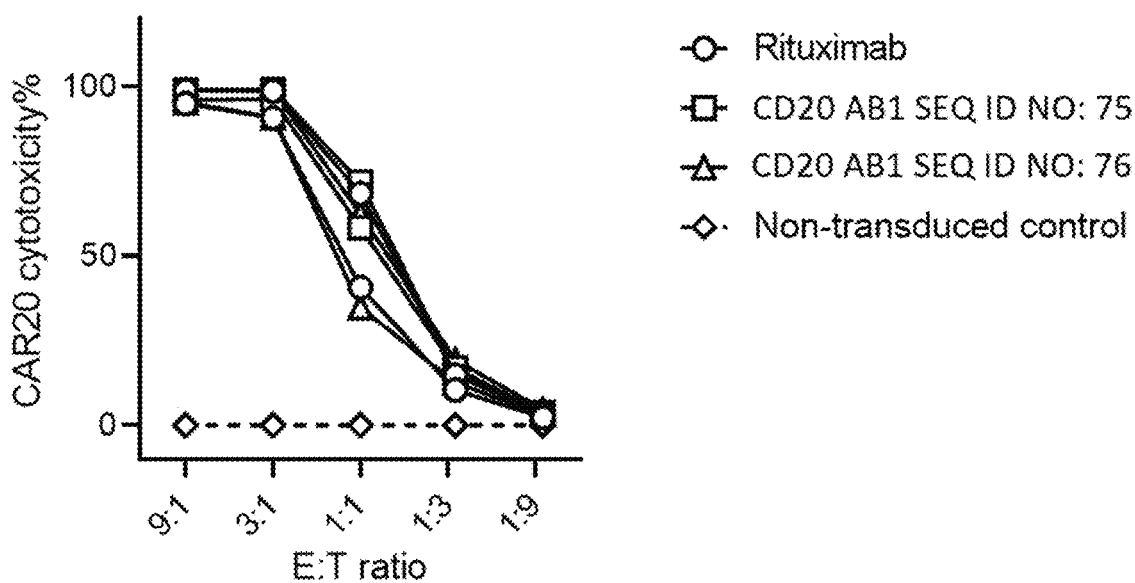
FIG. 12

PSEUDOTYPED VIRAL PARTICLES, COMPOSITIONS COMPRISING THE SAME, AND USES THEREOF

CROSS REFERENCE TO RELATED APPLICATIONS

This application is a continuation of, and claims priority to, U.S. patent application Ser. No. 18/647,283 filed Apr. 26, 2024, which is a continuation of U.S. patent application Ser. No. 18/157,421 filed 20 Jan. 2023, now U.S. Pat. No. 12,104,177 issued Oct. 1, 2024, which is a continuation of U.S. patent application Ser. No. 18/066,420 filed 15 Dec. 2022, now U.S. Pat. No. 11,767,366 issued 26 Sep. 2023, which claims the benefit of U.S. Provisional Application Ser. No. 63/289,888 filed 15 Dec. 2021, and U.S. Provisional Application Ser. No. 63/289,977 filed 15 Dec. 2021, and U.S. Provisional Application Ser. No. 63/266,044 filed 27 Dec. 2021, and U.S. Provisional Application Ser. No. 63/267,039 filed 21 Jan. 2022, each of which is hereby incorporated by reference in their entirety.

REFERENCE TO SEQUENCE LISTING SUBMITTED ELECTRONICALLY

The instant application contains a Sequence Listing which has been submitted electronically in XML format and is hereby incorporated by reference in its entirety. Said XML copy, created on 28 Nov. 2022, is named "148165.001401_SL.xml" and is 86.3 kilobytes in size.

BACKGROUND

Vesicular stomatitis virus (VSV) is an enveloped, negative-strand RNA virus that belongs to the Vesiculovirus genus of the Rhabdovirus family. It is an arbovirus which can infect insects, cattle, horses and pigs. VSV genome encodes five structural proteins among which include a single transmembrane glycoprotein (G). The glycoprotein is a classic type I membrane glycoprotein with an amino-terminal signal peptide, an ectodomain of about 450 amino acids, a single alpha helical transmembrane segment and a small intraviral carboxy-terminal domain. The signal peptide is cleaved in the lumen of the endoplasmic reticulum and the native glycoprotein consists in the ectodomain, the transmembrane domain and the intraviral domain.

G plays a critical role during the initial steps of virus infection (Molecular and Cellular Aspects of Rhabdovirus Entry. Viruses 4, 117-139), which is hereby incorporated by reference in its entirety. First, it is responsible for virus attachment to specific receptors. After binding, virions enter the cell by a clathrin-mediated endocytic pathway. In the acidic environment of the endocytic vesicle, G triggers the fusion between the viral and endosomal membranes, which releases the genome in the cytosol for the subsequent steps of infection. Fusion is catalyzed by a low-pH-induced large structural transition from a pre-toward a post-fusion conformation which are both trimeric (Roche, S., Bressanelli, S., Rey, F. A., and Gaudin, Y. (2006). Crystal structure of the low-pH form of the vesicular stomatitis virus glycoprotein G. Science 313, 187-191. Roche, S., Rey, F. A., Gaudin, Y., and Bressanelli, S. (2007). Structure of the prefusion form of the vesicular stomatitis virus glycoprotein g. Science 315, 843-848), each of which is hereby incorporated by reference in its entirety).

The polypeptide chain of G ectodomain folds into three distinct domains which are the fusion domain (FD), the pleckstrin homology domain (PHD), and the trimerization domain (TrD). During the structural transition, the FD, the PHD and the TrD retain their tertiary structure. Nevertheless, they undergo large rearrangements in their relative orientation due to secondary changes in hinge segments (S1 to S5) which refold during the low-pH induced conformational change (Roche et al., 2006; Roche et al., 2007).

It has been shown that low-density lipoprotein receptor (LDL-R) and other members of this receptor family serve as VSV receptors (Finkelshtein, D., Werman, A., Novick, D., Barak, S., and Rubinstein, M. (2013). LDL receptor and its family members serve as the cellular receptors for vesicular stomatitis virus. Proceedings of the National Academy of Sciences of the United States of America 110, 7306-7311, which is hereby incorporated by reference in its entirety). VSV-G can be used for pseudotyping other viruses and VSV-G-pseudotyped lentiviruses (VSV-G-LVs) exhibit the same broad tropism as VSV. However, this broad tropism can inhibit the selective targeting of specific cell types. Therefore, there is a need, for modified (mutated or mutant) VSV-G proteins that can be used to pseudotype viruses that abrogate its binding to the LDL receptor. The present embodiments, fulfill these needs as well as others.

The human CD7 molecule is a cell surface glycoprotein with a molecular weight of approximately 40 kDa belonging to the immunoglobulin superfamily. The CD7 molecule is mainly expressed on the surface of most thymocytes, more than 85% of the surface of peripheral blood T lymphocytes and the surface of natural killer cells. The embodiments disclosed herein provide for polypeptide and antibodies against CD7, compositions comprising the same, and uses thereof.

CD8 (cluster of differentiation 8) is a transmembrane glycoprotein which is a specific marker for a subclass of T-cells (which includes cytotoxic T-cells). Without wishing to be bound to a particular theory, CD8 assembles as either a heterodimer of the CD8 alpha and CD8 beta subunits or a CD8 alpha homodimer. The assembled dimeric CD8 complex acts as a co-receptor together with the T cell receptor (TCR) to recognize antigen presentation by MHC class I cells. CD8 plays a role in the development of T-cells and activation of mature T-cells. Changes in T-cell localization can reflect the progression of an immune response and can occur over time. The embodiments disclosed herein provide for polypeptide and antibodies against CD8, compositions comprising the same, and uses thereof.

BRIEF SUMMARY

In some embodiments, a VSV-G polypeptide is provided. In some embodiments, the VSV-G polypeptide comprises a mutation at position 182 of SEQ ID NO: 2. In some embodiments, the polypeptide comprises an I182E or I182D mutation as compared to SEQ ID NO: 2. In some embodiments, the VSV-G polypeptide comprises the sequence of SEQ ID NO: 4. In some embodiments, the VSV-G polypeptide comprises the sequence of SEQ ID NO: 5.

In some embodiments, the VSV-G polypeptide further comprises a mutation in the VSV-G protein that corresponds to a position of 8, 10, 47, 209, and/or 354 as compared to SEQ ID NO: 2. In some embodiments, the VSV-G polypeptide comprises a H8A and/or a K47Q substitution. In some embodiments, the VSV-G polypeptide comprises a substitution at position 10 as compared to SEQ ID NO: 2. In some embodiments, the substitution at position 10 is Q10A, Q10R, or Q10K.

In some embodiments, a VSV-G polypeptide is provided. In some embodiments, the VSV-G polypeptide comprises a substitution at position I182 and at least one of T214, and T352 of SEQ ID NO: 2. In some embodiments, the VSV-G polypeptide comprises a substitution at position I182, T214, and T352 of SEQ ID NO: 2. In some embodiments, the VSV-G polypeptide comprises the sequence of SEQ ID NO: 22. In some embodiments, the VSV-G polypeptide comprises the sequence of SEQ ID NO: 23. In some embodiments, the VSV-G polypeptide comprises the sequence of SEQ ID NO: 24. In some embodiments, the VSV-G polypeptide comprises the sequence of SEQ ID NO: 25.

In some embodiments, a nucleic acid molecule is provided. In some embodiments, the nucleic acid molecule encodes for the VSV-G polypeptide as provided for herein.

In some embodiments, a vector is provided comprising a nucleic acid molecule as provided for herein.

In some embodiments, a plasmid is provided comprising a nucleic acid molecule as provided for herein.

In some embodiments, a viral particle is provided. In some embodiments, the viral particle comprises a VSV-G polypeptide as provided for herein. In some embodiments, the viral particle further comprises a targeting moiety. In some embodiments, the viral particle further comprises a nucleic acid molecule encoding for a heterologous molecule of interest.

In some embodiments, a method of delivering a heterologous molecule of interest to a target cell is provided. In some embodiments, the method comprises contacting the cell with a viral vector comprising a VSV-G protein as provided for herein, a targeting moiety that binds to the target cell, and a nucleic acid molecule encoding a heterologous molecule of interest. In some embodiments, the heterologous molecule of interest is a chimeric antigen receptor.

In some embodiments, a method of delivering a heterologous molecule of interest to a target cell in a subject is provided. In some embodiments, the method comprises contacting the cell with a viral vector comprising a VSV-G protein as provided for herein, a targeting moiety that binds to the target cell, and a nucleic acid molecule encoding a heterologous molecule of interest. In some embodiments, the heterologous molecule of interest is a chimeric antigen receptor.

In some embodiments, a method of treating cancer in a subject is provided. In some embodiments, the method comprises contacting the cell with a viral vector comprising a VSV-G protein as provided for herein, a targeting moiety that binds to the target cell, and a nucleic acid molecule encoding a heterologous molecule of interest. In some embodiments, the heterologous molecule of interest is a chimeric antigen receptor.

In some embodiments, the targeting moiety of the viral particle binds to CD7. In some embodiments, the targeting moiety comprises a polypeptide comprising a heavy chain CDR1 having the amino acid sequence of SEQ ID NO: 35, a heavy chain CDR2 having the amino acid sequence of SEQ ID NO: 36, a heavy chain CDR3 having the amino acid sequence of SEQ ID NO: 37, a light chain CDR1 having the amino acid sequence of SEQ ID NO: 38, a light chain CDR2 having the amino acid sequence of SEQ ID NO: 39, a light chain CDR3 having the amino acid sequence of SEQ ID NO: 40. In some embodiments, the targeting moiety comprises a polypeptide comprising a heavy chain variable region having the amino acid sequence of SEQ ID NO: 47 and a light chain variable region having the amino acid sequence of SEQ ID NO: 48.

In some embodiments, the targeting moiety that binds to CD7 comprises a polypeptide comprising a sequence having at least 90% sequence identity to SEQ ID NO: 51, at least 95% sequence identity to SEQ ID NO: 51, at least 99% sequence identity to SEQ ID NO: 51, or a sequence as set forth in SEQ ID NO: 51. In some embodiments, the targeting moiety that binds to CD7 comprises a polypeptide comprising the sequence of SEQ ID NO: 51.

In some embodiments, the targeting moiety that binds to CD7 comprises a polypeptide comprising a sequence having at least 90% sequence identity to SEQ ID NO: 52, at least 95% sequence identity to SEQ ID NO: 52, at least 99% sequence identity to SEQ ID NO: 52, or a sequence as set forth in SEQ ID NO: 52. In some embodiments, the targeting moiety that binds to CD7 comprises a polypeptide comprising the sequence of SEQ ID NO: 52.

In some embodiments, the targeting moiety of the viral particle binds to CD8. In some embodiments, the targeting moiety comprises a polypeptide comprising a heavy chain CDR1 having the amino acid sequence of SEQ ID NO: 55, a heavy chain CDR2 having the amino acid sequence of SEQ ID NO: 56, a heavy chain CDR3 having the amino acid sequence of SEQ ID NO: 57, a light chain CDR1 having the amino acid sequence of SEQ ID NO: 58, a light chain CDR2 having the amino acid sequence of SEQ ID NO: 59, a light chain CDR3 having the amino acid sequence of SEQ ID NO: 60. In some embodiments, the targeting moiety comprises a polypeptide comprising a heavy chain variable region having the amino acid sequence of SEQ ID NO: 67 and a light chain variable region having the amino acid sequence of SEQ ID NO: 68.

In some embodiments, the targeting moiety that binds to CD8 comprises a polypeptide comprising a sequence having at least 90% sequence identity to SEQ ID NO: 69, at least 95% sequence identity to SEQ ID NO: 69, at least 99% sequence identity to SEQ ID NO: 69, or a sequence as set forth in SEQ ID NO: 69. In some embodiments, the targeting moiety that binds to CD7 comprises a polypeptide comprising the sequence of SEQ ID NO: 69.

In some embodiments, the targeting moiety that binds to CD7 comprises a polypeptide comprising a sequence having at least 90% sequence identity to SEQ ID NO: 70, at least 95% sequence identity to SEQ ID NO: 70, at least 99% sequence identity to SEQ ID NO: 70, or a sequence as set forth in SEQ ID NO: 70. In some embodiments, the targeting moiety that binds to CD7 comprises a polypeptide comprising the sequence of SEQ ID NO: 70.

In some embodiments, a method of delivering a heterologous molecule of interest to a target cell is provided. In some embodiments, the method comprises contacting the cell with a viral vector comprising a VSV-G protein as provided for herein, a targeting moiety as provided for herein that binds to the target cell, and a nucleic acid molecule encoding a heterologous molecule of interest. In some embodiments the targeting moiety binds to CD7. In some embodiments, the targeting moiety binds to CB8. In some embodiments, the heterologous molecule of interest is a chimeric antigen receptor.

In some embodiments, a method of delivering a heterologous molecule of interest to a target cell in a subject is provided. In some embodiments, the method comprises contacting the cell with a viral vector comprising a VSV-G protein as provided for herein, a targeting moiety as provided for herein that binds to the target cell, and a nucleic acid molecule encoding a heterologous molecule of interest. In some embodiments the targeting moiety binds to CD7. In some embodiments, the targeting moiety binds to CB8. In some embodiments, the heterologous molecule of interest is a chimeric antigen receptor.

In some embodiments, a method of treating cancer in a subject is provided. In some embodiments, the method comprises contacting the cell with a viral vector comprising a VSV-G protein as provided for herein, a targeting moiety as provided for herein that binds to the target cell, and a nucleic acid molecule encoding a heterologous molecule of interest. In some embodiments the targeting moiety binds to CD7. In some embodiments, the targeting moiety binds to CB8. In some embodiments, the heterologous molecule of interest is a chimeric antigen receptor.

BRIEF DESCRIPTION OF FIGURES

FIG. 1 Panel A illustrates the crystal structure of VSV-G bound to CR3 of the LDL-R. FIG. 1 Panel B illustrates the crystal structure of VSV-G bound to CR2 of the LDL-R.

FIG. 2 Panel A illustrates the titration of VSV-G constructs on SupT1 cells. FIG. 2 Panel B illustrates functional titer of each construct calculated from the titration in FIG. 2 Panel A.

FIG. 3 illustrates an alignment of the ectodomains of different VSV-G proteins from different strains.

FIG. 6 Panel M shows flow cytometry data of human PBMCs transduced with exemplary vectors comprising CD7 binders as disclosed herein.

FIG. 7 Panel M shows flow cytometry data of non-human primate PBMCs transduced with exemplary vectors comprising CD7 binders as disclosed herein.

FIG. 8 Panel B shows flow cytometry data of non-human primate PBMCs transduced with exemplary vectors comprising CD8 binders as disclosed herein.

FIG. 9 Panels A and B illustrate GFP or CAR transduction of SupT1 cells utilizing VSV-G pseudotyped lentiviral particles harboring CD7 or CD8 binders as provided for herein. FIG. 9 Panel A illustrates GFP transduction. FIG. 9 Panel B illustrates CAR transduction.

FIG. 10 Panel B illustrates the transduction of cells in the absence of the CD7 binder. FIG. 10 Panel C illustrates the transduction of human and non-human primate PBMCs in terms of MOI calculated from SupT1 titration. VSV-G* denotes VSV-G polypeptide comprising I182E, T214N, T352A, which corresponds to a mature polypeptide of SEQ ID NO: 23 or SEQ ID NO: 25 (with 1196E, T230N and T368A mutations (with leader sequence and adjusted numbering).

FIG. 11 Panels A and B illustrate the off target transduction of VSV-G* pseudotyped lentiviral particles harboring a CD7 binder in a panel of B-cell cell lines as compared to control SupT1 cells. FIG. 11 Panel A illustrates the data for GFP transduction. FIG. 11 Panel B illustrates the data for CAR20-T2A-GFP transduction. VSV-G* denotes a VSV-G polypeptide comprising I182E, T214N, and T352A mutations as provided for herein.

FIG. 12 Panels A and B illustrate the ability of VSV-G* pseudotyped lentiviral particles utilizing CD7 binders and a CD20-CAR transgene as provided for herein to kill Duadi lymphoma cells (FIG. 12 Panel A) or Raji lymphoma cells (FIG. 12 Panel B). CAR20 constructs utilized antigen binding domains comprising rituximab, or CD20AB1 SEQ ID NOs 75 or 76 as provided for herein.

FIG. 14 Panel A depicts the experimental design. FIG. 14 Panel B illustrates that mice receiving i.v. lentiviral particles as provided for herein prior to Raji tumor infusion had significantly lower tumor burden than mice receiving control (GFP) vector or untreated mice. Tumor burden measured via IVIS imaging.

FIG. 15 Panel A depicts the experimental design. FIG. 15 Panel B illustrates that mice receiving i.v. lentiviral particles as provided for herein after 6 days after Raji tumor infusion had their tumor burdens diminished below the limit of detection. Tumor burden measured via IVIS imaging.

DETAILED DESCRIPTION

Figure 1:
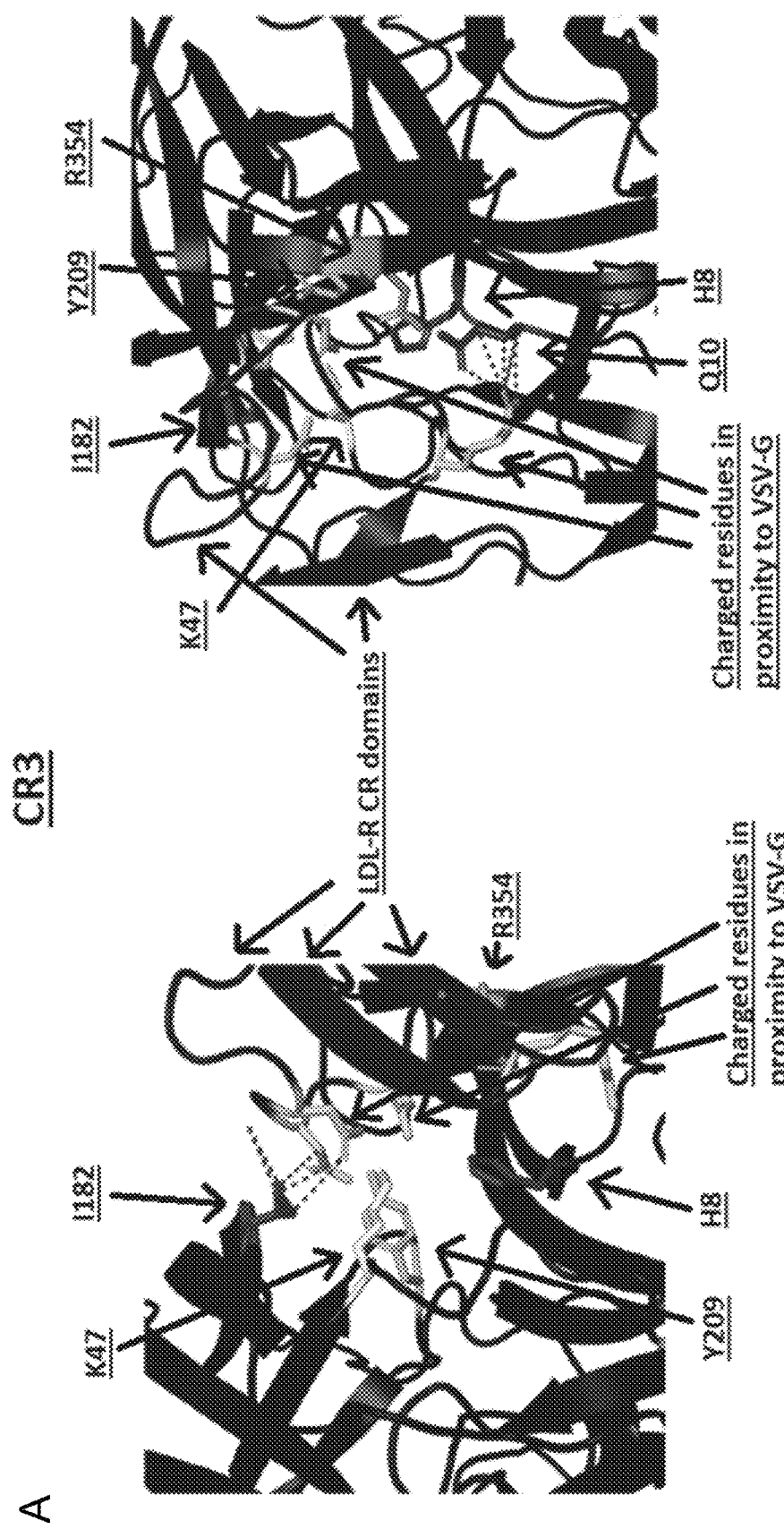
FIG. 1 Panels A and B illustrate crystal structures of VSV-G bound to LDL-R.
Figure 1:
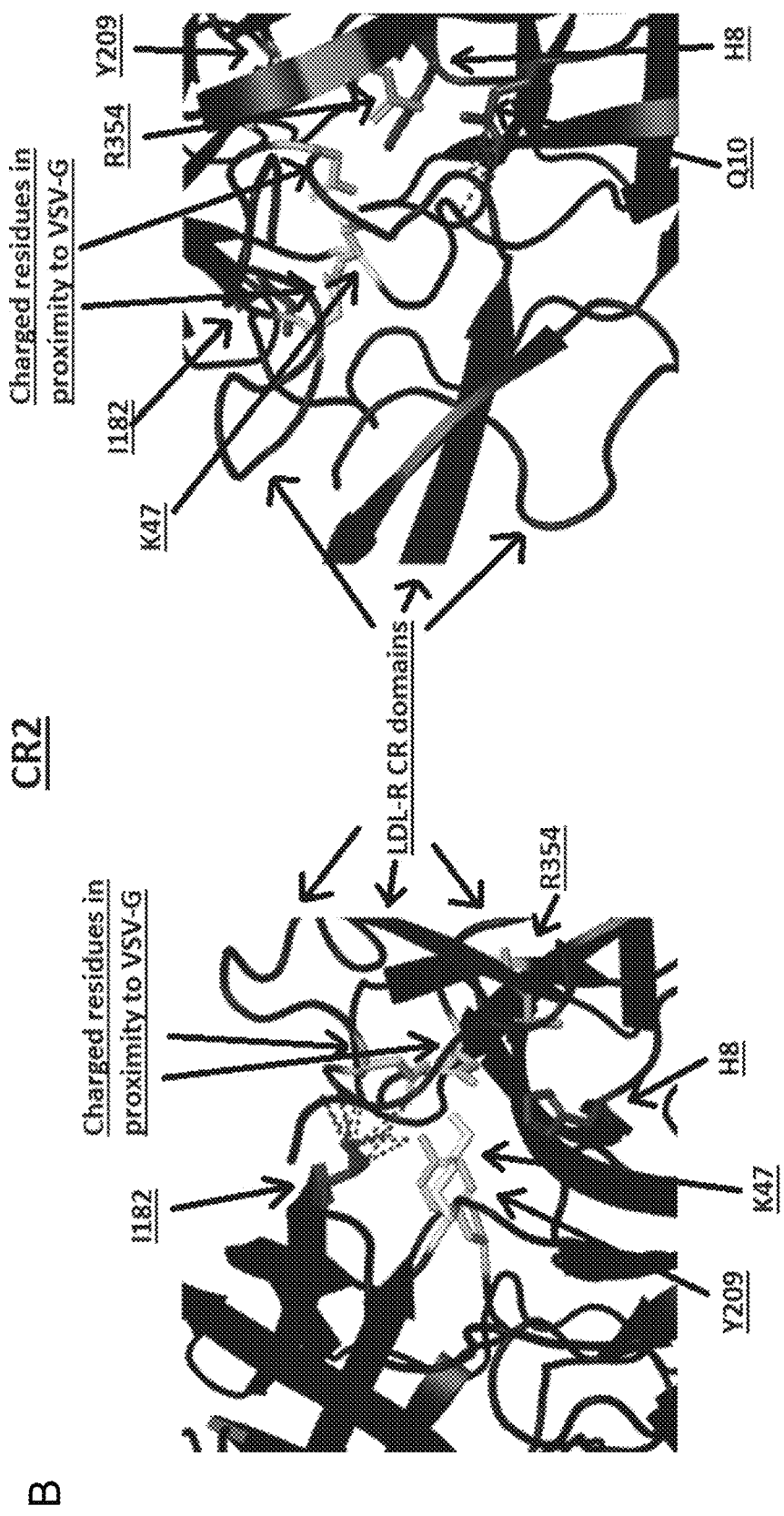

Provided for herein are mutant VSV-G proteins that can be used, for example, to pseudotype a virus, such as a lentivirus. In some embodiments, the pseudotyped viral-like particles are pseudotyped using viral glycoproteins of a vesicular stomatitis New Jersey virus strain, a vesicular stomatitis Indiana virus strain, a vesicular stomatitis Alagoas virus strain, a vesicular stromatitis Maraba virus strain, or a vesicular stomatitis Carajas virus strain.

The pseudotyped viruses comprising the mutant VSV-G proteins can be used in conjunction with a targeting moiety to facilitate the fusion of the pseudotyped virus with a specific cell or tissue based on the expression of the target on the cell or the tissue.

Unless defined otherwise, all technical and scientific terms have the same meaning as is commonly understood by one of ordinary skill in the art to which the embodiments disclosed belongs.

As used herein, the terms "a" or "an" means that "at least one" or "one or more" unless the context clearly indicates otherwise.

As used herein, the term "about" means that the numerical value is approximate and small variations would not significantly affect the practice of the disclosed embodiments. Where a numerical limitation is used, unless indicated otherwise by the context, "about" means the numerical value can vary by ±10% and remain within the scope of the disclosed embodiments. Additionally, where a phrase recites "about x to y," the term "about" modifies both x and y and can be used interchangeably with the phrase "about x to about y" unless context dictates differently.

"Activation," as used herein in reference to a T cell, refers to the state of a T cell that has been sufficiently stimulated to induce detectable cellular proliferation. Activation can also be associated with induced cytokine production, and detectable effector functions. The term "activated T cells" refers to, among other things, T cells that are undergoing cell division.

As used herein, to "alleviate" a disease means reducing the severity of one or more symptoms of the disease.

The term "antigen" as used herein is defined as a molecule that provokes an immune response. This immune response may involve either antibody production, or the activation of specific immunologically-competent cells, or both. The skilled artisan will understand that any macromolecule, including virtually all proteins or peptides, can serve as an antigen. The term "antigen" can also refer to a molecule that an antibody or antibody-like molecule can bind to or is recognized by the antibody or antibody-like molecule.

The term "antibody molecule," "antibody" or antigen binding domain, as that term is used herein, refers to a polypeptide, e.g., an immunoglobulin chain or fragment thereof, comprising at least one functional immunoglobulin variable domain sequence. An antibody molecule encompasses antibodies (e.g., full-length antibodies) and antibody fragments. In some embodiments, an antibody molecule comprises an antigen binding or functional fragment of a full-length antibody, or a full-length immunoglobulin chain. For example, a full-length antibody is an immunoglobulin (Ig) molecule (e.g., an IgG antibody) that is naturally occurring or formed by normal immunoglobulin gene fragment recombinatorial processes. In embodiments, an antibody molecule refers to an immunologically active, antigen binding portion of an immunoglobulin molecule, such as an antibody fragment. An antibody fragment, e.g., functional fragment, comprises a portion of an antibody, e.g., Fab, Fab', F(ab')2, F(ab)2, variable fragment (Fv), domain antibody (dAb), or single chain variable fragment (scFv). A functional antibody fragment binds to the same antigen as that recognized by the intact (e.g., full-length) antibody. The terms "antibody fragment" or "functional fragment" also include isolated fragments consisting of the variable regions, such as the "Fv" fragments consisting of the variable regions of the heavy and light chains or recombinant single chain polypeptide molecules in which light and heavy variable regions are connected by a peptide linker ("scFv proteins"). In some embodiments, an antibody fragment does not include portions of antibodies without antigen binding activity, such as Fc fragments or single amino acid residues. Exemplary antibody molecules include full-length antibodies and antibody fragments, e.g., dAb (domain antibody), single chain, Fab, Fab', and F(ab')2 fragments, and single chain variable fragments (scFvs).

The term "antibody molecule" also encompasses whole or antigen binding fragments of domain, or single domain, antibodies, which can also be referred to as "sdAb" or "VHH." Domain antibodies comprise either VH or VL that can act as stand-alone, antibody fragments. Additionally, domain antibodies include heavy-chain-only antibodies (HCAbs). Domain antibodies also include a CH2 domain of an IgG as the base scaffold into which CDR loops are grafted. It can also be generally defined as a polypeptide or protein comprising an amino acid sequence that is comprised of four framework regions interrupted by three complementarity determining regions. This is represented as FR1-CDR1-FR2-CDR2-FR3-CDR3-FR4. sdAbs can be produced in camelids such as llamas, but can also be synthetically generated using techniques that are well known in the art. The numbering of the amino acid residues of a sdAb or polypeptide is according to the general numbering for VH domains given by Kabat et al. ("Sequence of proteins of immunological interest," US Public Health Services, NIH Bethesda, MD, Publication No. 91, which is hereby incorporated by reference). According to this numbering, FR1 of a sdAb comprises the amino acid residues at positions 1-30, CDR1 of a sdAb comprises the amino acid residues at positions 31-36, FR2 of a sdAb comprises the amino acids at positions 36-49, CDR2 of a sdAb comprises the amino acid residues at positions 50-65, FR3 of a sdAb comprises the amino acid residues at positions 66-94, CDR3 of a sdAb comprises the amino acid residues at positions 95-102, and FR4 of a sdAb comprises the amino acid residues at positions 103-113. Domain antibodies are also described in WO2004041862 and WO2016065323, each of which is hereby incorporated by reference. The domain antibodies can be a targeting moiety as described herein.

As used herein, unless otherwise indicated, "antibody fragment" or "antigen binding fragment" refers to antigen binding fragments of antibodies, i.e. antibody fragments that retain the ability to bind specifically to the antigen bound by the full-length antibody, e.g. fragments that retain one or more CDR regions. Examples of antibody binding fragments include, but are not limited to, Fab, Fab', F(ab')$_2$, and Fv fragments; diabodies; linear antibodies; single-chain antibody molecules, e.g., sc-Fv; nanobodies (single domain antibody) and multispecific antibodies formed from antibody fragments.

A "Fab fragment" is comprised of one light chain and the $C_H1$ and variable regions of one heavy chain. The heavy chain of a Fab molecule cannot form a disulfide bond with another heavy chain molecule.

An "Fc" region contains two heavy chain fragments comprising the CH2 and CH3 domains of an antibody. The two heavy chain fragments are held together by two or more disulfide bonds and by hydrophobic interactions of the CH3 domains.

A "Fab' fragment" contains one light chain and a portion or fragment of one heavy chain that contains the $V_H$ domain and the $C_H1$ domain and also the region between the $C_H1$ and $CH_2$ domains, such that an interchain disulfide bond can be formed between the two heavy chains of two Fab' fragments to form a F(ab')$_2$ molecule.

A "F(ab')$_2$ fragment" contains two light chains and two heavy chains containing a portion of the constant region between the $C_H1$ and $C_H2$ domains, such that an interchain disulfide bond is formed between the two heavy chains. A F(ab')$_2$ fragment thus is composed of two Fab' fragments that are held together by a disulfide bond between the two heavy chains.

The "Fv region" comprises the variable regions from both the heavy and light chains, but lacks the constant regions.

The term "single-chain Fv" or "scFv" antibody refers to antibody fragments comprising the $V_H$ and $V_L$ domains of an antibody, wherein these domains are present in a single polypeptide chain. Generally, the Fv polypeptide further comprises a polypeptide linker between the VH and VL domains which enables the scFv to form the desired structure for antigen binding. For a review of scFv, see Pluckthun (1994) THE PHARMACOLOGY OF MONOCLONAL ANTIBODIES, vol. 113, Rosenburg and Moore eds. Springer-Verlag, New York, pp. 269-315. See also, International Patent Application Publication No. WO 88/01649 and U.S. Pat. Nos. 4,946,778 and 5,260,203.

Antibody molecules can be monospecific (e.g., monovalent or bivalent), bispecific (e.g., bivalent, trivalent, tetravalent, pentavalent, or hexavalent), trispecific (e.g., trivalent, tetravalent, pentavalent, or hexavalent), or with higher orders of specificity (e.g, tetraspecific) and/or higher orders of valency beyond hexavalency. An antibody molecule can comprise a functional fragment of a light chain variable region and a functional fragment of a heavy chain variable region, or heavy and light chains may be fused together into a single polypeptide.

Furthermore, antigens can be derived from recombinant or genomic DNA. A skilled artisan will understand that any DNA, which comprises a nucleotide sequences or a partial nucleotide sequence encoding a protein that elicits an immune response therefore encodes an "antigen" as that term is used herein. Furthermore, one skilled in the art will understand that an antigen need not be encoded solely by a full length nucleotide sequence of a gene. Moreover, a skilled artisan will understand that an antigen need not be encoded by a "gene" at all. It is readily apparent that an antigen can be generated synthesized or can be derived from a biological sample. Such a biological sample can include, but is not limited to a tissue sample, a tumor sample, a cell or a biological fluid.

In certain embodiments, monoclonal antibodies herein also include camelized single domain antibodies. See, e.g., Muyldermans et al. (2001) *Trends Biochem. Sci.* 26:230; Reichmann et al. (1999) *J. Immunol. Methods* 231:25; WO 94/04678; WO 94/25591; U.S. Pat. No. 6,005,079). In one embodiment, the present invention provides single domain antibodies comprising two $V_H$ domains with modifications such that single domain antibodies are formed.

As used herein, the term "diabodies" refers to small antibody fragments with two antigen-binding sites, which fragments comprise a heavy chain variable domain ($V_H$) connected to a light chain variable domain ($V_L$) in the same polypeptide chain ($V_H$-$V_L$ or $V_L$-$V_H$). By using a linker that is too short to allow pairing between the two domains on the same chain, the domains are forced to pair with the complementary domains of another chain and create two antigen-binding sites. Diabodies are described more fully in, e.g., EP 404,097; WO 93/11161; and Holliger et al. (1993) *Proc. Natl. Acad. Sci. USA* 90: 6444-6448. For a review of engineered antibody variants generally see Holliger and Hudson (2005) *Nat. Biotechnol.* 23:1126-1136.

"Isolated antibody" refers to the purification status of a binding compound and in such context means the molecule is substantially free of other biological molecules such as nucleic acids, proteins, lipids, carbohydrates, or other material such as cellular debris and growth media. Generally, the term "isolated" is not intended to refer to a complete absence of such material or to an absence of water, buffers, or salts, unless they are present in amounts that substantially interfere with experimental or therapeutic use of the binding compound as described herein.

The term "monoclonal antibody", as used herein, refers to population of substantially homogeneous antibodies, i.e., the antibody molecules comprising the population are identical in amino acid sequence except for possible naturally occurring mutations and/or post-translational modifications that may be present in minor amounts. In contrast, conventional (polyclonal) antibody preparations typically include a multitude of different antibodies having different amino acid sequences in their variable domains, particularly their CDRs, that are often specific for different epitopes. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al. (1975) *Nature* 256: 495, or may be made by recombinant DNA methods (see, e.g., U.S. Pat. No. 4,816,567). The "monoclonal antibodies" may also be isolated from phage antibody libraries using the techniques described in Clackson et al. (1991) *Nature* 352: 624-628 and Marks et al. (1991) *J. Mol. Biol.* 222: 581-597, for example. See also Presta (2005) *J. Allergy Clin. Immunol.* 116:731.

As used herein, the term "humanized antibody" refers to forms of antibodies that contain sequences from both human and non-human (e.g., murine, rat) antibodies. In general, the humanized antibody will comprise substantially all of at least one, and typically two, variable domains, in which all or substantially all of the hypervariable loops correspond to those of a non-human immunoglobulin, and all or substantially all of the framework (FR) regions are those of a human immunoglobulin sequence. The humanized antibody may optionally comprise at least a portion of a human immunoglobulin constant region (Fc).

The term "fully human antibody" refers to an antibody that comprises human immunoglobulin protein sequences only. A fully human antibody may contain murine carbohydrate chains if produced in a mouse, in a mouse cell, or in a hybridoma derived from a mouse cell. Similarly, "mouse antibody" refers to an antibody that comprises mouse immunoglobulin sequences only. Alternatively, a fully human antibody may contain rat carbohydrate chains if produced in a rat, in a rat cell, or in a hybridoma derived from a rat cell. Similarly, "rat antibody" refers to an antibody that comprises rat immunoglobulin sequences only.

In some embodiments, the basic antibody structural unit comprises a tetramer. Each tetramer includes two identical pairs of polypeptide chains, each pair having one "light" (about 25 kDa) and one "heavy" chain (about 50-70 kDa). The amino-terminal portion of each chain includes a variable region of about 100 to 110 or more amino acids primarily responsible for antigen recognition. The carboxy-terminal portion of the heavy chain may define a constant region primarily responsible for effector function. Typically, human light chains are classified as kappa and lambda light chains. Furthermore, human heavy chains are typically classified as mu, delta, gamma, alpha, or epsilon, and define the antibody's isotype as IgM, IgD, IgG, IgA, and IgE, respectively. Within light and heavy chains, the variable and constant regions are joined by a "J" region of about 12 or more amino acids, with the heavy chain also including a "D" region of about 10 more amino acids. See generally, *Fundamental Immunology* Ch. 7 (Paul, W., ed., 2nd ed. Raven Press, N.Y. (1989).

The variable regions of each light/heavy chain pair form the antibody binding site. Thus, in general, an intact antibody has two binding sites. However, in bifunctional or bispecific antibodies, the two binding sites are, in general, not the same.

Typically, the variable domains of both the heavy and light chains comprise three hypervariable regions, also called complementarity determining regions (CDRs), located within relatively conserved framework regions (FR). The CDRs are usually aligned by the framework regions, enabling binding to a specific epitope. In general, from N-terminal to C-terminal, both light and heavy chains variable domains comprise FR1, CDR1, FR2, CDR2, FR3, CDR3 and FR4. The assignment of amino acids to each domain is, generally, in accordance with the definitions of *Sequences of Proteins of Immunological Interest*, Kabat, et al.; National Institutes of Health, Bethesda, Md.; $5^{th}$ ed.; NIH Publ. No. 91-3242 (1991); Kabat (1978) Adv. Prot. Chem. 32:1-75; Kabat, et al., (1977) J. Biol. Chem. 252: 6609-6616; Chothia, et al., (1987) J Mol. Biol. 196:901-917 or Chothia, et al., (1989) Nature 342:878-883.

As used herein, the term "hypervariable region" refers to the amino acid residues of an antibody that are responsible for antigen-binding. The hypervariable region comprises amino acid residues from a "complementarity determining region" or "CDR" (i.e. residues 24-34 (CDRL1), 50-56 (CDRL2) and 89-97 (CDRL3) in the light chain variable domain and residues 31-35 (CDRH1), 50-65 (CDRH2) and 95-102 (CDRH3) in the heavy chain variable domain; Kabat et al. (1991) Sequences of Proteins of Immunological Interest, 5th Ed. Public Health Service, National Institutes of Health, Bethesda, Md.) and/or those residues from a "hypervariable loop" (i.e. residues 26-32 (CDRL1), 50-52 (CDRL2) and 91-96 (CDRL3) in the light chain variable domain and 26-32 (CDRH1), 53-55 (CDRH2) and 96-101 (CDRH3) in the heavy chain variable domain; Chothia and Lesk (1987) *J. Mol. Biol.* 196: 901-917). The CDRs can also be referenced according to the IMGT system for the identification of CDRs, which is described in Lefranc MP. Unique database numbering system for immunogenetic analysis. Immunol Today (1997) 18:509. As used herein, the term "framework" or "FR" residues refers to those variable domain residues other than the hypervariable region residues defined herein as CDR residues. CDRs provide the majority of contact residues for the binding of the antibody to the antigen or epitope. CDRs of interest can be derived from donor antibody variable heavy and light chain sequences, and include analogs of the naturally occurring CDRs, which analogs also share or retain the same antigen binding specificity and/or neutralizing ability as the donor antibody from which they were derived.

As used herein, "specific binding" or "immunospecific binding" or "binds immunospecifically" refer to antibody binding to a predetermined antigen at a much higher affinity than for another antigen(s). In some embodiments, the antibody binds the predetermined antigen with a dissociation constant ($K_D$) of $10^{-7}$ M or less, and such $K_D$ is at least two-fold less than its $K_D$ for binding to a non-specific antigen (e.g., BSA, casein, or another non-specific polypeptide).

Methods for determining mAb specificity and affinity by competitive inhibition can be found in Harlow, et al., Antibodies: A Laboratory Manual, Cold Spring Harbor Laboratory Press, Cold Spring Harbor, N.Y., 1988), Colligan et al., eds., Current Protocols in Immunology, Greene Publishing Assoc. and Wiley Interscience, N.Y., (1992, 1993), and Muller, Meth. Enzymol. 92:589 601 (1983), which references are entirely incorporated herein by reference.

As used herein, the term "individual" or "subject," or "patient" used interchangeably, means any animal, including mammals, such as mice, rats, other rodents, rabbits, dogs, cats, swine, cattle, sheep, horses, or primates, such as humans. In some embodiments, the subject is a human. A subject that is "in need thereof" refers to a subject that has been identified as requiring treatment for the condition that is to be treated and is treated with the specific intent of treating such condition. The conditions can be, for example, any of the conditions described herein.

As used herein, the terms "comprising" (and any form of comprising, such as "comprise", "comprises", and "comprised"), "having" (and any form of having, such as "have" and "has"), "including" (and any form of including, such as "includes" and "include"), or "containing" (and any form of containing, such as "contains" and "contain"), are inclusive or open-ended and do not exclude additional, unrecited elements or method steps. Any step or composition that uses the transitional phrase of "comprise" or "comprising" can also be said to describe the same with the transitional phase of "consisting of" or "consists."

As used herein, the term "contacting" means bringing together of two elements in an in vitro system or an in vivo system. For example, "contacting" virus or vector described herein with an individual or patient or cell includes the administration of the virus to an individual or patient, such as a human, as well as, for example, introducing a compound into a sample containing a cellular or purified preparation containing the cell.

As used herein, the term "fused" or "linked" when used in reference to a protein having different domains or heterologous sequences means that the protein domains are part of the same peptide chain that are connected to one another with either peptide bonds or other covalent bonding. The domains or section can be linked or fused directly to one another or another domain or peptide sequence can be between the two domains or sequences and such sequences would still be considered to be fused or linked to one another. In some embodiments, the various domains or proteins provided for herein are linked or fused directly to one another or a linker sequences, such as the glycine/serine sequences described herein link the two domains together.

A "disease" is a state of health of an animal wherein the animal cannot maintain homeostasis, and wherein if the disease is not ameliorated then the animal's health continues to deteriorate. In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

"Effective amount" or "therapeutically effective amount" are used interchangeably herein, and refer to an amount of a compound, formulation, material, or composition, as described herein effective to achieve a particular biological result or provides a therapeutic or prophylactic benefit. Such results may include, but are not limited to an amount that when administered to a mammal, causes a detectable level of immune cell activation compared to the immune cell activation detected in the absence of the composition. The immune response can be readily assessed by a plethora of art-recognized methods. The skilled artisan would understand that the amount of the composition administered herein varies and can be readily determined based on a number of factors such as the disease or condition being treated, the age and health and physical condition of the mammal being treated, the severity of the disease, the particular compound being administered, and the like.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

"Expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, such as cosmids, plasmids (e.g., naked or contained in liposomes) and viruses (e.g., Sendai viruses, lentiviruses, retroviruses, adenoviruses, and adeno-associated viruses) that incorporate the recombinant polynucleotide.

As used herein, the phrase "ex vivo" in reference to a cell being transduced, transfected or transformed ex vivo, refers to a cell being transduced, transfected or transformed outside of the subject, that is with the cells being removed from the subject before such cells are transduced, transfected or transformed.

"Identity" as used herein refers to the subunit sequence identity between two polymeric molecules such as between two nucleic acid or amino acid molecules, such as, between two polynucleotide or polypeptide molecules. When two amino acid sequences have the same residues at the same positions; e.g., if a position in each of two polypeptide molecules is occupied by an Arginine, then they are identical at that position. The identity or extent to which two amino acid or two nucleic acid sequences have the same residues at the same positions in an alignment is often expressed as a percentage. The identity between two amino acid or two nucleic acid sequences is a direct function of the number of matching or identical positions; e.g., if half of the positions in two sequences are identical, the two sequences are 50% identical; if 90% of the positions (e.g., 9 of 10), are matched or identical, the two amino acids sequences are 90% identical.

By "substantially identical" is meant a polypeptide or nucleic acid molecule exhibiting at least 50% identity to a reference amino acid sequence (for example, any one of the amino acid sequences described herein) or nucleic acid sequence (for example, any one of the nucleic acid sequences described herein). In some embodiments, such a sequence is at least 60%, 80% or 85%, or 90%, 95% or even 99% identical at the amino acid level or nucleic acid to the sequence used for comparison. Other percentages of identity in reference to specific sequences are described herein.

Sequence identity can be measured/determined using sequence analysis software (for example, Sequence Analysis Software Package of the Genetics Computer Group, University of Wisconsin Biotechnology Center, 1710 University Avenue, Madison, Wis. 53705, BLAST, BESTFIT, GAP, or PILEUP/PRETTYBOX programs). Such software matches identical or similar sequences by assigning degrees of homology to various substitutions, deletions, and/or other modifications. Conservative substitutions typically include substitutions within the following groups: glycine, alanine; valine, isoleucine, leucine; aspartic acid, glutamic acid, asparagine, glutamine; serine, threonine; lysine, arginine; and phenylalanine, tyrosine. In an exemplary approach to determining the degree of identity, a BLAST program may be used, with a probability score between e3 and e100 indicating a closely related sequence. In some embodiments, sequence identity is determined by using BLAST with the default settings.

To the extent embodiments provided for herein, includes composition comprising various proteins, these proteins may, in some instances, comprise amino acid sequences that have sequence identity to the amino acid sequences disclosed herein. Therefore, in certain embodiments, depending on the particular sequence, the degree of sequence identity is preferably greater than 50% (e.g. 60%, 70%, 75%, 80%, 85%, 90%, 91%, 92%, 93%, 94%, 95%, 96%, 97%, 98%, 99% or more) to the SEQ ID NOs disclosed herein. In addition to these percentages, other percentages of identity are provided for herein. Identity between polypeptides can be determined by the Smith-Waterman homology search algorithm as implemented in the MPSRCH program (Oxford Molecular), using an affine gap search with parameters gap open penalty—12 and gap extension penalty=1.

These proteins may, compared to the disclosed proteins, include one or more (e.g. 1, 2, 3, 4, 5, 6, 7, 8, 9, 10, etc.) conservative amino acid replacements i.e. replacements of one amino acid with another which has a related side chain. Genetically-encoded amino acids are generally divided into four families: (1) acidic i.e. aspartate, glutamate; (2) basic i.e. lysine, arginine, histidine; (3) non polar i.e. alanine, valine, leucine, isoleucine, proline, phenylalanine, methionine, tryptophan; and (4) uncharged polar i.e. glycine, asparagine, glutamine, cysteine, serine, threonine, tyrosine. Phenylalanine, tryptophan, and tyrosine are sometimes classified jointly as aromatic amino acids. In general, Substitution of single amino acids within these families does not have a major effect on the biological activity. The proteins may have one or more (e.g. 1, 2, 3, 4, 5, 6, 7, 8, 9, 10, etc.) single amino acid deletions relative to the disclosed protein sequences. The proteins may also include one or more (e.g. 1, 2, 3, 4, 5, 6, 7, 8, 9, 10, etc.) insertions (e.g. each of 1, 2, 3, 4 or 5 amino acids) relative to the disclosed protein sequences.

As used herein, the phrase "in vivo" in reference to a cell being transduced, transfected or transformed in vivo, refers to a cell being transduced, transfected or transformed in the subject without the cells being removed from the subject before such cells are transduced, transfected or transformed.

"Isolated" means altered or removed from the natural state. For example, a nucleic acid or a peptide naturally present in a living animal is not "isolated," but the same nucleic acid or peptide partially or completely separated from the coexisting materials of its natural state is "isolated." An isolated nucleic acid or protein can exist in substantially purified form, or can exist in a non-native environment such as, for example, a host cell.

A "lentivirus" as used herein refers to a genus of the Retroviridae family that is able to infect non-dividing cells. Non-limiting examples of lentiviruses are HIV, SIV, and FIV. Vectors or viral-like particles derived from lentiviruses can be used to transduce cells and deliver genes or other molecules and have them expressed in a cell either in vitro (ex-vivo) or in vivo.

By the term "modified" as used herein, is meant a changed state or structure of a molecule or cell as provided herein. Molecules may be modified in many ways, including chemically, structurally, and functionally, such as mutations, substitutions, insertions, or deletions (e.g. internal deletions truncations). Cells may be modified through the introduction of nucleic acids or the expression of heterologous proteins.

By the term "modulating," as used herein, is meant mediating an increase or decrease in the level of a response in a subject compared with the level of a response in the subject in the absence of a treatment or compound, and/or compared with the level of a response in an otherwise identical but untreated subject. The term encompasses perturbing and/or affecting a native signal or response thereby mediating a beneficial therapeutic response in a subject, such as, a human.

As used herein, the following abbreviations for the commonly occurring nucleic acid bases are used: "A" refers to adenosine, "C" refers to cytosine, "G" refers to guanosine, "T" refers to thymidine, and "U" refers to uridine.

Unless otherwise specified, a "nucleotide sequence encoding an amino acid sequence" includes all nucleotide sequences that are degenerate versions of each other and that encode the same amino acid sequence. The phrase nucleotide sequence that encodes a protein or an RNA may also include introns to the extent that the nucleotide sequence encoding the protein may in some version contain an intron(s).

The "Nipah virus" (NiV) is member of the family Paramyxoviridae, genus Henipavirus. Nipah virus is an enveloped virus with negative-stranded polarity and a non-segmented RNA genome consisting of helical nucleocapsids. Two strains of Nipah virus include, but are not limited to, the Malaysian (MY) and the Bangladesh (BD) strains.

The term "oligonucleotide" typically refers to short polynucleotides. It will be understood that when a nucleotide sequence is represented by a DNA sequence (i.e., A, T, C, G), this also provides the corresponding RNA sequence (i.e., A, U, C, G) in which "U" replaces "T."

"Parenteral" administration of a composition includes, e.g., subcutaneous (s.c.), intravenous (i.v.), intramuscular (i.m.), or intrasternal injection, or infusion techniques.

The term "polynucleotide" as used herein is defined as a chain of nucleotides. Furthermore, nucleic acids are polymers of nucleotides. Thus, the terms "nucleic acids" and "polynucleotides" as used herein are interchangeable. As used herein polynucleotides include, but are not limited to, all nucleic acid sequences which are obtained by any methods available in the art, including, without limitation, recombinant methods, i.e., the cloning of nucleic acid sequences from a recombinant library or a cell genome, using cloning technology and PCR, and the like, and by synthetic means.

As used herein, the terms "peptide," "polypeptide," and "protein" are used interchangeably, and refer to a compound comprised of a plurality of amino acid residues covalently linked by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. The polypeptides include natural peptides, recombinant peptides, synthetic peptides, or a combination thereof.

The term "pseudotyped" or "pseudotyped viral particle", as used herein, refers to a viral particle bearing glycoproteins derived from other viruses having envelopes or a viral vector encoding envelope glycoproteins from a virus that is different from the parental virus. The host range of the vector particles can thus be expanded or altered depending on the type of cell surface receptor used by the glycoprotein. For example, a virus can be pseudotyped with a VSV-G mutant protein as provided for herein or other virus glycoproteins, such as those provided for herein.

By the term "specifically binds," as used herein with respect to an antibody, is meant an antibody which recognizes a specific antigen, but does not substantially recognize or bind other molecules in a sample. For example, an antibody that specifically binds to an antigen from one species may also bind to that antigen from one or more species. But, such cross-species reactivity does not itself alter the classification of an antibody as specific. In another example, an antibody that specifically binds to an antigen may also bind to different allelic forms of the antigen. However, such cross reactivity does not itself alter the classification of an antibody as specific. In some instances, the terms "specific binding" or "specifically binding," can be used in reference to the interaction of an antibody, a protein, or a peptide with a second chemical species, to mean that the interaction is dependent upon the presence of a particular structure (e.g., an antigenic determinant or epitope) on the chemical species; for example, an antibody recognizes and binds to a specific protein structure rather than to proteins generally. If an antibody is specific for epitope "A", the presence of a molecule containing epitope A (or free, unlabeled A), in a reaction containing labeled "A" and the antibody, will reduce the amount of labeled A bound to the antibody. In some embodiments, the targeting moieties described herein that can be used to target the viral particles comprising the mutant VSV-G protein can specifically bind to their target.

The term "subject" includes living organisms, including those in which an immune response can be elicited (e.g., mammals). A "subject" or "patient," as used therein, may be a human or non-human mammal. Non-human mammals include, for example, livestock and pets, such as ovine, bovine, porcine, canine, non-human primates, feline and murine mammals. In some embodiments, the subject is human.

The term "therapeutic" as used herein means a treatment and/or prophylaxis. A therapeutic effect is obtained by suppression, remission, or eradication of a disease state.

The term "transfected" or "transformed" or "transduced" as used herein refers to a process by which exogenous nucleic acid is transferred or introduced into a cell. A "transfected" or "transformed" or "transduced" cell is one which has been transfected, transformed or transduced with exogenous nucleic acid. The cell includes the primary subject cell and its progeny. In some embodiments, the transfection, transformation, or transduction is performed or occurs in vivo.

To "treat" a disease as the term is used herein, means to reduce the frequency or severity of at least one sign or symptom of a disease or disorder experienced by a subject. As used herein, "inhibit" or "treat" or "treatment" also includes a postponement of development of the symptoms associated with a disorder and/or a reduction in the severity of the symptoms of such disorder. The terms further include ameliorating existing uncontrolled or unwanted symptoms, preventing additional symptoms, and ameliorating or preventing the underlying causes of such symptoms. Thus, the terms denote that a beneficial result has been conferred on a vertebrate subject with a disorder, disease or symptom, or with the potential to develop such a disorder, disease or symptom.

A "vector" is a composition of matter which comprises an isolated nucleic acid encoding a protein or a peptide. Numerous vectors are known in the art including, but not limited to, linear polynucleotides, plasmids, DNA, and RNA. Examples of viral vectors include, but are not limited to, Sendai viral vectors, adenoviral vectors, adeno-associated virus vectors, retroviral vectors, lentiviral vectors, and the like.

A "carrier" or "delivery vehicle" includes viral particles, viruses, polylysine compounds, and liposomes, which facilitate transfer of nucleic acid into cells. A carrier or delivery vehicle can also be used to deliver a protein or peptide to a cell.

Ranges: throughout this disclosure, various aspects of the embodiments can be presented in a range format. It should be understood that the description in range format is merely for convenience and brevity and should not be construed as an inflexible limitation. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range. Unless otherwise explicitly stated to the contrary, a range that is disclosed also includes the endpoints of the range.

Without being bound to any particular theory, the embodiments provided for herein have been found to show that a mutant VSV-G protein comprising a mutation at position 182 can be used to pseudotype a virus and transduce a cell when the virus comprises a targeting moiety. This mutation inhibits or reduces the VSV-G affinity to its natural co-receptor, the LDL-R. The mutant VSV-G proteins as provided can be used, in some embodiments, to transduce a target cell and deliver a heterologous molecule to the targeted cells.

In some embodiments, a VSV-G protein is provided that comprises a mutation at position 198 as compared to SEQ ID NO: 1 or at position 182 as compared to SEQ ID NO: 2. SEQ ID NO: 1 is the full length protein and SEQ ID NO: 2 is the ectodomain of the VSV-G protein. The 16-mer signal peptide of MKCLLYLAFLFIGVNC (SEQ ID NO: 26) as shown at the N-terminus of SEQ ID NO: 1 is cleaved leaving a protein of SEQ ID NO: 2. Thus, although a mutation may be referred to in the context of SEQ ID NO: 2, it should be understood to also be made in the context of SEQ ID NO: 1, which contains the leader sequence, and thus would be a position number that is 16 more than the position recited for SEQ ID NO: 2. In some embodiments, the mutation inhibits or decreases the binding of the VSV-G protein to the LDL receptor (LDL-R). In some embodiments, the mutation is a I182D mutation as compared to SEQ ID NO: 2. In some embodiments, the mutation is a I182E mutation as compared to SEQ ID NO: 2.

In some embodiments, a VSV-G protein is provided that comprises a mutation at position 198 as compared to SEQ ID NO: 10 or at position 182 as compared to SEQ ID NO: 11. SEQ ID NO: 10 is the full length protein and SEQ ID NO: 11 is the ectodomain of the VSV-G protein. The 16-mer signal peptide of MLSYLIFALVVSPILG (SEQ ID NO: 27) as shown at the N-terminus of SEQ ID NO: 10 is cleaved leaving a protein of SEQ ID NO: 11. Thus, although a mutation may be referred to in the context of SEQ ID NO: 11, it should be understood to also be made in the context of SEQ ID NO: 10, which contains the leader sequence, and thus would be a position number that is 16 more than the position recited for SEQ ID NO: 11. In some embodiments, the mutation inhibits or decreases the binding of the VSV-G protein to the LDL receptor (LDL-R). In some embodiments, the mutation is a T182D mutation as compared to SEQ ID NO: 11. In some embodiments, the mutation is a T182E mutation as compared to SEQ ID NO: 11.

In some embodiments, a VSV-G protein is provided that comprises a mutation at position 198 as compared to SEQ ID NO: 12 or at position 182 as compared to SEQ ID NO: 13. SEQ ID NO: 12 is the full length protein and SEQ ID NO: 13 is the ectodomain of the VSV-G protein. The 16-mer signal peptide of MLRLFLFCFLALGAHS (SEQ ID NO: 28) as shown at the N-terminus of SEQ ID NO: 12 is cleaved leaving a protein of SEQ ID NO: 13. Thus, although a mutation may be referred to in the context of SEQ ID NO: 13, it should be understood to also be made in the context of SEQ ID NO: 12, which contains the leader sequence, and thus would be a position number that is 16 more than the position recited for SEQ ID NO: 13. In some embodiments, the mutation inhibits or decreases the binding of the VSV-G protein to the LDL receptor (LDL-R). In some embodiments, the mutation is a A182D mutation as compared to SEQ ID NO: 13. In some embodiments, the mutation is a A182E mutation as compared to SEQ ID NO: 13.

In some embodiments, a VSV-G protein is provided that comprises a mutation at position 203 as compared to SEQ ID NO: 14 or at position 182 as compared to SEQ ID NO: 15. SEQ ID NO: 14 is the full length protein and SEQ ID NO: 15 is the ectodomain of the VSV-G protein. The 21-mer signal peptide of MKMKMVIAGLILCIGILPAIG (SEQ ID NO: 29) as shown at the N-terminus of SEQ ID NO: 14 is cleaved leaving a protein of SEQ ID NO: 15. Thus, although a mutation may be referred to in the context of SEQ ID NO: 15, it should be understood to also be made in the context of SEQ ID NO: 14, which contains the leader sequence, and thus would be a position number that is 21 more than the position recited for SEQ ID NO: 15. In some embodiments, the mutation inhibits or decreases the binding of the VSV-G protein to the LDL receptor (LDL-R). In some embodiments, the mutation is a V182D mutation as compared to SEQ ID NO: 15. In some embodiments, the mutation is a V182E mutation as compared to SEQ ID NO: 15.

In some embodiments, a VSV-G protein is provided that comprises a mutation at position 199 as compared to SEQ ID NO: 16 or at position 182 as compared to SEQ ID NO: 17. SEQ ID NO: 16 is the full length protein and SEQ ID NO: 17 is the ectodomain of the VSV-G protein. The 17-mer signal peptide of MTPAFILCMLLAGSSWA (SEQ ID NO: 30) as shown at the N-terminus of SEQ ID NO: 16 is cleaved leaving a protein of SEQ ID NO: 17. Thus, although a mutation may be referred to in the context of SEQ ID NO: 17, it should be understood to also be made in the context of SEQ ID NO: 16, which contains the leader sequence, and thus would be a position number that is 17 more than the position recited for SEQ ID NO: 17. In some embodiments, the mutation inhibits or decreases the binding of the VSV-G protein to the LDL receptor (LDL-R). In some embodiments, the mutation is a V182D mutation as compared to SEQ ID NO: 17. In some embodiments, the mutation is a V182E mutation as compared to SEQ ID NO: 17.

In some embodiments, a VSV-G protein is provided that comprises a mutation at position 199 as compared to SEQ ID NO: 18 or at position 182 as compared to SEQ ID NO: 19. SEQ ID NO: 18 is the full length protein and SEQ ID NO: 19 is the ectodomain of the VSV-G protein. The 17-mer signal peptide of MNFLLLTFIVLPLCSHA (SEQ ID NO: 31) as shown at the N-terminus of SEQ ID NO: 18 is cleaved leaving a protein of SEQ ID NO: 19. Thus, although a mutation may be referred to in the context of SEQ ID NO: 19, it should be understood to also be made in the context of SEQ ID NO: 18, which contains the leader sequence, and thus would be a position number that is 17 more than the position recited for SEQ ID NO: 19. In some embodiments, the mutation inhibits or decreases the binding of the VSV-G protein to the LDL receptor (LDL-R). In some embodiments, the mutation is a V182D mutation as compared to SEQ ID NO: 19. In some embodiments, the mutation is a V182E mutation as compared to SEQ ID NO: 19.

In some embodiments, a VSV-G protein is provided that comprises a mutation at position 199 as compared to SEQ ID NO: 20 or at position 182 as compared to SEQ ID NO: 21. SEQ ID NO: 20 is the full length protein and SEQ ID NO: 21 is the ectodomain of the VSV-G protein. The 17-mer signal peptide of MLVLYLLLSLLALGAQC (SEQ ID NO: 32) as shown at the N-terminus of SEQ ID NO: 20 is cleaved leaving a protein of SEQ ID NO: 21. Thus, although a mutation may be referred to in the context of SEQ ID NO: 21, it should be understood to also be made in the context of SEQ ID NO: 20, which contains the leader sequence, and thus would be a position number that is 17 more than the position recited for SEQ ID NO: 21. In some embodiments, the mutation inhibits or decreases the binding of the VSV-G protein to the LDL receptor (LDL-R). In some embodiments, the mutation is a I182D mutation as compared to SEQ ID NO: 21. In some embodiments, the mutation is a I182E mutation as compared to SEQ ID NO: 21.

As used herein, when a polypeptide is said to have a mutation as compared to a reference sequence, such comparison is based on an alignment such as using BlastP or ClustalW or ClutalOmega alignment software using default parameters. For example, position 182 can be found in SEQ ID NO: 2 and also as compared to the other strains as illustrated in FIG. 3. FIG. 3 illustrates a clustal alignment of the wild-type sequences of the ectodomains of the various strains of the VSV-G protein. The residue that is bolded and underlined are the residues that align to position 182 of SEQ ID NO: 2 of the various strains. SEQ ID NO: 2 refers to ectodomain of the VSV-G protein of the Indiana strain. SEQ ID NO: 11 refers to ectodomain of the VSV-G protein of the New Jersey strain. SEQ ID NO: 13 refers to ectodomain of the VSV-G protein of the Marraba strain. SEQ ID NO: 15 refers to ectodomain of the VSV-G protein of the Carajas strain. SEQ ID NO: 17 refers to ectodomain of the VSV-G protein of the Alagoa strain. SEQ ID NO: 19 refers to ectodomain of the VSV-G protein of the Cocal strain. SEQ ID NO: 21 refers to ectodomain of the VSV-G protein of the Morreton strain. Accordingly, the residue that aligns to residues 182 as compared to SEQ ID NO: 2 can also be mutated as provided for herein.

In some embodiments, the mutation at position 182 as compared to SEQ ID NO: 2 is not an alanine. In some embodiments, the mutation at position 182 as compared to SEQ ID NO: 2 is not a valine.

In some embodiments, the mutation at position 182 as compared to SEQ ID NO: 2 is I182S, I182H, I182T, I182Q, or I182N. In some embodiments, the mutation at position 182 as compared to SEQ ID NO: 11 is T182S, T182H, T182Q, or T182N. In some embodiments, the mutation at position 182 as compared to SEQ ID NO: 13 is A182S, A182H, A182T, A182Q, or A182N. In some embodiments, the mutation at position 182 as compared to SEQ ID NO: 15 is V182S, V182H, V182T, V182Q, or V182N. In some embodiments, the mutation at position 182 as compared to SEQ ID NO: 17 is V182S, V182H, V182T, V182Q, or V182N. In some embodiments, the mutation at position 182 as compared to SEQ ID NO: 19 is V182S, V182H, V182T, V182Q, or V182N. In some embodiments, the mutation at position 182 as compared to SEQ ID NO: 21 is I182S, I182H, I182T, I182Q, or I182N. In some embodiments, the mutation at position 182 is not a hydrophobic residue. In some embodiments, the mutation at position 182 is a charged residue. In some embodiments, the mutation at position 182 is a negatively charged residue.

Although, the mutations may be described in reference to SEQ ID NO: 1 or SEQ ID NO: 2, which is the VSV-G protein from the Indiana strain, the mutation can also be used in other strains of the VSV-G protein. For example, the mutation can be made in the New Jersey Strain of VSV-G, the Marraba strain of VSV-G, the Carajas strain of VSV-G, the Alagoa strain of VSV-G, the Cocal strain of VSV-G, or the Morreton strain of VSV-G. In some embodiments, the sequences of each are as provided herein. Examples of these can be found, for example in U.S. Patent Application Publication No. 20200216502, which is hereby incorporated by reference. For example, the wild-type full length or ectodomain of the New Jersey Strain of VSV-G are SEQ ID NO: 10 and SEQ ID NO: 11, respectively, the wild-type full length or ectodomain of Marraba strain of VSV-G are SEQ ID NO: 12 and SEQ ID NO: 13, respectively, the wild-type full length or ectodomain of Carajas strain of VSV-G are SEQ ID NO: 14 and SEQ ID NO: 15, respectively, the wild-type full length or ectodomain of Alagoa strain of VSV-G are SEQ ID NO: 16 and SEQ ID NO: 17, respectively, the wild-type full length or ectodomain of Cocal strain of VSV-G are SEQ ID NO: 18 and SEQ ID NO: 19, respectively, or the wild-type full length or ectodomain of Morreton strain of VSV-G are SEQ ID NO: 20 and SEQ ID NO: 21, respectively.

A VSV-G protein comprising a mutation at position 182 as compared to SEQ ID NO: 2 can also comprise other mutations, such as those described in U.S. Patent Application Publication No. 2020/0216502, which is hereby incorporated by reference in its entirety. For example, the VSV-G protein can comprise a mutation at a position that corresponds to positions of 8, 47, 209 and/or 354 of SEQ ID NO: 2.

In some embodiments, the substitution at position 8 is by any amino acid different from the amino acid indicated at that position in the sequence SEQ ID NO: 2, except Y. In some embodiments, the substitution at position 8 is by any amino acid different from the amino acid indicated at that position in the sequence SEQ ID NO: 2, except H. In some embodiments, the substitution at position 8 is by any amino acid different from the amino acid indicated at that position in the sequence SEQ ID NO: 2, except Q. In some embodiments, the substitution at position 8 is by any amino acid different from the amino acid indicated at that position in the sequence SEQ ID NO: 2, except Y or H or Q. In some embodiments, the substitution at position 8 is selected from alanine, arginine, asparagine, aspartic acid, cysteine, glutamic acid, glycine, isoleucine, valine, leucine, lysine, methionine, phenylalanine, proline, serine, threonine, or tryptophan. In some embodiments, the substitution at position 8 is selected from 8A, 8I, 8V, 8L, and the like. In some embodiments, the substitution at position 8 is selected from H8A, H8I, H8V, H8L, and the like.

In some embodiments, the substitution at position 209 is by any amino acid different from the amino acid indicated at that position in the sequence SEQ ID NO: 2, except H. In some embodiments, the substitution at position 209 is by any amino acid different from the amino acid indicated at that position in the sequence SEQ ID NO: 2, except Y. In some embodiments, the substitution at position 209 is by any amino acid different from the amino acid indicated at that position in the sequence SEQ ID NO: 2, except H or Y. In some embodiments, the substitution at position 209 is selected from alanine, arginine, asparagine, aspartic acid, cysteine, glutamic acid, glutamine, glycine, isoleucine, valine, leucine, lysine, methionine, phenylalanine, proline, serine, threonine, or tryptophan.

In some embodiments, the substitution at position 47 is by any amino acid different from the amino acid indicated at that position in the sequence SEQ ID NO: 2, except K. In some embodiments, the substitution at position 47 is by any amino acid different from the amino acid indicated at that position in the sequence SEQ ID NO: 2, except R. In some embodiments, the substitution at position 47 is by any amino acid different from the amino acid indicated at that position in the sequence SEQ ID NO: 2, except K or R. In some embodiments, the substitution at position 47 is selected from alanine, asparagine, aspartic acid, cysteine, glutamic acid, glutamine, glycine, histidine, isoleucine, valine, leucine, methionine, phenylalanine, proline, serine, threonine, tryptophan, or tyrosine. In some embodiments, the substitution at position 47 is selected from A, G, F, N, or Q. In some embodiments, the substitution at position 47 is selected from Q or N.

In some embodiments, the substitution at position 354 is by any amino acid different from the amino acid indicated at that position in the sequence SEQ ID NO: 2, except K. In some embodiments, the substitution at position 354 is by any amino acid different from the amino acid indicated at that position in the sequence SEQ ID NO: 2, except R. In some embodiments, the substitution at position 354 is by any amino acid different from the amino acid indicated at that position in the sequence SEQ ID NO: 2, except K or R. In some embodiments, the substitution at position 354 is selected from alanine, asparagine, aspartic acid, cysteine, glutamic acid, glutamine, glycine, histidine, isoleucine, valine, leucine, methionine, phenylalanine, proline, serine, threonine, tryptophan, or tyrosine. In some embodiments, the substitution at position 354 is selected from A, G, F, N, or Q.

In some embodiments, the substitution is at position 47 or at position 354, or at both positions 47 and 354 are, independently, substituted by A, G, F, N or Q. In some embodiments, the substitution at position 47 or at position 354, or at both positions 47 and 354 is, independently, A or Q or N.

In some embodiments, the VSV-G protein can comprise a mutation at a position that corresponds to positions of 8, 47, 209 and/or 354. In some embodiments, the VSV-G protein can comprise a mutation at a position that corresponds to position 8 as provided for herein, at position 47 as provided for herein, at position 209 as provided for herein, and/or position 354 as provided for herein. In some embodiments, the VSV-G protein can comprise a mutation at a position that corresponds to position 8 as provided for herein and at position 47 as provided for herein. In some embodiments, the VSV-G protein can comprise a mutation at a position that corresponds to position 8 as provided for herein and at position 209 as provided for herein. In some embodiments, the VSV-G protein can comprise a mutation at a position that corresponds to position 8 as provided for herein and at position 354 as provided for herein. In some embodiments, the VSV-G protein can comprise a mutation at a position that corresponds to position 47 as provided for herein and at position 209 as provided for herein. In some embodiments, the VSV-G protein can comprise a mutation at a position that corresponds to position 47 as provided for herein and at position 354 as provided for herein. In some embodiments, the VSV-G protein can comprise a mutation at a position that corresponds to position 209 as provided for herein and at position 354 as provided for herein. In some embodiments, the VSV-G protein can comprise a mutation at a position that corresponds to position 8 as provided for herein, at position 47 as provided for herein, and position 209 as provided for herein. In some embodiments, the VSV-G protein can comprise a mutation at a position that corresponds to position 8 as provided for herein, at position 47 as provided for herein, and position 354 as provided for herein. In some embodiments, the VSV-G protein can comprise a mutation at a position that corresponds to position 8 as provided for herein, at position 209 as provided for herein, and position 354 as provided for herein. In some embodiments, the VSV-G protein can comprise a mutation at a position that corresponds to position 47 as provided for herein, at position 209 as provided for herein, and position 354 as provided for herein. In some embodiments, the VSV-G protein can comprise a mutation at a position that corresponds to position 8 as provided for herein, at position 47 as provided for herein, at position 209 as provided for herein, and at position 354 as provided for herein.

In some embodiments, the substitution at position 8 is an alanine, i.e., H8A.

In some embodiments, the substitution at position 47 is Q or N or A, i.e., K47Q or K47N or K47A.

In some embodiments, the protein comprises a substitution at position 8 and/or a substitution at position 47. In some embodiments, the protein comprises a substitution at position 8 and a substitution at position 47. In some embodiments, the protein comprises a substitution at position 8 or a substitution at position 47. In some embodiments, the substitution at position 8 and/or a substitution at position 47 comprises a H8A and/or K47Q mutation.

In some embodiments, the protein comprises a mutation (substitution) at position 10. In some embodiments, the substitution/mutation is Q10A, Q10R, or Q10K.

In some non-limiting embodiments, the substitution at position 209 is A, i.e., Y209A.

In some non-limiting embodiments, the substitution at position 354 is A or Q, i.e. R354A or R354Q.

In some embodiments, a protein comprising a mutation at position 182 as compared to SEQ ID NO: 11 can also comprise other mutations, such as those described in U.S. Patent Application Publication No. 2020/0216502. For example, the VSV-G protein can comprise a mutation at a position analogous to positions of 8, 47, 209 and/or 354 of SEQ ID NO: 2. In some embodiments, the mutation in SEQ ID NO: 11 at a position analogous to positions of 8, 47, 209 and/or 354 of SEQ ID NO: 2 are as provided for herein.

In some embodiments, a protein comprising a mutation at position 182 as compared to SEQ ID NO: 13 can also comprise other mutations, such as those described in U.S. Patent Application Publication No. 2020/0216502. For example, the VSV-G protein can comprise a mutation at a position analogous to positions of 8, 47, 209 and/or 354 of SEQ ID NO: 2. In some embodiments, the mutation in SEQ ID NO: 13 at a position analogous to positions of 8, 47, 209 and/or 354 of SEQ ID NO: 2 are as provided for herein.

In some embodiments, a protein comprising a mutation at position 182 as compared to SEQ ID NO: 15 can also comprise other mutations, such as those described in U.S. Patent Application Publication No. 2020/0216502. For example, the VSV-G protein can comprise a mutation at a position analogous to positions of 8, 47, 209 and/or 354 of SEQ ID NO: 2. In some embodiments, the mutation in SEQ ID NO: 15 at a position analogous to positions of 8, 47, 209 and/or 354 of SEQ ID NO: 2 are as provided for herein.

In some embodiments, a protein comprising a mutation at position 182 as compared to SEQ ID NO: 17 can also comprise other mutations, such as those described in U.S. Patent Application Publication No. 2020/0216502. For example, the VSV-G protein can comprise a mutation at a position analogous to positions of 8, 47, 209 and/or 354 of SEQ ID NO: 2. In some embodiments, the mutation in SEQ ID NO: 17 at a position analogous to positions of 8, 47, 209 and/or 354 of SEQ ID NO: 2 are as provided for herein.

In some embodiments, a protein comprising a mutation at position 182 as compared to SEQ ID NO: 19 can also comprise other mutations, such as those described in U.S. Patent Application Publication No. 2020/0216502. For example, the VSV-G protein can comprise a mutation at a position analogous to positions of 8, 47, 209 and/or 354 of SEQ ID NO: 2. In some embodiments, the mutation in SEQ ID NO: 19 at a position analogous to positions of 8, 47, 209 and/or 354 of SEQ ID NO: 2 are as provided for herein.

In some embodiments, a protein comprising a mutation at position 182 as compared to SEQ ID NO: 21 can also comprise other mutations, such as those described in U.S. Patent Application Publication No. 2020/0216502. For example, the VSV-G protein can comprise a mutation at a position analogous to positions of 8, 47, 209 and/or 354 of SEQ ID NO: 2. In some embodiments, the mutation in SEQ ID NO: 21 at a position analogous to positions of 8, 47, 209 and/or 354 of SEQ ID NO: 2 are as provided for herein.

In some embodiments, a protein comprising a mutation at position 182 as compared to SEQ ID NO: 2 comprises a mutation at position 182 and at least, or about, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% identical as compared to SEQ ID NO: 2 (or SEQ ID NO: 1 if using the full length protein). In some embodiments, the protein is at least, or about, 80% identical to SEQ ID NO: 2. In some embodiments, the protein is at least, or about, 85% identical to SEQ ID NO: 2. In some embodiments, the protein is at least, or about, 90% identical to SEQ ID NO: 2. In some embodiments, the protein is at least, or about, 95% identical to SEQ ID NO: 2. In some embodiments, the mutation at position 182 is I182D or I182E mutation. In some embodiments, the mutation is I182D. In some embodiments, the mutation is I182E mutation. In some embodiments, the mutation is I182S, I182H, I182T, I182Q, or I182N mutation.

In some embodiments, a VSV-G is provided wherein the protein comprises the amino acid sequence of SEQ ID NO: 2 with a mutation at position 182 and at least, or about, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% identical as compared to SEQ ID NO: 2.

In some embodiments, a protein comprising a mutation at position 182 as compared to SEQ ID NO: 11 comprises a mutation at position 182 and at least, or about, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% identical as compared to SEQ ID NO: 11 (or SEQ ID NO: 10 if using the full length protein). In some embodiments, the polypeptide comprises a T182D or T182E mutation. In some embodiments, the VSV-G protein comprises a T182S, T182H, T182Q, or T182N mutation.

In some embodiments, a protein comprising a mutation at position 182 as compared to SEQ ID NO: 13 comprises a mutation at position 182 and at least, or about, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% identical as compared to SEQ ID NO: 13 (or SEQ ID NO: 12 if using the full length protein). In some embodiments, the polypeptide comprises a A182D or A182E mutation. In some embodiments, the VSV-G protein comprises a A182S, A182H, A182T, A182Q, or A182N mutation.

In some embodiments, a protein comprising a mutation at position 182 as compared to SEQ ID NO: 15 comprises a mutation at position 182 and at least, or about, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% identical as compared to SEQ ID NO: 15 (or SEQ ID NO: 14 if using the full length protein). In some embodiments, the polypeptide comprises a V182D or V182E mutation. In some embodiments, the VSV-G protein comprises a V182S, V182H, V182T, V182Q, or V182N mutation.

In some embodiments, a protein comprising a mutation at position 182 as compared to SEQ ID NO: 17 comprises a mutation at position 182 and at least, or about, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% identical as compared to SEQ ID NO: 17 (or SEQ ID NO: 16 if using the full length protein). In some embodiments, the polypeptide comprises a V182D or V182E mutation. In some embodiments, the VSV-G protein comprises a V182S, V182H, V182T, V182Q, or V182N mutation.

In some embodiments, a protein comprising a mutation at position 182 as compared to SEQ ID NO: 19 comprises a mutation at position 182 and at least, or about, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% identical as compared to SEQ ID NO: 19 (or SEQ ID NO: 18 if using the full length protein). In some embodiments, the polypeptide comprises a V182D or V182E mutation. In some embodiments, the VSV-G protein comprises a V182S, V182H, V182T, V182Q, or V182N mutation.

In some embodiments, a protein comprising a mutation at position 182 as compared to SEQ ID NO: 21 comprises a mutation at position 182 and at least, or about, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% identical as compared to SEQ ID NO: 21 (or SEQ ID NO: 20 if using the full length protein). In some embodiments, the polypeptide comprises a I182D or I182E mutation. In some embodiments, the VSV-G protein comprises a I182S, I182H, I182T, I182Q, or I182N mutation.

Viral Particles

The mutant VSV-G proteins can be used, for example, to pseudotype a virus, such as, but not limited to a lentivirus. Accordingly, in some embodiments, a viral particle comprising a mutant VSV-G protein as provided herein are provided. In some embodiments, the viral particle comprises a VSV-G protein comprising a mutation at position 198 as compared to SEQ ID NO: 1. In some embodiments, a protein comprising a mutation at position 182 as compared to SEQ ID NO: 2 comprises a mutation at position 182 and at least, or about, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% identical as compared to SEQ ID NO: 2 (or SEQ ID NO: 1 if using the full length protein). In some embodiments, the polypeptide comprises a I182D or I182E mutation as compared to SEQ ID NO: 2. In some embodiments, the VSV-G protein comprises a I182S, I182H, I182T, I182Q, or I182N mutation.

In some embodiments, the viral particle comprises a VSV-G protein comprising a mutation at position 198 as compared to SEQ ID NO: 10. In some embodiments, a protein comprising a mutation at position 182 as compared to SEQ ID NO: 11 comprises a mutation at position 182 and at least, or about, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% identical as compared to SEQ ID NO: 11 (or SEQ ID NO: 10 if using the full length protein). In some embodiments, the polypeptide comprises a T182D or T182E mutation as compared to SEQ ID NO: 11. In some embodiments, the VSV-G protein comprises a T182S, T182H, T182Q, or T182N mutation.

In some embodiments, the viral particle comprises a VSV-G protein comprising a mutation at position 198 as compared to SEQ ID NO: 12. In some embodiments, a protein comprising a mutation at position 182 as compared to SEQ ID NO: 13 comprises a mutation at position 182 and at least, or about, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% identical as compared to SEQ ID NO: 13 (or SEQ ID NO: 12 if using the full length protein). In some embodiments, the polypeptide comprises a A182D or A182E mutation as compared to SEQ ID NO: 13. In some embodiments, the VSV-G protein comprises a A182S, A182H, A182T, A182Q, or A182N mutation.

In some embodiments, the viral particle comprises a VSV-G protein comprising a mutation at position 203 as compared to SEQ ID NO: 14. In some embodiments, a protein comprising a mutation at position 182 as compared to SEQ ID NO: 15 comprises a mutation at position 182 and at least, or about, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% identical as compared to SEQ ID NO: 15 (or SEQ ID NO: 14 if using the full length protein). In some embodiments, the polypeptide comprises a V182D or V182E mutation as compared to SEQ ID NO: 15. In some embodiments, the VSV-G protein comprises a V182S, V182H, V182T, V182Q, or V182N mutation.

In some embodiments, the viral particle comprises a VSV-G protein comprising a mutation at position 199 as compared to SEQ ID NO: 16. In some embodiments, a protein comprising a mutation at position 182 as compared to SEQ ID NO: 17 comprises a mutation at position 182 and at least, or about, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% identical as compared to SEQ ID NO: 17 (or SEQ ID NO: 16 if using the full length protein). In some embodiments, the polypeptide comprises a V182D or V182E mutation as compared to SEQ ID NO: 17. In some embodiments, the VSV-G protein comprises a V182S, V182H, V182T, V182Q, or V182N mutation.

In some embodiments, the viral particle comprises a VSV-G protein comprising a mutation at position 199 as compared to SEQ ID NO: 18. In some embodiments, a protein comprising a mutation at position 182 as compared to SEQ ID NO: 19 comprises a mutation at position 182 and at least, or about, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% identical as compared to SEQ ID NO: 19 (or SEQ ID NO: 18 if using the full length protein). In some embodiments, the polypeptide comprises a V182D or V182E mutation as compared to SEQ ID NO: 19. In some embodiments, the VSV-G protein comprises a V182S, V182H, V182T, V182Q, or V182N mutation.

In some embodiments, the viral particle comprises a VSV-G protein comprising a mutation at position 199 as compared to SEQ ID NO: 20. In some embodiments, a protein comprising a mutation at position 182 as compared to SEQ ID NO: 21 comprises a mutation at position 182 and at least, or about, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% identical as compared to SEQ ID NO: 21 (or SEQ ID NO: 20 if using the full length protein). In some embodiments, the polypeptide comprises a I182D or I182E mutation as compared to SEQ ID NO: 21. In some embodiments, the VSV-G protein comprises a I182S, I182H, I182T, I182Q, or I182N mutation.

In some embodiments, the VSV-G protein further comprises a mutation at position that corresponds to positions 214 and/or 352 of SEQ ID NO: 2. In some embodiments, the residue that corresponds to position 214 of SEQ ID NO: 2 is T214. In some embodiments, the residue that corresponds to position 352 of SEQ ID NO: is T352. In some embodiments, the VSV-G protein comprises mutation that corresponds to T214N mutation as compared to SEQ ID NO: 2. In some embodiments, the VSV-G protein comprises mutation that corresponds to T352A mutation as compared to SEQ ID NO: 2. In some embodiments, the VSV-G protein comprises a T214N and T352A mutations as compared to SEQ ID NO: 2. These mutations can be combined with any other mutations as provided for herein. In some embodiments, the T214N and/or T352A mutations are combined with the I182E or I182D mutations. In some embodiments, a VSV-G protein comprises an amino acid sequence of SEQ ID NO: 22 and SEQ ID NO: 23, which combines the I182D or I182E, respectively, with the T214N and T352A mutations. The sequences are also illustrated below with the leader sequences, which are removed during protein processing.

VSV-G Protein_I196D, T230N and T368A mutations
(with leader sequence and adjusted numbering)
(SEQ ID NO: 24)
MKCLLYLAFLFIGVNCKFTIVFPHNQKGNWKNVPSNYHYCPSSSDLNWH

NDLIGTALQVKMPKSHKAIQADGWMCHASKWVTTCDFRWYGPKYITHSI

RSFTPSVEQCKESIEQTKQGTWLNPGFPPQSCGYATVTDAEAVIVQVTP

HHVLVDEYTGEWVDSQFINGKCSNYICPTVHNSTTWHSDYKVKGLCDSN

LDSMDITFFSEDGELSSLGKEGTGFRSNYFAYENGGKACKMQYCKHWGV

RLPSGVWFEMADKDLFAAARFPECPEGSSISAPSQTSVDVSLIQDVERI

-continued
LDYSLCQETWSKIRAGLPISPVDLSYLAPKNPGTGPAFTIINGTLKYFE

TRYIRVDIAAPILSRMVGMISGTTAERELWDDWAPYEDVEIGPNGVLRT

SSGYKFPLYMIGHGMLDSDLHLSSKAQVFEHPHIQDAASQLPDDESLFF

GDTGLSKNPIELVEGWFSSWKSSIASFFFIIGLIIGLFLVLRVGIHLCI

KLKHTKKRQIYTDIEMNRLGK

VSV-G Protein_I182D, T214N and T352A mutations
(without leader sequence)
(SEQ ID NO: 22)
KFTIVFPHNQKGNWKNVPSNYHYCPSSSDLNWHNDLIGTALQVKMPKSH

KAIQADGWMCHASKWVTTCDFRWYGPKYITHSIRSFTPSVEQCKESIEQ

TKQGTWLNPGFPPQSCGYATVTDAEAVIVQVTPHHVLVDEYTGEWVDSQ

FINGKCSNYICPTVHNSTTWHSDYKVKGLCDSNLDSMDITFFSEDGELS

SLGKEGTGFRSNYFAYENGGKACKMQYCKHWGVRLPSGVWFEMADKDLF

AAARFPECPEGSSISAPSQTSVDVSLIQDVERILDYSLCQETWSKIRAG

LPISPVDLSYLAPKNPGTGPAFTIINGTLKYFETRYIRVDIAAPILSRM

VGMISGTTAERELWDDWAPYEDVEIGPNGVLRTSSGYKFPLYMIGHGML

DSDLHLSSKAQVFEHPHIQDAASQLPDDESLFFGDTGLSKNPIELVEGW

FSSWKSSIASFFFIIGLIIGLFLVLRVGIHLCIKLKHTKKRQIYTDIEM

NRLGK

VSV-G Protein with I196E, T230N and T368A mutations
(with leader sequence and adjusted numbering)
(SEQ ID NO: 25)
MKCLLYLAFLFIGVNCKFTIVFPHNQKGNWKNVPSNYHYCPSSSDLNWH

NDLIGTALQVKMPKSHKAIQADGWMCHASKWVTTCDFRWYGPKYITHSI

RSFTPSVEQCKESIEQTKQGTWLNPGFPPQSCGYATVTDAEAVIVQVTP

HHVLVDEYTGEWVDSQFINGKCSNYICPTVHNSTTWHSDYKVKGLCDSN

LESMDITFFSEDGELSSLGKEGTGFRSNYFAYENGGKACKMQYCKHWGV

RLPSGVWFEMADKDLFAAARFPECPEGSSISAPSQTSVDVSLIQDVERI

LDYSLCQETWSKIRAGLPISPVDLSYLAPKNPGTGPAFTIINGTLKYFE

TRYIRVDIAAPILSRMVGMISGTTAERELWDDWAPYEDVEIGPNGVLRT

SSGYKFPLYMIGHGMLDSDLHLSSKAQVFEHPHIQDAASQLPDDESLFF

GDTGLSKNPIELVEGWFSSWKSSIASFFFIIGLIIGLFLVLRVGIHLCI

KLKHTKKRQIYTDIEMNRLGK

VSV-G Protein with I182E, T214N and T352A mutations
(without leader sequences)
(SEQ ID NO: 23)
KFTIVFPHNQKGNWKNVPSNYHYCPSSSDLNWHNDLIGTALQVKMPKSH

KAIQADGWMCHASKWVTTCDFRWYGPKYITHSIRSFTPSVEQCKESIEQ

TKQGTWLNPGFPPQSCGYATVTDAEAVIVQVTPHHVLVDEYTGEWVDSQ

FINGKCSNYICPTVHNSTTWHSDYKVKGLCDSNLESMDITFFSEDGELS

SLGKEGTGFRSNYFAYENGGKACKMQYCKHWGVRLPSGVWFEMADKDLF

AAARFPECPEGSSISAPSQTSVDVSLIQDVERILDYSLCQETWSKIRAG

LPISPVDLSYLAPKNPGTGPAFTIINGTLKYFETRYIRVDIAAPILSRM

VGMISGTTAERELWDDWAPYEDVEIGPNGVLRTSSGYKFPLYMIGHGML

DSDLHLSSKAQVFEHPHIQDAASQLPDDESLFFGDTGLSKNPIELVEGW

-continued
FSSWKSSIASFFFIIGLIIGLFLVLRVGIHLCIKLKHTKKRQIYTDIEM

NRLGK

The other strains of the VSV-G protein as described herein can also comprises the mutations that correspond to T214N and/or T352A in SEQ ID NO: 2 and as illustrated in SEQ ID NO: 22 and SEQ ID NO: 23.

In some embodiments, the composition comprises a mutation as described in Hwang et al., Gene Ther 2013 August; 20(8):807-15. (Epub 2013 Jan. 31), which is hereby incorporated by reference in its entirety. For example, the mutations can be. at positions 230, 368, 66, and/or 162 that corresponds to SEQ ID NO: 1. The positions will be 16 positions less as compared to SEQ ID NO: 2, when the leader sequence is removed. In some embodiments, the mutations at those positions are, for example, T230N, T368A, K66T, S162T, or any combination thereof. In some embodiments, the VSV-G protein comprises a T230N and a T368A mutation. In some embodiments, the VSV-G polypeptide comprises a K66T, S162T, T230N, and a T368A. These positions are those that correspond to the positions in the full length protein (SEQ ID NO: 1). In some embodiments, the VSV-G protein comprises T230N mutation, a T368A mutation, a K66T mutation, a S162T mutation, or any combination thereof. In some embodiments, the VSV-G protein further comprises one or more mutations in addition to the mutation that corresponds to position 182 of SEQ ID NO: 2, such as those described in U.S. Patent Application Publication No. 20200216502, which is hereby incorporated by reference in its entirety. For example, the VSV-G protein can further comprise a mutation at a position that corresponds to positions of 8, 47, 209 and/or 354 of SEQ ID NO: 2.

In some embodiments, the substitution at position 8 is by any amino acid different from the amino acid indicated at that position in the sequence SEQ ID NO: 2, except Y. In some embodiments, the substitution at position 209 is by any amino acid different from the amino acid indicated at that position in the sequence SEQ ID NO: 2, except H. In some embodiments, the substitution at position 47 is by any amino acid different from the amino acid indicated at that position in the sequence SEQ ID NO: 2, except K or R. In some embodiments, the substitution at position 354 is by any amino acid different from the amino acid indicated at that position in the sequence SEQ ID NO: 2, except K or R. In some embodiments, the substitution is at position 47 or at position 354, or at both positions 47 and 354 are substituted by A, G, F or Q. In some embodiments, the substitution is A or Q. In some embodiments, the substitution at position 8 is an alanine, i.e., H8A. In some embodiments, the substitution at position 47 is Q or N, i.e., K47Q or K47N. In some embodiments, the protein comprises a mutation (substitution) at position 10. In some embodiments, the substitution/mutation is Q10A, Q10R, or Q10K.

In some embodiments, the viral particle comprises a targeting moiety. The targeting moiety can be used to target the viral particle comprising the mutant VSV-G protein to a cell that expresses the target to which the targeting moiety binds to. In some embodiments, the targeting moiety is an antibody, a scFv antibody, an antigen binding domain, an ankyrin repeat (e.g., DARPIN), a VHH domain antibody, a nanobody, single domain antibody, a FN3 domain, or any combination thereof. The targeting moiety can be attached to the viral surface through an IgG Fc stalk. In some embodiments, the stalk comprises a transmembrane domain. In some embodiments, the transmembrane domain comprises a CD8 transmembrane domain. In some embodiments, the transmembrane domain comprises a CD28 transmembrane domain. In some embodiments, the targeting moiety is attached (fused or linked) an envelope glycoprotein G or H of a virus of the Paramyxoviridae family, such as a morbillivirus, such as Measles virus, or a henipavirus, such as Nipah virus, Cedar virus, or Hendra virus. In some embodiments, the targeting moiety can be attached (fused or linked) to a glycoprotein of a virus of the Rhabdoviridae family, such as a vesicular stomatitis New Jersey virus, a vesicular stomatitis Indiana virus, a vesicular stomatitis Alagoas virus, a vesicular stromatitis Maraba virus, a vesicular stomatitis Carajas virus, Parainfluenza virus, *Spodoptera frugiperda* rhabdovirus isolate Sf G, *Drosophila obscura* sigmavirus 10A, Wuhan insect virus 7, Perch virus, or Spring viremia of carp virus. In some embodiments, the VSV protein is the mutated proteins, such as those provided for herein. In some embodiments, the targeting moiety is attached to a glycoprotein of a virus of the Filoviridae family, such as Ebola virus or a glycoprotein of a virus of the Arenaviridae family, such as Machupo virus.

In some embodiments, the targeting moiety is a scFv. In some embodiments, the targeting moiety is a single domain antibody. In some embodiments, the targeting moiety is a VHH.

In some embodiments, the targeting moiety binds to CD7, CD8, cKit (CD117), CD4, CD3, CD5, CD6, CD2, TCR alpha, TCR beta, TCR gamma, TCR delta, CD10, CD34, CD110, CD33, CD14, CD68, CCR7, CD62L, CD25, CCR2, CCR3, CCR4, CCR5, CCR6, CCR7, or CXCR3, A glycosylated CD43 epitope expressed on acute leukemia or lymphoma but not on hematopoietic progenitors; A glycosylated CD43 epitope expressed on non-hematopoietic cancers; A kinase anchor protein 4 (AKAP-4); Adrenoceptor beta 3 (ADRB3); AFP; Anaplastic lymphoma kinase (ALK); Androgen receptor; Angiopoietin-binding cell surface receptor 2 (Tie 2); Auto antibody to desmoglein 1 (Dsg1); Auto antibody to desmoglein 3 (Dsg3); B7H3 (CD276); Biotin; Bone marrow stromal cell antigen 2 (BST2); BST1/CD157; Cancer/testis antigen 1 (NY-ESO-1); Cancer/testis antigen 2 (LAGE-la); Carbonic anhydrase IX (CA1X); Carcinoembryonic antigen (CEA); CCCTC-Binding Factor (Zinc Finger Protein)-Like (BORIS or Brother of the Regulator of Imprinted Sites); CCR4; CD5; CD19; CD20; CD22; CD24; CD30; CD32 (FCGR2A); CD33; CD34; CD38; CD44v6; CD72; CD79a; CD79b; CD97; CD99; CD123; CD171; CD179a; CD179b-IGL11; CD200R; CD276/B7H3; CD300 molecule-like family member f (CD300LF); CDH1-CD324; CDH6; CDH17; CDH19; Chromosome X open reading frame 61 (CXORF61); Claudin 6 (CLDN6); Claudin18.2 (CLD18A2 or CLDN18A.2); CMV pp65; C-MYC epitope Tag; Cripto; CS1 (also referred to as CD2 subset 1 or CRACC or SLAMF7 or CD319 or 19A24); CSF2RA (GM-CSFR-alpha); C-type lectin domain family 12 member A (CLEC12A); C-type lectin-like molecule-1 (CLL-1 or CLECL1); Cyclin B1; Cytochrome P450 IB 1 (CYP1B 1); DLL3; EBV-EBNA3c; EGF-bke module-containing mucin-like hormone receptor-like 2 (EMR2); Elongation factor 2 mutated (ELF2M); Ephrin B2; Ephrin type-A receptor 2 (EphA2); Epidermal growth factor receptor (EGFR); Epidermal growth factor receptor variant III (EGFRviii); Epithelial cell adhesion molecule (EPCAM); ERG; ETS trans-location-variant gene 6 located on chromosome 12p (ETV6-AML); Fc fragment of IgA receptor (FCAR or CD89); Fc receptor-like 5 (FCRL5); Fibroblast activation protein alpha (FAP); FITC; Fms Like Tyrosine Kinase 3 (FLT3); Folate receptor alpha (FRa or FR1); Folate receptor beta (FRb); Follicle stimulating hormone receptor (FSHR); Fos-related antigen 1; Fucosyl-GM1; G protein coupled receptor class C group 5 member D (GPRCSD); G protein-coupled receptor 20 (GPR20); GAD; Ganglioside G2 (GD2); Ganglioside GD3 (aNeu5Ac(2-8)aNeu5Ac(2-3)bDGalp(1-4)bDGlcp(1-1)Cer); Ganglioside GM3 (aNeu5Ac(2-3)bDClalp(1-4)bDGlcp(1-1)Cer); GD3; GFRalpha4; Glycoprotein 100 (gplOO); Glypican-3 (GPC3); Gonadotropin Hormone receptor (CGHR or GR); GpA33; GpNMB; GPRC5D; Guanylyl cyclase C (GCC); Heat shock protein 70-2 mutated (mut hsp70-2); Hepatitis A virus cellular receptor 1 (HAVCR1); Hexasaccharide portion of globoH glycoceramide (GloboH); High molecular weight-melanoma associated antigen (HMWMAA); HIV1 envelope glycoprotein; HLA; HLA-DOA; HLA-A; HLA-A2; HLA-B; HLA-C; HLA-DM; HLA-DOB; HLA-DP; HLA-DQ; HLA-DR; HLA-G; HTLV1-Tax; Human papilloma virus E6 (HPV E6); Human papilloma virus E7 (HPV E7); Human Telomerase reverse transcriptase (hTERT); IgE; IL13Ra2; IL1 1Ra; Immunoglobulin lambda-like polypeptide 1 (IGLL1); Influenza A hemagglutinin (HA); Insulin-like growth factor 1 receptor (IGF-I receptor); Interleukin 11 receptor alpha (IL-llRa); Interleukin-13 receptor subunit alpha-2 (IL-13Ra2 or CD213A2); Intestinal carboxyl esterase; KIT (CD117); KSHV K8.1; KSHV-gH; LAMP1; Legumain; Leukocyte immunoglobulin-like receptor subfamily A member 2 (LILRA2); Leukocyte-associated immunoglobulin-like receptor 1 (LAIR1); Leutenizing hormone receptor (LHR); Lewis(Y) antigen; Lews Ag; Livl; Locus K 9 (LY6K); Low conductance chloride channel; Lymphocyte antigen 6 complex; Lymphocyte antigen 75 (LY75); Lymphocyte-specific protein tyrosine kinase (LCK); Mammary gland differentiation antigen (NY-BR-1); Melanoma antigen recognized by T cells 1 (MelanA or MARTI); Melanoma-associated antigen 1 (MAGE-A1); Melanoma cancer testis antigen-1 (MAD-CT-1); Melanoma cancer testis antigen-2 (MAD-CT-2); Melanoma inhibitor of apoptosis (ML-IAP); Mesothelin; MPL; Mucin 1 cell surface associated (MUC1); N-Acetyl glucosaminyl-transferase V (NA17); Nectin-4; Neural cell adhesion molecule (NCAM); NKG2D; NYBR1; O-acetyl-GD2 ganglioside (OAcGD2); Olfactory receptor 51E2 (OR51E2); Oncogene fusion protein consisting of breakpoint cluster region (BCR) and Abelson murine leukemia viral oncogene homolog 1 (Abl) (bcr-abl); P53 mutant; Paired box protein Pax-3 (PAX3); Paired box protein Pax-5 (PAX5); Pannexin 3 (PANX3); PDL1; P-glycoprotein; Placenta-specific 1 (PLAC1); Platelet-derived growth factor receptor beta (PDGFR-beta); Polysialic acid; Proacrosin binding protein sp32 (OY-TES1); Prostase; Prostate carcinoma tumor antigen-1 (PCT A-1 or Galectin 8); Prostate stem cell antigen (PSCA); Prostate-specific membrane antigen (PSMA); Prostatic acid phosphatase (PAP); Prostein; Protease Serine 21 (Testisin or PRSS21); Proteasome (Prosome Macropain) Subunit Beta Type 9 (LMP2); PTK7; Ras G12V; Ras Homolog Family Member C (RhoC); Rat sarcoma (Ras) mutant; Receptor for Advanced Glycation Endproducts (RAGE-1); Receptor tyrosine kinase-like orphan receptor 1 (ROR1); Receptor tyrosine-protein kinase ERBB2 or Her-22/neu; Renal ubiquitous 1 (RUi); Renal ubiquitous 2 (RU2); Sarcoma translocation breakpoints; Serine 2 (TMPRSS2) ETS fusion gene; Sialyl Lewis adhesion molecule (sLe); SLAMF4; SLAMF6; Slea (CA19.9 or Sialyl Lewis Antigen); Sperm protein 17 (SPA17); Squamous Cell Carcinoma Antigen Recognized By T Cells 3 (SART3); Stage-specific embryonic antigen-4 (SSEA-4); STEAPI; Survivin; Synovial sarcoma X breakpoint 2 (SSX2); TCR Gamma Alternate Reading Frame Protein (TARP); TCR-beta1 chain; TCR-beta2 chain; TCR-delta chain; TCR-gamma chain; TCRgamma-delta; Telomerase; TGFbetaR2; The antigen recognized by TNT antibody; Thyroid stimulating hormone receptor (TSHR); Tim1-/HVCR1; Tissue Factor 1 (TF1); Tn ag; Tn antigen ((Tn Ag) or (GalNAca-Ser/Thr)); TNF receptor family member B cell maturation (BCMA); Transglutaminase 5 (TGS5); Transmembrane protease; TROP2; Tumor endothelial marker 1 (TEM1/CD248); Tumor endothelial marker 7-related (TEM7R); Tumor protein p53 (p53); Tumor-associated glycoprotein 72 (TAG72); Tyrosinase; Tyrosinase-related protein 2 (TRP-2); Uroplakin 2 (UPK2); Vascular endothelial growth factor receptor 2 (VEGFR2); V-myc avian myelocytomatosis viral oncogene neuroblastoma derived homolog (MYCN); Wilms tumor protein (WT1); or X Antigen Family Member 1A (XAGE1). In some embodiments, the targeting moiety binds to CD7. In some embodiments, the targeting moiety binds to CD8.

In some embodiments, the targeting moiety binds to a target that is present on a cell, such as an immune cell. In some embodiments, the cell is an immune cell, such as, but not limited to, T cell, B cell; NK cell, dendritic cell, neutrophils, macrophages, a cancer cell; or, for example, CD3+ T cell; CD4+ T cell; CD7+ T cell, CD8+ T cell; CD19+ B cell; CD19+ cancer cell; CD20+ B cell; CD20+ cancer cell; CD30+ lung epithelial cell; CD34+ haematopoietic stem cell; CD105+ endothelial cell; CD105+ haematopoietic stem cell; CD117+ haematopoietic stem cell; CD133+ cancer cell; EpCAM+ cancer cell; GluA2+ neuron; GluA4+ neuron; Haematopoietic stem cell; Hepatocyte; Her2/Neu+ cancer cell; NKG2D+ natural killer cell; SLC1A3+ astrocyte; SLC7A10+ adipocyte. In some embodiments, the cell is a T cell. In some embodiments, the cell is a B cell. In some embodiments, the cell is a CD7+ T cell and/or CD8+ T cell.

In some embodiments, the targeting moiety (a polypeptide) can bind to CD7.

In some embodiments, the polypeptide binds to CD7. In some embodiments, the polypeptide that binds to CD7 is an antibody which binds to non-human primate CD7. In some embodiments, the polypeptide that binds to CD7 is an antibody which binds to human CD7. The sequence of human CD7 (UniProtKB P09564) is as follows (SEQ ID NO: 33):

```
                                         (SEQ ID NO: 33)
MAGPPRLLLLLPLLLALARGLPGALAAQEVQQSPHCTTVPVGASVNITCS

TSGGLRGIYLRQLGPQPQDIIYYEDGVVPTTDRRFRGRIDFSGSQDNLT

ITMHRLQLSDTGTYTCQAITEVNVYGSGTLVLVTEEQSQGWHRCSDAPP

RASALPAPPTGSALPDPQTASALPDPPAASALPAALAVISFLLGLGLGV

ACVLARTQIKKLCSWRDKNSAACVVYEDMSHSRCNTLSSPNQYQ.
```

In some embodiments, the CD7 that the polypeptide binds to is expressed on the surface of a cell. In some embodiments, the cell is an immune cell. In some embodiments, the immune cell is a CD7+ T cell, CD4+ T cell, CD8+ T cell, NK cell, alpha-beta T cell, gamma-delta T cell, lymphoid progenitor cell, hematopoietic stem cell, myeloid cell, monocyte, macrophage, central memory T cell, effector memory T cell, stem-cell like memory T cells, naïve T cell, activated T cell, regulatory T cell (TReg), terminally differentiated effector memory T cell (TEMRA), resident memory T cell (TRM) or a T-cellCD8+ CCR7+.

In some embodiments, the antibody comprises a Fc region. The Fc region can be linked to the heavy or light chain of the antibody. In some embodiments, the Fc region is an IgG Fc. In some embodiments, the IgG is selected from IgG1, IgG2, IgG3, or IgG4. In some embodiments, the IgG fc is IgG1 Fc. In some embodiments, the antibody comprises an Fc constant region of SEQ ID NO: 34 as set forth below.

```
                                         (SEQ ID NO: 34)
ASTKGPSVFPLAPSSKSTSGGTAALGCLVKDYFPEPVTVSWNSGALTSG

VHTFPAVLQSSGLYSLSSVVTVPSSSLGTQTYICNVNHKPSNTKVDKKV

EPKSCDKTHTCPPCPAPELLGGPSVFLFPPKPKDTLMISRTPEVTCVVV

DVSHEDPEVKFNWYVDGVEVHNAKTKPREEQYNSTYRVVSVLTVLHQDW

LNGKEYKCKVSNKALPAPIEKTISKAKGQPREPQVYTLPPSRDELTKNQ

VSLTCLVKGFYPSDIAVEWESNGQPENNYKTTPPVLDSDGSFFLYSKLT

VDKSRWQQGNVFSCSVMHEALHNHYTQKSLSLSPGK
```

In some embodiments, the IgG fc is IgG2 Fc. In some embodiments, the antibody comprises an Fc constant region of SEQ ID NO: 71 as set forth below.

```
                                         (SEQ ID NO: 71)
STKGPSVFPLAPCSRSTSESTAALGCLVKDYFPEP

VTVSWNSGALTSGVHTFPAVLQSSGLYSLSSVVTV

PSSSLGTQTYTCNVDHKPSNTKVDKTVERKCCVEC

PPCPAPPVAGPSVFLFPPKPKDTLMISRTPEVTCV

VVDVSHEDPEVQFNWYVDGVEVHNAKTKPREEQFN

STFRVVSVLTVVHQDWLNGKEYKCKVSNKGLPAPI

EKTISKTKGQPREPQVYTLPPSREEMTKNQVSLTC

LVKGFYPSDIAVEWESNGQPENNYKTTPPMLDSDG

SFFLYSKLTVDKSRWQQGNVFSCSVMHEALHNHYT

QKSLSLSPGK
```

In some embodiments, the IgG fc is IgG4 Fc. In some embodiments, the antibody comprises an Fc constant region of SEQ ID NO: 72 as set forth below.

```
                                         (SEQ ID NO: 72)
STKGPSVFPLAPCSRSTSESTAALGCLVKDYFPEP

VTVSWNSGALTSGVHTFPAVLQSSGLYSLSSVVTV

PSSSLGTKTYTCNVDHKPSNTKVDKRVESKYGPPC

PSCPAPEFLGGPSVFLFPPKPKDTLMISRTPEVTC

VVVDVSQEDPEVQFNWYVDGVEVHNAKTKPREEQF

NSTYRVVSVLTVLHQDWLNGKEYKCKVSNKGLPSS

IEKTISKAKGQPREPQVYTLPPSQEEMTKNQVSLT

CLVKGFYPSDIAVEWESNGQPENNYKTTPPVLDSD

GSFFLYSRLTVDKSRWQEGNVFSCSVMHEALHNHY

TQKSLSLSLGK
```

In some embodiments, polypeptides (e.g. CD7-binding polypeptide) are provided herein. In some embodiments, antibodies (e.g. an anti-CD7 antibody) are provided herein.

In some embodiments, the antibody is a recombinant antibody that binds to CD7. In some embodiments, the CD7 protein is a human CD7 protein. In some embodiments, the CD7 protein is a non-human CD7 protein (e.g., mouse, rat, pig, dog, non-human primate). As used herein, the term "recombinant antibody" refers to an antibody that is not naturally occurring. In some embodiments, the term "recombinant antibody" refers to an antibody that is not isolated from a human subject.

In some embodiments, an antibody, or antigen binding fragment thereof is provided, wherein the antibody or antibody fragment comprises a peptide selected from the following table, which illustrate the CDRs based on Chothia numbering.

| Chothia CDRs | | | | | | |
|---|---|---|---|---|---|---|
| Ab ID No | HCDR1 | HCDR2 | HCDR3 | LCDR1 | LCDR2 | LCDR3 |
| CD7AB1 | GYPFTSY (SEQ ID NO: 35) | DPNSGD (SEQ ID NO: 36) | SPYYSN DNSMDY (SEQ ID NO: 37) | RASQSIGT SIH (SEQ ID NO: 38) | YASESIS (SEQ ID NO: 39) | QQSNSWPTT (SEQ ID NO: 40) |

In some embodiments, an antibody, or antigen binding fragment thereof is provided, wherein the antibody or antibody fragment comprises a peptide selected from the following table, which illustrate the CDRs based on Kabat numbering.

| Kabat CDRs | | | | | | |
|---|---|---|---|---|---|---|
| Ab ID No | HCDR1 | HCDR2 | HCDR3 | LCDR1 | LCDR2 | LCDR3 |
| CD7AB1 | SYWIH (SEQ ID NO: 41) | RIDPNSGD TKYNEKFKN (SEQ ID NO: 42) | SPYYSND NSMDY (SEQ ID NO: 37) | RASQSI GTSIH (SEQ ID NO: 38) | YASESIS (SEQ ID NO: 39) | QQSNSW PTT (SEQ ID NO: 40) |

In some embodiments, an antibody, or antigen binding fragment thereof is provided, wherein the antibody or antibody fragment comprises a peptide selected from the following table, which illustrate the CDRs based on IMGT numbering.

| IMGT CDRS | | | | | | |
|---|---|---|---|---|---|---|
| Ab ID No | HCDR1 | HCDR2 | HCDR3 | LCDR1 | LCDR2 | LCDR3 |
| CD7AB1 | GYPFTSYW (SEQ ID NO: 43) | IDPNSGDT (SEQ ID NO: 44) | ARSPYYSNDNQSIGTS SMDY (SEQ ID NO: 45) | QSIGTS (SEQ ID NO: 46) | YA | QQSNSWPTT (SEQ ID NO: 40) |

In some embodiments, a polypeptide, an antibody, or antibody binding fragment thereof, comprises a heavy or light chain CDR as provided in the tables above. In some embodiments, a polypeptide, an antibody, or antibody binding fragment thereof, comprises a heavy or light chain CDR as provided in the tables above and binds to non-human primate CD7. In some embodiments, a polypeptide, an antibody, or antibody binding fragment thereof, comprises a heavy or light chain CDR as provided in the tables above and binds to human CD7. In some embodiments, a polypeptide, an antibody, or antibody binding fragment thereof, comprises a light chain CDR having a sequence selected from SEQ ID NO: 38-40. In some embodiments, a polypeptide, an antibody, or antibody binding fragment thereof, comprises a light chain CDR having a sequence of SEQ ID NO: 38. In some embodiments, a polypeptide, an antibody, or antibody binding fragment thereof, comprises a light chain CDR having a sequence of SEQ ID NO: 39. In some embodiments, a polypeptide, an antibody, or antibody binding fragment thereof, comprises a light chain CDR having a sequence of SEQ ID NO: 40. In some embodiments, a polypeptide, an antibody, or antibody binding fragment thereof, comprises a heavy chain CDR having a sequence selected from SEQ ID NO: 35-37. In some embodiments, a polypeptide, an antibody, or antibody binding fragment thereof, comprises a heavy chain CDR having a sequence of SEQ ID NO: 35. In some embodiments, a polypeptide, an antibody, or antibody binding fragment thereof, comprises a heavy chain CDR having a sequence of SEQ ID NO: 36. In some embodiments, a polypeptide, an antibody, or antibody binding fragment thereof, comprises a heavy chain CDR having a sequence of SEQ ID NO: 37. The CDRs referenced in the embodiments throughout the present specification can be interchanged with the CDRs that are characterized by different formats, such as Kabat and IMGT.

In some embodiments, a polypeptide, an antibody, or antibody binding fragment thereof, comprises a light chain variable region having a LCDR1, a LCDR2, and a LCDR3, wherein the LCDR1 has a sequence of SEQ ID NO: 38, the LCDR2 has a sequence of SEQ ID NO: 39, and the LCDR3 has a sequence of SEQ ID NO: 40.

In some embodiments, a polypeptide, an antibody, or antibody binding fragment thereof, comprises a light chain variable region having a LCDR1, a LCDR2, and a LCDR3, wherein the LCDR1 has a sequence of SEQ ID NO: 46, the LCDR2 has a sequence of YA, and the LCDR3 has a sequence of SEQ ID NO: 40.

In some embodiments, a polypeptide, an antibody, or antibody binding fragment thereof, comprises a heavy chain variable region having a HCDR1, a HCDR2, and a HCDR3, wherein the HCDR1 has a sequence of SEQ ID NO: 35, the HCDR2 has a sequence of SEQ ID NO: 36, and the HCDR3 has a sequence of SEQ ID NO: 37.

In some embodiments, a polypeptide, an antibody, or antibody binding fragment thereof, comprises a heavy chain variable region having a HCDR1, a HCDR2, and a HCDR3, wherein the HCDR1 has a sequence of SEQ ID NO: 41, the HCDR2 has a sequence of SEQ ID NO: 42, and the HCDR3 has a sequence of SEQ ID NO: 37.

In some embodiments, a polypeptide, an antibody, or antibody binding fragment thereof, comprises a heavy chain variable region having a HCDR1, a HCDR2, and a HCDR3, wherein the HCDR1 has a sequence of SEQ ID NO: 43, the HCDR2 has a sequence of SEQ ID NO: 44, and the HCDR3 has a sequence of SEQ ID NO: 45.

In some embodiments, a polypeptide, an antibody or antibody binding fragment thereof, comprises: (i) a light chain having any one of the foregoing recited combinations of LCDR1, LCDR2, and LCDR3 sequences; and (ii) a heavy chain having any one of the foregoing recited combinations of HCDR1, HCDR2, and HCDR3 sequences.

The different CDR motifs can be combined in any combination including those not depicted in the table above. For example, the following embodiments are provided as non-limiting examples of such combinations.

In some embodiments, a polypeptide, an antibody, or antigen binding fragment thereof, comprises: (i) a light chain variable region comprising light chain CDR1, CDR2, and CDR3 sequences, wherein the light chain CDR1 sequence has the amino acid sequence of SEQ ID NO: 38; the light chain CDR2 has the amino acid sequence of SEQ ID NO: 39; and the light chain CDR3 sequence has the amino acid sequence of SEQ ID NO: 40; and (ii) a heavy chain variable region comprising heavy chain CDR1, CDR2, and CDR3 sequences, wherein the heavy chain CDR1 sequence has the amino acid sequence of SEQ ID NO: 35; the heavy chain CDR2 sequence has the amino acid sequence of SEQ ID NO: 36; and the heavy chain CDR3 sequence has the amino acid sequence of SEQ ID NO: 37; or variants of any of the foregoing.

In some embodiments, a polypeptide, an antibody, or antigen binding fragment thereof, comprises: (i) a light chain variable region comprising light chain CDR1, CDR2, and CDR3 sequences, wherein the light chain CDR1 sequence has the amino acid sequence of SEQ ID NO: 38; the light chain CDR2 has the amino acid sequence of SEQ ID NO: 39; and the light chain CDR3 sequence has the amino acid sequence of SEQ ID NO: 40; and (ii) a heavy chain variable region comprising heavy chain CDR1, CDR2, and CDR3 sequences, wherein the heavy chain CDR1 sequence has the amino acid sequence of SEQ ID NO: 41; the heavy chain CDR2 sequence has the amino acid sequence of SEQ ID NO: 42; and the heavy chain CDR3 sequence has the amino acid sequence of SEQ ID NO: 37; or variants of any of the foregoing.

In some embodiments, a polypeptide, an antibody, or antigen binding fragment thereof, comprises: (i) a light chain variable region comprising light chain CDR1, CDR2, and CDR3 sequences, wherein the light chain CDR1 sequence has the amino acid sequence of SEQ ID NO: 46; the light chain CDR2 has the amino acid sequence of YA; and the light chain CDR3 sequence has the amino acid sequence of SEQ ID NO: 40; and (ii) a heavy chain variable region comprising heavy chain CDR1, CDR2, and CDR3 sequences, wherein the heavy chain CDR1 sequence has the amino acid sequence of SEQ ID NO: 43; the heavy chain CDR2 sequence has the amino acid sequence of SEQ ID NO: 44; and the heavy chain CDR3 sequence has the amino acid sequence of SEQ ID NO: 45; or variants of any of the foregoing.

In some embodiments, the light chain variable region CDR1 is replaced with any of the other light chain CDR1 sequences. In some embodiments, the light chain variable region CDR2 is replaced with any of the other light chain CDR2 sequences. In some embodiments, the light chain variable region CDR3 is replaced with any of the other light chain CDR3 sequences. In some embodiments, the heavy chain variable region CDR1 is replaced with any of the other heavy chain CDR1 sequences. In some embodiments, the heavy chain variable region CDR2 is replaced with any of the other heavy chain CDR2 sequences. In some embodiments, the heavy chain variable region CDR3 is replaced with any of the other heavy chain CDR3 sequences.

In some embodiments, the polypeptide comprises a heavy chain variable region peptide having one of the following sequences, or a variant thereof:

| SEQ ID NO: | AB ID NO. | Sequence |
|---|---|---|
| 47 | CD7AB1 | QVQLQQPGAELVKPGASVKLSC KASGYPFTSYWIHWVKQRPGRG LEWLGRIDPNSGDTKYNEKFKN KATLTVDKSSTTAYMQLSSLTS EDSAVYYCARSPYYSNDNSMDY WGQGTSVTVSS |

In some embodiments, the polypeptide comprises a light chain variable region peptide having one of the following sequences, or a variant thereof:

| SEQ ID NO: | AB ID NO. | Sequence |
|---|---|---|
| 48 | CD7AB1 | DILLTQSPAILSVSPGERVSFS CRASQSIGTSIHWYQQRTNDSP RLLIKYASESISGIPSRFSGSG SGTDFTLSINSVESEDIADYYC QQSNSWPTTFGGGTKLEIKR |

In some embodiments, a polypeptide, an antibody, or antigen binding fragment thereof, comprises a $V_H$ peptide of SEQ ID NO: 47. In some embodiments, a polypeptide, an antibody, or antigen binding fragment thereof, comprises a $V_L$ peptide of SEQ ID NO: 48. In some embodiments, a polypeptide, an antibody, or antigen binding fragment thereof, comprises a $V_H$ peptide and a $V_L$ peptide, wherein the wherein the $V_H$ peptide comprises a sequence of SEQ ID NO: 47, or a variant thereof, and the $V_L$ peptide comprises a sequence of SEQ ID NO: 48, or a variant thereof. In some embodiments, a polypeptide, an antibody, or antigen binding fragment thereof, comprises a $V_H$ peptide and a $V_L$ peptide, wherein the wherein the $V_H$ peptide comprises a sequence of SEQ ID NO: 47, or a variant thereof, and the $V_L$ peptide comprises a sequence of SEQ ID NO: 48, or a variant thereof, and the polypeptide, the antibody, or antigen binding fragment thereof, binds to non-human primate CD7. In some embodiments, a polypeptide, an antibody, or antigen binding fragment thereof, comprises a $V_H$ peptide and a $V_L$ peptide, wherein the $V_H$ peptide comprises a sequence of SEQ ID NO: 47, or a variant thereof, and the $V_L$ peptide comprises a sequence of SEQ ID NO: 48, or a variant thereof, and the polypeptide, the antibody, or antigen binding fragment thereof, binds to human CD7. In some embodiments, the $V_H$ peptide comprises a sequence of SEQ ID NO: 47; and the $V_L$ peptide comprises a sequence of SEQ ID NO: 48.

The VH and the VL sequences can be in any format, including, but not limited to an scFv format where the VH and VL regions are linked with a peptide linker. Examples of peptide linkers that can be used to link various peptides provided for herein include, but are not limited to: (GGGGS)$_n$ (SEQ ID NO: 49), wherein each n is independently 1-5. In some embodiments, n is 1. In some embodiments, n is 2. In some embodiments, n is 3. In some embodiments, n is 4. In some embodiments, n is 5. In some embodiments, the variable regions are not linked with a peptide linker. In some embodiments, the polypeptide comprises SEQ ID NO: 47 and SEQ ID NO: 48.

In some embodiments, the VH and VL polypeptides are linked to a Fc region. In some embodiments, the Fc region is as provided for herein. In some embodiments, the Fc region comprises an amino acid sequence of SEQ ID NO: 34, SEQ ID NO: 71, or SEQ ID NO: 72 as provided for herein. As provided for herein, the heavy chain can be linked to a Fc region. Non-limiting mutations in the Fc region are provided for herein. In some embodiments, the Fc region further comprises a transmembrane domain. Examples of transmembrane domains include, but are not limited to, a CD8 or CD28 ("CD8/CD28") transmembrane domain. In some embodiments, the Fc region further comprises a CD8 transmembrane domain. In some embodiments, the Fc region further comprises a CD28 transmembrane domain. In some embodiments, the Fc region comprising a transmembrane domain further comprises an Env incorporation motif. In some embodiments, the Fc region comprising a CD8/CD28 transmembrane domain further comprises an Env incorporation motif. In some embodiments, the VH and VL polypeptides provided herein are linked to an Fc region comprising a transmembrane domain. In some embodiments, the VH and VL polypeptides provided herein are linked to an Fc region comprising a CD8/CD28 transmembrane domain. In some embodiments, the VH and VL polypeptides provided herein are linked to an Fc region comprising a CD8/CD28 transmembrane domain and an Env incorporation motif. In some embodiments, the VH and VL polypeptides provided herein linked to an Fc region comprising a CD8/CD28 transmembrane domain are anchored to the plasma membrane on the surface of a cell. In some embodiments, the cell is an immune cell, such as those provided herein. In some embodiments, the VH having a sequence as set forth in SEQ ID NO: 47 and VL having a sequence as set forth in SEQ ID NO: 48 are linked to an Fc region comprising a transmembrane domain. In some embodiments, the VH having a sequence as set forth in SEQ ID NO: 47 and VL having a sequence as set forth in SEQ ID NO: 48 are linked to an Fc region comprising a CD8/CD28 transmembrane domain. In some embodiments, the VH having a sequence as set forth in SEQ ID NO: 47 and VL having a sequence as set forth in SEQ ID NO: 48 are linked to an Fc region comprising a CD8/CD28 transmembrane domain and an Env incorporation motif. In some embodiments, the VH having a sequence as set forth in SEQ ID NO: 47 and VL having a sequence as set forth in SEQ ID NO: 48 linked to an Fc region comprising a CD8/CD28 transmembrane domain are anchored to the plasma membrane on the surface of a cell. In some embodiments, the cell is an immune cell, such as those provided herein.

In some embodiments, the $V_H$ peptide comprising a sequence that is at least 85%, 86%, 87%, 88%, 89%, 90%, 91%, 92%, 93%, 94%, 95%, 96%, 97%, 98%, or 99% identical to a sequence of SEQ ID NO: 47; and the $V_L$ peptide comprising a sequence that is at least 85%, 86%, 87%, 88%, 89%, 90%, 91%, 92%, 93%, 94%, 95%, 96%, 97%, 98%, or 99% identical to a sequence of SEQ ID NO: 48 are linked to an Fc region comprising a transmembrane domain. In some embodiments, the VH peptide comprising a sequence that is at least 85%, 86%, 87%, 88%, 89%, 90%, 91%, 92%, 93%, 94%, 95%, 96%, 97%, 98%, or 99% identical to a sequence of SEQ ID NO: 47; and the $V_L$ peptide comprising a sequence that is at least 85%, 86%, 87%, 88%, 89%, 90%, 91%, 92%, 93%, 94%, 95%, 96%, 97%, 98%, or 99% identical to a sequence of SEQ ID NO: 48 are linked to an Fc region comprising a CD8/CD28 transmembrane domain. In some embodiments, the $V_H$ peptide comprising a sequence that is at least 85%, 86%, 87%, 88%, 89%, 90%, 91%, 92%, 93%, 94%, 95%, 96%, 97%, 98%, or 99% identical to a sequence of SEQ ID NO: 47; and the $V_L$ peptide comprising a sequence that is at least 85%, 86%, 87%, 88%, 89%, 90%, 91%, 92%, 93%, 94%, 95%, 96%, 97%, 98%, or 99% identical to a sequence of SEQ ID NO: 48 are linked to an Fc region comprising a CD8/CD28 transmembrane domain and an Env incorporation motif. In some embodiments, the $V_H$ peptide comprising a sequence that is at least 85%, 86%, 87%, 88%, 89%, 90%, 91%, 92%, 93%, 94%, 95%, 96%, 97%, 98%, or 99% identical to a sequence of SEQ ID NO: 47; and the $V_L$ peptide comprising a sequence that is at least 85%, 86%, 87%, 88%, 89%, 90%, 91%, 92%, 93%, 94%, 95%, 96%, 97%, 98%, or 99% identical to a sequence of SEQ ID NO: 48 linked to an Fc region comprising a CD8/CD28 transmembrane domain are anchored to the plasma membrane on the surface of a cell. In some embodiments, the cell is an immune cell, such as those provided herein.

In some embodiments, a polypeptide comprises a $V_H$ peptide and a $V_L$ peptide, wherein the $V_H$ peptide comprises a sequence that is at least 85%, 86%, 87%, 88%, 89%, 90%, 91%, 92%, 93%, 94%, 95%, 96%, 97%, 98%, or 99% identical to a sequence of SEQ ID NO: 47; and the VL peptide comprises a sequence that is at least 85%, 86%, 87%, 88%, 89%, 90%, 91%, 92%, 93%, 94%, 95%, 96%, 97%, 98%, or 99% identical to a sequence of SEQ ID NO: 48.

In some embodiments, a polypeptide comprises a $V_H$ peptide and a $V_L$ peptide, wherein the $V_H$ peptide comprises a sequence that is at least 85%, 86%, 87%, 88%, 89%, 90%, 91%, 92%, 93%, 94%, 95%, 96%, 97%, 98%, or 99% identical to a sequence of SEQ ID NO: 47; and the VL peptide comprises a sequence that is at least 85%, 86%, 87%, 88%, 89%, 90%, 91%, 92%, 93%, 94%, 95%, 96%, 97%, 98%, or 99% identical to a sequence of SEQ ID NO: 48; provided that the $V_H$ peptide and a $V_L$ peptide comprises a light chain CDR having a sequence of SEQ ID NO: 38-40; and/or a heavy chain CDR having a sequence of SEQ ID NO: 35-37. In some embodiments, a polypeptide comprises a $V_H$ peptide and a $V_L$ peptide, wherein the $V_H$ peptide comprises a sequence that is at least 85%, 86%, 87%, 88%, 89%, 90%, 91%, 92%, 93%, 94%, 95%, 96%, 97%, 98%, or 99% identical to a sequence of SEQ ID NO: 47; and the $V_L$ peptide comprises a sequence that is at least 85%, 86%, 87%, 88%, 89%, 90%, 91%, 92%, 93%, 94%, 95%, 96%, 97%, 98%, or 99% identical to a sequence of SEQ ID NO: 48; provided that the $V_H$ peptide and a $V_L$ peptide comprise a light chain CDR1 having a sequence of SEQ ID NO: 38; a light chain CDR2 having a sequence of SEQ ID NO: 39; a light chain CDR3 having a sequence of SEQ ID NO: 40; and/or a heavy chain CDR1 having a sequence of SEQ ID NO: 35; a heavy chain CDR2 having a sequence of SEQ ID NO: 36; and a heavy chain CDR3 having a sequence of SEQ ID NO: 37. In some embodiments, the CDRs in the $V_H$ or $V_L$ chain are as set forth in the combinations provided for herein.

In some embodiments, a polypeptide comprises a $V_H$ peptide and a $V_L$ peptide, wherein the $V_H$ peptide comprises a sequence that is at least 85%, 86%, 87%, 88%, 89%, 90%, 91%, 92%, 93%, 94%, 95%, 96%, 97%, 98%, or 99% identical to a sequence of SEQ ID NO: 47; and the $V_L$ peptide comprises a sequence that is at least 85%, 86%, 87%, 88%, 89%, 90%, 91%, 92%, 93%, 94%, 95%, 96%, 97%, 98%, or 99% identical to a sequence of SEQ ID NO: 48; provided that the $V_L$ peptide comprises a LCDR1 having a sequence of SEQ ID NO: 38; a LCDR2 having a sequence of SEQ ID NO: 39; and a LCDR3 having a sequence of SEQ ID NO: 40; and the $V_H$ peptide comprises a HCDR1 having a sequence of SEQ ID NO: 35; a HCDR2 having a sequence of SEQ ID NO: 36; and a HCDR3 having a sequence of SEQ ID NO: 37.

In some embodiments, a polypeptide comprises a $V_H$ peptide and a $V_L$ peptide, wherein the $V_H$ peptide comprises a sequence that is at least 85%, 86%, 87%, 88%, 89%, 90%, 91%, 92%, 93%, 94%, 95%, 96%, 97%, 98%, or 99% identical to a sequence of SEQ ID NO: 47; and the $V_L$ peptide comprises a sequence that is at least 85%, 86%, 87%, 88%, 89%, 90%, 91%, 92%, 93%, 94%, 95%, 96%, 97%, 98%, or 99% identical to a sequence of SEQ ID NO: 48; provided that the $V_L$ peptide comprises a LCDR1 having a sequence of SEQ ID NO: 38, wherein the LCDR1 comprises at most 1 conservative amino acid substitution, a LCDR2 having a sequence of SEQ ID NO: 39, wherein the LCDR2 comprises at most 1 conservative amino acid substitution, and a LCDR3 having a sequence of SEQ ID NO: 40, wherein the LCDR3 comprises at most 1 conservative amino acid substitution; and the $V_H$ peptide comprises a HCDR1 having a sequence of SEQ ID NO: 35, wherein the HCDR1 comprises at most 1 conservative amino acid substitution, a HCDR2 having a sequence of SEQ ID NO: 36, wherein the HCDR2 comprises at most 1 conservative amino acid substitution, and a HCDR3 having a sequence of SEQ ID NO: 37, wherein the HCDR3 comprises at most 1 conservative amino acid substitution.

In some embodiments, a polypeptide comprises a $V_H$ peptide and a $V_L$ peptide, wherein the $V_H$ peptide comprises a sequence that is at least 85%, 86%, 87%, 88%, 89%, 90%, 91%, 92%, 93%, 94%, 95%, 96%, 97%, 98%, or 99% identical to a sequence of SEQ ID NO: 47; and the $V_L$ peptide comprises a sequence that is at least 85%, 86%, 87%, 88%, 89%, 90%, 91%, 92%, 93%, 94%, 95%, 96%, 97%, 98%, or 99% identical to a sequence of SEQ ID NO: 48; provided that the $V_H$ peptide and a $V_L$ peptide comprise a light chain CDR1 having a sequence of SEQ ID NO: 38; a light chain CDR2 having a sequence of SEQ ID NO: 39; a light chain CDR1 having a sequence of SEQ ID NO: 40; and/or a heavy chain CDR1 having a sequence of SEQ ID NO: 41; a heavy chain CDR2 having a sequence of SEQ ID NO: 42; and a heavy chain CDR3 having a sequence of SEQ ID NO: 37. In some embodiments, the CDRs in the $V_H$ or $V_L$ chain are as set forth in the combinations provided for herein.

In some embodiments, a polypeptide comprises a $V_H$ peptide and a $V_L$ peptide, wherein the $V_H$ peptide comprises a sequence that is at least 85%, 86%, 87%, 88%, 89%, 90%, 91%, 92%, 93%, 94%, 95%, 96%, 97%, 98%, or 99% identical to a sequence of SEQ ID NO: 47; and the $V_L$ peptide comprises a sequence that is at least 85%, 86%, 87%, 88%, 89%, 90%, 91%, 92%, 93%, 94%, 95%, 96%, 97%, 98%, or 99% identical to a sequence of SEQ ID NO: 48; provided that the $V_L$ peptide comprises a LCDR1 having a sequence of SEQ ID NO: 38; a LCDR2 having a sequence of SEQ ID NO: 39; and a LCDR3 having a sequence of SEQ ID NO: 40; and the $V_H$ peptide comprises a HCDR1 having a sequence of SEQ ID NO: 41; a HCDR2 having a sequence of SEQ ID NO: 42; and a HCDR3 having a sequence of SEQ ID NO: 37.

In some embodiments, a polypeptide comprises a $V_H$ peptide and a $V_L$ peptide, wherein the $V_H$ peptide comprises a sequence that is at least 85%, 86%, 87%, 88%, 89%, 90%, 91%, 92%, 93%, 94%, 95%, 96%, 97%, 98%, or 99% identical to a sequence of SEQ ID NO: 47; and the $V_L$ peptide comprises a sequence that is at least 85%, 86%, 87%, 88%, 89%, 90%, 91%, 92%, 93%, 94%, 95%, 96%, 97%, 98%, or 99% identical to a sequence of SEQ ID NO: 48; provided that the $V_L$ peptide comprises a LCDR1 having a sequence of SEQ ID NO: 38, wherein the LCDR1 comprises at most 1 conservative amino acid substitution, a LCDR2 having a sequence of SEQ ID NO: 39, wherein the LCDR2 comprises at most 1 conservative amino acid substitution, and a LCDR3 having a sequence of SEQ ID NO: 40, wherein the LCDR3 comprises at most 1 conservative amino acid substitution; and the $V_H$ peptide comprises a HCDR1 having a sequence of SEQ ID NO: 41, wherein the HCDR1 comprises at most 1 conservative amino acid substitution, a HCDR2 having a sequence of SEQ ID NO: 42, wherein the HCDR2 comprises at most 1 conservative amino acid substitution, and a HCDR3 having a sequence of SEQ ID NO: 37, wherein the HCDR3 comprises at most 1 conservative amino acid substitution.

In some embodiments, a polypeptide comprises a $V_H$ peptide and a $V_L$ peptide, wherein the $V_H$ peptide comprises a sequence that is at least 85%, 86%, 87%, 88%, 89%, 90%, 91%, 92%, 93%, 94%, 95%, 96%, 97%, 98%, or 99% identical to a sequence of SEQ ID NO: 47; and the $V_L$ peptide comprises a sequence that is at least 85%, 86%, 87%, 88%, 89%, 90%, 91%, 92%, 93%, 94%, 95%, 96%, 97%, 98%, or 99% identical to a sequence of SEQ ID NO: 48; provided that the $V_H$ peptide and a $V_L$ peptide comprise a light chain CDR1 having a sequence of SEQ ID NO: 46; a light chain CDR2 having a sequence of YA; a light chain CDR1 having a sequence of SEQ ID NO: 40; and/or a heavy chain CDR1 having a sequence of SEQ ID NO: 43; a heavy chain CDR2 having a sequence of SEQ ID NO: 44; and a heavy chain CDR3 having a sequence of SEQ ID NO: 45. In some embodiments, the CDRs in the $V_H$ or $V_L$ chain are as set forth in the combinations provided for herein.

In some embodiments, a polypeptide comprises a $V_H$ peptide and a $V_L$ peptide, wherein the $V_H$ peptide comprises a sequence that is at least 85%, 86%, 87%, 88%, 89%, 90%, 91%, 92%, 93%, 94%, 95%, 96%, 97%, 98%, or 99% identical to a sequence of SEQ ID NO: 47; and the $V_L$ peptide comprises a sequence that is at least 85%, 86%, 87%, 88%, 89%, 90%, 91%, 92%, 93%, 94%, 95%, 96%, 97%, 98%, or 99% identical to a sequence of SEQ ID NO: 48; provided that the $V_L$ peptide comprises a LCDR1 having a sequence of SEQ ID NO: 46; a LCDR2 having a sequence of YA; and a LCDR3 having a sequence of SEQ ID NO: 40; and the $V_H$ peptide comprises a HCDR1 having a sequence of SEQ ID NO: 43; a HCDR2 having a sequence of SEQ ID NO: 44; and a HCDR3 having a sequence of SEQ ID NO: 45.

In some embodiments, a polypeptide comprises a $V_H$ peptide and a $V_L$ peptide, wherein the $V_H$ peptide comprises a sequence that is at least 85%, 86%, 87%, 88%, 89%, 90%, 91%, 92%, 93%, 94%, 95%, 96%, 97%, 98%, or 99% identical to a sequence of SEQ ID NO: 47; and the $V_L$ peptide comprises a sequence that is at least 85%, 86%, 87%, 88%, 89%, 90%, 91%, 92%, 93%, 94%, 95%, 96%, 97%, 98%, or 99% identical to a sequence of SEQ ID NO: 48; provided that the $V_L$ peptide comprises a LCDR1 having a sequence of SEQ ID NO: 46, wherein the LCDR1 comprises at most 1 conservative amino acid substitution, a LCDR2 having a sequence of YA, wherein the LCDR2 comprises at most 1 conservative amino acid substitution, and a LCDR3 having a sequence of SEQ ID NO: 40, wherein the LCDR3 comprises at most 1 conservative amino acid substitution; and the $V_H$ peptide comprises a HCDR1 having a sequence of SEQ ID NO: 43, wherein the HCDR1 comprises at most 1 conservative amino acid substitution, a HCDR2 having a sequence of SEQ ID NO: 44, wherein the HCDR2 comprises at most 1 conservative amino acid substitution, and a HCDR3 having a sequence of SEQ ID NO: 45, wherein the HCDR3 comprises at most 1 conservative amino acid substitution.

In some embodiments, a polypeptide comprises a $V_H$ peptide and a $V_L$ peptide, wherein the $V_H$ peptide comprises a sequence of SEQ ID NO: 47 and the $V_L$ peptide comprises a sequence of SEQ ID NO: 48.

In some embodiments, a polypeptide as provided herein binds to non-human primate CD7. In some embodiments, a polypeptide as provided herein binds to human CD7.

As provided for herein, the different polypeptides ($V_H$ or $V_L$) described herein can be linked with a peptide linker or not linked with a peptide linker and instead for a continuous sequence. In some embodiments, the peptide linker comprises a sequence of (GGGGS)$_n$ (SEQ ID NO: 49), wherein each n is independently 1-5. In some embodiments, n is 1. In some embodiments, n is 2. In some embodiments, n is 3. In some embodiments, n is 4. In some embodiments, n is 5. The linked peptide format can be represented by a formula of $V_H$-Z-$V_L$ or $V_L$-Z-$V_H$, wherein Z is the peptide linker. In some embodiments, Z is (GGGGS)$_n$ (SEQ ID NO: 49), wherein each n is independently 1-5.

In some embodiments, a polypeptide comprising the linked peptide represented by a formula of $V_L$-Z-$V_H$ comprises a heavy chain variable region as set forth in SEQ ID NO: 47 linked via a linker sequence GGGGSGGGGSGGGGSGGGGS (SEQ ID NO: 50) to a light chain variable region as set forth in SEQ ID NO: 48. In some embodiments, a polypeptide comprising a $V_L$ linked via a peptide linker to a $V_H$ has the sequence as set forth below, (SEQ ID NO: 51)
DILLTQSPAILSVSPGERVSFSCRASQSIGTSI

HWYQQRTNDSPRLLIKYASESISGIPSRFSGSG

SGTDFTLSINSVESEDIADYYCQQSNSWPTTFG

GGTKLEIKRGGGGSGGGGSGGGGSGGGGSQVQL

QQPGAELVKPGASVKLSCKASGYPFTSYWIHWV

KQRPGRGLEWLGRIDPNSGDTKYNEKFKNKATL

-continued
TVDKSSTTAYMQLSSLTSEDSAVYYCARSPYYS

NDNSMDYWGQGTSVTVSS.

In some embodiments, a polypeptide comprises a sequence that is at least 85%, 86%, 87%, 88%, 89%, 90%, 91%, 92%, 93%, 94%, 95%, 96%, 97%, 98%, or 99% identical to a sequence of SEQ ID NO: 51. In some embodiments, a polypeptide comprises a sequence that is at least 90% identical to a sequence of SEQ ID NO: 51. In some embodiments, a polypeptide comprises a sequence that is at least 95% identical to a sequence of SEQ ID NO: 51. In some embodiments, a polypeptide comprises a sequence that is at least 99% identical to a sequence of SEQ ID NO: 51. In some embodiments, a polypeptide comprises a sequence as set forth in SEQ ID NO: 51. In some embodiments, the polypeptide as set forth in SEQ ID NO: 51 is an antibody, or an antigen binding fragment thereof. In some embodiments, the antibody is an anti-CD7 antibody.

In some embodiments, a polypeptide comprising the linked peptide represented by a formula of $V_H$-Z-$V_L$ comprises a light chain variable region as set forth in SEQ ID NO: 48 linked via a linker sequence GGGGSGGGGSGGGGSGGGGS (SEQ ID NO: 50) to a heavy chain variable region as set forth in SEQ ID NO: 49. In some embodiments, a polypeptide comprising a $V_H$ linked via a peptide linker to a $V_L$ has the sequence as set forth below, (SEQ ID NO: 52)
QVQLQQPGAELVKPGASVKLSCKASGYPFTSYWIH

WVKQRPGRGLEWLGRIDPNSGDTKYNEKFKNKATL

TVDKSSTTAYMQLSSLTSEDSAVYYCARSPYYSND

NSMDYWGQGTSVTVSSGGGGSGGGGSGGGGSGGGG

SDILLTQSPAILSVSPGERVSFSCRASQSIGTSIH

WYQQRTNDSPRLLIKYASESISGIPSRFSGSGSGT

DFTLSINSVESEDIADYYCQQSNSWPTTFGGGTKL

EIKR

In some embodiments, a polypeptide comprises a sequence that is at least 85%, 86%, 87%, 88%, 89%, 90%, 91%, 92%, 93%, 94%, 95%, 96%, 97%, 98%, or 99% identical to a sequence of SEQ ID NO: 52. In some embodiments, a polypeptide comprises a sequence that is at least 90% identical to a sequence of SEQ ID NO: 52. In some embodiments, a polypeptide comprises a sequence that is at least 95% identical to a sequence of SEQ ID NO: 52. In some embodiments, a polypeptide comprises a sequence that is at least 99% identical to a sequence of SEQ ID NO: 52. In some embodiments, a polypeptide comprises a sequence as set forth in SEQ ID NO: 52. In some embodiments, the polypeptide as set forth in SEQ ID NO: 52 is an antibody, or an antigen binding fragment thereof. In some embodiments, the antibody is an anti-CD7 antibody. In some embodiments, the anti-CD7 antibody binds to non-human primate CD7. In some embodiments, the anti-CD7 antibody binds to human CD7.

In some embodiments, a polypeptide comprises a sequence that is at least 85%, 86%, 87%, 88%, 89%, 90%, 91%, 92%, 93%, 94%, 95%, 96%, 97%, 98%, or 99% identical to a sequence of SEQ ID NO: 51 and comprises an Fc region, such as those provided herein. In some embodiments, a polypeptide comprises a sequence that is at least 85%, 86%, 87%, 88%, 89%, 90%, 91%, 92%, 93%, 94%, 95%, 96%, 97%, 98%, or 99% identical to a sequence of SEQ ID NO: 51 and comprises an Fc region, such as those provided herein, and a transmembrane domain, such as those provided herein. In some embodiments, a polypeptide comprises a sequence that is at least 85%, 86%, 87%, 88%, 89%, 90%, 91%, 92%, 93%, 94%, 95%, 96%, 97%, 98%, or 99% identical to a sequence of SEQ ID NO: 51 and comprises an Fc region, such as those provided herein, and a CD8/CD28 transmembrane domain. In some embodiments, a polypeptide comprises a sequence that is at least 85%, 86%, 87%, 88%, 89%, 90%, 91%, 92%, 93%, 94%, 95%, 96%, 97%, 98%, or 99% identical to a sequence of SEQ ID NO: 51 and comprises an Fc region, such as those provided herein, a transmembrane domain, such as those provided herein, and an Env incorporation motif.

In some embodiments, a polypeptide comprises a sequence that is at least 85%, 86%, 87%, 88%, 89%, 90%, 91%, 92%, 93%, 94%, 95%, 96%, 97%, 98%, or 99% identical to a sequence of SEQ ID NO: 52 and comprises an Fc region, such as those provided herein. In some embodiments, a polypeptide comprises a sequence that is at least 85%, 86%, 87%, 88%, 89%, 90%, 91%, 92%, 93%, 94%, 95%, 96%, 97%, 98%, or 99% identical to a sequence of SEQ ID NO: 52 and comprises an Fc region, such as those provided herein, and a transmembrane domain, such as those provided herein. In some embodiments, a polypeptide comprises a sequence that is at least 85%, 86%, 87%, 88%, 89%, 90%, 91%, 92%, 93%, 94%, 95%, 96%, 97%, 98%, or 99% identical to a sequence of SEQ ID NO: 52 and comprises an Fc region, such as those provided herein, and a CD8/CD28 transmembrane domain. In some embodiments, a polypeptide comprises a sequence that is at least 85%, 86%, 87%, 88%, 89%, 90%, 91%, 92%, 93%, 94%, 95%, 96%, 97%, 98%, or 99% identical to a sequence of SEQ ID NO: 52 and comprises an Fc region, such as those provided herein, a transmembrane domain, such as those provided herein, and an Env incorporation motif.

As provided for herein, the polypeptide, antibodies, or antigen binding fragments thereof can be variants of the sequences.

The sequences of the polypeptides or antibodies can be modified to yield human IgG antibodies. The conversion of the sequences provided herein can be modified to yield other types of antibodies. The CDRs can also be linked to other antibodies, proteins, or molecules to create antibody fragments that bind CD7.

In some embodiments, a polypeptide or an antibody as provided herein is a targeting moiety on the surface of an engineered viral particle. In some embodiments, the targeting moiety allows for binding to a target cell. In some embodiments, the targeting moiety is a CD7 binding moiety, such as a polypeptide or an antibody as provided herein. In some embodiments, the targeting moiety comprises a sequence that is at least 85%, 86%, 87%, 88%, 89%, 90%, 91%, 92%, 93%, 94%, 95%, 96%, 97%, 98%, or 99% identical to a sequence of SEQ ID NO: 51. In some embodiments, the targeting moiety comprises a sequence that is at least 90% identical to a sequence of SEQ ID NO: 51. In some embodiments, the targeting moiety comprises a sequence that is at least 95% identical to a sequence of SEQ ID NO: 51. In some embodiments, the targeting moiety comprises a sequence that is at least 99% identical to a sequence of SEQ ID NO: 51. In some embodiments, the targeting moiety comprises a sequence as set forth in SEQ ID NO: 51. In some embodiments, the targeting moiety as set forth in SEQ ID NO: 51 is an antibody, or an antigen binding fragment thereof. In some embodiments, the targeting moiety is an anti-CD7 antibody.

In some embodiments, a polypeptide or an antibody as provided for herein is a targeting moiety on the surface of an engineered viral particle. In some embodiments, the engineered viral particle is a pseudotyped viral-like particle. In some embodiments, the targeting moiety allows for binding to a target cell. In some embodiments, the targeting moiety is a CD7 binding moiety, such as a polypeptide or an antibody as provided herein. In some embodiments, the targeting moiety comprises a sequence that is at least 85%, 86%, 87%, 88%, 89%, 90%, 91%, 92%, 93%, 94%, 95%, 96%, 97%, 98%, or 99% identical to a sequence of SEQ ID NO: 52. In some embodiments, the targeting moiety comprises a sequence that is at least 90% identical to a sequence of SEQ ID NO: 52. In some embodiments, the targeting moiety comprises a sequence that is at least 95% identical to a sequence of SEQ ID NO: 52. In some embodiments, the targeting moiety comprises a sequence that is at least 99% identical to a sequence of SEQ ID NO: 52. In some embodiments, the targeting moiety comprises a sequence as set forth in SEQ ID NO: 52. In some embodiments, the targeting moiety as set forth in SEQ ID NO: 52 is an antibody, or an antigen binding fragment thereof. In some embodiments, the targeting moiety is an anti-CD7 antibody. In some embodiments, the anti-CD7 antibody binds to non-human primate CD7. In some embodiments, the anti-CD7 antibody binds to human CD7.

In some embodiments, a polypeptide comprises a sequence having a sequence as set forth in SEQ ID NO: 51 and comprises an Fc region, such as those provided herein. In some embodiments, a polypeptide comprises a sequence having a sequence as set forth in SEQ ID NO: 51 and comprises an Fc region, such as those provided herein, and a transmembrane domain, such as those provided herein. In some embodiments, a polypeptide comprises a sequence having a sequence as set forth in SEQ ID NO: 51 and comprises an Fc region, such as those provided herein, and a CD8/CD28 transmembrane domain. In some embodiments, a polypeptide comprises a sequence having a sequence as set forth in SEQ ID NO: 51 and comprises an Fc region, such as those provided herein, a transmembrane domain, such as those provided herein, and an Env incorporation motif.

In some embodiments, a polypeptide comprises a sequence having a sequence as set forth in SEQ ID NO: 52 and comprises an Fc region, such as those provided herein. In some embodiments, a polypeptide comprises a sequence having a sequence as set forth in SEQ ID NO: 52 and comprises an Fc region, such as those provided herein, and a transmembrane domain, such as those provided herein. In some embodiments, a polypeptide comprises a sequence having a sequence as set forth in SEQ ID NO: 52 and comprises an Fc region, such as those provided herein, and a CD8/CD28 transmembrane domain. In some embodiments, a polypeptide comprises a sequence having a sequence as set forth in SEQ ID NO: 52 and comprises an Fc region, such as those provided herein, a transmembrane domain, such as those provided herein, and an Env incorporation motif.

In some embodiments, the targeting moiety (a polypeptide) can bind to CD8.

In some embodiments, the polypeptide binds to CD8. In some embodiments, the polypeptide binds to CD8-alpha. In some embodiments, the polypeptide binds to CD8-beta. In some embodiments, the polypeptide binds to CD8 heterodimer. In some embodiments, the CD8 heterodimer comprises CD8-alpha and CD8-beta subunits. In some embodiments, the polypeptide binds to CD8-alpha homodimer. In some embodiments, the polypeptide that binds to CD8 is an antibody which binds to non-human primate CD8. In some embodiments, the antibody that binds to non-human primate CD8 is an antibody which binds to non-human primate CD8-alpha. In some embodiments, the antibody that binds to non-human primate CD8 is an antibody which binds to non-human primate CD8-beta. In some embodiments, the antibody that binds to non-human primate CD8 is an antibody which binds to non-human primate CD8-alpha homodimer. In some embodiments, the antibody that binds to non-human primate CD8 is an antibody which binds to non-human primate CD8 heterodimer. In some embodiments, the polypeptide that binds to CD8 is an antibody which binds to human CD8. In some embodiments, the antibody that binds to human CD8 is an antibody which binds to human CD8-alpha. In some embodiments, the antibody that binds to human CD8 is an antibody which binds to human CD8-beta. In some embodiments, the antibody that binds to human CD8 is an antibody which binds to human CD8-alpha homodimer. In some embodiments, the antibody that binds to human CD8 is an antibody which binds to human CD8 heterodimer. The sequence of human CD8-alpha (UniProtKB Q8 TAW8) is as follows (SEQ ID NO: 53):

```
                                        (SEQ ID NO: 53)
MALPVTALLLPLALLLHAARPSQFRVSPLDRTWNL

GETVELKCQVLLSNPTSGCSWLFQPRGAAASPTFL

LYLSQNKPKAAEGLDTQRFSGKRLGDTFVLTLSDF

RRENEGCYFCSALSNSIMYFSHFVPVFLPAKPTTT

PAPRPPTPAPTIASQPLSLRPEACRPAAGGAVHTR

GLDFACDIYIWAPLAGTCGVLLLSLVITLYCNHRN

RRRVCKCPRPVVKSGDKPSLSARYV.
```

The sequence of human CD8-beta (UniProtKB Q8TD28) is as follows (SEQ ID NO: 54):

```
                                        (SEQ ID NO: 54)
MRPRLWLLLAAQLTVLHGNSVLQQTPAYIKVQTNK

MVMLSCEAKISLSNMRIYWLRQRQAPSSDSHHEFL

ALWDSAKGTIHGEEVEQEKIAVFRDASRFILNLTS

VKPEDSGIYFCMIVGSPELTFGKGTQLSVVDFLPT

TAQPTKKSTLKKRVCRLPRPETQKGPLCSPITLGL

LVAGVLVLLVSLGVAIHLCCRRRRARLRFMKQLYK.
```

In some embodiments, the CD8 that the polypeptide binds to is expressed on the surface of a cell. In some embodiments, the cell is an immune cell. In some embodiments, the immune cell is a CD7+ T cell, CD4+ T cell, CD8+ T cell, NK cell, alpha-beta T cell, gamma-delta T cell, lymphoid progenitor cell, hematopoietic stem cell, myeloid cell, monocyte, macrophage, central memory T cell, effector memory T cell, stem-cell like memory T cells, naïve T cell, activated T cell, regulatory T cell (TReg), terminally differentiated effector memory T cell (TEMRA), resident memory T cell (TRM) or a T-cellCD8+ CCR7+. In some embodiments, the cell is a CD8+ T cell. In some embodiments, the cell is a CD8+ cell.

In some embodiments, the antibody comprises a Fc region. The Fc region can be linked to the heavy or light chain of the antibody. In some embodiments, the Fc region is an IgG Fc. In some embodiments, the IgG is selected from IgG1, IgG2, IgG3, or IgG4. In some embodiments, the IgG Fc is IgG1 Fc. In some embodiments, the antibody comprises an Fc constant region as set forth below.

```
                                        (SEQ ID NO: 34)
ASTKGPSVFPLAPSSKSTSGGTAALGCLVKDYFPE

PVTVSWNSGALTSGVHTFPAVLQSSGLYSLSSVVT

VPSSSLGTQTYICNVNHKPSNTKVDKKVEPKSCDK

THTCPPCPAPELLGGPSVFLFPPKPKDTLMISRTP

EVTCVVVDVSHEDPEVKFNWYVDGVEVHNAKTKPR

EEQYNSTYRVVSVLTVLHQDWLNGKEYKCKVSNKA

LPAPIEKTISKAKGQPREPQVYTLPPSRDELTKNQ

VSLTCLVKGFYPSDIAVEWESNGQPENNYKTTPPV

LDSDGSFFLYSKLTVDKSRWQQGNVFSCSVMHEAL

HNHYTQKSLSLSPGK
```

In some embodiments, the IgG fc is IgG2 Fc. In some embodiments, the antibody comprises an Fc constant region of SEQ ID NO: 71 as set forth below.

```
                                        (SEQ ID NO: 71)
STKGPSVFPLAPCSRSTSESTAALGCLVKDYFPEP

VTVSWNSGALTSGVHTFPAVLQSSGLYSLSSVVTV

PSSSLGTQTYTCNVDHKPSNTKVDKTVERKCCVEC

PPCPAPPVAGPSVFLFPPKPKDTLMISRTPEVTCV

VVDVSHEDPEVQFNWYVDGVEVHNAKTKPREEQFN

STFRVVSVLTVVHQDWLNGKEYKCKVSNKGLPAPI

EKTISKTKGQPREPQVYTLPPSREEMTKNQVSLTC

LVKGFYPSDIAVEWESNGQPENNYKTTPPMLDSDG

SFFLYSKLTVDKSRWQQGNVFSCSVMHEALHNHYT

QKSLSLSPGK
```

In some embodiments, the IgG fc is IgG4 Fc. In some embodiments, the antibody comprises an Fc constant region of SEQ ID NO: 72 as set forth below.

```
                                        (SEQ ID NO: 72)
STKGPSVFPLAPCSRSTSESTAALGCLVKDYFPEP

VTVSWNSGALTSGVHTFPAVLQSSGLYSLSSVVTV

PSSSLGTKTYTCNVDHKPSNTKVDKRVESKYGPPC

PSCPAPEFLGGPSVFLFPPKPKDTLMISRTPEVTC

VVDVSQEDPEVQFNWYVDGVEVHNAKTKPREEQF

NSTYRVVSVLTVLHQDWLNGKEYKCKVSNKGLPSS
```

```
IEKTISKAKGQPREPQVYTLPPSQEEMTKNQVSLT

CLVKGFYPSDIAVEWESNGQPENNYKTTPPVLDSD

GSFFLYSRLTVDKSRWQEGNVFSCSVMHEALHNHY

TQKSLSLSLGK
```

In some embodiments, polypeptides (e.g. CD8-binding polypeptide) are provided herein. In some embodiments, antibodies (e.g. an anti-CD8 antibody) are provided herein. In some embodiments, the antibody is a recombinant antibody that binds to CD8. In some embodiments, the CD8 protein is a human CD8 protein. In some embodiments, the CD8 protein is a non-human CD8 protein (e.g., mouse, rat, pig, dog, non-human primate). As used herein, the term "recombinant antibody" refers to an antibody that is not naturally occurring. In some embodiments, the term "recombinant antibody" refers to an antibody that is not isolated from a human subject.

In some embodiments, an antibody, or antigen binding fragment thereof is provided, wherein the antibody or antibody fragment comprises a peptide selected from the following table, which illustrate the CDRs based on Chothia numbering.

In some embodiments, a polypeptide, an antibody, or antibody binding fragment thereof, comprises a heavy or light chain CDR as provided in the tables above. In some embodiments, a polypeptide, an antibody, or antibody binding fragment thereof, comprises a heavy or light chain CDR as provided in the tables above and binds to non-human primate CD8. In some embodiments, a polypeptide, an antibody, or antibody binding fragment thereof, comprises a heavy or light chain CDR as provided in the tables above and binds to human CD8. In some embodiments, a polypeptide, an antibody, or antibody binding fragment thereof, comprises a light chain CDR having a sequence selected from SEQ ID NO: 58-60. In some embodiments, a polypeptide, an antibody, or antibody binding fragment thereof, comprises a light chain CDR having a sequence of SEQ ID NO: 58. In some embodiments, a polypeptide, an antibody, or antibody binding fragment thereof, comprises a light chain CDR having a sequence of SEQ ID NO: 59. In some embodiments, a polypeptide, an antibody, or antibody binding fragment thereof, comprises a light chain CDR having a sequence of SEQ ID NO: 60. In some embodiments, a polypeptide, an antibody, or antibody binding fragment thereof, comprises a heavy chain CDR having a sequence selected from SEQ ID NO: 55-57. In some embodiments, a polypeptide, an antibody, or antibody binding fragment thereof, comprises a heavy chain CDR having a sequence of SEQ ID NO: 55. In some embodiments, a polypeptide, an antibody, or antibody binding fragment thereof, comprises a heavy chain CDR having a sequence of SEQ ID NO: 56. In some embodiments, a polypeptide, an antibody, or antibody binding fragment thereof, comprises a heavy chain CDR having a sequence of SEQ ID NO: 57. The CDRs referenced in the embodiments throughout the present specification can

| Chothia CDRs | | | | | | |
|---|---|---|---|---|---|---|
| Ab ID No | HCDR1 | HCDR2 | HCDR3 | LCDR1 | LCDR2 | LCDR3 |
| CD8AB1 | RYTFTDY (SEQ ID NO: 55) | YPYNGG (SEQ ID NO: 56) | DHRYNEGVS FDY (SEQ ID NO: 57) | RASESVDG FGNSFMN (SEQ ID NO: 58) | LASNLES (SEQ ID NO: 59) | QQNNEDPYT (SEQ ID NO: 60) |

In some embodiments, an antibody, or antigen binding fragment thereof is provided, wherein the antibody or antibody fragment comprises a peptide selected from the following table which illustrate the CDRs based on Kabat numbering.

| Kabat CDRs | | | | | | |
|---|---|---|---|---|---|---|
| Ab ID No | HCDR1 | HCDR2 | HCDR3 | LCDR1 | LCDR2 | LCDR3 |
| CD8AB1 | DYNLH (SEQ ID NO: 61) | FIYPYNGGT GYNQKFKN (SEQ ID NO: 62) | DHRYNEGVSF DY (SEQ ID NO: 57) | RASESVDG FGNSFMN (SEQ ID NO: 58) | LASNLES (SEQ ID NO: 59) | QQNNEDPYT (SEQ ID NO: 60) |

In some embodiments, an antibody, or antigen binding fragment thereof is provided, wherein the antibody or antibody fragment comprises a peptide selected from the following table, which illustrate the CDRs based on IMGT numbering.

| IMGT CDRs | | | | | | |
|---|---|---|---|---|---|---|
| Ab ID No | HCDR1 | HCDR2 | HCDR3 | LCDR1 | LCDR2 | LCDR3 |
| CD8AB1 | RYTFTD YN (SEQ ID NO: 63) | TYPYNGGT (SEQ ID NO: 64) | ARDHRYNEGV SFDY (SEQ ID NO: 65) | ESVDGFGN SF (SEQ ID NO: 66) | LA | QQNNEDPYT (SEQ ID NO: 60) | be interchanged with the CDRs that are characterized by different formats, such as Kabat and IMGT.

In some embodiments, a polypeptide, an antibody, or antibody binding fragment thereof, comprises a light chain variable region having a LCDR1, a LCDR2, and a LCDR3, wherein the LCDR1 has a sequence of SEQ ID NO: 58, the LCDR2 has a sequence of SEQ ID NO: 59, and the LCDR3 has a sequence of SEQ ID NO: 60.

In some embodiments, a polypeptide, an antibody, or antibody binding fragment thereof, comprises a light chain variable region having a LCDR1, a LCDR2, and a LCDR3, wherein the LCDR1 has a sequence of SEQ ID NO: 66, the LCDR2 has a sequence of LA, and the LCDR3 has a sequence of SEQ ID NO: 60.

In some embodiments, a polypeptide, an antibody, or antibody binding fragment thereof, comprises a heavy chain variable region having a HCDR1, a HCDR2, and a HCDR3, wherein the HCDR1 has a sequence of SEQ ID NO: 55, the HCDR2 has a sequence of SEQ ID NO: 56, and the HCDR3 has a sequence of SEQ ID NO: 57.

In some embodiments, a polypeptide, an antibody, or antibody binding fragment thereof, comprises a heavy chain variable region having a HCDR1, a HCDR2, and a HCDR3, wherein the HCDR1 has a sequence of SEQ ID NO: 61, the HCDR2 has a sequence of SEQ ID NO: 62, and the HCDR3 has a sequence of SEQ ID NO: 57.

In some embodiments, a polypeptide, an antibody, or antibody binding fragment thereof, comprises a heavy chain variable region having a HCDR1, a HCDR2, and a HCDR3, wherein the HCDR1 has a sequence of SEQ ID NO: 63, the HCDR2 has a sequence of SEQ ID NO: 64, and the HCDR3 has a sequence of SEQ ID NO: 65.

In some embodiments, a polypeptide, an antibody or antibody binding fragment thereof, comprises: (i) a light chain having any one of the foregoing recited combinations of LCDR1, LCDR2, and LCDR3 sequences; and (ii) a heavy chain having any one of the foregoing recited combinations of HCDR1, HCDR2, and HCDR3 sequences.

The different CDR motifs can be combined in any combination including those not depicted in the table above. For example, the following embodiments are provided as non-limiting examples of such combinations.

In some embodiments, a polypeptide, an antibody, or antigen binding fragment thereof, comprises: (i) a light chain variable region comprising light chain CDR1, CDR2, and CDR3 sequences, wherein the light chain CDR1 sequence has the amino acid sequence of SEQ ID NO: 58; the light chain CDR2 has the amino acid sequence of SEQ ID NO: 59; and the light chain CDR3 sequence has the amino acid sequence of SEQ ID NO: 60; and (ii) a heavy chain variable region comprising heavy chain CDR1, CDR2, and CDR3 sequences, wherein the heavy chain CDR1 sequence has the amino acid sequence of SEQ ID NO: 55; the heavy chain CDR2 sequence has the amino acid sequence of SEQ ID NO: 56; and the heavy chain CDR3 sequence has the amino acid sequence of SEQ ID NO: 57; or variants of any of the foregoing.

In some embodiments, a polypeptide, an antibody, or antigen binding fragment thereof, comprises: (i) a light chain variable region comprising light chain CDR1, CDR2, and CDR3 sequences, wherein the light chain CDR1 sequence has the amino acid sequence of SEQ ID NO: 58; the light chain CDR2 has the amino acid sequence of SEQ ID NO: 59; and the light chain CDR3 sequence has the amino acid sequence of SEQ ID NO: 60; and (ii) a heavy chain variable region comprising heavy chain CDR1, CDR2, and CDR3 sequences, wherein the heavy chain CDR1 sequence has the amino acid sequence of SEQ ID NO: 61; the heavy chain CDR2 sequence has the amino acid sequence of SEQ ID NO: 62; and the heavy chain CDR3 sequence has the amino acid sequence of SEQ ID NO: 57; or variants of any of the foregoing.

In some embodiments, a polypeptide, an antibody, or antigen binding fragment thereof, comprises: (i) a light chain variable region comprising light chain CDR1, CDR2, and CDR3 sequences, wherein the light chain CDR1 sequence has the amino acid sequence of SEQ ID NO: 66; the light chain CDR2 has the amino acid sequence of LA; and the light chain CDR3 sequence has the amino acid sequence of SEQ ID NO: 60; and (ii) a heavy chain variable region comprising heavy chain CDR1, CDR2, and CDR3 sequences, wherein the heavy chain CDR1 sequence has the amino acid sequence of SEQ ID NO: 63; the heavy chain CDR2 sequence has the amino acid sequence of SEQ ID NO: 64; and the heavy chain CDR3 sequence has the amino acid sequence of SEQ ID NO: 65; or variants of any of the foregoing.

In some embodiments, the light chain variable region CDR1 is replaced with any of the other light chain CDR1 sequences. In some embodiments, the light chain variable region CDR2 is replaced with any of the other light chain CDR2 sequences. In some embodiments, the light chain variable region CDR3 is replaced with any of the other light chain CDR3 sequences. In some embodiments, the heavy chain variable region CDR1 is replaced with any of the other heavy chain CDR1 sequences. In some embodiments, the heavy chain variable region CDR2 is replaced with any of the other heavy chain CDR2 sequences. In some embodiments, the heavy chain variable region CDR3 is replaced with any of the other heavy chain CDR3 sequences.

In some embodiments, the polypeptide comprises a heavy chain variable region peptide having one of the following sequences, or a variant thereof:

| SEQ ID NO: | AB ID NO. | Sequence |
|---|---|---|
| 67 | CD8AB1 | EVQLQQSGPELVKPGASVKISCKASRYTFTDYN LHWVKLSHEKSLEWIGFIYPYNGGTGYNQKFKN KAKLTVDYSSSTAYMELRSLTSVDAAVYYCARD HRYNEGVSFDYWGQGTTLTVSS |

In some embodiments, the polypeptide comprises a light chain variable region peptide having one of the following sequences, or a variant thereof:

| SEQ ID NO: | AB ID NO. | Sequence |
|---|---|---|
| 68 | CD8AB1 | NIVLTQSPASLAVSLGQRATISCRASESVDGFG NSFMNWYQQKPGQSPKLLIYLASNLESGVPARF SGSGSRTDFTLTIDPVEADDAATYYCQQNNEDP YTFGGGTKLEIKR |

In some embodiments, a polypeptide, an antibody, or antigen binding fragment thereof, comprises a $V_H$ peptide of SEQ ID NO: 67. In some embodiments, a polypeptide, an antibody, or antigen binding fragment thereof, comprises a $V_L$ peptide of SEQ ID NO: 68. In some embodiments, a polypeptide, an antibody, or antigen binding fragment thereof, comprises a $V_H$ peptide and a $V_L$ peptide, wherein the wherein the $V_H$ peptide comprises a sequence of SEQ ID NO: 67, or a variant thereof, and the $V_L$ peptide comprises a sequence of SEQ ID NO: 68, or a variant thereof. In some embodiments, a polypeptide, an antibody, or antigen binding fragment thereof, comprises a $V_H$ peptide and a $V_L$ peptide, wherein the wherein the $V_H$ peptide comprises a sequence of SEQ ID NO: 67, or a variant thereof, and the $V_L$ peptide comprises a sequence of SEQ ID NO: 68, or a variant thereof, and the polypeptide, the antibody, or antigen binding fragment thereof, binds to non-human primate CD8. In some embodiments, a polypeptide, an antibody, or antigen binding fragment thereof, comprises a $V_H$ peptide and a $V_L$ peptide, wherein the wherein the $V_H$ peptide comprises a sequence of SEQ ID NO: 67, or a variant thereof, and the $V_L$ peptide comprises a sequence of SEQ ID NO: 68, or a variant thereof, and the polypeptide, the antibody, or antigen binding fragment thereof, binds to human CD8. In some embodiments, the $V_H$ peptide comprises a sequence of SEQ ID NO: 67; and the $V_L$ peptide comprises a sequence of SEQ ID NO: 68.

The VH and the VL sequences can be in any format, including, but not limited to an scFv format where the VH and VL regions are linked with a peptide linker. Examples of peptide linkers that can be used to link various peptides provided for herein include, but are not limited to: (GGGGS)$_n$ (SEQ ID NO: 49), wherein each n is independently 1-5. In some embodiments, n is 1. In some embodiments, n is 2. In some embodiments, n is 3. In some embodiments, n is 4. In some embodiments, n is 5. In some embodiments, the variable regions are not linked with a peptide linker. In some embodiments, the polypeptide comprises SEQ ID NO: 67 and SEQ ID NO: 68.

In some embodiments, the VH and VL polypeptides are linked to a Fc region. In some embodiments, the Fc region is as provided for herein. As provided for herein, the heavy chain can be linked to a Fc region. Non-limiting mutations in the Fc region are provided for herein. In some embodiments, the Fc region further comprises a transmembrane domain. Examples of transmembrane domains include, but are not limited to, a CD8/CD28 transmembrane domain. In some embodiments, the Fc region further comprises a CD8 or CD28 ("CD8/CD28") transmembrane domain. In some embodiments, the Fc region further comprises a CD8 transmembrane domain. In some embodiments, the Fc region further comprises a CD28 transmembrane domain. In some embodiments, the Fc region comprising a transmembrane domain further comprises an Env incorporation motif. In some embodiments, the Fc region comprising a CD8/CD28 transmembrane domain further comprises an Env incorporation motif. In some embodiments, the VH and VL polypeptides provided herein are linked to an Fc region comprising a transmembrane domain. In some embodiments, the VH and VL polypeptides provided herein are linked to an Fc region comprising a CD8/CD28 transmembrane domain. In some embodiments, the VH and VL polypeptides provided herein are linked to an Fc region comprising a CD8/CD28 transmembrane domain and an Env incorporation motif. In some embodiments, the VH and VL polypeptides provided herein linked to an Fc region comprising a CD8/CD28 transmembrane domain are anchored to the plasma membrane on the surface of a cell. In some embodiments, the cell is an immune cell, such as those provided herein. In some embodiments, the VH having a sequence as set forth in SEQ ID NO: 67 and VL having a sequence as set forth in SEQ ID NO: 68 are linked to an Fc region comprising a transmembrane domain. In some embodiments, the VH having a sequence as set forth in SEQ ID NO: 67 and VL having a sequence as set forth in SEQ ID NO: 68 are linked to an Fc region comprising a CD8/CD28 transmembrane domain. In some embodiments, the VH having a sequence as set forth in SEQ ID NO: 67 and VL having a sequence as set forth in SEQ ID NO: 68 are linked to an Fc region comprising a CD8/CD28 transmembrane domain and an Env incorporation motif. In some embodiments, the VH having a sequence as set forth in SEQ ID NO: 67 and VL having a sequence as set forth in SEQ ID NO: 68 linked to an Fc region comprising a CD8/CD28 transmembrane domain are anchored to the plasma membrane on the surface of a cell. In some embodiments, the cell is an immune cell, such as those provided herein.

In some embodiments, the $V_H$ peptide comprising a sequence that is at least 85%, 86%, 87%, 88%, 89%, 90%, 91%, 92%, 93%, 94%, 95%, 96%, 97%, 98%, or 99% identical to a sequence of SEQ ID NO: 67; and the $V_L$ peptide comprising a sequence that is at least 85%, 86%, 87%, 88%, 89%, 90%, 91%, 92%, 93%, 94%, 95%, 96%, 97%, 98%, or 99% identical to a sequence of SEQ ID NO: 68 are linked to an Fc region comprising a transmembrane domain. In some embodiments, the $V_H$ peptide comprising a sequence that is at least 85%, 86%, 87%, 88%, 89%, 90%, 91%, 92%, 93%, 94%, 95%, 96%, 97%, 98%, or 99% identical to a sequence of SEQ ID NO: 67; and the $V_L$ peptide comprising a sequence that is at least 85%, 86%, 87%, 88%, 89%, 90%, 91%, 92%, 93%, 94%, 95%, 96%, 97%, 98%, or 99% identical to a sequence of SEQ ID NO: 68 are linked to an Fc region comprising a CD8/CD28 transmembrane domain. In some embodiments, the $V_H$ peptide comprising a sequence that is at least 85%, 86%, 87%, 88%, 89%, 90%, 91%, 92%, 93%, 94%, 95%, 96%, 97%, 98%, or 99% identical to a sequence of SEQ ID NO: 67; and the $V_L$ peptide comprising a sequence that is at least 85%, 86%, 87%, 88%, 89%, 90%, 91%, 92%, 93%, 94%, 95%, 96%, 97%, 98%, or 99% identical to a sequence of SEQ ID NO: 68 are linked to an Fc region comprising a CD8/CD28 transmembrane domain and an Env incorporation motif. In some embodiments, the $V_H$ peptide comprising a sequence that is at least 85%, 86%, 87%, 88%, 89%, 90%, 91%, 92%, 93%, 94%, 95%, 96%, 97%, 98%, or 99% identical to a sequence of SEQ ID NO: 67; and the $V_L$ peptide comprising a sequence that is at least 85%, 86%, 87%, 88%, 89%, 90%, 91%, 92%, 93%, 94%, 95%, 96%, 97%, 98%, or 99% identical to a sequence of SEQ ID NO: 68 linked to an Fc region comprising a CD8/CD28 transmembrane domain are anchored to the plasma membrane on the surface of a cell. In some embodiments, the cell is an immune cell, such as those provided herein.

In some embodiments, a polypeptide comprises a $V_H$ peptide and a $V_L$ peptide, wherein the $V_H$ peptide comprises a sequence that is at least 85%, 86%, 87%, 88%, 89%, 90%, 91%, 92%, 93%, 94%, 95%, 96%, 97%, 98%, or 99% identical to a sequence of SEQ ID NO: 67; and the $V_L$ peptide comprises a sequence that is at least 85%, 86%, 87%, 88%, 89%, 90%, 91%, 92%, 93%, 94%, 95%, 96%, 97%, 98%, or 99% identical to a sequence of SEQ ID NO: 68.

In some embodiments, a polypeptide comprises a $V_H$ peptide and a $V_L$ peptide, wherein the $V_H$ peptide comprises a sequence that is at least 85%, 86%, 87%, 88%, 89%, 90%, 91%, 92%, 93%, 94%, 95%, 96%, 97%, 98%, or 99% identical to a sequence of SEQ ID NO: 67; and the $V_L$ peptide comprises a sequence that is at least 85%, 86%, 87%, 88%, 89%, 90%, 91%, 92%, 93%, 94%, 95%, 96%, 97%, 98%, or 99% identical to a sequence of SEQ ID NO: 68; provided that the $V_H$ peptide and a $V_L$ peptide comprises a light chain CDR having a sequence of SEQ ID NO: 58-60; and/or a heavy chain CDR having a sequence of SEQ ID NO: 55-57. In some embodiments, a polypeptide comprises a $V_H$ peptide and a $V_L$ peptide, wherein the $V_H$ peptide comprises a sequence that is at least 85%, 86%, 87%, 88%, 89%, 90%, 91%, 92%, 93%, 94%, 95%, 96%, 97%, 98%, or 99% identical to a sequence of SEQ ID NO: 67; and the $V_L$ peptide comprises a sequence that is at least 85%, 86%, 87%, 88%, 89%, 90%, 91%, 92%, 93%, 94%, 95%, 96%, 97%, 98%, or 99% identical to a sequence of SEQ ID NO: 68; provided that the $V_H$ peptide and a $V_L$ peptide comprise a light chain CDR1 having a sequence of SEQ ID NO: 58; a light chain CDR2 having a sequence of SEQ ID NO: 59; a light chain CDR3 having a sequence of SEQ ID NO: 60; and/or a heavy chain CDR1 having a sequence of SEQ ID NO: 55; a heavy chain CDR2 having a sequence of SEQ ID NO: 56; and a heavy chain CDR3 having a sequence of SEQ ID NO: 57. In some embodiments, the CDRs in the $V_H$ or $V_L$ chain are as set forth in the combinations provided for herein.

In some embodiments, a polypeptide comprises a $V_H$ peptide and a $V_L$ peptide, wherein the $V_H$ peptide comprises a sequence that is at least 85%, 86%, 87%, 88%, 89%, 90%, 91%, 92%, 93%, 94%, 95%, 96%, 97%, 98%, or 99% identical to a sequence of SEQ ID NO: 67; and the $V_L$ peptide comprises a sequence that is at least 85%, 86%, 87%, 88%, 89%, 90%, 91%, 92%, 93%, 94%, 95%, 96%, 97%, 98%, or 99% identical to a sequence of SEQ ID NO: 68; provided that the $V_L$ peptide comprises a LCDR1 having a sequence of SEQ ID NO: 58; a LCDR2 having a sequence of SEQ ID NO: 59; and a LCDR3 having a sequence of SEQ ID NO: 60; and the $V_H$ peptide comprises a HCDR1 having a sequence of SEQ ID NO: 55; a HCDR2 having a sequence of SEQ ID NO: 56; and a HCDR3 having a sequence of SEQ ID NO: 57.

In some embodiments, a polypeptide comprises a $V_H$ peptide and a $V_L$ peptide, wherein the $V_H$ peptide comprises a sequence that is at least 85%, 86%, 87%, 88%, 89%, 90%, 91%, 92%, 93%, 94%, 95%, 96%, 97%, 98%, or 99% identical to a sequence of SEQ ID NO: 67; and the $V_L$ peptide comprises a sequence that is at least 85%, 86%, 87%, 88%, 89%, 90%, 91%, 92%, 93%, 94%, 95%, 96%, 97%, 98%, or 99% identical to a sequence of SEQ ID NO: 68; provided that the $V_L$ peptide comprises a LCDR1 having a sequence of SEQ ID NO: 58, wherein the LCDR1 comprises at most 1 conservative amino acid substitution, a LCDR2 having a sequence of SEQ ID NO: 59, wherein the LCDR2 comprises at most 1 conservative amino acid substitution, and a LCDR3 having a sequence of SEQ ID NO: 60, wherein the LCDR3 comprises at most 1 conservative amino acid substitution; and the $V_H$ peptide comprises a HCDR1 having a sequence of SEQ ID NO: 55, wherein the HCDR1 comprises at most 1 conservative amino acid substitution, a HCDR2 having a sequence of SEQ ID NO: 56, wherein the HCDR2 comprises at most 1 conservative amino acid substitution, and a HCDR3 having a sequence of SEQ ID NO: 57, wherein the HCDR3 comprises at most 1 conservative amino acid substitution.

In some embodiments, a polypeptide comprises a $V_H$ peptide and a $V_L$ peptide, wherein the $V_H$ peptide comprises a sequence that is at least 85%, 86%, 87%, 88%, 89%, 90%, 91%, 92%, 93%, 94%, 95%, 96%, 97%, 98%, or 99% identical to a sequence of SEQ ID NO: 67; and the $V_L$ peptide comprises a sequence that is at least 85%, 86%, 87%, 88%, 89%, 90%, 91%, 92%, 93%, 94%, 95%, 96%, 97%, 98%, or 99% identical to a sequence of SEQ ID NO: 68; provided that the $V_H$ peptide and a $V_L$ peptide comprise a light chain CDR1 having a sequence of SEQ ID NO: 58; a light chain CDR2 having a sequence of SEQ ID NO: 59; a light chain CDR3 having a sequence of SEQ ID NO: 60; and/or a heavy chain CDR1 having a sequence of SEQ ID NO: 61; a heavy chain CDR2 having a sequence of SEQ ID NO: 62; and a heavy chain CDR3 having a sequence of SEQ ID NO: 57. In some embodiments, the CDRs in the $V_H$ or $V_L$ chain are as set forth in the combinations provided for herein.

In some embodiments, a polypeptide comprises a $V_H$ peptide and a $V_L$ peptide, wherein the $V_H$ peptide comprises a sequence that is at least 85%, 86%, 87%, 88%, 89%, 90%, 91%, 92%, 93%, 94%, 95%, 96%, 97%, 98%, or 99% identical to a sequence of SEQ ID NO: 67; and the $V_L$ peptide comprises a sequence that is at least 85%, 86%, 87%, 88%, 89%, 90%, 91%, 92%, 93%, 94%, 95%, 96%, 97%, 98%, or 99% identical to a sequence of SEQ ID NO: 68; provided that the $V_L$ peptide comprises a LCDR1 having a sequence of SEQ ID NO: 58; a LCDR2 having a sequence of SEQ ID NO: 59; and a LCDR3 having a sequence of SEQ ID NO: 60; and the $V_H$ peptide comprises a HCDR1 having a sequence of SEQ ID NO: 61; a HCDR2 having a sequence of SEQ ID NO: 62; and a HCDR3 having a sequence of SEQ ID NO: 57.

In some embodiments, a polypeptide comprises a $V_H$ peptide and a $V_L$ peptide, wherein the $V_H$ peptide comprises a sequence that is at least 85%, 86%, 87%, 88%, 89%, 90%, 91%, 92%, 93%, 94%, 95%, 96%, 97%, 98%, or 99% identical to a sequence of SEQ ID NO: 67; and the $V_L$ peptide comprises a sequence that is at least 85%, 86%, 87%, 88%, 89%, 90%, 91%, 92%, 93%, 94%, 95%, 96%, 97%, 98%, or 99% identical to a sequence of SEQ ID NO: 68; provided that the $V_L$ peptide comprises a LCDR1 having a sequence of SEQ ID NO: 58, wherein the LCDR1 comprises at most 1 conservative amino acid substitution, a LCDR2 having a sequence of SEQ ID NO: 59, wherein the LCDR2 comprises at most 1 conservative amino acid substitution, and a LCDR3 having a sequence of SEQ ID NO: 60, wherein the LCDR3 comprises at most 1 conservative amino acid substitution; and the $V_H$ peptide comprises a HCDR1 having a sequence of SEQ ID NO: 61, wherein the HCDR1 comprises at most 1 conservative amino acid substitution, a HCDR2 having a sequence of SEQ ID NO: 62, wherein the HCDR2 comprises at most 1 conservative amino acid substitution, and a HCDR3 having a sequence of SEQ ID NO: 57, wherein the HCDR3 comprises at most 1 conservative amino acid substitution.

In some embodiments, a polypeptide comprises a $V_H$ peptide and a $V_L$ peptide, wherein the $V_H$ peptide comprises a sequence that is at least 85%, 86%, 87%, 88%, 89%, 90%, 91%, 92%, 93%, 94%, 95%, 96%, 97%, 98%, or 99% identical to a sequence of SEQ ID NO: 67; and the $V_L$ peptide comprises a sequence that is at least 85%, 86%, 87%, 88%, 89%, 90%, 91%, 92%, 93%, 94%, 95%, 96%, 97%, 98%, or 99% identical to a sequence of SEQ ID NO: 68; provided that the $V_H$ peptide and a $V_L$ peptide comprise a light chain CDR1 having a sequence of SEQ ID NO: 66; a light chain CDR2 having a sequence of LA; a light chain CDR3 having a sequence of SEQ ID NO: 60; and/or a heavy chain CDR1 having a sequence of SEQ ID NO: 63; a heavy chain CDR2 having a sequence of SEQ ID NO: 64; and a heavy chain CDR3 having a sequence of SEQ ID NO: 65. In some embodiments, the CDRs in the $V_H$ or $V_L$ chain are as set forth in the combinations provided for herein.

In some embodiments, a polypeptide comprises a $V_H$ peptide and a $V_L$ peptide, wherein the $V_H$ peptide comprises a sequence that is at least 85%, 86%, 87%, 88%, 89%, 90%, 91%, 92%, 93%, 94%, 95%, 96%, 97%, 98%, or 99% identical to a sequence of SEQ ID NO: 67; and the $V_L$ peptide comprises a sequence that is at least 85%, 86%, 87%, 88%, 89%, 90%, 91%, 92%, 93%, 94%, 95%, 96%, 97%, 98%, or 99% identical to a sequence of SEQ ID NO: 68; provided that the $V_L$ peptide comprises a LCDR1 having a sequence of SEQ ID NO: 66; a LCDR2 having a sequence of LA; and a LCDR3 having a sequence of SEQ ID NO: 60; and the $V_H$ peptide comprises a HCDR1 having a sequence of SEQ ID NO: 63; a HCDR2 having a sequence of SEQ ID NO: 64; and a HCDR3 having a sequence of SEQ ID NO: 65.

In some embodiments, a polypeptide comprises a $V_H$ peptide and a $V_L$ peptide, wherein the $V_H$ peptide comprises a sequence that is at least 85%, 86%, 87%, 88%, 89%, 90%, 91%, 92%, 93%, 94%, 95%, 96%, 97%, 98%, or 99% identical to a sequence of SEQ ID NO: 67; and the $V_L$ peptide comprises a sequence that is at least 85%, 86%, 87%, 88%, 89%, 90%, 91%, 92%, 93%, 94%, 95%, 96%, 97%, 98%, or 99% identical to a sequence of SEQ ID NO: 68; provided that the $V_L$ peptide comprises a LCDR1 having a sequence of SEQ ID NO: 66, wherein the LCDR1 comprises at most 1 conservative amino acid substitution, a LCDR2 having a sequence of LA, wherein the LCDR2 comprises at most 1 conservative amino acid substitution, and a LCDR3 having a sequence of SEQ ID NO: 60, wherein the LCDR3 comprises at most 1 conservative amino acid substitution; and the $V_H$ peptide comprises a HCDR1 having a sequence of SEQ ID NO: 63, wherein the HCDR1 comprises at most 1 conservative amino acid substitution, a HCDR2 having a sequence of SEQ ID NO: 64, wherein the HCDR2 comprises at most 1 conservative amino acid substitution, and a HCDR3 having a sequence of SEQ ID NO: 65, wherein the HCDR3 comprises at most 1 conservative amino acid substitution.

In some embodiments, a polypeptide comprises a $V_H$ peptide and a $V_L$ peptide, wherein the $V_H$ peptide comprises a sequence of SEQ ID NO: 67 and the $V_L$ peptide comprises a sequence of SEQ ID NO: 68.

In some embodiments, a polypeptide as provided herein binds to non-human primate CD8. In some embodiments, a polypeptide as provided herein binds to human CD8.

As provided for herein, the different polypeptides ($V_H$ or $V_L$) described herein can be linked with a peptide linker or not linked with a peptide linker and instead for a continuous sequence. In some embodiments, the peptide linker comprises a sequence of (GGGGS)$_n$ (SEQ ID NO: 49), wherein each n is independently 1-5. In some embodiments, n is 1. In some embodiments, n is 2. In some embodiments, n is 3. In some embodiments, n is 4. In some embodiments, n is 5. The linked peptide format can be represented by a formula of $V_H$-Z-$V_L$ or $V_L$-Z-$V_H$, wherein Z is the peptide linker. In some embodiments, Z is (GGGGS)$_n$ (SEQ ID NO: 49), wherein each n is independently 1-5.

In some embodiments, a polypeptide comprising the linked peptide represented by a formula of $V_L$-Z-$V_H$ comprises a heavy chain variable region as set forth in SEQ ID NO: 67 linked via a linker sequence GGGGSGGGGSGGGGSGGGGS (SEQ ID NO: 50) to a light chain variable region as set forth in SEQ ID NO: 68. In some embodiments, a polypeptide comprising a $V_L$ linked via a peptide linker to a $V_H$ has the sequence as set forth below,

```
                                        (SEQ ID NO: 69)
NIVLTQSPASLAVSLGQRATISCRASESVDGFGNSFMNWYQQKPGQSPK

LLIYLASNLESGVPARFSGSGSRTDFTLTIDPVEADDAATYYCQQNNED

PYTFGGGTKLEIKRGGGGSGGGGSGGGGSGGGGSEVQLQQSGPELVKPG

ASVKISCKASRYTFTDYNLHWVKLSHEKSLEWIGFIYPYNGGTGYNQKF

KNKAKLTVDYSSSTAYMELRSLTSVDAAVYYCARDHRYNEGVSFDYWGQ

GTTLTVSS.
```

In some embodiments, a polypeptide comprises a sequence that is at least 85%, 86%, 87%, 88%, 89%, 90%, 91%, 92%, 93%, 94%, 95%, 96%, 97%, 98%, or 99% identical to a sequence of SEQ ID NO: 69. In some embodiments, a polypeptide comprises a sequence that is at least 90% identical to a sequence of SEQ ID NO: 69. In some embodiments, a polypeptide comprises a sequence that is at least 95% identical to a sequence of SEQ ID NO: 69. In some embodiments, a polypeptide comprises a sequence that is at least 99% identical to a sequence of SEQ ID NO: 69. In some embodiments, a polypeptide comprises a sequence as set forth in SEQ ID NO: 69. In some embodiments, the polypeptide as set forth in SEQ ID NO: 69 is an antibody, or an antigen binding fragment thereof. In some embodiments, the antibody is an anti-CD8 antibody.

In some embodiments, a polypeptide comprising the linked peptide represented by a formula of $V_H$-Z-$V_L$ comprises a light chain variable region as set forth in SEQ ID NO: 68 linked via a linker sequence GGGGSGGGGSGGGGSGGGGS (SEQ ID NO: 50) to a heavy chain variable region as set forth in SEQ ID NO: 67. In some embodiments, a polypeptide comprising a $V_H$ linked via a peptide linker to a $V_L$ has the sequence as set forth below,

```
                                        (SEQ ID NO: 70)
EVQLQQSGPELVKPGASVKISCKASRYTFTDYNLHWVKLSHEKSLEWIG

FIYPYNGGTGYNQKFKNKAKLTVDYSSSTAYMELRSLTSVDAAVYYCAR

DHRYNEGVSFDYWGQGTTLTVSSGGGGSGGGGSGGGGSGGGGSNIVLTQ

SPASLAVSLGQRATISCRASESVDGFGNSFMNWYQQKPGQSPKLLIYLA

SNLESGVPARFSGSGSRTDFTLTIDPVEADDAATYYCQQNNEDPYTFGG

GTKLEIKR.
```

In some embodiments, a polypeptide comprises a sequence that is at least 85%, 86%, 87%, 88%, 89%, 90%, 91%, 92%, 93%, 94%, 95%, 96%, 97%, 98%, or 99% identical to a sequence of SEQ ID NO: 70. In some embodiments, a polypeptide comprises a sequence that is at least 90% identical to a sequence of SEQ ID NO: 70. In some embodiments, a polypeptide comprises a sequence that is at least 95% identical to a sequence of SEQ ID NO: 70. In some embodiments, a polypeptide comprises a sequence that is at least 99% identical to a sequence of SEQ ID NO: 70. In some embodiments, a polypeptide comprises a sequence as set forth in SEQ ID NO: 70. In some embodiments, the polypeptide as set forth in SEQ ID NO: 70 is an antibody, or an antigen binding fragment thereof. In some embodiments, the antibody is an anti-CD8 antibody. In some embodiments, the anti-CD8 antibody binds to non-human primate CD8. In some embodiments, the anti-CD8 antibody binds to human CD8.

In some embodiments, a polypeptide comprises a sequence that is at least 85%, 86%, 87%, 88%, 89%, 90%, 91%, 92%, 93%, 94%, 95%, 96%, 97%, 98%, or 99% identical to a sequence of SEQ ID NO: 69 and comprises an Fc region, such as those provided herein. In some embodiments, a polypeptide comprises a sequence that is at least 85%, 86%, 87%, 88%, 89%, 90%, 91%, 92%, 93%, 94%, 95%, 96%, 97%, 98%, or 99% identical to a sequence of SEQ ID NO: 69 and comprises an Fc region, such as those provided herein, and a transmembrane domain, such as those provided herein. In some embodiments, a polypeptide comprises a sequence that is at least 85%, 86%, 87%, 88%, 89%, 90%, 91%, 92%, 93%, 94%, 95%, 96%, 97%, 98%, or 99% identical to a sequence of SEQ ID NO: 69 and comprises an Fc region, such as those provided herein, and a CD8/CD28 transmembrane domain. In some embodiments, a polypeptide comprises a sequence that is at least 85%, 86%, 87%, 88%, 89%, 90%, 91%, 92%, 93%, 94%, 95%, 96%, 97%, 98%, or 99% identical to a sequence of SEQ ID NO: 69 and comprises an Fc region, such as those provided herein, a transmembrane domain, such as those provided herein, and an Env incorporation motif.

In some embodiments, a polypeptide comprises a sequence that is at least 85%, 86%, 87%, 88%, 89%, 90%, 91%, 92%, 93%, 94%, 95%, 96%, 97%, 98%, or 99% identical to a sequence of SEQ ID NO: 70 and comprises an Fc region, such as those provided herein. In some embodiments, a polypeptide comprises a sequence that is at least 85%, 86%, 87%, 88%, 89%, 90%, 91%, 92%, 93%, 94%, 95%, 96%, 97%, 98%, or 99% identical to a sequence of SEQ ID NO: 70 and comprises an Fc region, such as those provided herein, and a transmembrane domain, such as those provided herein. In some embodiments, a polypeptide comprises a sequence that is at least 85%, 86%, 87%, 88%, 89%, 90%, 91%, 92%, 93%, 94%, 95%, 96%, 97%, 98%, or 99% identical to a sequence of SEQ ID NO: 70 and comprises an Fc region, such as those provided herein, and a CD8/CD28 transmembrane domain. In some embodiments, a polypeptide comprises a sequence that is at least 85%, 86%, 87%, 88%, 89%, 90%, 91%, 92%, 93%, 94%, 95%, 96%, 97%, 98%, or 99% identical to a sequence of SEQ ID NO: 70 and comprises an Fc region, such as those provided herein, a transmembrane domain, such as those provided herein, and an Env incorporation motif.

As provided for herein, the polypeptide, antibodies, or antigen binding fragments thereof can be variants of the sequences.

The sequences of the polypeptides or antibodies can be modified to yield human IgG antibodies. The conversion of the sequences provided herein can be modified to yield other types of antibodies. The CDRs can also be linked to other antibodies, proteins, or molecules to create antibody fragments that bind CD8.

In some embodiments, a polypeptide or an antibody as provided herein is a targeting moiety on the surface of an engineered viral particle. In some embodiments, the targeting moiety allows for binding to a target cell. In some embodiments, the targeting moiety is a CD8 binding moiety, such as a polypeptide or an antibody as provided herein. In some embodiments, the targeting moiety comprises a sequence that is at least 85%, 86%, 87%, 88%, 89%, 90%, 91%, 92%, 93%, 94%, 95%, 96%, 97%, 98%, or 99% identical to a sequence of SEQ ID NO: 69. In some embodiments, the targeting moiety comprises a sequence that is at least 90% identical to a sequence of SEQ ID NO: 69. In some embodiments, the targeting moiety comprises a sequence that is at least 95% identical to a sequence of SEQ ID NO: 69. In some embodiments, the targeting moiety comprises a sequence that is at least 99% identical to a sequence of SEQ ID NO: 69. In some embodiments, the targeting moiety comprises a sequence as set forth in SEQ ID NO: 69. In some embodiments, the targeting moiety as set forth in SEQ ID NO: 69 is an antibody, or an antigen binding fragment thereof. In some embodiments, the targeting moiety is an anti-CD8 antibody.

In some embodiments, a polypeptide or an antibody as provided for herein is a targeting moiety on the surface of an engineered viral particle. In some embodiments, the engineered viral particle is a pseudotyped viral-like particle. In some embodiments, the targeting moiety allows for binding to a target cell. In some embodiments, the targeting moiety is a CD8 binding moiety, such as a polypeptide or an antibody as provided herein. In some embodiments, the targeting moiety comprises a sequence that is at least 85%, 86%, 87%, 88%, 89%, 90%, 91%, 92%, 93%, 94%, 95%, 96%, 97%, 98%, or 99% identical to a sequence of SEQ ID NO: 70. In some embodiments, the targeting moiety comprises a sequence that is at least 90% identical to a sequence of SEQ ID NO: 70. In some embodiments, the targeting moiety comprises a sequence that is at least 95% identical to a sequence of SEQ ID NO: 70. In some embodiments, the targeting moiety comprises a sequence that is at least 99% identical to a sequence of SEQ ID NO: 70. In some embodiments, the targeting moiety comprises a sequence as set forth in SEQ ID NO: 70. In some embodiments, the targeting moiety as set forth in SEQ ID NO: 70 is an antibody, or an antigen binding fragment thereof. In some embodiments, the targeting moiety is an anti-CD8 antibody. In some embodiments, the anti-CD8 antibody binds to non-human primate CD8. In some embodiments, the anti-CD8 antibody binds to human CD8.

In some embodiments, a polypeptide comprises a sequence having a sequence as set forth in SEQ ID NO: 69 and comprises an Fc region, such as those provided herein. In some embodiments, a polypeptide comprises a sequence having a sequence as set forth in SEQ ID NO: 69 and comprises an Fc region, such as those provided herein, and a transmembrane domain, such as those provided herein. In some embodiments, a polypeptide comprises a sequence having a sequence as set forth in SEQ ID NO: 69 and comprises an Fc region, such as those provided herein, and a CD8/CD28 transmembrane domain. In some embodiments, a polypeptide comprises a sequence having a sequence as set forth in SEQ ID NO: 69 and comprises an Fc region, such as those provided herein, a transmembrane domain, such as those provided herein, and an Env incorporation motif.

In some embodiments, a polypeptide comprises a sequence having a sequence as set forth in SEQ ID NO: 70 and comprises an Fc region, such as those provided herein. In some embodiments, a polypeptide comprises a sequence having a sequence as set forth in SEQ ID NO: 70 and comprises an Fc region, such as those provided herein, and a transmembrane domain, such as those provided herein. In some embodiments, a polypeptide comprises a sequence having a sequence as set forth in SEQ ID NO: 70 and comprises an Fc region, such as those provided herein, and a CD8/CD28 transmembrane domain. In some embodiments, a polypeptide comprises a sequence having a sequence as set forth in SEQ ID NO: 70 and comprises an Fc region, such as those provided herein, a transmembrane domain, such as those provided herein, and an Env incorporation motif.

Although, the binders that bind to CD7 and CD8 are illustrated, in part, with a mutant VSV-G protein, other fusogenic proteins can also be used in place of the VSV-G protein. For example, in some embodiments, the pseudotyped viral-like particles can pseudotyped using viral glycoproteins other than VSV-G.

In some embodiments, viral particle can be pseudotyped using a viral glycoprotein from, for example, VSV. In some embodiments, viral particle can be pseudotyped using a viral glycoprotein from, for example, the Paramyxoviridae family. In some embodiments, the pseudotyped viral-like particles are pseudotyped using viral glycoproteins of morbillivirus, such as Measles virus. In some embodiments, the pseudotyped viral-like particles are pseudotyped using viral glycoproteins of the Measles virus. In some embodiments, the pseudotyped viral-like particles are pseudotyped using viral glycoproteins of henipavirus, such as Nipah virus, Cedar virus, or Hendra virus. In some embodiments, the pseudotyped viral-like particles are pseudotyped using viral glycoproteins of the Nipah virus. In some embodiments, a polypeptide or an antibody as provided herein is linked via a linker to an envelope glycoprotein G or H of a virus of the Paramyxoviridae family. In some embodiments, the virus of the Paramyxoviridae family is a morbillivirus, such as Measles virus. In some embodiments, the virus of the Paramyxoviridae family is a henipavirus, such as Nipah virus, Cedar virus, or Hendra virus.

In some embodiments, the pseudotyped viral-like particles comprising the targeting moieties provided for herein are pseudotyped with viral glycoproteins of viruses of the Rhabdoviridae family. In some embodiments, the pseudotyped viral-like particles are pseudotyped using viral glycoproteins of a vesicular stomatitis New Jersey virus, a vesicular stomatitis Indiana virus, a vesicular stomatitis Alagoas virus, a vesicular stomatitis Maraba virus, or a vesicular stomatitis Carajas virus. In some embodiments, a polypeptide or an antibody as provided herein is linked via a linker to a glycoprotein of a virus of the Rhabdoviridae family. In some embodiments, the virus of the Rhabdoviridae family is the vesicular stomatitis New Jersey virus, the vesicular stomatitis Indiana virus, the vesicular stomatitis Alagoas virus, the vesicular stomatitis Maraba virus, or the vesicular stomatitis Carajas virus.

In some embodiments, the pseudotyped viral-like particles comprising the targeting moieties provided for herein are pseudotyped with viral glycoproteins of the Parainfluezna virus, *Spodoptera frugiperda* virus, *Drosophila obscura* sigmavirus, Wuhan insect virus 7, Spring viremia of carp virus, or Perch virus. In some embodiments, a polypeptide or an antibody as provided herein is linked via a linker to a glycoprotein of a virus of the Rhabdoviridae family. In some embodiments, the virus of the Rhabdoviridae family is a Parainfluezna virus. In some embodiments, the virus of the Rhabdoviridae family is a *Spodoptera frugiperda* virus. In some embodiments, the virus of the Rhabdoviridae family is a *Drosophila obscura* sigmavirus. In some embodiments, the virus of the Rhabdoviridae family is a Wuhan insect virus 7. In some embodiments, the virus of the Rhabdoviridae family is a Spring viremia of carp virus. In some embodiments, the virus of the Rhabdoviridae family is a Perch virus. In some embodiments, a polypeptide or an antibody as provided herein is linked via a linker to a Parainfluezna virus glycoprotein. In some embodiments, a polypeptide or an antibody as provided herein is linked via a linker to a *Spodoptera frugiperda* rhabdovirus isolate Sf G virus glycoprotein.

In some embodiments, the pseudotyped viral-like particles comprising the targeting moieties provided for herein are pseudotyped with viral glycoproteins of viruses of the Arenaviridae family. In some embodiments, the pseudotyped viral-like particles are pseudotyped using viral glycoproteins of the Machupo virus. In some embodiments, a polypeptide or an antibody as provided herein is linked via a linker to a glycoprotein of a virus of the Arenaviridae family. In some embodiments, the virus of the Arenaviridae family is a Machupo virus.

In some embodiments, the viral particle comprising a mutant VSV-G protein (or other viral glycorptein) and/or or targeting moiety as provided for herein comprises a nucleic acid molecule encoding for a heterologous molecule of interest or "cargo." For example, heterologous molecule of interest is meant to refer to any product that may be encoded by a nucleic acid molecule. As non-limiting examples, "cargo" or "heterologous molecule of interest" may refer to an siRNA, an shRNA, a peptide, a polypeptide, a protein, a viral payload, a viral genome, or a combination thereof. In some embodiments, the polypeptide is a chimeric antigen receptor ("CAR"). In some embodiments, the heterologous molecule of interest is an siRNA, an shRNA, a non-coding RNA (e.g. a guide RNA for a CRISPR system), a peptide, a polypeptide, a protein, a viral payload, a viral genome, a chimeric antigen receptor ("CAR"), or a combination thereof. In some embodiments, the heterologous molecule of interest is a CAR.

A "chimeric antigen receptor" or "CAR" as used herein refers to an antigen-binding domain that is fused, directly, or indirectly (e.g. via a hinge or transmembrane domain to an intracellular signaling domain capable of activating or stimulating an immune cell. Most commonly, the CAR's extracellular binding domain is composed of a single chain variable fragment (scFv) derived from fusing the variable heavy and light regions of a murine or humanized monoclonal antibody. Alternatively, scFvs may be used that are derived from Fab's (instead of from an antibody, e.g., obtained from Fab libraries). In various embodiments, this scFv is fused to a transmembrane domain and then to an intracellular signaling domain. However, the antigen binding domain can be any molecule that can bind to the to target on the cell. For example, the antigen binding domain of a CAR can be an antibody, a scFv antibody, an antigen binding domain, an ankyrin repeat (e.g. DARPIN), a VHH domain antibody, a nanobody, single domain antibody, a FN3 domain, or any combination thereof. In some embodiments, a CAR includes those that solely provide CD3ζ signals upon antigen binding. In some embodiments, the CAR includes those that provide both costimulation (e.g. CD28 or CD137) and activation (CD3 ζ). In some embodiments, the CARs include those that provide multiple costimulation (e.g. CD28 and CD137) and activation (CD3ζ). In various embodiments, the CAR is selected to have high affinity or avidity for the antigen. In some embodiments, the antigen-binding domain binds to CD20. In some embodiments, the antigen-binding domain comprises a CD20 antibody, or fragment thereof. In some embodiments, antibody fragments are as provided for herein, such as but not limited to a scFv antibody, an antigen binding domain, an ankyrin repeat (e.g. DARPIN), a VHH domain antibody, a nanobody, single domain antibody, a FN3 domain, or any combination thereof.

In some embodiments, the antigen-binding domain of the CAR comprises a $V_H$ domain, a $V_L$ domain, or a $V_H$ and a $V_L$ domain. In some embodiments, the $V_H$ domain comprises an amino acid sequence having at least 75%, 80%, 85%, 85%, 87%, 88%, 89%, 90%, 91%, 92%, 93%, 94%, 95%, 96%, 97%, 98%, 99%, or 100% identity to SEQ ID NO: 73, or any value or range in-between.

(SEQ ID NO: 73)
EVQLVESGGGLVQPGRSLRLSCAASGFTFNDYAMHWVRQAPGKGLEWVS

TISWNSGSIGYADSVKGRFTISRDNAKKSLYLQMNSLRAEDTALYYCAK

DIQYGNYYYGMDVWGQGTTVTVSS

In some embodiments, the $V_H$ domain comprises an amino acid sequence having at least 90% identity to SEQ ID NO: 73. In some embodiments, the $V_H$ domain comprises an amino acid sequence having at least 95% identity to SEQ ID NO: 73. In some embodiments, the $V_H$ domain comprises an amino acid sequence having at least 98% identity to SEQ ID NO: 73. In some embodiments, the $V_H$ domain comprises an amino acid sequence having at least 99% identity to SEQ ID NO: 73. In some embodiments, the $V_H$ domain comprises an amino acid sequence having the sequence of SEQ ID NO: 73.

In some embodiments, the $V_L$ domain comprises an amino acid sequence having at least 75%, 80%, 85%, 85%, 87%, 88%, 89%, 90%, 91%, 92%, 93%, 94%, 95%, 96%, 97%, 98%, 99%, or 100% identity to SEQ ID NO: 74, or any value or range in-between.

(SEQ ID NO: 74)
EIVLTQSPATLSLSPGERATLSCRASQSVSSYLAWYQQKPGQAPRLLIY

DASNRATGIPARFSGSGSGTDFTLTISSLEPEDFAVYYCQQRSNWPITF

GQGTRLEIK

In some embodiments, the $V_L$ domain comprises an amino acid sequence having at least 90% identity to SEQ ID NO: 74. In some embodiments, the $V_L$ domain comprises an amino acid sequence having at least 95% identity to SEQ ID NO: 74. In some embodiments, the $V_L$ domain comprises an amino acid sequence having at least 98% identity to SEQ ID NO: 74. In some embodiments, the $V_L$ domain comprises an amino acid sequence having at least 99% identity to SEQ ID NO: 74. In some embodiments, the $V_L$ domain comprises an amino acid sequence having the sequence of SEQ ID NO: 74.

In some embodiments, the antigen-binding domain of the CAR comprises a $V_H$ domain and a $V_L$ domain. In some embodiments, the $V_H$ and $V_L$ domain are not linked by a linker peptide. In some embodiments, the $V_H$ and $V_L$ domain are linked by a linker peptide, such as those as provided for herein, including but not limited to: (GGGGS)$_n$ (SEQ ID NO: 49), wherein each n is independently 1-5. In some embodiment n is 1. In some embodiment n is 2. In some embodiment n is 3. In some embodiment n is 4. In some embodiment n is 5.

In some embodiments, the antigen-binding domain of the CAR comprising a $V_H$ domain and a $V_L$ domain comprises a $V_H$ domain having at least 75%, 80%, 85%, 85%, 87%, 88%, 89%, 90%, 91%, 92%, 93%, 94%, 95%, 96%, 97%, 98%, 99%, or 100% identity to SEQ ID NO: 73, and comprises a $V_L$ having at least 75%, 80%, 85%, 85%, 87%, 88%, 89%, 90%, 91%, 92%, 93%, 94%, 95%, 96%, 97%, 98%, 99%, or 100% identity to SEQ ID NO: 74. In some embodiments, the antigen-binding domain of the CAR comprising a $V_H$ domain and a $V_L$ domain comprises a $V_H$ domain having at least 75%, 80%, 85%, 85%, 87%, 88%, 89%, 90%, 91%, 92%, 93%, 94%, 95%, 96%, 97%, 98%, 99%, or 100% identity to SEQ ID NO: 73, and comprises a $V_L$ having at least 90% identity to SEQ ID NO: 74. In some embodiments, the antigen-binding domain of the CAR comprising a $V_H$ domain and a $V_L$ domain comprises a $V_H$ domain having at least 75%, 80%, 85%, 85%, 87%, 88%, 89%, 90%, 91%, 92%, 93%, 94%, 95%, 96%, 97%, 98%, 99%, or 100% identity to SEQ ID NO: 73, and comprises a $V_L$ having at least 95% identity to SEQ ID NO: 74. In some embodiments, the antigen-binding domain of the CAR comprising a $V_H$ domain and a $V_L$ domain comprises a $V_H$ domain having at least 75%, 80%, 85%, 85%, 87%, 88%, 89%, 90%, 91%, 92%, 93%, 94%, 95%, 96%, 97%, 98%, 99%, or 100% identity to SEQ ID NO: 73, and comprises a $V_L$ having at least 98% identity to SEQ ID NO: 74. In some embodiments, the antigen-binding domain of the CAR comprising a $V_H$ domain and a $V_L$ domain comprises a $V_H$ domain having at least 75%, 80%, 85%, 85%, 87%, 88%, 89%, 90%, 91%, 92%, 93%, 94%, 95%, 96%, 97%, 98%, 99%, or 100% identity to SEQ ID NO: 73, and comprises a $V_L$ having at least 99% identity to SEQ ID NO: 74. In some embodiments, the antigen-binding domain of the CAR comprising a $V_H$ domain and a $V_L$ domain comprises a $V_H$ domain having at least 75%, 80%, 85%, 85%, 87%, 88%, 89%, 90%, 91%, 92%, 93%, 94%, 95%, 96%, 97%, 98%, 99%, or 100% identity to SEQ ID NO: 73, and comprises a $V_L$ having the sequence of SEQ ID NO: 74. In some embodiments, the antigen-binding domain of the CAR comprising a $V_H$ domain and a $V_L$ domain comprises a $V_H$ domain having at least 90% identity to SEQ ID NO: 73, and comprises a $V_L$ having at least 75%, 80%, 85%, 85%, 87%, 88%, 89%, 90%, 91%, 92%, 93%, 94%, 95%, 96%, 97%, 98%, 99%, or 100% identity to SEQ ID NO: 74. In some embodiments, the antigen-binding domain of the CAR comprising a $V_H$ domain and a $V_L$ domain comprises a $V_H$ domain having at least 95% identity to SEQ ID NO: 73, and comprises a $V_L$ having at least 75%, 80%, 85%, 85%, 87%, 88%, 89%, 90%, 91%, 92%, 93%, 94%, 95%, 96%, 97%, 98%, 99%, or 100% identity to SEQ ID NO: 74. In some embodiments, the antigen-binding domain of the CAR comprising a $V_H$ domain and a $V_L$ domain comprises a $V_H$ domain having at least 98% identity to SEQ ID NO: 73, and comprises a $V_L$ having at least 75%, 80%, 85%, 85%, 87%, 88%, 89%, 90%, 91%, 92%, 93%, 94%, 95%, 96%, 97%, 98%, 99%, or 100% identity to SEQ ID NO: 74. In some embodiments, the antigen-binding domain of the CAR comprising a $V_H$ domain and a $V_L$ domain comprises a $V_H$ domain having at least 99% identity to SEQ ID NO: 73, and comprises a $V_L$ having at least 75%, 80%, 85%, 85%, 87%, 88%, 89%, 90%, 91%, 92%, 93%, 94%, 95%, 96%, 97%, 98%, 99%, or 100% identity to SEQ ID NO: 74. In some embodiments, the antigen-binding domain of the CAR comprising a $V_H$ domain and a $V_L$ domain comprises a $V_H$ domain having an amino acid sequence of SEQ ID NO: 73, and comprises a $V_L$ having at least 75%, 80%, 85%, 85%, 87%, 88%, 89%, 90%, 91%, 92%, 93%, 94%, 95%, 96%, 97%, 98%, 99%, or 100% identity to SEQ ID NO: 74. In some embodiments, the antigen-binding domain of the CAR comprising a $V_H$ domain and a $V_L$ domain comprises a $V_H$ domain having at least 90% identity to SEQ ID NO: 73, and comprises a $V_L$ having at least 90% identity to SEQ ID NO: 74. In some embodiments, the antigen-binding domain of the CAR comprising a $V_H$ domain and a $V_L$ domain comprises a $V_H$ domain having at least 95% identity to SEQ ID NO: 73, and comprises a $V_L$ having at least 90% identity to SEQ ID NO: 74. In some embodiments, the antigen-binding domain of the CAR comprising a $V_H$ domain and a $V_L$ domain comprises a $V_H$ domain having at least 90% identity to SEQ ID NO: 73, and comprises a $V_L$ having at least 95% identity to SEQ ID NO: 74. In some embodiments, the antigen-binding domain of the CAR comprising a $V_H$ domain and a $V_L$ domain comprises a $V_H$ domain having at least 95% identity to SEQ ID NO: 73, and comprises a $V_L$ having at least 95% identity to SEQ ID NO: 74. In some embodiments, the antigen-binding domain of the CAR comprising a $V_H$ domain and a $V_L$ domain comprises a $V_H$ domain having at least 98% identity to SEQ ID NO: 73, and comprises a $V_L$ having at least 98% identity to SEQ ID NO: 74. In some embodiments, the antigen-binding domain of the CAR comprising a $V_H$ domain and a $V_L$ domain comprises a $V_H$ domain having at least 99% identity to SEQ ID NO: 73, and comprises a $V_L$ having at least 99% identity to SEQ ID NO: 74. In some embodiments, the antigen-binding domain of the CAR comprising a $V_H$ domain and a $V_L$ domain comprises a $V_H$ domain having an amino acid sequence of SEQ ID NO: 73, and comprises a $V_L$ having an amino acid sequence of SEQ ID NO: 74.

In some embodiments, the antigen-binding domain of the CAR comprises a formula of $V_H$-Z-$V_L$, wherein $V_H$ is a heavy chain variable region comprising the amino acid sequence of SEQ ID NO: 73, Z is a linker comprising the amino acid sequence GGGGSGGGGSGGGGS (SEQ ID NO: 77), and $V_L$ is a light chain variable region comprising the amino acid sequence of SEQ ID NO: 74. In some embodiments, the antigen-binding domain of the CAR comprising a formula of $V_H$-Z-$V_L$ has an amino acid sequence as set forth below:

(SEQ ID NO: 75)
EVQLVESGGGLVQPGRSLRLSCAASGFTFNDYAMHWVRQAPGKGLEWVS

TISWNSGSIGYADSVKGRFTISRDNAKKSLYLQMNSLRAEDTALYYCAK

DIQYGNYYYGMDVWGQGTTVTVSSGGGGSGGGGSGGGGSEIVLTQSPAT

LSLSPGERATLSCRASQSVSSYLAWYQQKPGQAPRLLIYDASNRATGIP

ARFSGSGSGTDFTLTISSLEPEDFAVYYCQQRSNWPITFGQGTRLEIK

In some embodiments, the antigen-binding domain of the CAR comprises an amino acid sequence having at least 85%, 86%, 87%, 88%, 89%, 90%, 91%, 92%, 93%, 94%, 95%, 96%, 97%, 98%, 99%, or 100% identity to a sequence of SEQ ID NO: 75. In some embodiments, the antigen-binding domain of the CAR comprises an amino acid sequence having at least 90% identity to a sequence of SEQ ID NO: 75. In some embodiments, the antigen-binding domain of the CAR comprises an amino acid sequence having at least 95% identity to a sequence of SEQ ID NO: 75. In some embodiments, the antigen-binding domain of the CAR comprises an amino acid sequence having at least 98% identity to a sequence of SEQ ID NO: 75. In some embodiments, the antigen-binding domain of the CAR comprises an amino acid sequence having at least 99% identity to a sequence of SEQ ID NO: 75. In some embodiments, the antigen-binding domain of the CAR comprises the amino acid sequence of SEQ ID NO: 75.

In some embodiments, the antigen-binding domain of the CAR comprises a formula of $V_L$-Z-$V_H$, wherein $V_L$ is a light chain variable region comprising the amino acid sequence of SEQ ID NO: 74, Z is a linker comprising the amino acid sequence GGGGSGGGGSGGGGS (SEQ ID NO: 77), and $V_H$ is a light chain variable region comprising the amino acid sequence of SEQ ID NO: 73. In some embodiments, the antigen-binding domain of the CAR comprising a formula of $V_L$-Z-$V_H$ has an amino acid sequence as set forth below:

(SEQ ID NO: 76)
EIVLTQSPATLSLSPGERATLSCRASQSVSSYLAWYQQKPGQAPRLLIY

DASNRATGIPARFSGSGSGTDFTLTISSLEPEDFAVYYCQQRSNWPITF

GQGTRLEIKGGGGSGGGGSGGGGSEVQLVESGGGLVQPGRSLRLSCAAS

GFTFNDYAMHWVRQAPGKGLEWVSTISWNSGSIGYADSVKGRFTISRDN

AKKSLYLQMNSLRAEDTALYYCAKDIQYGNYYYGMDVWGQGTTVTVSS

In some embodiments, the antigen-binding domain of the CAR comprises an amino acid sequence having at least 85%, 86%, 87%, 88%, 89%, 90%, 91%, 92%, 93%, 94%, 95%, 96%, 97%, 98%, 99%, or 100% identity to a sequence of SEQ ID NO: 76. In some embodiments, the antigen-binding domain of the CAR comprises an amino acid sequence having at least 90% identity to a sequence of SEQ ID NO: 76. In some embodiments, the antigen-binding domain of the CAR comprises an amino acid sequence having at least 95% identity to a sequence of SEQ ID NO: 76. In some embodiments, the antigen-binding domain of the CAR comprises an amino acid sequence having at least 98% identity to a sequence of SEQ ID NO: 76. In some embodiments, the antigen-binding domain of the CAR comprises an amino acid sequence having at least 99% identity to a sequence of SEQ ID NO: 76. In some embodiments, the antigen-binding domain of the CAR comprises the amino acid sequence of SEQ ID NO: 76.

In some embodiments, the antigen-binding domain of the CAR comprises a $V_H$ domain, a $V_L$ domain, or a $V_H$ and a $V_L$ domain. In some embodiments, the $V_H$ domain comprises an amino acid sequence having at least 75%, 80%, 85%, 85%, 87%, 88%, 89%, 90%, 91%, 92%, 93%, 94%, 95%, 96%, 97%, 98%, 99%, or 100% identity to SEQ ID NO: 78, or any value or range in-between.

(SEQ ID NO: 78)
DIVLTQSPAILSASPGEKVTMTCRASSSVNYMDWYQKKPGSSPKPWIYA

TSNLASGVPARFSGSGSGTSYSLTISRVEAEDAATYYCQQWSFNPPTFG

GGTKLEIKGSTS

In some embodiments, the $V_H$ domain comprises an amino acid sequence having at least 90% identity to SEQ ID NO: 78. In some embodiments, the $V_H$ domain comprises an amino acid sequence having at least 95% identity to SEQ ID NO: 78. In some embodiments, the $V_H$ domain comprises an amino acid sequence having at least 98% identity to SEQ ID NO: 78. In some embodiments, the $V_H$ domain comprises an amino acid sequence having at least 99% identity to SEQ ID NO: 78. In some embodiments, the $V_H$ domain comprises an amino acid sequence having the sequence of SEQ ID NO: 78.

In some embodiments, the $V_L$ domain comprises an amino acid sequence having at least 75%, 80%, 85%, 85%, 87%, 88%, 89%, 90%, 91%, 92%, 93%, 94%, 95%, 96%, 97%, 98%, 99%, or 100% identity to SEQ ID NO: 79, or any value or range in-between.

(SEQ ID NO: 79)
EVQLQQSGAELVKPGASVKMSCKASGYTFTSYNMHWVKQTPGQGLEWIG

AIYPGNGDTSYNQKFKGKATLTADKSSSTAYMQLSSLTSEDSADYYCAR

SNYYGSSYWFFDVWGAGTTVTVSS

In some embodiments, the $V_L$ domain comprises an amino acid sequence having at least 90% identity to SEQ ID NO: 79. In some embodiments, the $V_L$ domain comprises an amino acid sequence having at least 95% identity to SEQ ID NO: 79. In some embodiments, the $V_L$ domain comprises an amino acid sequence having at least 98% identity to SEQ ID NO: 79. In some embodiments, the $V_L$ domain comprises an amino acid sequence having at least 99% identity to SEQ ID NO: 79. In some embodiments, the $V_L$ domain comprises an amino acid sequence having the sequence of SEQ ID NO: 79.

In some embodiments, the antigen-binding domain of the CAR comprising a $V_H$ domain and a $V_L$ domain comprises a $V_H$ domain having at least 75%, 80%, 85%, 85%, 87%, 88%, 89%, 90%, 91%, 92%, 93%, 94%, 95%, 96%, 97%, 98%, 99%, or 100% identity to SEQ ID NO: 78, and comprises a $V_L$ having at least 75%, 80%, 85%, 85%, 87%, 88%, 89%, 90%, 91%, 92%, 93%, 94%, 95%, 96%, 97%, 98%, 99%, or 100% identity to SEQ ID NO: 79. In some embodiments, the antigen-binding domain of the CAR comprising a $V_H$ domain and a $V_L$ domain comprises a $V_H$ domain having at least 75%, 80%, 85%, 85%, 87%, 88%, 89%, 90%, 91%, 92%, 93%, 94%, 95%, 96%, 97%, 98%, 99%, or 100% identity to SEQ ID NO: 78, and comprises a $V_L$ having at least 90% identity to SEQ ID NO: 79. In some embodiments, the antigen-binding domain of the CAR comprising a $V_H$ domain and a $V_L$ domain comprises a $V_H$ domain having at least 75%, 80%, 85%, 85%, 87%, 88%, 89%, 90%, 91%, 92%, 93%, 94%, 95%, 96%, 97%, 98%, 99%, or 100% identity to SEQ ID NO: 78, and comprises a $V_L$ having at least 95% identity to SEQ ID NO: 79. In some embodiments, the antigen-binding domain of the CAR comprising a $V_H$ domain and a $V_L$ domain comprises a $V_H$ domain having at least 75%, 80%, 85%, 85%, 87%, 88%, 89%, 90%, 91%, 92%, 93%, 94%, 95%, 96%, 97%, 98%, 99%, or 100% identity to SEQ ID NO: 78, and comprises a $V_L$ having at least 98% identity to SEQ ID NO: 79. In some embodiments, the antigen-binding domain of the CAR comprising a $V_H$ domain and a $V_L$ domain comprises a $V_H$ domain having at least 75%, 80%, 85%, 85%, 87%, 88%, 89%, 90%, 91%, 92%, 93%, 94%, 95%, 96%, 97%, 98%, 99%, or 100% identity to SEQ ID NO: 78, and comprises a $V_L$ having at least 99% identity to SEQ ID NO: 79. In some embodiments, the antigen-binding domain of the CAR comprising a $V_H$ domain and a $V_L$ domain comprises a $V_H$ domain having at least 75%, 80%, 85%, 85%, 87%, 88%, 89%, 90%, 91%, 92%, 93%, 94%, 95%, 96%, 97%, 98%, 99%, or 100% identity to SEQ ID NO: 78, and comprises a $V_L$ having the sequence of SEQ ID NO: 79. In some embodiments, the antigen-binding domain of the CAR comprising a $V_H$ domain and a $V_L$ domain comprises a $V_H$ domain having at least 90% identity to SEQ ID NO: 78, and comprises a $V_L$ having at least 75%, 80%, 85%, 85%, 87%, 88%, 89%, 90%, 91%, 92%, 93%, 94%, 95%, 96%, 97%, 98%, 99%, or 100% identity to SEQ ID NO: 79. In some embodiments, the antigen-binding domain of the CAR comprising a $V_H$ domain and a $V_L$ domain comprises a $V_H$ domain having at least 95% identity to SEQ ID NO: 78, and comprises a $V_L$ having at least 75%, 80%, 85%, 85%, 87%, 88%, 89%, 90%, 91%, 92%, 93%, 94%, 95%, 96%, 97%, 98%, 99%, or 100% identity to SEQ ID NO: 79. In some embodiments, the antigen-binding domain of the CAR comprising a $V_H$ domain and a $V_L$ domain comprises a $V_H$ domain having at least 98% identity to SEQ ID NO: 78, and comprises a $V_L$ having at least 75%, 80%, 85%, 85%, 87%, 88%, 89%, 90%, 91%, 92%, 93%, 94%, 95%, 96%, 97%, 98%, 99%, or 100% identity to SEQ ID NO: 79. In some embodiments, the antigen-binding domain of the CAR comprising a $V_H$ domain and a $V_L$ domain comprises a $V_H$ domain having at least 99% identity to SEQ ID NO: 78, and comprises a $V_L$ having at least 75%, 80%, 85%, 85%, 87%, 88%, 89%, 90%, 91%, 92%, 93%, 94%, 95%, 96%, 97%, 98%, 99%, or 100% identity to SEQ ID NO: 79. In some embodiments, the antigen-binding domain of the CAR comprising a $V_H$ domain and a $V_L$ domain comprises a $V_H$ domain having an amino acid sequence of SEQ ID NO: 78, and comprises a $V_L$ having at least 75%, 80%, 85%, 85%, 87%, 88%, 89%, 90%, 91%, 92%, 93%, 94%, 95%, 96%, 97%, 98%, 99%, or 100% identity to SEQ ID NO: 79. In some embodiments, the antigen-binding domain of the CAR comprising a $V_H$ domain and a $V_L$ domain comprises a $V_H$ domain having at least 90% identity to SEQ ID NO: 78, and comprises a $V_L$ having at least 90% identity to SEQ ID NO: 79. In some embodiments, the antigen-binding domain of the CAR comprising a $V_H$ domain and a $V_L$ domain comprises a $V_H$ domain having at least 95% identity to SEQ ID NO: 78, and comprises a $V_L$ having at least 90% identity to SEQ ID NO: 79. In some embodiments, the antigen-binding domain of the CAR comprising a $V_H$ domain and a $V_L$ domain comprises a $V_H$ domain having at least 90% identity to SEQ ID NO: 78, and comprises a $V_L$ having at least 95% identity to SEQ ID NO: 79. In some embodiments, the antigen-binding domain of the CAR comprising a $V_H$ domain and a $V_L$ domain comprises a $V_H$ domain having at least 95% identity to SEQ ID NO: 78, and comprises a $V_L$ having at least 95% identity to SEQ ID NO: 79. In some embodiments, the antigen-binding domain of the CAR comprising a $V_H$ domain and a $V_L$ domain comprises a $V_H$ domain having at least 98% identity to SEQ ID NO: 78, and comprises a $V_L$ having at least 98% identity to SEQ ID NO: 79. In some embodiments, the antigen-binding domain of the CAR comprising a $V_H$ domain and a $V_L$ domain comprises a $V_H$ domain having at least 99% identity to SEQ ID NO: 78, and comprises a $V_L$ having at least 99% identity to SEQ ID NO: 79. In some embodiments, the antigen-binding domain of the CAR comprising a $V_H$ domain and a $V_L$ domain comprises a $V_H$ domain having an amino acid sequence of SEQ ID NO: 78, and comprises a $V_L$ having an amino acid sequence of SEQ ID NO: 79.

In some embodiments, the antigen-binding domain of the CAR comprises a formula of $V_H$-Z-$V_L$, wherein $V_H$ is a heavy chain variable region comprising the amino acid sequence of SEQ ID NO: 78, Z is a linker comprising the amino acid sequence GGGGSGGGGSGGGGS (SEQ ID NO: 77), and $V_L$ is a light chain variable region comprising the amino acid sequence of SEQ ID NO: 79. In some embodiments, the antigen-binding domain of the CAR comprising a formula of $V_H$-Z-$V_L$ has an amino acid sequence as set forth below:

```
                                      (SEQ ID NO: 80)
DIVLTQSPAILSASPGEKVTMTCRASSSVNYMDWYQKKPGSSPKPWIYA

TSNLASGVPARFSGSGSGTSYSLTISRVEAEDAATYYCQQWSFNPPTFG

GGTKLEIKGSTSGGGGSGGGGSGGGGSSEVQLQQSGAELVKPGASVKMS

CKASGYTFTSYNMHWVKQTPGQGLEWIGAIYPGNGDTSYNQKFKGKATL

TADKSSSTAYMQLSSLTSEDSADYYCARSNYYGSSYWFFDVWGAGTTVT

VSS
```

In some embodiments, the antigen-binding domain of the CAR comprises an amino acid sequence having at least 85%, 86%, 87%, 88%, 89%, 90%, 91%, 92%, 93%, 94%, 95%, 96%, 97%, 98%, 99%, or 100% identity to a sequence of SEQ ID NO: 80. In some embodiments, the antigen-binding domain of the CAR comprises an amino acid sequence having at least 90% identity to a sequence of SEQ ID NO: 80. In some embodiments, the antigen-binding domain of the CAR comprises an amino acid sequence having at least 95% identity to a sequence of SEQ ID NO: 80. In some embodiments, the antigen-binding domain of the CAR comprises an amino acid sequence having at least 98% identity to a sequence of SEQ ID NO: 80. In some embodiments, the antigen-binding domain of the CAR comprises an amino acid sequence having at least 99% identity to a sequence of SEQ ID NO: 80. In some embodiments, the antigen-binding domain of the CAR comprises the amino acid sequence of SEQ ID NO: 80.

In some embodiments, the antigen-binding domain of the CAR comprises a formula of $V_L$-Z-$V_H$, wherein $V_L$ is a light chain variable region comprising the amino acid sequence of SEQ ID NO: 79, Z is a linker comprising the amino acid sequence GGGGSGGGGSGGGGS (SEQ ID NO: 77), and $V_H$ is a light chain variable region comprising the amino acid sequence of SEQ ID NO: 78. In some embodiments, the antigen-binding domain of the CAR comprising a formula of $V_L$-Z-$V_H$ has an amino acid sequence as set forth below:

```
                                          (SEQ ID NO: 81)
SEVQLQQSGAELVKPGASVKMSCKASGYTFTSYNMHWVKQTPGQGLEWI

GAIYPGNGDTSYNQKFKGKATLTADKSSSTAYMQLSSLTSEDSADYYCA

RSNYYGSSYWFFDVWGAGTTVTVSSGGGGSGGGGSGGGGSDIVLTQSPA

ILSASPGEKVTMTCRASSSVNYMDWYQKKPGSSPKPWIYATSNLASGVP

ARFSGSGSGTSYSLTISRVEAEDAATYYCQQWSFNPPTFGGGTKLEIKG

STS
```

In some embodiments, the antigen-binding domain of the CAR comprises an amino acid sequence having at least 85%, 86%, 87%, 88%, 89%, 90%, 91%, 92%, 93%, 94%, 95%, 96%, 97%, 98%, 99%, or 100% identity to a sequence of SEQ ID NO: 81. In some embodiments, the antigen-binding domain of the CAR comprises an amino acid sequence having at least 90% identity to a sequence of SEQ ID NO: 81. In some embodiments, the antigen-binding domain of the CAR comprises an amino acid sequence having at least 95% identity to a sequence of SEQ ID NO: 81. In some embodiments, the antigen-binding domain of the CAR comprises an amino acid sequence having at least 98% identity to a sequence of SEQ ID NO: 81. In some embodiments, the antigen-binding domain of the CAR comprises an amino acid sequence having at least 99% identity to a sequence of SEQ ID NO: 81. In some embodiments, the antigen-binding domain of the CAR comprises the amino acid sequence of SEQ ID NO: 81.

In some embodiments, the antigen-binding domain of the CAR comprises rituximab, ocrelizumab, obinutuzumab, ofatumumab, ibritumomab tiuxetan, tositumomab, or ublituximab. In some embodiment, the antigen-binding domain comprises rituximab. In some embodiment, the antigen-binding domain comprises ofatumumab. In some embodiments, the CAR comprises the 4-1BB domain as well. These are merely illustrative in nature and are not limiting to the present embodiments and any chimeric antigen receptor can be delivered in conjunction with the viral particles and vectors provided for herein. These are non-limiting examples of CARs and any CAR construct could be encoded for by the nucleic acid molecule.

In some embodiments, the pseudotyped viral particle further comprises a heterologous nucleic acid molecule encoding a cargo of interest. The nucleic acid molecule may be useful for modulating the expression of a target gene. In some embodiments, the cargo can be used to modulate the activity of a cell or express a protein that is trafficked to the surface of the target cell. Therefore, in some embodiments, the nucleic acid may comprise an siRNA or an shRNA. The nucleic acid may also encode for a cargo of interest. Therefore, in some embodiments, the cargo of interest may comprise a polypeptide or portion thereof, a protein or portion thereof, a chimeric antigen receptor or portion thereof, or a tumor antigen or a portion thereof. In some embodiments, the cargo of interest is an antibody that is produced by the virus, which can then be secreted by the cell that is infected with the virus. The term "protein" can refer to any polypeptide that carries a native function in a cellular environment. Therefore, in some embodiments, the protein encoded by the nucleic acid cargo of interest may comprise an enzyme, a nuclear receptor, a transporter, a ribosomal protein, a membrane bound protein, a cytoplasmic protein, a G-protein coupled receptor, a voltage gated ion channel, a secretory protein, a mitochondria protein, a cytokine, a chimeric antigen receptor, a tumor antigen, or a portion or chimeric species thereof.

Without being bound to any particular theory, the viral particle comprising the mutant VSV-G protein or other viral glycoprotein as provided for herein that comprises a targeting moiety can be used to express the heterologous molecule of interest in the target cell. Thus, for example, the CAR can be expressed in a T cell that is targeted by a viral particle pseudotyped with a VSV-G protein as provided for herein. Where the T cell is the intended target the viral particle can comprise a targeting moiety that binds to a target on the surface of a T cell, such as, but not limited to CD2, CD3, CD4, CD5, CD7 or CD8. In some embodiments, the target is CD2. In some embodiments, the target is CD3. In some embodiments, the target is CD4. In some embodiments, the target is CD5. In some embodiments, the target is CD6. In some embodiments, the target is CD7. In some embodiments, the target is CD8.

Also provided herein are viral particles comprising a targeting moiety that binds to CD7 or CD8, or a pharmaceutical composition comprising the same. In some the viral particle comprises a targeting moiety that binds to CD7. In some the viral particle comprises a targeting moiety that binds to CD7.

In some embodiments, the viral particle that comprises a targeting moiety that binds to CD7 or CD8 is a pseudotyped viral particle. The viral particle can be pseudotyped with a viral glycoprotein, such as those, but not limited to, described herein. In some embodiments, the viral particle is pseudotyped with a VSV-G protein or mutant thereof, including, but not limited to, those provided for herein. The targeting moiety can be any antibody that or binder that binds to CD7 or CD8. Non-limiting examples are provided for herein.

In addition to being pseudotyped, the viral particles comprising a targeting moiety that binds to CD7 or CD8 can comprise a heterologous nucleic acid molecule encoding a molecule of interest. This can be, for example, a siRNA, an shRNA, a non-coding RNA (e.g. a guide RNA for a CRISPR system), a peptide, a polypeptide, a protein, a viral payload, a viral genome, or a combination thereof. In some embodiments, the heterologous molecule of interest is a chimeric antigen receptor ("CAR").

In some embodiments, the pseudotyped viral particle is a recombinant lentivirus. In some embodiments, the recombinant pseudotyped viral particle is replication competent. In some embodiments, the recombinant pseudotyped viral particle is replication incompetent.

In some embodiments, a pharmaceutical composition is provided comprising any composition, particle, or component provided for herein, such as an envelope pseudotyped viral particles or vectors as provided for herein, i.e. a particle that comprises a VSV-G mutant protein provided for herein or other viral glycoprotein, or particles that comprise a targeting moiety and/or a heterologous nucleic acid molecule as provided for herein.

In some embodiments, methods of delivering a cargo of interest to a cell are provided. In some embodiments, the methods comprise contacting the cell with the pseudotyped viral-like particles or viral vectors as provided for herein, or a pharmaceutical composition comprising the same.

In some embodiments, methods of delivering a cargo of interest to a cell in a subject are provided. In some embodiments, the methods comprise administering to the subject the pseudotyped viral-like particles or viral vectors as provided for herein, or a pharmaceutical composition comprising the same. In some embodiments, the cargo is a chimeric antigen receptor or as otherwise provided for herein.

In some embodiments, methods for of delivering a chimeric antigen receptor to a T-cell in a subject are provided. In some embodiments, the methods comprising administering to the subject the pseudotyped viral-like particles or viral vectors as provided for herein, or a pharmaceutical composition comprising the same, wherein the pseudotyped viral-like particle or viral vector comprises a heterologous nucleic acid molecule encoding the chimeric antigen receptor.

Also provided herein are nucleic acid molecules encoding a mutant VSV-G protein as provided for herein.

Also provided herein are nucleic acid molecules encoding a targeting moiety, such as those provided for herein.

Methods of making the viral like particles or vectors are also provided. In some embodiments, the methods comprise making a viral like particles or vectors comprising a mutant VSV-G protein or other viral glycoprotein. In some embodiments, the methods comprise transfecting or transducing a packaging cell line with the nucleic acid molecules encoding a mutant VSV-G protein or another viral glycoprotein as provided for herein under conditions sufficient to produce the pseudotyped viral-like particles or viral vectors. In some embodiments, the methods comprise transfecting or transducing a packaging cell line with the plurality of nucleic acid molecules provided for herein under conditions sufficient to produce the pseudotyped viral-like particles or viral vectors and optionally with a targeting moiety, such as one that binds to a target antigen, such as those provided for herein. In some embodiments, the targeting moiety binds to CD7 or CD8. In some embodiments, the targeting moiety comprises a sequence that binds to CD7 or CD8, such as those provided for herein. In some embodiments, methods further comprise isolating the pseudotyped viral-like particle or viral vector. In some embodiments, the nucleic acid molecules also comprise a nucleic acid molecule encoding a targeting moiety and/or a cargo that is to be delivered by the viral vector that is produced.

Accordingly, in some embodiments, cells are provided comprising heterologous nucleic acid molecules that encode the components to produce the virus. Packaging cell lines are known in the art and can be modified with the molecules of interest to produce the viral particle of interest.

For example, a cell or population of cells is provided that comprises one or more heterologous nucleic acid molecules encoding for a targeting moiety and/or a viral glycoprotein. In some embodiments, the cell comprises heterologous nucleic acid molecules encoding for a targeting moiety and a viral glycoprotein. In some embodiments, the heterologous nucleic acid molecules comprise a nucleic acid sequence encoding for a targeting moiety that binds to CD7 or CD8. In some embodiments, the targeting moiety that is encoded for comprises an amino acid sequence as provided for herein. In some embodiments, the viral glycoprotein encoded for is any viral glycoprotein that can function as a fusogenic protein to facilitate entry of the viral particle into a cell that expresses CD7 or CD8. In some embodiments, the viral glycoprotein is wild-type or a mutant VSV-G protein, such as those provided for herein. Other viral glycoproteins that can be encoded for are also described herein and can be used.

The viral particles provided for herein can be produced or made by, for example, culturing the cell under conditions sufficient to make the viral particle. In some embodiments, the cell is what is called a packaging cell line that provides components of the virus to produce the viral particle. These can be structural or non-structural viral components or proteins.

Also provided for herein are methods of treating cancer in a subject. In some embodiments, the methods comprise administering to the subject the pseudotyped viral-like particles or viral vectors as provided for herein, or a pharmaceutical composition comprising the same, wherein the pseudotyped viral-like particle or viral vector comprises a heterologous nucleic acid molecule encoding the chimeric antigen receptor.

Also provided herein are methods of treating a disease in a subject in need thereof.

In some embodiments, the methods provided include, but are not limited to, methods of treating a disease in a subject in need thereof, comprising administering to the subject the viral particle(s) provided herein to treat the disease.

In certain embodiments, the disease is a cancer. In addition, the compositions provided for herein can be used in methods for the treatment of any condition related to a cancer, such as a cell-mediated immune response against a tumor cell(s), where it is desirable to treat or alleviate the disease. The types of cancers to be treated include, but are not limited to, carcinoma, blastoma, sarcoma, certain leukemia or lymphoid malignancies, benign and malignant tumors, malignancies e.g., sarcomas, carcinomas, and melanomas. Other exemplary cancers include, but are not limited to, breast cancer, prostate cancer, ovarian cancer, cervical cancer, skin cancer, pancreatic cancer, colorectal cancer, renal cancer, liver cancer, brain cancer, lymphoma, leukemia, lung cancer, thyroid cancer, and the like. In some embodiments, the cancer is the cancer is carcinoma, blastoma, sarcoma, leukemia, lymphoid malignancies, benign tumors, malignant tumors, sarcoma, carcinoma, melanoma, breast cancer, prostate cancer, ovarian cancer, cervical cancer, skin cancer, pancreatic cancer, colorectal cancer, renal cancer, liver cancer, brain cancer, lymphoma, leukemia, lung cancer, thyroid cancer, B cell related cancer or T cell related cancer. The cancers may be non-solid tumors (such as hematological tumors) or solid tumors. Adult tumors/cancers and pediatric tumors/cancers are also included. In one embodiment, the cancer is a hematological tumor. In one embodiment, the cancer is a carcinoma. In one embodiment, the cancer is a sarcoma. In one embodiment, the cancer is a leukemia. In one embodiment the cancer is a solid tumor.

Solid tumors are abnormal masses of tissue that usually do not contain cysts or liquid areas. Solid tumors can be benign or malignant. Different types of solid tumors are named for the type of cells that form them (such as sarcomas, carcinomas, and lymphomas). Examples of solid tumors, such as sarcomas and carcinomas, include fibrosarcoma, myxosarcoma, liposarcoma, chondrosarcoma, osteosarcoma, synovioma, mesothelioma, Ewing's tumor, leiomyosarcoma, rhabdomyosarcoma, colon carcinoma, lymphoid malignancy, pancreatic cancer, breast cancer, lung cancers, ovarian cancer, prostate cancer, hepatocellular carcinoma, squamous cell carcinoma, basal cell carcinoma, adenocarcinoma, sweat gland carcinoma, medullary thyroid carcinoma, papillary thyroid carcinoma, pheochromocytomas sebaceous gland carcinoma, papillary carcinoma, papillary adenocarcinomas, medullary carcinoma, bronchogenic carcinoma, renal cell carcinoma, hepatoma, bile duct carcinoma, choriocarcinoma, Wilms' tumor, cervical cancer, testicular tumor, seminoma, bladder carcinoma, melanoma, CNS tumors (such as a glioma (such as brainstem glioma and mixed gliomas), glioblastoma (also known as glioblastoma multiforme) astrocytoma, CNS lymphoma, germinoma, medulloblastoma, Schwannoma craniopharyogioma, ependymoma, pinealoma, hemangioblastoma, acoustic neuroma, oligodendroglioma, menangioma, neuroblastoma, retinoblastoma and brain metastases).

Carcinomas that can be amenable to therapy by the methods disclosed herein include, but are not limited to, esophageal carcinoma, hepatocellular carcinoma, basal cell carcinoma (a form of skin cancer), squamous cell carcinoma (various tissues), bladder carcinoma, including transitional cell carcinoma (a malignant neoplasm of the bladder), bronchogenic carcinoma, colon carcinoma, colorectal carcinoma, gastric carcinoma, lung carcinoma, including small cell carcinoma and non-small cell carcinoma of the lung, adrenocortical carcinoma, thyroid carcinoma, pancreatic carcinoma, breast carcinoma, ovarian carcinoma, prostate carcinoma, adenocarcinoma, sweat gland carcinoma, sebaceous gland carcinoma, papillary carcinoma, papillary adenocarcinoma, cystadenocarcinoma, medullary carcinoma, renal cell carcinoma, ductal carcinoma in situ or bile duct carcinoma, choriocarcinoma, seminoma, embryonal carcinoma, Wilm's tumor, cervical carcinoma, uterine carcinoma, testicular carcinoma, osteogenic carcinoma, epithelial carcinoma, and nasopharyngeal carcinoma.

In certain exemplary embodiments, the compositions provided herein can be used in methods to treat a myeloma, or a condition related to myeloma. Examples of myeloma or conditions related thereto include, without limitation, light chain myeloma, non-secretory myeloma, monoclonal gamopathy of undertermined significance (MGUS), plasmacytoma (e.g., solitary, multiple solitary, extramedullary plasmacytoma), amyloidosis, and multiple myeloma. In some embodiments, methods of treating multiple myeloma are provided. In some embodiments, the multiple myeloma is refractory myeloma. In some embodiments, the multiple myeloma is relapsed myeloma.

In certain exemplary embodiments, the in vivo modified immune cells produced using the compositions provided herein are used to treat a melanoma, or a condition related to melanoma. Examples of melanoma or conditions related thereto include, without limitation, superficial spreading melanoma, nodular melanoma, lentigo maligna melanoma, acral lentiginous melanoma, amelanotic melanoma, or melanoma of the skin (e.g., cutaneous, eye, vulva, vagina, rectum melanoma). In some embodiments, the melanoma is cutaneous melanoma. In some embodiments, the melanoma is refractory melanoma. In some embodiments, the melanoma is relapsed melanoma.

In some embodiments, the compositions provided herein are used to treat a sarcoma, or a condition related to sarcoma. Examples of sarcoma or conditions related thereto include, without limitation, angiosarcoma, chondrosarcoma, chordoma, endotheliosarcoma, Ewing's sarcoma, fibrosarcoma, gastrointestinal stromal tumor, leiomyosarcoma, liposarcoma, lymphangiosarcoma, lymphangioendotheliosarcoma, mesothelioma, malignant peripheral nerve sheath tumor, myxosarcoma, osteogenic sarcoma, osteosarcoma, pleomorphic sarcoma, rhabdomyosarcoma, synovioma, synovial sarcoma, and other soft tissue sarcomas. In some embodiments, the sarcoma is synovial sarcoma. In some embodiments, the sarcoma is liposarcoma such as myxoid/round cell liposarcoma, differentiated/dedifferentiated liposarcoma, or pleomorphic liposarcoma. In some embodiments, the sarcoma is myxoid/round cell liposarcoma. In some embodiments, the sarcoma is refractory sarcoma. In some embodiments, the sarcoma is relapsed sarcoma.

In some embodiments, the subject has been treated with a therapeutic agent targeting the disease or condition, e.g. the tumor, prior to administration of the composition. In some aspects, the subject is refractory or non-responsive to the other therapeutic agent. In some embodiments, the subject has persistent or relapsed disease, e.g., following treatment with another therapeutic intervention, including chemotherapy, radiation, and/or hematopoietic stem cell transplantation (HSCT), e.g., allogenic HSCT. In some embodiments, the administration effectively treats the subject despite the subject having become resistant to another therapy.

In some embodiments, the subject is responsive to the other therapeutic agent, and treatment with the therapeutic agent reduces disease burden. In some aspects, the subject is initially responsive to the therapeutic agent, but exhibits a relapse of the disease or condition over time. In some embodiments, the subject has not relapsed. In some such embodiments, the subject is determined to be at risk for relapse, such as at a high risk of relapse, and thus the composition is administered prophylactically, e.g., to reduce the likelihood of or prevent relapse. In some aspects, the subject has not received prior treatment with another therapeutic agent.

The administration of the compositions may be carried out in any convenient manner known to those of skill in the art. For example, the compositions may be administered to a subject by aerosol inhalation, injection, ingestion, transfusion, implantation or transplantation. The compositions described herein may be administered to a patient transarterially, subcutaneously, intradermally, intratumorally, intranodally, intramedullary, intramuscularly, by intravenous (i.v.) injection, intraperitoneally, intranasally, intracranially, or intraosseously. In other instances, the compositions are injected directly into a site of a local disease site in the subject, a lymph node, an organ, a tumor, and the like.

For the prevention or treatment of disease, the appropriate dosage may depend on the type of disease to be treated, the severity and course of the disease, whether the composition is administered for preventive or therapeutic purposes, previous therapy, the subject's clinical history and response to the treatment, and the discretion of the attending physician. The composition is, in some embodiments, suitably administered to the subject at one time or over a series of treatments.

In some embodiments, the composition is administered as part of a combination treatment, such as simultaneously with or sequentially with, in any order, another therapeutic intervention, such as an antibody or produced cell or receptor or agent, such as a cytotoxic or therapeutic agent. The composition(s), in some embodiments, is co-administered with one or more additional therapeutic agents or in connection with another therapeutic intervention, either simultaneously or sequentially in any order. In some contexts, the composition is co-administered with another therapy sufficiently close in time such that the composition enhances the effect of one or more additional therapeutic agents, or vice versa. In some embodiments, the composition is administered prior to the one or more additional therapeutic agents. In some embodiments, the composition is administered after the one or more additional therapeutic agents. In some embodiments, the one or more additional agents includes a cytokine, such as IL-2, for example, to enhance persistence. In some embodiments, the methods comprise administration of a chemotherapeutic agent. In some embodiments, the methods do not comprise the administration of a chemotherapeutic agent.

In certain embodiments, the compositions may be administered to a subject in combination with an immune checkpoint antibody (e.g., an anti-PD1, anti-CTLA-4, or anti-PDL1 antibody). For example, viral vectors may be administered in combination with an antibody or antibody fragment targeting, for example, PD-1 (programmed death 1 protein). Examples of anti-PD-1 antibodies include, but are not limited to, pembrolizumab (KEYTRUDA®, formerly lambrolizumab, also known as MK-3475), and nivolumab (BMS-936558, MDX-1106, ONO-4538, OPDIVO®) or an antigen-binding fragment thereof. In certain embodiments, the compositions may be administered in combination with an anti-PD-L1 antibody or antigen-binding fragment thereof. Examples of anti-PD-L1 antibodies include, but are not limited to, BMS-936559, MPDL3280A (TECENTRIQ®, Atezolizumab), and MEDI4736 (Durvalumab, Imfinzi). In certain embodiments, the composition may be administered in combination with an anti-CTLA-4 antibody or antigen-binding fragment thereof. An example of an anti-CTLA-4 antibody includes, but is not limited to, Ipilimumab (trade name Yervoy). Other types of immune checkpoint modulators may also be used including, but not limited to, small molecules, siRNA, miRNA, and CRISPR systems. Immune checkpoint modulators may be administered before, after, or concurrently with the viral vector. In certain embodiments, combination treatment comprising an immune checkpoint modulator may increase the therapeutic efficacy of a therapy comprising a composition as provided herein. The other therapeutic can be administered simultaneously, before, or after the compositions provided herein are administered to the subject.

In certain embodiments, the subject is provided a secondary treatment. Secondary treatments include but are not limited to chemotherapy, radiation, surgery, and medications. In some embodiments, the subject is not provided a secondary treatment.

In some embodiments, the methods are performed without a lymphodepletion step, such as the administration of cyclophosphamide and/or fludarabine.

In some embodiments, the subject can be administered a conditioning therapy after the administration of the compositions to kill certain immune cells that are not transduced with the CAR encoded by the compositions. This can be done by including a selection marker that is encoded by the nucleic acid cargo of interest. In some embodiments, the conditioning therapy comprises administering an effective amount of cyclophosphamide to the subject. In some embodiments, the conditioning therapy comprises administering an effective amount of fludarabine to the subject. In some embodiments, the conditioning therapy comprises administering an effective amount of a combination of cyclophosphamide and fludarabine to the subject.

In some embodiments, a specific dosage regimen of the present disclosure includes a lymphodepletion step after the administration of the composition. In an exemplary embodiment, the lymphodepletion step includes administration of cyclophosphamide and/or fludarabine.

In some embodiments, the lymphodepletion step includes administration of cyclophosphamide at a dose of between about 200 mg/m2/day and about 2000 mg/m2/day (e.g., 200 mg/m2/day, 300 mg/m2/day, or 500 mg/m2/day). In an exemplary embodiment, the dose of cyclophosphamide is about 300 mg/m2/day. In some embodiments, the lymphodepletion step includes administration of fludarabine at a dose of between about 20 mg/m2/day and about 900 mg/m2/day (e.g., 20 mg/m2/day, 25 mg/m2/day, 30 mg/m2/day, or 60 mg/m2/day). In an exemplary embodiment, the dose of fludarabine is about 30 mg/m2/day.

In some embodiment, the lymphodepletion step includes administration of cyclophosphamide at a dose of between about 200 mg/m2/day and about 2000 mg/m2/day (e.g., 200 mg/m2/day, 300 mg/m2/day, or 500 mg/m2/day), and fludarabine at a dose of between about 20 mg/m2/day and about 900 mg/m2/day (e.g., 20 mg/m2/day, 25 mg/m2/day, 30 mg/m2/day, or 60 mg/m2/day). In an exemplary embodiment, the lymphodepletion step includes administration of cyclophosphamide at a dose of about 300 mg/m2/day, and fludarabine at a dose of about 30 mg/m2/day.

In an exemplary embodiment, the dosing of cyclophosphamide is 300 mg/m2/day over three days, and the dosing of fludarabine is 30 mg/m2/day over three days.

It is known in the art that one of the adverse effects of the use of CAR T cells can be the onset of immune activation, known as cytokine release syndrome (CRS). CRS is immune activation resulting in elevated inflammatory cytokines. CRS is a known on-target toxicity, development of which likely correlates with efficacy. Clinical and laboratory measures range from mild CRS (constitutional symptoms and/or grade-2 organ toxicity) to severe CRS (sCRS; grade ≥3 organ toxicity, aggressive clinical intervention, and/or potentially life threatening). Clinical features include: high fever, malaise, fatigue, myalgia, nausea, anorexia, tachycardia/hypotension, capillary leak, cardiac dysfunction, renal impairment, hepatic failure, and disseminated intravascular coagulation. Dramatic elevations of cytokines including interferon-gamma, granulocyte macrophage colony-stimulating factor, IL-10, and IL-6 have been shown following CAR T-cell infusion. One CRS signature is elevation of cytokines including IL-6 (severe elevation), IFN-gamma, TNF-alpha (moderate), and IL-2 (mild). Elevations in clinically available markers of inflammation including ferritin and C-reactive protein (CRP) have also been observed to correlate with the CRS syndrome. The presence of CRS generally correlates with expansion and progressive immune activation of adoptively transferred cells. It has been demonstrated that the degree of CRS severity is dictated by disease burden at the time of infusion as patients with high tumor burden experience a more sCRS.

Accordingly, in some embodiments, the methods comprise, following the diagnosis of CRS, appropriate CRS management strategies to mitigate the physiological symptoms of uncontrolled inflammation without dampening the antitumor efficacy of the in vivo generated cells (e.g., CAR T cells). CRS management strategies are known in the art. For example, systemic corticosteroids may be administered to rapidly reverse symptoms of sCRS (e.g., grade 3 CRS) without compromising initial antitumor response.

In some embodiments, an anti-IL-6R antibody may be administered. An example of an anti-IL-6R antibody is the Food and Drug Administration-approved monoclonal antibody tocilizumab, also known as atlizumab (marketed as Actemra, or RoActemra). Tocilizumab is a humanized monoclonal antibody against the interleukin-6 receptor (IL-6R). Administration of tocilizumab has demonstrated near-immediate reversal of CRS.

CRS is generally managed based on the severity of the observed syndrome and interventions are tailored as such. CRS management decisions may be based upon clinical signs and symptoms and response to interventions, not solely on laboratory values alone.

Mild to moderate cases generally are treated with symptom management with fluid therapy, non-steroidal anti-inflammatory drug (NSAID) and antihistamines as needed for adequate symptom relief More severe cases include patients with any degree of hemodynamic instability; with any hemodynamic instability, the administration of tocilizumab is recommended. The first-line management of CRS may be tocilizumab, in some embodiments, at the labeled dose of 8 mg/kg IV over 60 minutes (not to exceed 800 mg/dose); tocilizumab can be repeated Q8 hours. If suboptimal response to the first dose of tocilizumab, additional doses of tocilizumab may be considered. Tocilizumab can be administered alone or in combination with corticosteroid therapy. Patients with continued or progressive CRS symptoms, inadequate clinical improvement in 12-18 hours or poor response to tocilizumab, may be treated with high-dose corticosteroid therapy, generally hydrocortisone 100 mg IV or methylprednisolone 1-2 mg/kg. In patients with more severe hemodynamic instability or more severe respiratory symptoms, patients may be administered high-dose corticosteroid therapy early in the course of the CRS. CRS management guidance may be based on published standards (Lee et al. (2019) Biol Blood Marrow Transplant, doi.org/10.1016/j.bbmt.2018.12.758; Neelapu et al. (2018) Nat Rev Clin Oncology, 15:47; Teachey et al. (2016) Cancer Discov, 6(6):664-679).

Features consistent with Macrophage Activation Syndrome (MAS) or Hemophagocytic lymphohistiocytosis (HLH) have been observed in patients treated with CAR-T therapy (Henter, 2007), coincident with clinical manifestations of the CRS. MAS appears to be a reaction to immune activation that occurs from the CRS, and should therefore be considered a manifestation of CRS. MAS is similar to HLH (also a reaction to immune stimulation). The clinical syndrome of MAS is characterized by high grade non-remitting fever, cytopenias affecting at least two of three lineages, and hepatosplenomegaly. It is associated with high serum ferritin, soluble interleukin-2 receptor, and triglycerides, and a decrease of circulating natural killer (NK) activity.

In some embodiments, methods of treating cancer in a subject in need thereof are provided, the methods comprising administering to the subject any of the compositions, such as the viral particle(s), provided herein.

The compositions disclosed herein can comprise a pharmaceutical composition, and for example include a pharmaceutically acceptable carrier, and/or a pharmaceutical formulation.

The term "pharmaceutical formulation" refers to a preparation which is in such form as to permit the biological activity of an active ingredient contained therein to be effective, and which contains no additional components which are unacceptably toxic to a subject to which the formulation would be administered. A "pharmaceutically acceptable carrier" refers to an ingredient in a pharmaceutical formulation, other than an active ingredient, which is nontoxic to a subject. A pharmaceutically acceptable carrier includes, but is not limited to, a buffer, excipient, stabilizer, or preservative. In some aspects, the choice of carrier is determined in part by the particular cell and/or by the method of administration. Accordingly, there are a variety of suitable formulations. For example, the pharmaceutical composition can contain preservatives. Suitable preservatives may include, for example, methylparaben, propylparaben, sodium benzoate, and benzalkonium chloride. In some aspects, a mixture of two or more preservatives is used. The preservative or mixtures thereof are typically present in an amount of about 0.0001% to about 2% by weight of the total composition. Carriers are described, e.g., by Remington's Pharmaceutical Sciences 16th edition, Osol, A. Ed. (1980). Pharmaceutically acceptable carriers are generally nontoxic to recipients at the dosages and concentrations employed, and include, but are not limited to: buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as polyethylene glycol (PEG).

Buffering agents in some aspects are included in the compositions. Suitable buffering agents include, for example, citric acid, sodium citrate, phosphoric acid, potassium phosphate, and various other acids and salts. In some aspects, a mixture of two or more buffering agents is used. The buffering agent or mixtures thereof are typically present in an amount of about 0.001% to about 4% by weight of the total composition. Methods for preparing administrable pharmaceutical compositions are known. Exemplary methods are described in more detail in, for example, Remington: The Science and Practice of Pharmacy, Lippincott Williams & Wilkins; 21st ed. (May 1, 2005).

The formulations can include aqueous solutions. The formulation or composition may also contain more than one active ingredient useful for the particular indication, disease, or condition being treated with the composition, preferably those with activities complementary to the composition, where the respective activities do not adversely affect one another. Such active ingredients are suitably present in combination in amounts that are effective for the purpose intended. Thus, in some embodiments, the pharmaceutical composition further includes other pharmaceutically active agents or drugs, such as chemotherapeutic agents, e.g., asparaginase, busulfan, carboplatin, cisplatin, daunorubicin, doxorubicin, fluorouracil, gemcitabine, hydroxyurea, methotrexate, paclitaxel, rituximab, vinblastine, and/or vincristine. The pharmaceutical composition in some embodiments contains the composition in amounts effective to treat or prevent the disease or condition, such as a therapeutically effective or prophylactically effective amount. Therapeutic or prophylactic efficacy in some embodiments is monitored by periodic assessment of treated subjects. The desired dosage can be delivered by a single bolus administration of the composition, by multiple bolus administrations of the composition, or by continuous infusion administration of the composition. In some embodiments, the pharmaceutical composition does not include a chemotherapeutic.

Formulations include those for oral, intravenous, intraperitoneal, subcutaneous, pulmonary, transdermal, intramuscular, intranasal, buccal, sublingual, or suppository administration. In some embodiments, the composition is administered parenterally. The term "parenteral," as used herein, includes intravenous, intramuscular, subcutaneous, rectal, vaginal, and intraperitoneal administration. In some embodiments, the composition is administered to the subject using peripheral systemic delivery by intravenous, intraperitoneal, or subcutaneous injection. Compositions in some embodiments are provided as sterile liquid preparations, e.g., isotonic aqueous solutions, suspensions, emulsions, dispersions, or viscous compositions, which may in some aspects be buffered to a selected pH. Liquid preparations are normally easier to prepare than gels, other viscous compositions, and solid compositions. Additionally, liquid compositions are somewhat more convenient to administer, especially by injection. Viscous compositions, on the other hand, can be formulated within the appropriate viscosity range to provide longer contact periods with specific tissues. Liquid or viscous compositions can comprise carriers, which can be a solvent or dispersing medium containing, for example, water, saline, phosphate buffered saline, polyol (for example, glycerol, propylene glycol, liquid polyethylene glycol) and suitable mixtures thereof.

Sterile injectable solutions can be prepared by incorporating the composition in a solvent, such as in admixture with a suitable carrier, diluent, or excipient such as sterile water, physiological saline, glucose, dextrose, or the like. The compositions can contain auxiliary substances such as wetting, dispersing, or emulsifying agents (e.g., methylcellulose), pH buffering agents, gelling or viscosity enhancing additives, preservatives, flavoring agents, and/or colors, depending upon the route of administration and the preparation desired. Standard texts may in some aspects be consulted to prepare suitable preparations.

Various additives which enhance the stability and sterility of the compositions, including antimicrobial preservatives, antioxidants, chelating agents, and buffers, can be added. Prevention of the action of microorganisms can be ensured by various antibacterial and antifungal agents, for example, parabens, chlorobutanol, phenol, and sorbic acid. Prolonged absorption of the injectable pharmaceutical form can be brought about by the use of agents delaying absorption, for example, aluminum monostearate and gelatin.

The formulations to be used for in vivo administration are generally sterile. Sterility may be readily accomplished, e.g., by filtration through sterile filtration membranes.

The embodiments provided for herein can be used for many purposes, since the a pseudotyped virus capable of fusing with a target cell can be used to deliver a gene or other heterologous sequence of interest.

ENUMERATED EMBODIMENTS

In some embodiments, the following embodiments are provided:

1. A VSV-G polypeptide comprising a mutation that corresponds to a mutation at position 182 of SEQ ID NO: 2.

2. The VSV-G polypeptide of embodiment 1, wherein the protein comprises an amino acid sequence of SEQ ID NO: 2 with a mutation at position 182 and has at least 70% identity to SEQ ID NO: 2.

3. The VSV-G polypeptide of embodiments 1 or 2, wherein the polypeptide comprises a I182E or I182D mutation as compared to SEQ ID NO: 2.

4. The VSV-G polypeptide of any one of embodiments 1-3, wherein the polypeptide comprises an amino acid sequence of SEQ ID NO: 1 with a mutation at position 198 and at least 70% identity to SEQ ID NO: 2.

5. The VSV-G polypeptide of any one of embodiments 1-4, wherein the polypeptide comprises a mutation that corresponds to I182D or I182E as compared to a sequence of SEQ ID NO: 2.

6. The VSV-G polypeptide of any one of embodiments 1-5, wherein the polypeptide comprises an amino acid sequence at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% identical to an amino acid sequence of SEQ ID NO: 4.

7. The VSV-G polypeptide of any one of embodiments 1-5, wherein the polypeptide comprises a sequence of SEQ ID NO: 4.

8. The VSV-polypeptide of any one of embodiments 1-5, wherein the polypeptide comprises an amino acid sequence at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% identical to an amino acid sequence of SEQ ID NO: 5.

9. The VSV-G polypeptide of any one of embodiments 1-5, wherein the polypeptide comprises a sequence of SEQ ID NO: 5.

10. The VSV-G polypeptide of any one of embodiments 1-9, further comprising a mutation in the VSV-G protein that corresponds to a mutation as described in US 2020/0216502, which is hereby incorporated by reference in its entirety.

11. The VSV-G polypeptide of any one of embodiments 1-10, further comprising a mutation in the VSV-G protein that corresponds to a position of 8, 10, 47, 209 and/or 354 as compared to SEQ ID NO: 2.

12. The VSV-G polypeptide of any one of embodiments 1-11, further comprising a mutation that corresponds to position 8 in SEQ ID NO: 2, wherein the mutation is any amino acid different from the amino acid indicated at that position in SEQ ID NO: 2, except Y.

13. The VSV-G polypeptide of any one of embodiments 1-12, further comprising a mutation that corresponds to position 209 in SEQ ID NO: 2, wherein the mutation is any amino acid different from the amino acid indicated at that position in SEQ ID NO: 2, except H.

14. The VSV-G polypeptide of any one of embodiments 1-13, further comprising a mutation that corresponds to position 47 in SEQ ID NO: 2, wherein the mutation is any amino acid different from the amino acid indicated at that position in SEQ ID NO: 2, except K or R.

15. The VSV-G polypeptide of any one of embodiments 1-14, further comprising a mutation that corresponds to position 354 in SEQ IDNO: 2, wherein the mutation is any amino acid different from the amino acid indicated at that position in SEQ ID NO: 2, except K or R.

16. The VSV-G polypeptide of any one of embodiments 1-15, further comprising a mutation that corresponds to position 10 in SEQ ID NO: 2, wherein the mutation is any amino acid different from the amino acid indicated at that position in SEQ ID NO: 2, except Q or N.

17. The VSV-G polypeptide of any one of embodiments 1-16, wherein the protein comprises a substitution at position 47 or at position 354, or at both positions 47 and 354, wherein each position is, independently, substituted by A, G, F, Q, or N.

18. The VSV-G polypeptide of any one of embodiments 1-17, wherein the protein comprises a substitution at position 8, wherein the substitution is H8A, H8I, H8V, H8L, and the like.

19. The VSV-G polypeptide of any one of embodiments 1-18, wherein the protein comprises a substitution at position 47, wherein the substitution is K47Q or K47N.

20. The VSV-G polypeptide of any one of embodiments 1-19, wherein the protein comprises a substitution H8A and/or K47Q mutation.

21. The VSV-G polypeptide of any one of embodiments 1-20, wherein the protein comprises a substitution at position 10, such as Q10A, Q10R, or Q10K substitution.

22. The VSV-G polypeptide of any one of embodiments 1-21, further comprising a mutation that corresponds to a mutation at positions 214 and/or 352 of SEQ ID NO: 2.

23. The VSV-G polypeptide of embodiment 22, wherein the polypeptide comprises a T214N and/or T352A mutation.

24. A VSV-G polypeptide comprising a substitution at positions I182 and at least one of T214, and T352 of SEQ ID NO: 2.

25. The VSV-G polypeptide of embodiment 24, wherein the polypeptide comprises substitutions at positions I182, T214, and T352 of SEQ ID NO: 2.

26. The VSV-G polypeptide of embodiments 24 or 25, wherein the substitution at position 182 is I182D or I182E, the substitution at position 214 is T214N, and the substitution at position 352 is T352A.

27. The VSV-G polypeptide of any one of embodiments 24-26, wherein the polypeptide comprises a sequence of SEQ ID NO: 22, SEQ ID NO: 23, SEQ ID NO: 24 or SEQ ID NO: 25.

28. The VSV-G polypeptide of any one of embodiments 24-26, wherein the polypeptide comprises a sequence of SEQ ID NO: 22.

29. The VSV-G polypeptide of any one of embodiments 24-26, wherein the polypeptide comprises a sequence of SEQ ID NO: 23.

30. The VSV-G polypeptide of any one of embodiments 24-26, wherein the polypeptide comprises a sequence of SEQ ID NO: 24.

31. The VSV-G polypeptide of any one of embodiments 24-26, wherein the polypeptide comprises a sequence of SEQ ID NO: 25.

32. A nucleic acid molecule encoding the VSV-G polypeptide of any one of embodiments 1-31.

33. A vector comprising the nucleic acid molecule of embodiment 32.

34. A plasmid comprising the nucleic acid molecule of embodiment 32.

35. A viral particle comprising the polypeptide of any one of embodiments 1-31.

36. The viral particle of embodiment 35, further comprising a targeting moiety.

37. The viral particle of embodiments 35 or 36, wherein the viral particle is a pseudotyped lentivirus.

38. The viral particle of any one of embodiments 35-37, wherein the viral particle further comprises a nucleic acid molecule encoding a heterologous molecule of interest.

39. The viral particle of embodiment 38, wherein the heterologous molecule of interest is an siRNA, an shRNA, a non-coding RNA (e.g. a guide RNA for a CRISPR system), a peptide, a polypeptide, a protein, a viral payload, a viral genome, or a combination thereof.

40. The viral particle of embodiments 38 or 39, wherein the heterologous molecule of interest is a chimeric antigen receptor ("CAR").

41. The viral particle of any one of embodiments 35-40, wherein the targeting moiety binds to an immune cell, such as a T cell, B cell; NK cell, dendritic cell, neutrophils, macrophages, a cancer cell; or, for example, CD3+ T cell; CD4+ T cell; CD7+ T cell, CD8+ T cell; CD19+ B cell; CD19+ cancer cell; CD20+ B cell; "CD20+ cancer cell, CD30+ lung epithelial cell; CD34+ haematopoietic stem cell; CD105+ endothelial cell; CD105+ haematopoietic stem cell; CD117+ haematopoietic stem cell; CD133+ cancer cell; EpCAM+ cancer cell; GluA2+ neuron; GluA4+ neuron; Haematopoietic stem cell; Hepatocyte; Her2/Neu+ cancer cell; NKG2D+ natural killer cell; SLC1A3+ astrocyte; SLC7A10+ adipocyte.

42. The viral particle of any one of embodiments 35-41, wherein the targeting moiety binds to CD7, CD8, cKit (CD117), CD4, CD3, CD5, CD6, CD2, TCR alpha, TCR beta, TCR gamma, TCR delta, CD10, CD34, CD110, CD33, CD14, CD68, CCR7, CD62L, CD25, CCR2, CCR3, CCR4, CCR5, CCR6, CCR7, or CXCR3, A glycosylated CD43 epitope expressed on acute leukemia or lymphoma but not on hematopoietic progenitors; A glycosylated CD43 epitope expressed on non-hematopoietic cancers; A kinase anchor protein 4 (AKAP-4); Adrenoceptor beta 3 (ADRB3); AFP; Anaplastic lymphoma kinase (ALK); Androgen receptor; Angiopoietin-binding cell surface receptor 2 (Tie 2); Auto antibody to desmoglein 1 (Dsg1); Auto antibody to desmoglein 3 (Dsg3); B7H3 (CD276); Biotin; Bone marrow stromal cell antigen 2 (BST2); BST1/CD157; Cancer/testis antigen 1 (NY-ESO-1); Cancer/testis antigen 2 (LAGE-la); Carbonic anhydrase IX (CA1X); Carcinoembryonic antigen (CEA); CCCTC-Binding Factor (Zinc Finger Protein)-Like (BORIS or Brother of the Regulator of Imprinted Sites); CCR4; CD5; CD19; CD20; CD22; CD24; CD30; CD32 (FCGR2A); CD33; CD34; CD38; CD44v6; CD72; CD79a; CD79b; CD97; CD99; CD123; CD171; CD179a; CD179b-IGL11; CD200R; CD276/B7H3; CD300 molecule-like family member f (CD300LF); CDH1-CD324; CDH6; CDH17; CDH19; Chromosome X open reading frame 61 (CXORF61); Claudin 6 (CLDN6); Claudin18.2 (CLD18A2 or CLDN18A.2); CMV pp65; C-MYC epitope Tag; Cripto; CS1 (also referred to as CD2 subset 1 or CRACC or SLAMF7 or CD319 or 19A24); CSF2RA (GM-CSFR-alpha); C-type lectin domain family 12 member A (CLEC12A); C-type lectin-like molecule-1 (CLL-1 or CLECL1); Cyclin B1; Cytochrome P450 IB 1 (CYP1B 1); DLL3; EBV-EBNA3c; EGF-bke module-containing mucin-like hormone receptor-like 2 (EMR2); Elongation factor 2 mutated (ELF2M); Ephrin B2; Ephrin type-A receptor 2 (EphA2); Epidermal growth factor receptor (EGFR); Epidermal growth factor receptor variant III (EGFRviii); Epithelial cell adhesion molecule (EPCAM); ERG; ETS translocation-variant gene 6 located on chromosome 12p (ETV6-AML); Fc fragment of IgA receptor (FCAR or CD89); Fc receptor-like 5 (FCRL5); Fibroblast activation protein alpha (FAP); FITC; Fms Like Tyrosine Kinase 3 (FLT3); Folate receptor alpha (FRa or FR1); Folate receptor beta (FRb); Follicle stimulating hormone receptor (FSHR); Fos-related antigen 1; Fucosyl-GM1; G protein coupled receptor class C group 5 member D (GPRC5D); G protein-coupled receptor 20 (GPR20); GAD; Ganglioside G2 (GD2); Ganglioside GD3 (aNeu5Ac(2-8)aNeu5Ac(2-3)bDGalp(1-4)bDGlcp(1-1)Cer); Ganglioside GM3 (aNeu5Ac(2-3)bDClalp(1-4)bDGlcp(1-1)Cer); GD3; GFRalpha4; Glycoprotein 100 (gplOO); Glypican-3 (GPC3); Gonadotropin Hormone receptor (CGHR or GR); GpA33; GpNMB; GPRC5D; Guanylyl cyclase C (GCC); Heat shock protein 70-2 mutated (mut hsp70-2); Hepatitis A virus cellular receptor 1 (HAVCR1); Hexasaccharide portion of globoH glycoceramide (GloboH); High molecular weight-melanoma associated antigen (HMWMAA); HIVi envelope glycoprotein; HLA; HLA-DOA; HLA-A; HLA-A2; HLA-B; HLA-C; HLA-DM; HLA-DOB; HLA-DP; HLA-DQ; HLA-DR; HLA-G; HTLVl-Tax; Human papilloma virus E6 (HPV E6); Human papilloma virus E7 (HPV E7); Human Telomerase reverse transcriptase (hTERT); IgE; IL13Ra2; IL11Ra; Immunoglobulin lambda-like polypeptide 1 (IGLL1); Influenza A hemagglutinin (HA); Insulin-like growth factor 1 receptor (IGF-I receptor); Interleukin 11 receptor alpha (IL-llRa); Interleukin-13 receptor subunit alpha-2 (IL-13Ra2 or CD213A2); Intestinal carboxyl esterase; KIT (CD117); KSHV K8.1; KSHV-gH; LAMP1; Legumain; Leukocyte immunoglobulin-like receptor subfamily A member 2 (LILRA2); Leukocyte-associated immunoglobulin-like receptor 1 (LAIR1); Leutenizing hormone receptor (LHR); Lewis(Y) antigen; Lews Ag; Livl; Locus K 9 (LY6K); Low conductance chloride channel; Lymphocyte antigen 6 complex; Lymphocyte antigen 75 (LY75); Lymphocyte-specific protein tyrosine kinase (LCK); Mammary gland differentiation antigen (NY-BR-1); Melanoma antigen recognized by T cells 1 (MelanA or MARTI); Melanoma-associated antigen 1 (MAGE-A1); Melanoma cancer testis antigen-1 (MAD-CT-1); Melanoma cancer testis antigen-2 (MAD-CT-2); Melanoma inhibitor of apoptosis (ML-IAP); Mesothelin; MPL; Mucin 1 cell surface associated (MUC1); N-Acetyl glucosaminyl-transferase V (NA17); Nectin-4; Neural cell adhesion molecule (NCAM); NKG2D; NYBR1; O-acetyl-GD2 ganglioside (OAcGD2); Olfactory receptor 51E2 (OR51E2); Oncogene fusion protein consisting of breakpoint cluster region (BCR) and Abelson murine leukemia viral oncogene homolog 1 (Abl) (bcr-abl); P53 mutant; Paired box protein Pax-3 (PAX3); Paired box protein Pax-5 (PAX5); Pannexin 3 (PANX3); PDL1; P-glycoprotein; Placenta-specific 1 (PLAC1); Platelet-derived growth factor receptor beta (PDGFR-beta); Polysialic acid; Proacrosin binding protein sp32 (OY-TES1); Prostase; Prostate carcinoma tumor antigen-1 (PCT A-1 or Galectin 8); Prostate stem cell antigen (PSCA); Prostate-specific membrane antigen (PSMA); Prostatic acid phosphatase (PAP); Prostein; Protease Serine 21 (Testisin or PRSS21); Proteasome (Prosome Macropain) Subunit Beta Type 9 (LMP2); PTK7; Ras G12V; Ras Homolog Family Member C (RhoC); Rat sarcoma (Ras) mutant; Receptor for Advanced Glycation Endproducts (RAGE-1); Receptor tyrosine kinase-like orphan receptor 1 (ROR1); Receptor tyrosine-protein kinase ERBB2 or Her-22/neu; Renal ubiquitous 1 (RUi); Renal ubiquitous 2 (RU2); Sarcoma translocation breakpoints; Serine 2 (TMPRSS2) ETS fusion gene; Sialyl Lewis adhesion molecule (sLe); SLAMF4; SLAMF6; Slea (CA19.9 or Sialyl Lewis Antigen); Sperm protein 17 (SPA17); Squamous Cell Carcinoma Antigen Recognized By T Cells 3 (SART3); Stage-specific embryonic antigen-4 (SSEA-4); STEAPI; Survivin; Synovial sarcoma X breakpoint 2 (SSX2); TCR Gamma Alternate Reading Frame Protein (TARP); TCR-beta1 chain; TCR-beta2 chain; TCR-delta chain; TCR-gamma chain; TCRgamma-delta; Telomerase; TGFbetaR2; The antigen recognized by TNT antibody; Thyroid stimulating hormone receptor (TSHR); Timl-/HVCR1; Tissue Factor 1 (TF1); Tn ag; Tn antigen ((Tn Ag) or (GalNAca-Ser/Thr)); TNF receptor family member B cell maturation (BCMA); Transglutaminase 5 (TGS5); Transmembrane protease; TROP2; Tumor endothelial marker 1 (TEM1/CD248); Tumor endothelial marker 7-related (TEM7R); Tumor protein p53 (p53); Tumor-associated glycoprotein 72 (TAG72); Tyrosinase; Tyrosinase-related protein 2 (TRP-2); Uroplakin 2 (UPK2); Vascular endothelial growth factor receptor 2 (VEGFR2); V-myc avian myelocytomatosis viral oncogene neuroblastoma derived homolog (MYCN); Wilms tumor protein (WTi); or X Antigen Family Member 1A (XAGE1).

43. The viral particle of any one of embodiments 35-42, wherein the targeting moiety is an antibody, a scFv antibody, an antigen binding domain, an ankyrin repeat (e.g., DARPIN), a VHH domain antibody, a nanobody, single domain antibody, a FN3 domain, or any combination thereof.

44. The viral particle of any one of embodiments 35-43, wherein the targeting moiety is attached to the viral surface through
   an IgG Fc stalk;
   an envelope glycoprotein G or H of a virus of the Paramyxoviridae family, such as a morbillivirus, such as Measles virus, or a henipavirus, such as Nipah virus, Cedar virus, or Hendra virus;
   a glycoprotein of a virus of the Rhabdoviridae family, such as a vesicular stomatitis New Jersey virus, a vesicular stomatitis Indiana virus, a vesicular stomatitis Alagoas virus, a vesicular stomatitis Maraba virus, a vesicular stomatitis Carajas virus, Parainfluenza virus, *Spodoptera frugiperda* rhabdovirus isolate Sf G, *Drosophila obscura* sigmavirus 10A, Wuhan insect virus 7, Perch virus, or Spring viremia of carp virus;
   a glycoprotein of a virus of the Filoviridae family, such as Ebola virus; or
   a glycoprotein of a virus of the Arenaviridae family, such as Machupo virus.

45. The viral particle of embodiment 44, wherein the stalk comprises a transmembrane domain, such as, but not limited to a CD8 or CD28 transmembrane domain.

46. A method of delivering a heterologous molecule to a target cell, the method comprising contacting the cell with a viral vector comprising:
   a) the VSV-G protein of any one of embodiments 1-31;
   b) a targeting moiety that binds to the target cell; and
   c) a nucleic acid molecule encoding the heterologous molecule.

47. The method of embodiment 46, wherein the target cell is an immune cell, such as a T cell, B cell; NK cell, dendritic cell, neutrophils, macrophages, a cancer cell; or, for example, CD3+ T cell; CD4+ T cell; CD7+ T cell, CD8+ T cell; CD19+ B cell; CD19+ cancer cell; CD20+ B cell; CD30+ lung epithelial cell; CD34+ haematopoietic stem cell; CD105+ endothelial cell; CD105+ haematopoietic stem cell; CD117+ haematopoietic stem cell; CD133+ cancer cell; EpCAM+ cancer cell; GluA2+ neuron; GluA4+ neuron; Haematopoietic stem cell; Hepatocyte; Her2/Neu+ cancer cell; NKG2D+ natural killer cell; SLC1A3+ astrocyte; SLC7A10+ adipocyte.

48. The method of embodiments 46 or 47, wherein the targeting moiety binds to CD7, CD8, cKit (CD117), CD4, CD3, CD5, CD6, CD2, TCR alpha, TCR beta, TCR gamma, TCR delta, CD10, CD34, CD110, CD33, CD14, CD68, CCR7, CD62L, CD25, CCR2, CCR3, CCR4, CCR5, CCR6, CCR7, or CXCR3, A glycosylated CD43 epitope expressed on acute leukemia or lymphoma but not on hematopoietic progenitors; A glycosylated CD43 epitope expressed on non-hematopoietic cancers; A kinase anchor protein 4 (AKAP-4); Adrenoceptor beta 3 (ADRB3); AFP; Anaplastic lymphoma kinase (ALK); Androgen receptor; Angiopoietin-binding cell surface receptor 2 (Tie 2); Auto antibody to desmoglein 1 (Dsg1); Auto antibody to desmoglein 3 (Dsg3); B7H3 (CD276); Biotin; Bone marrow stromal cell antigen 2 (BST2); BST1/CD157; Cancer/testis antigen 1 (NY-ESO-1); Cancer/testis antigen 2 (LAGE-la); Carbonic anhydrase IX (CA1X); Carcinoembryonic antigen (CEA); CCCTC-Binding Factor (Zinc Finger Protein)-Like (BORIS or Brother of the Regulator of Imprinted Sites); CCR4; CD5; CD19; CD20; CD22; CD24; CD30; CD32 (FCGR2A); CD33; CD34; CD38; CD44v6; CD72; CD79a; CD79b; CD97; CD99; CD123; CD171; CD179a; CD179b-IGL11; CD200R; CD276/B7H3; CD300 molecule-like family member f (CD300LF); CDH1-CD324; CDH6; CDH17; CDH19; Chromosome X open reading frame 61 (CXORF61); Claudin 6 (CLDN6); Claudin18.2 (CLD18A2 or CLDN18A.2); CMV pp65; C-MYC epitope Tag; Cripto; CS1 (also referred to as CD2 subset 1 or CRACC or SLAMF7 or CD319 or 19A24); CSF2RA (GM-CSFR-alpha); C-type lectin domain family 12 member A (CLEC12A); C-type lectin-like molecule-1 (CLL-1 or CLECL1); Cyclin B1; Cytochrome P450 IB 1 (CYP1B 1); DLL3; EBV-EBNA3c; EGF-bke module-containing mucin-like hormone receptor-like 2 (EMR2); Elongation factor 2 mutated (ELF2M); Ephrin B2; Ephrin type-A receptor 2 (EphA2); Epidermal growth factor receptor (EGFR); Epidermal growth factor receptor variant III (EGFRviii); Epithelial cell adhesion molecule (EPCAM); ERG; ETS translocation-variant gene 6 located on chromosome 12p (ETV6-AML); Fc fragment of IgA receptor (FCAR or CD89); Fc receptor-like 5 (FCRL5); Fibroblast activation protein alpha (FAP); FITC; Fms Like Tyrosine Kinase 3 (FLT3); Folate receptor alpha (FRa or FR1); Folate receptor beta (FRb); Follicle stimulating hormone receptor (FSHR); Fos-related antigen 1; Fucosyl-GM1; G protein coupled receptor class C group 5 member D (GPRCSD); G protein-coupled receptor 20 (GPR20); GAD; Ganglioside G2 (GD2); Ganglioside GD3 (aNeu5Ac(2-8)aNeu5Ac(2-3)bDGalp(1-4)bDGlcp(1-1)Cer); Ganglioside GM3 (aNeu5Ac(2-3)bDClalp(1-4)bDGlcp(1-1)Cer); GD3; GFRalpha4; Glycoprotein 100 (gplOO); Glypican-3 (GPC3); Gonadotropin Hormone receptor (CGHR or GR); GpA33; GpNMB; GPRC5D; Guanylyl cyclase C (GCC); Heat shock protein 70-2 mutated (mut hsp70-2); Hepatitis A virus cellular receptor 1 (HAVCR1); Hexasaccharide portion of globoH glycoceramide (GloboH); High molecular weight-melanoma associated antigen (HMWMAA); HIVi envelope glycoprotein; HLA; HLA-DOA; HLA-A; HLA-A2; HLA-B; HLA-C; HLA-DM; HLA-DOB; HLA-DP; HLA-DQ; HLA-DR; HLA-G; HTLVl-Tax; Human papilloma virus E6 (HPV E6); Human papilloma virus E7 (HPV E7); Human Telomerase reverse transcriptase (hTERT); IgE; ILI3Ra2; IL11Ra; Immunoglobulin lambda-like polypeptide 1 (IGLL1); Influenza A hemagglutinin (HA); Insulin-like growth factor 1 receptor (IGF-I receptor); Interleukin 11 receptor alpha (IL-llRa); Interleukin-13 receptor subunit alpha-2 (IL-13Ra2 or CD213A2); Intestinal carboxyl esterase; KIT (CD117); KSHV K8.1; KSHV-gH; LAMP1; Legumain; Leukocyte immunoglobulin-like receptor subfamily A member 2 (LILRA2); Leukocyte-associated immunoglobulin-like receptor 1 (LAIR1); Leutenizing hormone receptor (LHR); Lewis(Y) antigen; Lews Ag; Livl; Locus K 9 (LY6K); Low conductance chloride channel; Lymphocyte antigen 6 complex; Lymphocyte antigen 75 (LY75); Lymphocyte-specific protein tyrosine kinase (LCK); Mammary gland differentiation antigen (NY-BR-1); Melanoma antigen recognized by T cells 1 (MelanA or MARTI); Melanoma-associated antigen 1 (MAGE-A1); Melanoma cancer testis antigen-1 (MAD-CT-1); Melanoma cancer testis antigen-2 (MAD-CT-2); Melanoma inhibitor of apoptosis (ML-IAP); Mesothelin; MPL; Mucin 1 cell surface associated (MUC1); N-Acetyl glucosaminyl-transferase V (NA17); Nectin-4; Neural cell adhesion molecule (NCAM); NKG2D; NYBR1; O-acetyl-GD2 ganglioside (OAcGD2); Olfactory receptor 51E2 (OR51E2); Oncogene fusion protein consisting of breakpoint cluster region (BCR) and Abelson murine leukemia viral oncogene homolog 1 (Abl) (bcr-abl); P53 mutant; Paired box protein Pax-3 (PAX3); Paired box protein Pax-5 (PAX5); Pannexin 3 (PANX3); PDL1; P-glycoprotein; Placenta-specific 1 (PLAC1); Platelet-derived growth factor receptor beta (PDGFR-beta); Polysialic acid; Proacrosin binding protein sp32 (OY-TES1); Prostase; Prostate carcinoma tumor antigen-1 (PCT A-1 or Galectin 8); Prostate stem cell antigen (PSCA); Prostate-specific membrane antigen (PSMA); Prostatic acid phosphatase (PAP); Prostein; Protease Serine 21 (Testisin or PRSS21); Proteasome (Prosome Macropain) Subunit Beta Type 9 (LMP2); PTK7; Ras G12V; Ras Homolog Family Member C (RhoC); Rat sarcoma (Ras) mutant; Receptor for Advanced Gly III cation Endproducts (RAGE-1); Receptor tyrosine kinase-like orphan receptor 1 (ROR1); Receptor tyrosine-protein kinase ERBB2 or Her-22/neu; Renal ubiquitous 1 (RUl); Renal ubiquitous 2 (RU2); Sarcoma translocation breakpoints; Serine 2 (TMPRSS2) ETS fusion gene; Sialyl Lewis adhesion molecule (sLe); SLAMF4; SLAMF6; Slea (CA19.9 or Sialyl Lewis Antigen); Sperm protein 17 (SPA17); Squamous Cell Carcinoma Antigen Recognized By T Cells 3 (SART3); Stage-specific embryonic antigen-4 (SSEA-4); STEAPI; Survivin; Synovial sarcoma X breakpoint 2 (SSX2); TCR Gamma Alternate Reading Frame Protein (TARP); TCR-beta1 chain; TCR-beta2 chain; TCR-delta chain; TCR-gamma chain; TCRgamma-delta; Telomerase; TGFbetaR2; The antigen recognized by TNT antibody; Thyroid stimulating hormone receptor (TSHR); Timl-/HVCR1; Tissue Factor 1 (TF1); Tn ag; Tn antigen ((Tn Ag) or (GalNAca-Ser/Thr)); TNF receptor family member B cell maturation (BCMA); Transglutaminase 5 (TGS5); Transmembrane protease; TROP2; Tumor endothelial marker 1 (TEM1/CD248); Tumor endothelial marker 7-related (TEM7R); Tumor protein p53 (p53); Tumor-associated glycoprotein 72 (TAG72); Tyrosinase; Tyrosinase-related protein 2 (TRP-2); Uroplakin 2 (UPK2); Vascular endothelial growth factor receptor 2 (VEGFR2); V-myc avian myelocytomatosis viral oncogene neuroblastoma derived homolog (MYCN); Wilms tumor protein (WT1); or X Antigen Family Member 1A (XAGE1) on the target cell.

49. A method of delivering a heterologous molecule to a target cell in a subject, the method comprising administering to the subject a viral vector comprising:

a) the VSV-G polypeptide of any one of embodiments 1-31;

b) a targeting moiety that binds to the target cell; and c) a nucleic acid molecule encoding the heterologous molecule.

50. The method of embodiment 49, wherein the target cell is an immune cell, such as a T cell, B cell; NK cell, dendritic cell, neutrophils, macrophages, a cancer cell; or, for example, CD3+ T cell; CD4+ T cell; CD7+ T cell, CD8+ T cell; CD19+ B cell; CD19+ cancer cell; CD20+ B cell; CD20+ cancer cell; CD30+ lung epithelial cell; CD34+ haematopoietic stem cell; CD105+ endothelial cell; CD105+ haematopoietic stem cell; CD117+ haematopoietic stem cell; CD133+ cancer cell; EpCAM+ cancer cell; GluA2+ neuron; GluA4+ neuron; Haematopoietic stem cell; Hepatocyte; Her2/Neu+ cancer cell; NKG2D+ natural killer cell; SLC1A3+ astrocyte; SLC7A10+ adipocyte.

51. The method of embodiments 49 or 50, wherein the targeting moiety binds to CD7, CD8, cKit (CD117), CD4, CD3, CD5, CD6, CD2, TCR alpha, TCR beta, TCR gamma, TCR delta, CD10, CD34, CD110, CD33, CD14, CD68, CCR7, CD62L, CD25, CCR2, CCR3, CCR4, CCR5, CCR6, CCR7, or CXCR3, A glycosylated CD43 epitope expressed on acute leukemia or lymphoma but not on hematopoietic progenitors; A glycosylated CD43 epitope expressed on non-hematopoietic cancers; A kinase anchor protein 4 (AKAP-4); Adrenoceptor beta 3 (ADRB3); AFP; Anaplastic lymphoma kinase (ALK); Androgen receptor; Angiopoietin-binding cell surface receptor 2 (Tie 2); Auto antibody to desmoglein 1 (Dsg1); Auto antibody to desmoglein 3 (Dsg3); B7H3 (CD276); Biotin; Bone marrow stromal cell antigen 2 (BST2); BST1/CD157; Cancer/testis antigen 1 (NY-ESO-1); Cancer/testis antigen 2 (LAGE-la); Carbonic anhydrase IX (CA1X); Carcinoembryonic antigen (CEA); CCCTC-Binding Factor (Zinc Finger Protein)-Like (BORIS or Brother of the Regulator of Imprinted Sites); CCR4; CD5; CD19; CD20; CD22; CD24; CD30; CD32 (FCGR2A); CD33; CD34; CD38; CD44v6; CD72; CD79a; CD79b; CD97; CD99; CD123; CD171; CD179a; CD179b-IGL11; CD200R; CD276/B7H3; CD300 molecule-like family member f (CD300LF); CDH1-CD324; CDH6; CDH17; CDH19; Chromosome X open reading frame 61 (CXORF61); Claudin 6 (CLDN6); Claudin18.2 (CLD18A2 or CLDN18A.2); CMV pp65; C-MYC epitope Tag; Cripto; CS1 (also referred to as CD2 subset 1 or CRACC or SLAMF7 or CD319 or 19A24); CSF2RA (GM-CSFR-alpha); C-type lectin domain family 12 member A (CLEC12A); C-type lectin-like molecule-1 (CLL-1 or CLECL1); Cyclin B1; Cytochrome P450 IB 1 (CYP1B 1); DLL3; EBV-EBNA3c; EGF-bke module-containing mucin-like hormone receptor-like 2 (EMR2); Elongation factor 2 mutated (ELF2M); Ephrin B2; Ephrin type-A receptor 2 (EphA2); Epidermal growth factor receptor (EGFR); Epidermal growth factor receptor variant III (EGFRviii); Epithelial cell adhesion molecule (EPCAM); ERG; ETS translocation-variant gene 6 located on chromosome 12p (ETV6-AML); Fc fragment of IgA receptor (FCAR or CD89); Fc receptor-like 5 (FCRL5); Fibroblast activation protein alpha (FAP); FITC; Fms Like Tyrosine Kinase 3 (FLT3); Folate receptor alpha (FRa or FR1); Folate receptor beta (FRb); Follicle stimulating hormone receptor (FSHR); Fos-related antigen 1; Fucosyl-GM1; G protein coupled receptor class C group 5 member D (GPRCSD); G protein-coupled receptor 20 (GPR20); GAD; Ganglioside G2 (GD2); Ganglioside GD3 (aNeu5Ac(2-8)aNeu5Ac(2-3) bDGalp(1-4)bDGlcp(1-1)Cer); Ganglioside GM3 (aNeu5Ac(2-3)bDClalp(1-4)bDGlcp(1-1)Cer); GD3; GFRalpha4; Glycoprotein 100 (gplOO); Glypican-3 (GPC3); Gonadotropin Hormone receptor (CGHR or GR); GpA33; GpNMB; GPRC5D; Guanylyl cyclase C (GCC); Heat shock protein 70-2 mutated (mut hsp70-2); Hepatitis A virus cellular receptor 1 (HAVCR1); Hexasaccharide portion of globoH glycoceramide (GloboH); High molecular weight-melanoma associated antigen (HMWMAA); HIVi envelope glycoprotein; HLA; HLA-DOA; HLA-A; HLA-A2; HLA-B; HLA-C; HLA-DM; HLA-DOB; HLA-DP; HLA-DQ; HLA-DR; HLA-G; HTLVl-Tax; Human papilloma virus E6 (HPV E6); Human papilloma virus E7 (HPV E7); Human Telomerase reverse transcriptase (hTERT); IgE; ILI3Ra2; IL11Ra; Immunoglobulin lambda-like polypeptide 1 (IGLL1); Influenza A hemagglutinin (HA); Insulin-like growth factor 1 receptor (IGF-I receptor); Interleukin 11 receptor alpha (IL-llRa); Interleukin-13 receptor subunit alpha-2 (IL-13Ra2 or CD213A2); Intestinal carboxyl esterase; KIT (CD117); KSHV K8.1; KSHV-gH; LAMP1; Legumain; Leukocyte immunoglobulin-like receptor subfamily A member 2 (LILRA2); Leukocyte-associated immunoglobulin-like receptor 1 (LAIR1); Leutenizing hormone receptor (LHR); Lewis(Y) antigen; Lews Ag; Livl; Locus K 9 (LY6K); Low conductance chloride channel; Lymphocyte antigen 6 complex; Lymphocyte antigen 75 (LY75); Lymphocyte-specific protein tyrosine kinase (LCK); Mammary gland differentiation antigen (NY-BR-1); Melanoma antigen recognized by T cells 1 (MelanA or MARTI); Melanoma-associated antigen 1 (MAGE-A1); Melanoma cancer testis antigen-1 (MAD-CT-1); Melanoma cancer testis antigen-2 (MAD-CT-2); Melanoma inhibitor of apoptosis (ML-IAP); Mesothelin; MPL; Mucin 1 cell surface associated (MUC1); N-Acetyl glucosaminyl-transferase V (NA17); Nectin-4; Neural cell adhesion molecule (NCAM); NKG2D; NYBR1; O-acetyl-GD2 ganglioside (OAcGD2); Olfactory receptor 51E2 (OR51E2); Oncogene fusion protein consisting of breakpoint cluster region (BCR) and Abelson murine leukemia viral oncogene homolog 1 (Abl) (bcr-abl); P53 mutant; Paired box protein Pax-3 (PAX3); Paired box protein Pax-5 (PAX5); Pannexin 3 (PANX3); PDL1; P-glycoprotein; Placenta-specific 1 (PLAC1); Platelet-derived growth factor receptor beta (PDGFR-beta); Polysialic acid; Proacrosin binding protein sp32 (OY-TES1); Prostase; Prostate carcinoma tumor antigen-1 (PCT A-1 or Galectin 8); Prostate stem cell antigen (PSCA); Prostate-specific membrane antigen (PSMA); Prostatic acid phosphatase (PAP); Prostein; Protease Serine 21 (Testisin or PRSS21); Proteasome (Prosome Macropain) Subunit Beta Type 9 (LMP2); PTK7; Ras G12V; Ras Homolog Family Member C (RhoC); Rat sarcoma (Ras) mutant; Receptor for Advanced Glycation Endproducts (RAGE-1); Receptor tyrosine kinase-like orphan receptor 1 (ROR1); Receptor tyrosine-protein kinase ERBB2 or Her-22/neu; Renal ubiquitous 1 (RUl); Renal ubiquitous 2 (RU2); Sarcoma translocation breakpoints; Serine 2 (TMPRSS2) ETS fusion gene; Sialyl Lewis adhesion molecule (sLe); SLAMF4; SLAMF6; Slea (CA19.9 or Sialyl Lewis Antigen); Sperm protein 17 (SPA17); Squamous Cell Carcinoma Antigen Recognized By T Cells 3 (SART3); Stage-specific embryonic antigen-4 (SSEA-4); STEAPI; Survivin; Synovial sarcoma X breakpoint 2 (SSX2); TCR Gamma Alternate Reading Frame Protein (TARP); TCR-beta1 chain; TCR-beta2 chain; TCR-delta chain; TCR-gamma chain; TCRgamma-delta; Telomerase; TGFbetaR2; The antigen recognized by TNT antibody; Thyroid stimulating hormone receptor (TSHR); Timl-/HVCR1; Tissue Factor 1 (TF1); Tn ag; Tn antigen ((Tn Ag) or (GalNAca-Ser/Thr)); TNF receptor family member B cell maturation (BCMA); Transglutaminase 5 (TGS5); Transmembrane protease; TROP2; Tumor endothelial marker 1 (TEM1/CD248); Tumor endothelial marker 7-related (TEM7R); Tumor protein p53 (p53); Tumor-associated glycoprotein 72 (TAG72); Tyrosinase; Tyrosinase-related protein 2 (TRP-2); Uroplakin 2 (UPK2); Vascular endothelial growth factor receptor 2 (VEGFR2); V-myc avian myelocytomatosis viral oncogene neuroblastoma derived homolog (MYCN); Wilms tumor protein (WT1); or X Antigen Family Member 1A (XAGE1) on the target cell.

52. The method of any one of embodiments 46-51, wherein the heterologous molecule is an siRNA, an shRNA, a non-coding RNA (e.g. a guide RNA for a CRISPR system), a peptide, a polypeptide, a protein, a viral payload, a viral genome, or a combination thereof, such as a chimeric antigen receptor ("CAR").

53. A method of treating cancer in a subject, the method comprising administering to the subject a viral vector comprising:
   a) the VSV-G polypeptide of any one of embodiments 1-31;
   b) a targeting moiety that binds to the target cell; and
   c) a nucleic acid molecule encoding the heterologous molecule.

54. The method of embodiment 53, wherein the heterologous molecule is a chimeric antigen receptor.

55. The method of embodiments 53 or 54, wherein the target cell is an immune cell, such as a T cell, B cell; NK cell, dendritic cell, neutrophils, macrophages, a cancer cell; or, for example, CD3+ T cell; CD4+ T cell; CD7+ T cell, CD8+ T cell; CD19+ B cell; CD19+ cancer cell; CD20+B cell; CD30+ lung epithelial cell; CD34+ haematopoietic stem cell; CD105+ endothelial cell; CD105+ haematopoietic stem cell; CD117+ haematopoietic stem cell; CD133+ cancer cell; EpCAM+ cancer cell; GluA2+ neuron; GluA4+ neuron; Haematopoietic stem cell; Hepatocyte; Her2/Neu+ cancer cell; NKG2D+ natural killer cell; SLC1A3+ astrocyte; SLC7A10+ adipocyte.

56. The method of any one of embodiments 53-55, wherein the targeting moiety binds to CD7, CD8, cKit (CD117), CD4, CD3, CD5, CD6, CD2, TCR alpha, TCR beta, TCR gamma, TCR delta, CD10, CD34, CD110, CD33, CD14, CD68, CCR7, CD62L, CD25, CCR2, CCR3, CCR4, CCR5, CCR6, CCR7, or CXCR3, A glycosylated CD43 epitope expressed on acute leukemia or lymphoma but not on hematopoietic progenitors; A glycosylated CD43 epitope expressed on non-hematopoietic cancers; A kinase anchor protein 4 (AKAP-4); Adrenoceptor beta 3 (ADRB3); AFP; Anaplastic lymphoma kinase (ALK); Androgen receptor; Angiopoietin-binding cell surface receptor 2 (Tie 2); Auto antibody to desmoglein 1 (Dsg1); Auto antibody to desmoglein 3 (Dsg3); B7H3 (CD276); Biotin; Bone marrow stromal cell antigen 2 (BST2); BST1/CD157; Cancer/testis antigen 1 (NY-ESO-1); Cancer/testis antigen 2 (LAGE-la); Carbonic anhydrase IX (CA1X); Carcinoembryonic antigen (CEA); CCCTC-Binding Factor (Zinc Finger Protein)-Like (BORIS or Brother of the Regulator of Imprinted Sites); CCR4; CD5; CD19; CD20; CD22; CD24; CD30; CD32 (FCGR2A); CD33; CD34; CD38; CD44v6; CD72; CD79a; CD79b; CD97; CD99; CD123; CD171; CD179a; CD179b-IGL11; CD200R; CD276/B7H3; CD300 molecule-like family member f (CD300LF); CDH1-CD324; CDH6; CDH17; CDH19; Chromosome X open reading frame 61 (CXORF61); Claudin 6 (CLDN6); Claudin18.2 (CLD18A2 or CLDN18A.2); CMV pp65; C-MYC epitope Tag; Cripto; CS1 (also referred to as CD2 subset 1 or CRACC or SLAMF7 or CD319 or 19A24); CSF2RA (GM-CSFR-alpha); C-type lectin domain family 12 member A (CLEC12A); C-type lectin-like molecule-1 (CLL-1 or CLECL1); Cyclin B1; Cytochrome P450 IB 1 (CYP1B 1); DLL3; EBV-EBNA3c; EGF-bke module-containing mucin-like hormone receptor-like 2 (EMR2); Elongation factor 2 mutated (ELF2M); Ephrin B2; Ephrin type-A receptor 2 (EphA2); Epidermal growth factor receptor (EGFR); Epidermal growth factor receptor variant III (EGFRviii); Epithelial cell adhesion molecule (EPCAM); ERG; ETS translocation-variant gene 6 located on chromosome 12p (ETV6-AML); Fc fragment of IgA receptor (FCAR or CD89); Fc receptor-like 5 (FCRL5); Fibroblast activation protein alpha (FAP); FITC; Fms Like Tyrosine Kinase 3 (FLT3); Folate receptor alpha (FRa or FR1); Folate receptor beta (FRb); Follicle stimulating hormone receptor (FSHR); Fos-related antigen 1; Fucosyl-GM1; G protein coupled receptor class C group 5 member D (GPRC5D); G protein-coupled receptor 20 (GPR20); GAD; Ganglioside G2 (GD2); Ganglioside GD3 (aNeu5Ac(2-8)aNeu5Ac(2-3)bDGalp(1-4)bDGlcp(1-1)Cer); Ganglioside GM3 (aNeu5Ac(2-3)bDClalp(1-4)bDGlcp(1-1)Cer); GD3; GFRalpha4; Glycoprotein 100 (gplOO); Glypican-3 (GPC3); Gonadotropin Hormone receptor (CGHR or GR); GpA33; GpNMB; GPRC5D; Guanylyl cyclase C (GCC); Heat shock protein 70-2 mutated (mut hsp70-2); Hepatitis A virus cellular receptor 1 (HAVCR1); Hexasaccharide portion of globoH glycoceramide (GloboH); High molecular weight-melanoma associated antigen (HMWMAA); HIVi envelope glycoprotein; HLA; HLA-DOA; HLA-A; HLA-A2; HLA-B; HLA-C; HLA-DM; HLA-DOB; HLA-DP; HLA-DQ; HLA-DR; HLA-G; HTLVl-Tax; Human papilloma virus E6 (HPV E6); Human papilloma virus E7 (HPV E7); Human Telomerase reverse transcriptase (hTERT); IgE; IL13Ra2; IL11Ra; Immunoglobulin lambda-like polypeptide 1 (IGLL1); Influenza A hemagglutinin (HA); Insulin-like growth factor 1 receptor (IGF-I receptor); Interleukin 11 receptor alpha (IL-llRa); Interleukin-13 receptor subunit alpha-2 (IL-13Ra2 or CD213A2); Intestinal carboxyl esterase; KIT (CD117); KSHV K8.1; KSHV-gH; LAMP1; Legumain; Leukocyte immunoglobulin-like receptor subfamily A member 2 (LILRA2); Leukocyte-associated immunoglobulin-like receptor 1 (LAIR1); Leutenizing hormone receptor (LHR); Lewis(Y) antigen; Lews Ag; Livl; Locus K 9 (LY6K); Low conductance chloride channel; Lymphocyte antigen 6 complex; Lymphocyte antigen 75 (LY75); Lymphocyte-specific protein tyrosine kinase (LCK); Mammary gland differentiation antigen (NY-BR-1); Melanoma antigen recognized by T cells 1 (MelanA or MARTI); Melanoma-associated antigen 1 (MAGE-A1); Melanoma cancer testis antigen-1 (MAD-CT-1); Melanoma cancer testis antigen-2 (MAD-CT-2); Melanoma inhibitor of apoptosis (ML-IAP); Mesothelin; MPL; Mucin 1 cell surface associated (MUC1); N-Acetyl glucosaminyl-transferase V (NA17); Nectin-4; Neural cell adhesion molecule (NCAM); NKG2D; NYBR1; O-acetyl-GD2 ganglioside (OAcGD2); Olfactory receptor 51E2 (OR51E2); Oncogene fusion protein consisting of breakpoint cluster region (BCR) and Abelson murine leukemia viral oncogene homolog 1 (Abl) (bcr-abl); P53 mutant; Paired box protein Pax-3 (PAX3); Paired box protein Pax-5 (PAX5); Pannexin 3 (PANX3); PDL1; P-glycoprotein; Placenta-specific 1 (PLAC1); Platelet-derived growth factor receptor beta (PDGFR-beta); Polysialic acid; Proacrosin binding protein sp32 (OY-TES1); Prostase; Prostate carcinoma tumor antigen-1 (PCT A-1 or Galectin 8); Prostate stem cell antigen (PSCA); Prostate-specific membrane antigen (PSMA); Prostatic acid phosphatase (PAP); Prostein; Protease Serine 21 (Testisin or PRSS21); Proteasome (Prosome Macropain) Subunit Beta Type 9 (LMP2); PTK7; Ras G12V; Ras Homolog Family Member C (RhoC); Rat sarcoma (Ras) mutant; Receptor for Advanced Glycation Endproducts (RAGE-1); Receptor tyrosine kinase-like orphan receptor 1 (ROR1); Receptor tyrosine-protein kinase ERBB2 or Her-22/neu; Renal ubiquitous 1 (RUi); Renal ubiquitous 2 (RU2); Sarcoma translocation breakpoints; Serine 2 (TMPRSS2) ETS fusion gene; Sialyl Lewis adhesion molecule (sLe); SLAMF4; SLAMF6; Slea (CA19.9 or Sialyl Lewis Antigen); Sperm protein 17 (SPA17); Squamous Cell Carcinoma Antigen Recognized By T Cells 3 (SART3); Stage-specific embryonic antigen-4 (SSEA-4); STEAPI; Survivin; Synovial sarcoma X breakpoint 2 (SSX2); TCR Gamma Alternate Reading Frame Protein (TARP); TCR-beta1 chain; TCR-beta2 chain; TCR-delta chain; TCR-gamma chain; TCRgamma-delta; Telomerase; TGFbetaR2; The antigen recognized by TNT antibody; Thyroid stimulating hormone receptor (TSHR); Timl-/HVCR1; Tissue Factor 1 (TF1); Tn ag; Tn antigen ((Tn Ag) or (GalNAca-Ser/Thr)); TNF receptor family member B cell maturation (BCMA); Transglutaminase 5 (TGS5); Transmembrane protease; TROP2; Tumor endothelial marker 1 (TEM1/CD248); Tumor endothelial marker 7-related (TEM7R); Tumor protein p53 (p53); Tumor-associated glycoprotein 72 (TAG72); Tyrosinase; Tyrosinase-related protein 2 (TRP-2); Uroplakin 2 (UPK2); Vascular endothelial growth factor receptor 2 (VEGFR2); V-myc avian myelocytomatosis viral oncogene neuroblastoma derived homolog (MYCN); Wilms tumor protein (WTi); or X Antigen Family Member 1A (XAGEi) on the target cell.

57. The method of any one of embodiments 53-56, wherein the cancer is a cancer as provided for herein, such as a T cell or B cell disorder.

58. The viral particle of any one of embodiments 35-45, wherein the targeting moiety binds to CD7.

59. The viral particle of embodiment 58, wherein the targeting moiety that binds to CD7 comprises a polypeptide comprising: (i) a heavy chain variable region comprising heavy chain CDR1, CDR2, and CDR3 sequences, wherein the heavy chain CDR1 sequence has the amino acid sequence of SEQ ID NO: 35; the heavy chain CDR2 has the amino acid sequence of SEQ ID NO: 36; and the heavy chain CDR3 sequence has the amino acid sequence of SEQ ID NO: 37, or variants of any of the foregoing; and (ii) a light chain variable region comprising light chain CDR1, CDR2, and CDR3 sequences, wherein the light chain CDR1 sequence has the amino acid sequence of SEQ ID NO: 38; the light chain CDR2 sequence has the amino acid sequence of SEQ ID NO: 39; and the light chain CDR3 sequence has the amino acid sequence of SEQ ID NO: 40; or variants of any of the foregoing.

60. The viral particle of embodiment 59, wherein the heavy chain comprises a heavy chain variable region having at least 90% sequence identity to SEQ ID NO: 47, wherein the polypeptide maintains the sequences of HCDR1 as set forth in SEQ ID NO: 35; HCDR2 as set forth in SEQ ID NO: 36; and HCDR3 as set forth in SEQ ID NO: 37.

61. The viral particle of embodiments 59 and 60, wherein the light chain comprises: a light chain variable region having at least 90% sequence identity to SEQ ID NO: 48, wherein the polypeptide maintains the sequences of LCDR1 as set forth in SEQ ID NO: 38; LCDR2 as set forth in SEQ ID NO: 39; and LCDR3 as set forth in SEQ ID NO: 40.

62. The viral particle of any one of embodiments 59-61, wherein the polypeptide comprises a heavy chain and a light chain comprising: a heavy chain variable region of the heavy chain having at least 90% sequence identity to SEQ ID NO: 47, and a light chain variable region of the light chain having at least 90% sequence identity to SEQ ID NO: 48, wherein polypeptide maintains the sequences of HCDR1 as set forth in SEQ ID NO: 35; HCDR2 as set forth in SEQ ID NO: 36; HCDR3 as set forth in SEQ ID NO: 37; LCDR1 as set forth in SEQ ID NO: 38; LCD2 as set forth in SEQ ID NO: 39; and LCDR3 as set forth in SEQ ID NO: 40.

63. The viral particle of any one of embodiments 59-62, wherein the light chain and a heavy chain comprise: a heavy chain variable region of the heavy chain having at least 90% sequence identity to SEQ ID NO: 47; and a light chain variable region of the light chain having at least 90% sequence identity to SEQ ID NO: 48.

64. The viral particle of any one of embodiments 59-63, wherein the light chain and a heavy chain comprise: a heavy chain variable region of the heavy chain having at least 95% sequence identity to SEQ ID NO: 47; and a light chain variable region of the light chain having at least 95% sequence identity to SEQ ID NO: 48.

65. The viral particle of any one of embodiments 59-64, wherein the light chain and a heavy chain comprise: a heavy chain variable region of the heavy chain having at least 99% sequence identity to SEQ ID NO: 47; and a light chain variable region of the light chain having at least 99% sequence identity to SEQ ID NO: 48.

66. The viral particle of any one of embodiments 59-65, wherein the light chain and a heavy chain comprise: a heavy chain variable region comprising SEQ ID NO: 47, and a light chain variable region comprising SEQ ID NO: 48.

67. The viral particle of any one of embodiments 59-66, wherein the heavy chain variable region and the light chain variable region are, or are not, linked by a linker, such as a peptide linker, which can be for example, a glycine/serine linker.

68. The viral particle of embodiment 67, wherein the peptide linker comprises a sequence of (GGGGS)n (SEQ ID NO: 49), wherein n is independently 1-5.

69. The viral particle of any one of embodiments 58-68, wherein the targeting moiety that binds to CD7 comprises a polypeptide comprising a sequence having at least 90% sequence identity to SEQ ID NO: 51, at least 95% sequence identity to SEQ ID NO: 51, at least 99% sequence identity to SEQ ID NO: 51, or a sequence as set forth in SEQ ID NO: 51.

70. The viral particle of any one of embodiments 58-68, wherein the targeting moiety that binds to CD7 comprises a polypeptide comprising a sequence having at least 90% sequence identity to SEQ ID NO: 52, having at least 95% sequence identity to SEQ ID NO: 52, having at least 99% sequence identity to SEQ ID NO: 52, or a sequence as set forth in SEQ ID NO: 52.

71. The viral particle of any one of embodiments 35-45, wherein the targeting moiety binds to CD8.

72. The viral particle of embodiment 71, wherein the targeting moiety comprises a polypeptide that comprises: a heavy chain variable region comprising heavy chain CDR1, CDR2, and CDR3 sequences, wherein the heavy chain CDR1 sequence has the amino acid sequence of SEQ ID NO: 55; the heavy chain CDR2 has the amino acid sequence of SEQ ID NO: 56; and the heavy chain CDR3 sequence has the amino acid sequence of SEQ ID NO: 57, or variants of any of the foregoing; and (ii) a light chain variable region comprising light chain CDR1, CDR2, and CDR3 sequences, wherein the light chain CDR1 sequence has the amino acid sequence of SEQ ID NO: 58; the light chain CDR2 sequence has the amino acid sequence of SEQ ID NO: 59; and the light chain CDR3 sequence has the amino acid sequence of SEQ ID NO: 60; or variants of any of the foregoing.

73. The viral particle of embodiment 72, wherein the targeting moiety comprises a heavy chain that comprises a heavy chain variable region having at least 90% sequence identity to SEQ ID NO: 67, wherein the polypeptide maintains the sequences of HCDR1 as set forth in SEQ ID NO: 55; HCDR2 as set forth in SEQ ID NO: 56; and HCDR3 as set forth in SEQ ID NO: 57.

74. The viral particle of embodiment 72 or 73, wherein the CD8 targeting moiety comprises a light chain that comprises a light chain variable region having at least 90% sequence identity to SEQ ID NO: 68, wherein the polypeptide maintains the sequences of LCDR1 as set forth in SEQ ID NO: 58; LCDR2 as set forth in SEQ ID NO: 59; and LCDR3 as set forth in SEQ ID NO: 60.

75. The viral particle of any one of embodiments 72-74, wherein the CD8 targeting moiety comprises a polypeptide comprising a heavy chain and a light chain comprising: a heavy chain variable region of the heavy chain having at least 90% sequence identity to SEQ ID NO: 67, and a light chain variable region of the light chain having at least 90% sequence identity to SEQ ID NO: 68, wherein polypeptide maintains the sequences of HCDR1 as set forth in SEQ ID NO: 55; HCDR2 as set forth in SEQ ID NO: 56; HCDR3 as set forth in SEQ ID NO: 57; LCDR1 as set forth in SEQ ID NO: 58; LCD2 as set forth in SEQ ID NO: 59; and LCDR3 as set forth in SEQ ID NO: 60.

76. The viral particle of any one of embodiments 72-75, wherein the CD8 targeting moiety comprises a polypeptide comprising a light chain and a heavy chain comprising: a heavy chain variable region of the heavy chain having at least 90% sequence identity to SEQ ID NO: 67; and a light chain variable region of the light chain having at least 90% sequence identity to SEQ ID NO: 68.

77. The viral particle of any one of embodiments 72-75, wherein the CD8 targeting moiety comprises a polypeptide comprising a light chain and a heavy chain comprising: a heavy chain variable region of the heavy chain having at least 95% sequence identity to SEQ ID NO: 67; and a light chain variable region of the light chain having at least 95% sequence identity to SEQ ID NO: 68.

78. The viral particle of any one of embodiments 72-75, wherein the CD8 targeting moiety comprises a polypeptide comprising a light chain and a heavy chain comprising: a heavy chain variable region of the heavy chain having at least 99% sequence identity to SEQ ID NO: 67; and a light chain variable region of the light chain having at least 99% sequence identity to SEQ ID NO: 68.

79. The viral particle of embodiment 71, wherein the CD8 targeting moiety comprises a polypeptide comprising a light chain and a heavy chain comprising: wherein the heavy chain variable region comprises SEQ ID NO: 67, and the light chain variable region comprises SEQ ID NO: 68.

80. The viral particle of any one of embodiments 72-79, wherein the heavy chain variable region and the light chain variable region are, or are not, linked by a linker, such as a peptide linker.

81. The viral particle of embodiment 80, wherein the peptide linker is a glycine/serine linker.

82. The viral particle of embodiments 80 or 81, wherein the peptide linker comprises a sequence of (GGGGS)$_n$ (SEQ ID NO: 49), wherein each n is independently 1-5.

83. The viral particle of any one of embodiments 71-82, wherein the targeting moiety that binds to CD8 comprises a polypeptide comprising a sequence having at least 90% sequence identity to SEQ ID NO: 69, at least 95% sequence identity to SEQ ID NO: 69, at least 99% sequence identity to SEQ ID NO: 69, or a sequence as set forth in SEQ ID NO: 69.

84. The viral particle of any one of embodiments 71-82, wherein the targeting moiety that binds to CD8 comprises a polypeptide comprising a sequence having at least 90% sequence identity to SEQ ID NO: 70, having at least 95% sequence identity to SEQ ID NO: 70, having at least 99% sequence identity to SEQ ID NO: 70, or a sequence as set forth in SEQ ID NO: 70.

85. The method of any one of embodiments 46-57, wherein the targeting moiety that binds to the target cell binds to CD7.

86. The method of embodiment 85, wherein the targeting moiety comprises a polypeptide comprising: (i) a heavy chain variable region comprising heavy chain CDR1, CDR2, and CDR3 sequences, wherein the heavy chain CDR1 sequence has the amino acid sequence of SEQ ID NO: 35; the heavy chain CDR2 has the amino acid sequence of SEQ ID NO: 36; and the heavy chain CDR3 sequence has the amino acid sequence of SEQ ID NO: 37, or variants of any of the foregoing; and (ii) a light chain variable region comprising light chain CDR1, CDR2, and CDR3 sequences, wherein the light chain CDR1 sequence has the amino acid sequence of SEQ ID NO: 38; the light chain CDR2 sequence has the amino acid sequence of SEQ ID NO: 39; and the light chain CDR3 sequence has the amino acid sequence of SEQ ID NO: 40; or variants of any of the foregoing.

87. The method of embodiment 86, wherein the heavy chain comprises a heavy chain variable region having at least 90% sequence identity to SEQ ID NO: 47, wherein the polypeptide maintains the sequences of HCDR1 as set forth in SEQ ID NO: 35; HCDR2 as set forth in SEQ ID NO: 36; and HCDR3 as set forth in SEQ ID NO: 37.

88. The method of embodiments 86 and 87, wherein the light chain comprises: a light chain variable region having at least 90% sequence identity to SEQ ID NO: 48, wherein the polypeptide maintains the sequences of LCDR1 as set forth in SEQ ID NO: 38; LCDR2 as set forth in SEQ ID NO: 39; and LCDR3 as set forth in SEQ ID NO: 40.

89. The method of any one of embodiments 86-88, wherein the polypeptide comprises a heavy chain and a light chain comprising: a heavy chain variable region of the heavy chain having at least 90% sequence identity to SEQ ID NO: 47, and a light chain variable region of the light chain having at least 90% sequence identity to SEQ ID NO: 48, wherein polypeptide maintains the sequences of HCDR1 as set forth in SEQ ID NO: 35; HCDR2 as set forth in SEQ ID NO: 36; HCDR3 as set forth in SEQ ID NO: 37; LCDR1 as set forth in SEQ ID NO: 38; LCD2 as set forth in SEQ ID NO: 39; and LCDR3 as set forth in SEQ ID NO: 40.

90. The method of any one of embodiments 86-89, wherein the light chain and a heavy chain comprise: a heavy chain variable region of the heavy chain having at least 90% sequence identity to SEQ ID NO: 47; and a light chain variable region of the light chain having at least 90% sequence identity to SEQ ID NO: 48.

91. The method of any one of embodiments 86-90, wherein the light chain and a heavy chain comprise: a heavy chain variable region of the heavy chain having at least 95% sequence identity to SEQ ID NO: 47; and a light chain variable region of the light chain having at least 95% sequence identity to SEQ ID NO: 48.

92. The method of any one of embodiments 86-91, wherein the light chain and a heavy chain comprise: a heavy chain variable region of the heavy chain having at least 99% sequence identity to SEQ ID NO: 47; and a light chain variable region of the light chain having at least 99% sequence identity to SEQ ID NO: 48.

93. The method of any one of embodiments 86-92, wherein the light chain and a heavy chain comprise: a heavy chain variable region comprising SEQ ID NO: 47, and a light chain variable region comprising SEQ ID NO: 48.

94. The method of any one of embodiments 86-93, wherein the heavy chain variable region and the light chain variable region are, or are not, linked by a linker, such as a peptide linker, which can be for example, a glycine/serine linker.

95. The method of embodiment 94, wherein the peptide linker comprises a sequence of (GGGGS)$_n$ (SEQ ID NO: 49), wherein n is independently 1-5.

96. The method of any one of embodiments 85-95, wherein the targeting moiety that binds to CD7 comprises a polypeptide comprising a sequence having at least 90% sequence identity to SEQ ID NO: 51, at least 95% sequence identity to SEQ ID NO: 51, at least 99% sequence identity to SEQ ID NO: 51, or a sequence as set forth in SEQ ID NO: 51.

97. The method of any one of embodiments 85-95, wherein the targeting moiety that binds to CD7 comprises a polypeptide comprising a sequence having at least 90% sequence identity to SEQ ID NO: 52, having at least 95% sequence identity to SEQ ID NO: 52, having at least 99% sequence identity to SEQ ID NO: 52, or a sequence as set forth in SEQ ID NO: 52.

98. The method of any one of embodiments 46-57, wherein the targeting moiety that binds to the target cell binds to CD8.

99. The method of embodiment 98, wherein the targeting moiety comprises a polypeptide that comprises: a heavy chain variable region comprising heavy chain CDR1, CDR2, and CDR3 sequences, wherein the heavy chain CDR1 sequence has the amino acid sequence of SEQ ID NO: 55; the heavy chain CDR2 has the amino acid sequence of SEQ ID NO: 56; and the heavy chain CDR3 sequence has the amino acid sequence of SEQ ID NO: 57, or variants of any of the foregoing; and (ii) a light chain variable region comprising light chain CDR1, CDR2, and CDR3 sequences, wherein the light chain CDR1 sequence has the amino acid sequence of SEQ ID NO: 58; the light chain CDR2 sequence has the amino acid sequence of SEQ ID NO: 59; and the light chain CDR3 sequence has the amino acid sequence of SEQ ID NO: 60; or variants of any of the foregoing.

100. The method of embodiment 99, wherein the targeting moiety comprises a heavy chain that comprises a heavy chain variable region having at least 90% sequence identity to SEQ ID NO: 67, wherein the polypeptide maintains the sequences of HCDR1 as set forth in SEQ ID NO: 55; HCDR2 as set forth in SEQ ID NO: 56; and HCDR3 as set forth in SEQ ID NO: 57.

101. The method of embodiment 99 or 100, wherein the CD8 targeting moiety comprises a light chain that comprises a light chain variable region having at least 90% sequence identity to SEQ ID NO: 68, wherein the polypeptide maintains the sequences of LCDR1 as set forth in SEQ ID NO: 58; LCDR2 as set forth in SEQ ID NO: 59; and LCDR3 as set forth in SEQ ID NO: 60.

102. The method of any one of embodiments 99-101, wherein the CD8 targeting moiety comprises a polypeptide comprising a heavy chain and a light chain comprising: a heavy chain variable region of the heavy chain having at least 90% sequence identity to SEQ ID NO: 67, and a light chain variable region of the light chain having at least 90% sequence identity to SEQ ID NO: 68, wherein polypeptide maintains the sequences of HCDR1 as set forth in SEQ ID NO: 55; HCDR2 as set forth in SEQ ID NO: 56; HCDR3 as set forth in SEQ ID NO: 57; LCDR1 as set forth in SEQ ID NO: 58; LCD2 as set forth in SEQ ID NO: 59; and LCDR3 as set forth in SEQ ID NO: 60.

103. The method of any one of embodiments 99-102, wherein the CD8 targeting moiety comprises a polypeptide comprising a light chain and a heavy chain comprising: a heavy chain variable region of the heavy chain having at least 90% sequence identity to SEQ ID NO: 67; and a light chain variable region of the light chain having at least 90% sequence identity to SEQ ID NO: 68.

104. The method of any one of embodiments 99-102, wherein the CD8 targeting moiety comprises a polypeptide comprising a light chain and a heavy chain comprising: a heavy chain variable region of the heavy chain having at least 95% sequence identity to SEQ ID NO: 67; and a light chain variable region of the light chain having at least 95% sequence identity to SEQ ID NO: 68.

105. The method of any one of embodiments 99-102, wherein the CD8 targeting moiety comprises a polypeptide comprising a light chain and a heavy chain comprising: a heavy chain variable region of the heavy chain having at least 99% sequence identity to SEQ ID NO: 67; and a light chain variable region of the light chain having at least 99% sequence identity to SEQ ID NO: 68.

106. The method of embodiment 98, wherein the CD8 targeting moiety comprises a polypeptide comprising a light chain and a heavy chain comprising: wherein the heavy chain variable region comprises SEQ ID NO: 67, and the light chain variable region comprises SEQ ID NO: 68.

107. The method of any one of embodiments 99-106, wherein the heavy chain variable region and the light chain variable region are, or are not, linked by a linker, such as a peptide linker.

108. The method of embodiment 107, wherein the peptide linker is a glycine/serine linker.

109. The method of embodiments 107 or 108, wherein the peptide linker comprises a sequence of (GGGGS)$_n$ (SEQ ID NO: 49), wherein each n is independently 1-5.

110. The method of any one of embodiments 98-109, wherein the targeting moiety that binds to CD8 comprises a polypeptide comprising a sequence having at least 90% sequence identity to SEQ ID NO: 69, at least 95% sequence identity to SEQ ID NO: 69, at least 99% sequence identity to SEQ ID NO: 69, or a sequence as set forth in SEQ ID NO: 69.

111. The method of any one of embodiments 98-109, wherein the targeting moiety that binds to CD8 comprises a polypeptide comprising a sequence having at least 90% sequence identity to SEQ ID NO: 70, having at least 95% sequence identity to SEQ ID NO: 70, having at least 99% sequence identity to SEQ ID NO: 70, or a sequence as set forth in SEQ ID NO: 70.

112. The viral particle of any one of embodiments 40-45 or 58-84, wherein the CAR comprises an antigen binding domain having an amino acid sequence having at least 85%, 86%, 87%, 88%, 89%, 90%, 91%, 92%, 93%, 94%, 95%, 96%, 97%, 98%, 99%, or 100% identity to SEQ ID NO: 75.

113. The viral particle of embodiment 112, wherein the CAR comprises an antigen binding domain having an amino acid sequence having at least 90% identity to SEQ ID NO: 75.

114. The viral particle of embodiment 112, wherein the CAR comprises an antigen binding domain having an amino acid sequence having at least 95% identity to SEQ ID NO: 75.

115. The viral particle of embodiment 112, wherein the CAR comprises an antigen binding domain having an amino acid sequence having at least 98% identity to SEQ ID NO: 75.

116. The viral particle of embodiment 112, wherein the CAR comprises an antigen binding domain having an amino acid sequence having at least 99% identity to SEQ ID NO: 75.

117. The viral particle of embodiment 112, wherein the CAR comprises an antigen binding domain having an amino acid sequence having the amino acid sequence of SEQ ID NO: 75.

118. The viral particle of any one of embodiments 40-45 or 58-84, wherein the CAR comprises an antigen binding domain having an amino acid sequence having at least 85%, 86%, 87%, 88%, 89%, 90%, 91%, 92%, 93%, 94%, 95%, 96%, 97%, 98%, 99%, or 100% identity to SEQ ID NO: 76.

119. The viral particle of embodiment 118, wherein the CAR comprises an antigen binding domain having an amino acid sequence having at least 90% identity to SEQ ID NO: 76.

120. The viral particle of embodiment 118, wherein the CAR comprises an antigen binding domain having an amino acid sequence having at least 95% identity to SEQ ID NO: 76.

121. The viral particle of embodiment 118, wherein the CAR comprises an antigen binding domain having an amino acid sequence having at least 98% identity to SEQ ID NO: 76.

122. The viral particle of embodiment 118, wherein the CAR comprises an antigen binding domain having an amino acid sequence having at least 99% identity to SEQ ID NO: 76.

123. The viral particle of embodiment 118, wherein the CAR comprises an antigen binding domain having an amino acid sequence having the amino acid sequence of SEQ ID NO: 76.

124. The method of any one of embodiments 46-57 or 85-111 wherein the heterologous molecule of interest is a chimeric antigen receptor (CAR), and wherein the CAR comprises an antigen binding domain having an amino acid sequence having at least 85%, 86%, 87%, 88%, 89%, 90%, 91%, 92%, 93%, 94%, 95%, 96%, 97%, 98%, 99%, or 100% identity to SEQ ID NO: 75.

125. The method of embodiment 124, wherein the CAR comprises an antigen binding domain having an amino acid sequence having at least 90% identity to SEQ ID NO: 75.

126. The method of embodiment 124, wherein the CAR comprises an antigen binding domain having an amino acid sequence having at least 95% identity to SEQ ID NO: 75.

127. The method of embodiment 124, wherein the CAR comprises an antigen binding domain having an amino acid sequence having at least 98% identity to SEQ ID NO: 75.

128. The method of embodiment 124, wherein the CAR comprises an antigen binding domain having an amino acid sequence having at least 99% identity to SEQ ID NO: 75.

129. The method of embodiment 124, wherein the CAR comprises an antigen binding domain having the amino acid sequence of SEQ ID NO: 75.

130. The method of any one of embodiments 46-57 or 85-111 wherein the heterologous molecule of interest is a chimeric antigen receptor (CAR), and wherein the CAR comprises an antigen binding domain having an amino acid sequence having at least 85%, 86%, 87%, 88%, 89%, 90%, 91%, 92%, 93%, 94%, 95%, 96%, 97%, 98%, 99%, or 100% identity to SEQ ID NO: 76.

131. The method of embodiment 130, wherein the CAR comprises an antigen binding domain having an amino acid sequence having at least 90% identity to SEQ ID NO: 76.

132. The method of embodiment 130, wherein the CAR comprises an antigen binding domain having an amino acid sequence having at least 95% identity to SEQ ID NO: 76.

133. The method of embodiment 130, wherein the CAR comprises an antigen binding domain having an amino acid sequence having at least 98% identity to SEQ ID NO: 76.

134. The method of embodiment 130, wherein the CAR comprises an antigen binding domain having an amino acid sequence having at least 99% identity to SEQ ID NO: 76.

135. The method of embodiment 130, wherein the CAR comprises an antigen binding domain having the amino acid sequence of SEQ ID NO: 76.

136. A viral particle comprising a targeting moiety that binds to CD7 or CD8, or a pharmaceutical composition comprising the same.

137. The viral particle of embodiment 136, or a pharmaceutical composition comprising the same, wherein the targeting moiety that binds to CD7 comprises a polypeptide comprising: (i) a heavy chain variable region comprising heavy chain CDR1, CDR2, and CDR3 sequences, wherein the heavy chain CDR1 sequence has the amino acid sequence of SEQ ID NO: 35; the heavy chain CDR2 has the amino acid sequence of SEQ ID NO: 36; and the heavy chain CDR3 sequence has the amino acid sequence of SEQ ID NO: 37, or variants of any of the foregoing; and (ii) a light chain variable region comprising light chain CDR1, CDR2, and CDR3 sequences, wherein the light chain CDR1 sequence has the amino acid sequence of SEQ ID NO: 38; the light chain CDR2 sequence has the amino acid sequence of SEQ ID NO: 39; and the light chain CDR3 sequence has the amino acid sequence of SEQ ID NO: 40; or variants of any of the foregoing.

138. The viral particle of embodiment 137, or a pharmaceutical composition comprising the same, wherein the targeting moiety comprises a heavy chain comprising a heavy chain variable region having at least 90% sequence identity to SEQ ID NO: 47, wherein the polypeptide maintains the sequences of HCDR1 as set forth in SEQ ID NO: 35; HCDR2 as set forth in SEQ ID NO: 36; and HCDR3 as set forth in SEQ ID NO: 37.

139. The viral particle of embodiment 137, or a pharmaceutical composition comprising the same, wherein the targeting moiety comprises a light chain comprising: a light chain variable region having at least 90% sequence identity to SEQ ID NO: 48, wherein the polypeptide maintains the sequences of LCDR1 as set forth in SEQ ID NO: 38; LCDR2 as set forth in SEQ ID NO: 39; and LCDR3 as set forth in SEQ ID NO: 40.

140. The viral particle of embodiment 137, or a pharmaceutical composition comprising the same, wherein the targeting moiety that binds to CD7 comprises a polypeptide comprises a heavy chain and a light chain comprising: a heavy chain variable region of the heavy chain having at least 90% sequence identity to SEQ ID NO: 47, and a light chain variable region of the light chain having at least 90% sequence identity to SEQ ID NO: 48, wherein polypeptide maintains the sequences of HCDR1 as set forth in SEQ ID NO: 35; HCDR2 as set forth in SEQ ID NO: 36; HCDR3 as set forth in SEQ ID NO: 37; LCDR1 as set forth in SEQ ID NO: 38; LCD2 as set forth in SEQ ID NO: 39; and LCDR3 as set forth in SEQ ID NO: 40.

141. The viral particle of embodiment 137, or a pharmaceutical composition comprising the same, wherein the targeting moiety comprises a light chain and a heavy chain, wherein the light chain and a heavy chain comprise: a heavy chain variable region of the heavy chain having at least 90% sequence identity to SEQ ID NO: 47; and a light chain variable region of the light chain having at least 90% sequence identity to SEQ ID NO: 48.

141. The viral particle of embodiment 141, or a pharmaceutical composition comprising the same, wherein the light chain and a heavy chain comprise: a heavy chain variable region of the heavy chain having at least 95% sequence identity to SEQ ID NO: 47; and a light chain variable region of the light chain having at least 95% sequence identity to SEQ ID NO: 48.

142. The viral particle embodiment 141, or a pharmaceutical composition comprising the same, wherein the light chain and a heavy chain comprise: a heavy chain variable region of the heavy chain having at least 99% sequence identity to SEQ ID NO: 47; and a light chain variable region of the light chain having at least 99% sequence identity to SEQ ID NO: 48.

143. The viral particle embodiment 141, or a pharmaceutical composition comprising the same, wherein the light chain and a heavy chain comprise: a heavy chain variable region comprising SEQ ID NO: 47, and a light chain variable region comprising SEQ ID NO: 48.

144. The viral particle of embodiment 136, or a pharmaceutical composition comprising the same, wherein the targeting moiety that binds to CD7 comprises a polypeptide comprising a sequence having at least 90% sequence identity to SEQ ID NO: 51, at least 95% sequence identity to SEQ ID NO: 51, at least 99% sequence identity to SEQ ID NO: 51, or a sequence as set forth in SEQ ID NO: 51.

145. The viral particle of embodiment 136, or a pharmaceutical composition comprising the same, wherein the targeting moiety that binds to CD7 comprises a polypeptide comprising a sequence having at least 90% sequence identity to SEQ ID NO: 52, having at least 95% sequence identity to SEQ ID NO: 52, having at least 99% sequence identity to SEQ ID NO: 52, or a sequence as set forth in SEQ ID NO: 52.

146. The viral particle of embodiment 136, or a pharmaceutical composition comprising the same, wherein the targeting moiety binds to CD8.

147. The viral particle of embodiment 146, or a pharmaceutical composition comprising the same, wherein the targeting moiety comprises a polypeptide that comprises: a heavy chain variable region comprising heavy chain CDR1, CDR2, and CDR3 sequences, wherein the heavy chain CDR1 sequence has the amino acid sequence of SEQ ID NO: 55; the heavy chain CDR2 has the amino acid sequence of SEQ ID NO: 56; and the heavy chain CDR3 sequence has the amino acid sequence of SEQ ID NO: 57, or variants of any of the foregoing; and (ii) a light chain variable region comprising light chain CDR1, CDR2, and CDR3 sequences, wherein the light chain CDR1 sequence has the amino acid sequence of SEQ ID NO: 58; the light chain CDR2 sequence has the amino acid sequence of SEQ ID NO: 59; and the light chain CDR3 sequence has the amino acid sequence of SEQ ID NO: 60; or variants of any of the foregoing.

148. The viral particle of embodiment 146, or a pharmaceutical composition comprising the same, wherein the targeting moiety comprises a heavy chain that comprises a heavy chain variable region having at least 90% sequence identity to SEQ ID NO: 67, wherein the polypeptide maintains the sequences of HCDR1 as set forth in SEQ ID NO: 55; HCDR2 as set forth in SEQ ID NO: 56; and HCDR3 as set forth in SEQ ID NO: 57.

149. The viral particle of embodiment 146, or a pharmaceutical composition comprising the same, wherein the CD8 targeting moiety comprises a light chain that comprises a light chain variable region having at least 90% sequence identity to SEQ ID NO: 68, wherein the polypeptide maintains the sequences of LCDR1 as set forth in SEQ ID NO: 58; LCDR2 as set forth in SEQ ID NO: 59; and LCDR3 as set forth in SEQ ID NO: 60.

150. The viral particle of embodiment 146, or a pharmaceutical composition comprising the same, wherein the CD8 targeting moiety comprises a polypeptide comprising a heavy chain and a light chain comprising: a heavy chain variable region of the heavy chain having at least 90% sequence identity to SEQ ID NO: 67, and a light chain variable region of the light chain having at least 90% sequence identity to SEQ ID NO: 68, wherein polypeptide maintains the sequences of HCDR1 as set forth in SEQ ID NO: 55; HCDR2 as set forth in SEQ ID NO: 56; HCDR3 as set forth in SEQ ID NO: 57; LCDR1 as set forth in SEQ ID NO: 58; LCD2 as set forth in SEQ ID NO: 59; and LCDR3 as set forth in SEQ ID NO: 60.

150. The viral particle of embodiment 146, or a pharmaceutical composition comprising the same, wherein the CD8 targeting moiety comprises a polypeptide comprising a light chain and a heavy chain comprising: a heavy chain variable region of the heavy chain having at least 90% sequence identity to SEQ ID NO: 67; and a light chain variable region of the light chain having at least 90% sequence identity to SEQ ID NO: 68.

151. The viral particle of embodiment 146, or a pharmaceutical composition comprising the same, wherein the CD8 targeting moiety comprises a polypeptide comprising a light chain and a heavy chain comprising: a heavy chain variable region of the heavy chain having at least 95% sequence identity to SEQ ID NO: 67; and a light chain variable region of the light chain having at least 95% sequence identity to SEQ ID NO: 68.

152. The viral particle of embodiment 146, or a pharmaceutical composition comprising the same, wherein the CD8 targeting moiety comprises a polypeptide comprising a light chain and a heavy chain comprising: a heavy chain variable region of the heavy chain having at least 99% sequence identity to SEQ ID NO: 67; and a light chain variable region of the light chain having at least 99% sequence identity to SEQ ID NO: 68.

153. The viral particle of embodiment 146, or a pharmaceutical composition comprising the same, wherein the CD8 targeting moiety comprises a polypeptide comprising a light chain and a heavy chain comprising: wherein the heavy chain variable region comprises SEQ ID NO: 67, and the light chain variable region comprises SEQ ID NO: 68.

154. The viral particle of embodiment 146, or a pharmaceutical composition comprising the same, wherein the targeting moiety that binds to CD8 comprises a polypeptide comprising a sequence having at least 90% sequence identity to SEQ ID NO: 69, at least 95% sequence identity to SEQ ID NO: 69, at least 99% sequence identity to SEQ ID NO: 69, or a sequence as set forth in SEQ ID NO: 69.

155. The viral particle of embodiment 146, or a pharmaceutical composition comprising the same, wherein the targeting moiety that binds to CD8 comprises a polypeptide comprising a sequence having at least 90% sequence identity to SEQ ID NO: 70, having at least 95% sequence identity to SEQ ID NO: 70, having at least 99% sequence identity to SEQ ID NO: 70, or a sequence as set forth in SEQ ID NO: 70.

156. The viral particle of any one of embodiments 136-155, or a pharmaceutical composition comprising the same, wherein the viral particle is a lentivirus derived viral particle.

157. The viral particle of any one of embodiments 136-156, or a pharmaceutical composition comprising the same, wherein the viral particle comprises a heterologous fusogenic protein, such as a glycoprotein from such as those provided for herein.

158. The viral particle of embodiment 157, or a pharmaceutical composition comprising the same, wherein the fusogenic protein is a VSV-G protein.

159. The viral particle of embodiment 158, or a pharmaceutical composition comprising the same, wherein the VSV-G protein is a mutant VSV-G protein.

160. The viral particle of embodiment 159, or a pharmaceutical composition comprising the same, wherein the mutant VSV-G protein abrogates binding to its natural co-receptor, such as LDL-R.

161. The viral particle of embodiment 159, or a pharmaceutical composition comprising the same, wherein the mutant VSV-G protein comprises a polypeptide of any one of embodiments 1-30.

162. The viral particle of embodiment 159, or a pharmaceutical composition comprising the same, wherein the viral particle comprises a nucleic acid molecule encoding a chimeric antigen receptor.

163. The viral particle of embodiment 162, or a pharmaceutical composition comprising the same, wherein the chimeric antigen receptor comprises an antigen binding domain that binds to CD20.

164. The viral particle of embodiment 163, or a pharmaceutical composition comprising the same, wherein the antigen binding domain that binds to CD20 comprises a $V_H$ and $V_L$ as provided for herein.

165. A method of delivering a heterologous molecule to a CD7+ or CD8+ target cell or a method of treating cancer in a subject, the method comprising contacting a cell with, or administering to the subject, a pseudotyped viral vector comprising a targeting moiety that specifically binds to CD7 or CD8 on the target cell and a nucleic acid molecule encoding the heterologous molecule, wherein:
  i) the targeting moiety that binds to CD7 comprises:
    a polypeptide comprising: (i) a heavy chain variable region comprising heavy chain CDR1, CDR2, and CDR3 sequences, wherein the heavy chain CDR1 sequence has the amino acid sequence of SEQ ID NO: 35; the heavy chain CDR2 has the amino acid sequence of SEQ ID NO: 36; and the heavy chain CDR3 sequence has the amino acid sequence of SEQ ID NO: 37, or variants of any of the foregoing; and (ii) a light chain variable region comprising light chain CDR1, CDR2, and CDR3 sequences, wherein the light chain CDR1 sequence has the amino acid sequence of SEQ ID NO: 38; the light chain CDR2 sequence has the amino acid sequence of SEQ ID NO: 39; and the light chain CDR3 sequence has the amino acid sequence of SEQ ID NO: 40; or variants of any of the foregoing;
    a heavy chain comprising a heavy chain variable region having at least 90% sequence identity to SEQ ID NO: 47, wherein the polypeptide maintains the sequences of HCDR1 as set forth in SEQ ID NO: 35; HCDR2 as set forth in SEQ ID NO: 36; and HCDR3 as set forth in SEQ ID NO: 37;
    a light chain comprising: a light chain variable region having at least 90% sequence identity to SEQ ID NO: 48, wherein the polypeptide maintains the sequences of LCDR1 as set forth in SEQ ID NO: 38; LCDR2 as set forth in SEQ ID NO: 39; and LCDR3 as set forth in SEQ ID NO: 40;
    a polypeptide comprises a heavy chain and a light chain comprising: a heavy chain variable region of the heavy chain having at least 90% sequence identity to SEQ ID NO: 47, and a light chain variable region of the light chain having at least 90% sequence identity to SEQ ID NO: 48, wherein polypeptide maintains the sequences of HCDR1 as set forth in SEQ ID NO: 35; HCDR2 as set forth in SEQ ID NO: 36; HCDR3 as set forth in SEQ ID NO: 37; LCDR1 as set forth in SEQ ID NO: 38; LCD2 as set forth in SEQ ID NO: 39; and LCDR3 as set forth in SEQ ID NO: 40;
    a light chain and a heavy chain, wherein the light chain and a heavy chain comprise: a heavy chain variable region of the heavy chain having at least 90% sequence identity to SEQ ID NO: 47; and a light chain variable region of the light chain having at least 90% sequence identity to SEQ ID NO: 48;
    a heavy chain variable region of the heavy chain having at least 95% sequence identity to SEQ ID NO: 47; and a light chain variable region of the light chain having at least 95% sequence identity to SEQ ID NO: 48;
    a heavy chain variable region of the heavy chain having at least 99% sequence identity to SEQ ID NO: 47; and a light chain variable region of the light chain having at least 99% sequence identity to SEQ ID NO: 48;
    a heavy chain variable region comprising SEQ ID NO: 47, and a light chain variable region comprising SEQ ID NO: 48; a polypeptide comprising a sequence having at least 90% sequence identity to SEQ ID NO: 51, at least 95% sequence identity to SEQ ID NO: 51, at least 99% sequence identity to SEQ ID NO: 51, or a sequence as set forth in SEQ ID NO: 51; or a polypeptide comprising a sequence having at least 90% sequence identity to SEQ ID NO: 52, having at least 95% sequence identity to SEQ ID NO: 52, having at least 99% sequence identity to SEQ ID NO: 52, or a sequence as set forth in SEQ ID NO: 52; or
  ii) the targeting moiety that binds to CD8 comprises:
    a polypeptide that comprises: a heavy chain variable region comprising heavy chain CDR1, CDR2, and CDR3 sequences, wherein the heavy chain CDR1 sequence has the amino acid sequence of SEQ ID NO: 55; the heavy chain CDR2 has the amino acid sequence of SEQ ID NO: 56; and the heavy chain CDR3 sequence has the amino acid sequence of SEQ ID NO: 57, or variants of any of the foregoing; and (ii) a light chain variable region comprising light chain CDR1, CDR2, and CDR3 sequences, wherein the light chain CDR1 sequence has the amino acid sequence of SEQ ID NO: 58; the light chain CDR2 sequence has the amino acid sequence of SEQ ID NO: 59; and the light chain CDR3 sequence has the amino acid sequence of SEQ ID NO: 60; or variants of any of the foregoing;
    a heavy chain that comprises a heavy chain variable region having at least 90% sequence identity to SEQ ID NO: 67, wherein the polypeptide maintains the sequences of HCDR1 as set forth in SEQ ID NO: 55; HCDR2 as set forth in SEQ ID NO: 56; and HCDR3 as set forth in SEQ ID NO: 57;
    a light chain that comprises a light chain variable region having at least 90% sequence identity to SEQ ID NO: 68, wherein the polypeptide maintains the sequences of LCDR1 as set forth in SEQ ID NO: 58; LCDR2 as set forth in SEQ ID NO: 59; and LCDR3 as set forth in SEQ ID NO: 60;
    a polypeptide comprising a heavy chain and a light chain comprising: a heavy chain variable region of the heavy chain having at least 90% sequence identity to SEQ ID NO: 67, and a light chain variable region of the light chain having at least 90% sequence identity to SEQ ID NO: 68, wherein polypeptide maintains the sequences of HCDR1 as set forth in SEQ ID NO: 55; HCDR2 as set forth in SEQ ID NO: 56; HCDR3 as set forth in SEQ ID NO: 57; LCDR1 as set forth in SEQ ID NO: 58; LCD2 as set forth in SEQ ID NO: 59; and LCDR3 as set forth in SEQ ID NO: 60;

a polypeptide comprising a light chain and a heavy chain comprising: a heavy chain variable region of the heavy chain having at least 90% sequence identity to SEQ ID NO: 67; and a light chain variable region of the light chain having at least 90% sequence identity to SEQ ID NO: 68;

a polypeptide comprising a light chain and a heavy chain comprising: a heavy chain variable region of the heavy chain having at least 95% sequence identity to SEQ ID NO: 67; and a light chain variable region of the light chain having at least 95% sequence identity to SEQ ID NO: 68;

a polypeptide comprising a light chain and a heavy chain comprising: a heavy chain variable region of the heavy chain having at least 99% sequence identity to SEQ ID NO: 67; and a light chain variable region of the light chain having at least 99% sequence identity to SEQ ID NO: 68;

a polypeptide comprising a light chain and a heavy chain comprising: wherein the heavy chain variable region comprises SEQ ID NO: 67, and the light chain variable region comprises SEQ ID NO: 68;

a polypeptide comprising a sequence having at least 90% sequence identity to SEQ ID NO: 69, at least 95% sequence identity to SEQ ID NO: 69, at least 99% sequence identity to SEQ ID NO: 69, or a sequence as set forth in SEQ ID NO: 69; or a polypeptide comprising a sequence having at least 90% sequence identity to SEQ ID NO: 70, having at least 95% sequence identity to SEQ ID NO: 70, having at least 99% sequence identity to SEQ ID NO: 70, or a sequence as set forth in SEQ ID NO: 70.

166. The method of embodiment 165, wherein the pseudotyped viral particle is a pseudotyped lentivirus derived viral particle.

167. The method of embodiments 165 or 166, wherein the pseudotyped viral particle comprises a heterologous fusogenic protein, such as a glycoprotein from those provided for herein.

168. The method of embodiment 167, wherein the fusogenic protein is a VSV-G protein.

169. The method of embodiment 168, wherein the VSV-G protein is a mutant VSV-G protein.

170. The method of embodiment 169, wherein the mutant VSV-G protein abrogates binding to its natural co-receptor, such as LDL-R.

171. The method of embodiment 169, wherein the mutant VSV-G protein comprises a polypeptide of any one of embodiments 1-30.

172. The method of any one of embodiments 165-171, wherein the heterologous nucleic acid molecule encodes for an siRNA, an shRNA, a non-coding RNA, a peptide, a polypeptide, a protein, a viral payload, a viral genome, a chimeric antigen receptor ("CAR") or a combination thereof.

173. The method of embodiment 172, wherein the heterologous nucleic acid molecule encodes for a chimeric antigen receptor.

174. The method of embodiment 173, wherein the chimeric antigen receptor comprises an antigen binding domain that binds to CD20.

175. The method of embodiment 174, wherein the antigen binding domain that binds to CD20 comprises a $V_H$ and $V_L$ as provided for herein and linked polypeptides comprising the same.

176. A cell comprising one or more heterologous nucleic acid molecules encoding for a targeting moiety and a viral glycoprotein.

177. The cell of embodiment 176, wherein the heterologous nucleic acid molecules comprise a nucleic acid sequence encoding for a targeting moiety that binds to CD7 or CD8.

178. The cell of embodiment 177, wherein the nucleic acid sequence encoding for a targeting moiety that binds to CD7 encodes for a polypeptide comprising: (i) a heavy chain variable region comprising heavy chain CDR1, CDR2, and CDR3 sequences, wherein the heavy chain CDR1 sequence has the amino acid sequence of SEQ ID NO: 35; the heavy chain CDR2 has the amino acid sequence of SEQ ID NO: 36; and the heavy chain CDR3 sequence has the amino acid sequence of SEQ ID NO: 37, or variants of any of the foregoing; and (ii) a light chain variable region comprising light chain CDR1, CDR2, and CDR3 sequences, wherein the light chain CDR1 sequence has the amino acid sequence of SEQ ID NO: 38; the light chain CDR2 sequence has the amino acid sequence of SEQ ID NO: 39; and the light chain CDR3 sequence has the amino acid sequence of SEQ ID NO: 40; or variants of any of the foregoing.

179. The cell of embodiment 177, wherein the nucleic acid molecule that encodes for a targeting moiety that binds CD7 encodes for a polypeptide comprising a heavy chain comprising a heavy chain variable region having at least 90% sequence identity to SEQ ID NO: 47, wherein the polypeptide maintains the sequences of HCDR1 as set forth in SEQ ID NO: 35; HCDR2 as set forth in SEQ ID NO: 36; and HCDR3 as set forth in SEQ ID NO: 37.

180. The cell of embodiment 177, wherein the nucleic acid molecule that encodes for a targeting moiety that binds CD7 encodes for a polypeptide comprising a light chain comprising: a light chain variable region having at least 90% sequence identity to SEQ ID NO: 48, wherein the polypeptide maintains the sequences of LCDR1 as set forth in SEQ ID NO: 38; LCDR2 as set forth in SEQ ID NO: 39; and LCDR3 as set forth in SEQ ID NO: 40.

181. The cell of embodiment 166, wherein the nucleic acid molecule that encodes for a targeting moiety that binds CD7 encodes for a polypeptide comprising a heavy chain and a light chain comprising: a heavy chain variable region of the heavy chain having at least 90% sequence identity to SEQ ID NO: 47, and a light chain variable region of the light chain having at least 90% sequence identity to SEQ ID NO: 48, wherein polypeptide maintains the sequences of HCDR1 as set forth in SEQ ID NO: 35; HCDR2 as set forth in SEQ ID NO: 36; HCDR3 as set forth in SEQ ID NO: 37; LCDR1 as set forth in SEQ ID NO: 38; LCD2 as set forth in SEQ ID NO: 39; and LCDR3 as set forth in SEQ ID NO: 40.

182. The cell of embodiment 177, wherein the nucleic acid molecule that encodes for a targeting moiety that binds CD7 encodes for a polypeptide comprising a light chain and a heavy chain, wherein the light chain and a heavy chain comprise: a heavy chain variable region of the heavy chain having at least 90% sequence identity to SEQ ID NO: 47; and a light chain variable region of the light chain having at least 90% sequence identity to SEQ ID NO: 48.

183. The cell of embodiment 177, wherein the nucleic acid molecule that encodes for a targeting moiety that binds CD7 encodes for a polypeptide comprising a light chain and a heavy chain that comprise: a heavy chain variable region of the heavy chain having at least 95% sequence identity to SEQ ID NO: 47; and a light chain variable region of the light chain having at least 95% sequence identity to SEQ ID NO: 48.

184. The cell of embodiment 183, wherein the light chain and the heavy chain comprise: a heavy chain variable region of the heavy chain having at least 99% sequence identity to SEQ ID NO: 47; and a light chain variable region of the light chain having at least 99% sequence identity to SEQ ID NO: 48.

185. The cell of embodiment 183, wherein the light chain and the heavy chain comprise: a heavy chain variable region comprising SEQ ID NO: 47, and a light chain variable region comprising SEQ ID NO: 48.

186. The cell of embodiment 177, wherein the nucleic acid sequence encoding for a targeting moiety that binds to CD7 encodes for a polypeptide comprising a sequence having at least 90% sequence identity to SEQ ID NO: 51, at least 95% sequence identity to SEQ ID NO: 51, at least 99% sequence identity to SEQ ID NO: 51, or a sequence as set forth in SEQ ID NO: 51.

187. The cell of embodiment 177, wherein the nucleic acid sequence encoding for a targeting moiety that binds to CD7 encodes for a polypeptide comprising a sequence having at least 90% sequence identity to SEQ ID NO: 52, having at least 95% sequence identity to SEQ ID NO: 52, having at least 99% sequence identity to SEQ ID NO: 52, or a sequence as set forth in SEQ ID NO: 52.

188. The cell of embodiment 177, wherein the nucleic acid sequence encoding for a targeting moiety that binds to CD8.

189. The cell of embodiment 188, wherein the targeting moiety comprises a polypeptide that comprises: a heavy chain variable region comprising heavy chain CDR1, CDR2, and CDR3 sequences, wherein the heavy chain CDR1 sequence has the amino acid sequence of SEQ ID NO: 55; the heavy chain CDR2 has the amino acid sequence of SEQ ID NO: 56; and the heavy chain CDR3 sequence has the amino acid sequence of SEQ ID NO: 57, or variants of any of the foregoing; and (ii) a light chain variable region comprising light chain CDR1, CDR2, and CDR3 sequences, wherein the light chain CDR1 sequence has the amino acid sequence of SEQ ID NO: 58; the light chain CDR2 sequence has the amino acid sequence of SEQ ID NO: 59; and the light chain CDR3 sequence has the amino acid sequence of SEQ ID NO: 60; or variants of any of the foregoing.

190. The cell of embodiment 188, wherein the targeting moiety comprises a heavy chain that comprises a heavy chain variable region having at least 90% sequence identity to SEQ ID NO: 67, wherein the polypeptide maintains the sequences of HCDR1 as set forth in SEQ ID NO: 55; HCDR2 as set forth in SEQ ID NO: 56; and HCDR3 as set forth in SEQ ID NO: 57.

191. The cell of embodiment 188, wherein the CD8 targeting moiety comprises a light chain that comprises a light chain variable region having at least 90% sequence identity to SEQ ID NO: 68, wherein the polypeptide maintains the sequences of LCDR1 as set forth in SEQ ID NO: 58; LCDR2 as set forth in SEQ ID NO: 59; and LCDR3 as set forth in SEQ ID NO: 60.

192. The cell of embodiment 188, wherein the CD8 targeting moiety comprises a polypeptide comprising a heavy chain and a light chain comprising: a heavy chain variable region of the heavy chain having at least 90% sequence identity to SEQ ID NO: 67, and a light chain variable region of the light chain having at least 90% sequence identity to SEQ ID NO: 68, wherein polypeptide maintains the sequences of HCDR1 as set forth in SEQ ID NO: 55; HCDR2 as set forth in SEQ ID NO: 56; HCDR3 as set forth in SEQ ID NO: 57; LCDR1 as set forth in SEQ ID NO: 58; LCD2 as set forth in SEQ ID NO: 59; and LCDR3 as set forth in SEQ ID NO: 60.

193. The cell of embodiment 188, wherein the CD8 targeting moiety comprises a polypeptide comprising a light chain and a heavy chain comprising: a heavy chain variable region of the heavy chain having at least 90% sequence identity to SEQ ID NO: 67; and a light chain variable region of the light chain having at least 90% sequence identity to SEQ ID NO: 68.

194. The cell of embodiment 188, wherein the CD8 targeting moiety comprises a polypeptide comprising a light chain and a heavy chain comprising: a heavy chain variable region of the heavy chain having at least 95% sequence identity to SEQ ID NO: 67; and a light chain variable region of the light chain having at least 95% sequence identity to SEQ ID NO: 68.

195. The cell of embodiment 188, wherein the CD8 targeting moiety comprises a polypeptide comprising a light chain and a heavy chain comprising: a heavy chain variable region of the heavy chain having at least 99% sequence identity to SEQ ID NO: 67; and a light chain variable region of the light chain having at least 99% sequence identity to SEQ ID NO: 68.

196. The cell of embodiment 188, wherein the CD8 targeting moiety comprises a polypeptide comprising a light chain and a heavy chain comprising: wherein the heavy chain variable region comprises SEQ ID NO: 67, and the light chain variable region comprises SEQ ID NO: 68.

197. The cell of embodiment 188, wherein the targeting moiety that binds to CD8 comprises a polypeptide comprising a sequence having at least 90% sequence identity to SEQ ID NO: 69, at least 95% sequence identity to SEQ ID NO: 69, at least 99% sequence identity to SEQ ID NO: 69, or a sequence as set forth in SEQ ID NO: 69.

198. The cell of embodiment 188, wherein the targeting moiety that binds to CD8 comprises a polypeptide comprising a sequence having at least 90% sequence identity to SEQ ID NO: 70, having at least 95% sequence identity to SEQ ID NO: 70, having at least 99% sequence identity to SEQ ID NO: 70, or a sequence as set forth in SEQ ID NO: 70.

199. The cells of any one of embodiments 176-198, wherein the heterologous nucleic acid molecule encoding the viral glycoprotein is a glycoprotein of any one of embodiments 1-30.

200. A cell comprising the nucleic acid molecule of embodiment 31, the vector of embodiment 32, or the plasmid of embodiment 33.

201. A method of making a viral particle comprising culturing the cell of any one of embodiments 176-198 under conditions sufficient to make the viral particle.

EXAMPLES

The following examples are illustrative, but not limiting, of the compounds, compositions, particles, polypeptids, and methods described herein. Other suitable modifications and adaptations known to those skilled in the art are within the scope of the following embodiments.

Example 1: Mutation at Position 182 of VSV-G Abrogates LDL-R Interaction, but Retains Fusing Properties Plasmids/Sequences. All VSV-G plasmids were derived from pCMV-VSV-G Envelope Vector (Cell Bio Labs, catalog RV-110). Point mutations and combinations thereof were introduced using site directed mutagenesis (New England Biolabs). Individual mutations H8A and K47Q were previously shown to partially "blind" VSV-G, reducing its binding to LDL-R, the native cellular receptor for VSV (PMID: 29531262, DOI: 10.1038/s41467-018-03432-4). In this experiment, a single binder molecule consisting of a CD7-targeting scFv (clone MT701) fused to an IgG "stalk" bearing a CD28 transmembrane domain was used.

Cells. HEK293T cells were grown in DMEM with 10% FBS. SupT1 cells were maintained in RPMI media with 10% FBS. Human PBMCs were purchased from AllCells and cultured in X-Vivo 10 (Lonza) supplemented with 20 ng/mL IL-2 (Peprotech). PBMCs were activated 48 hours prior to transduction using anti-CD3/CD28 Dynabeads (Cell Therapy Systems).

Generation of lentiviral particles. The recombinant lentiviral particles co-expressing VSV-G glycoprotein and binder molecules were generated by plasmid transection into HEK293T cells using Lipofectamine 3000 (ThermoFisher Scientific). A total of 5 plasmids were transfected: (1) plasmid expressing the VSV-G glycoprotein, (2) plasmid expressing the binder protein (3) plasmid expressing the lentiviral transfer genome encoding for eGFP, (4) plasmid expressing gag-pol, and (5) plasmid expressing rev. Transfected cell supernatant was harvested 48 hours later. Virus in the cell supernatant was concentrated by centrifugation through a sucrose cushion and resuspended in PBS. Lentiviral particle titer was determined using the Lenti-X p24 Rapid Titer Kit (Takara Bio, San Jose, CA).

Lentivirus transduction assay. A series of 10-fold dilutions (in cell culture media) of the concentrated lentivirus was performed and used to infect SupT1 and activated human PBMCs. Media was replaced 6 hours later, and the transduced cells were analyzed by flow cytometry on days 4 and 7 after transduction. Cells were stained with a viability stain and an anti-CD7 antibody to detect CD7 positive cells (PeCy7 mouse-anti-human CD7, clone CD7-6B7, BD Biosciences). Expression of eGFP was measured to calculate transduction efficiency.

Structure-guided design of novel blinding mutations. Using a published crystal structures of VSV-G bound to CR2 and CR3 of the LDL-R (pdb 5OYL and 5OY9, respectively), we identified two putative positions in VSV-G with side chains oriented toward the binding interface on LDL-R (FIG. 1). Residue Q10 (SEQ ID NO: 2) appeared to form several interactions with residues in both CR2 and CR3. In CR3, this included interactions with a positively charged arginine residue. Thus, three substitutions were tested: Q10A to reduce side-chain interactions that potentially stabilize LDL-R binding and Q10R and Q10K to create electrostatic repulsion.

Residue I182 (SEQ ID NO: 2) appeared to contact several residues in both CR2 and CR3 as well. Three substitutions were tested: I182A to reduce side-chain interactions that potentially stabilize LDL-R binding and I182D and I182E to create electrostatic repulsion against the primary binding interfaces on LDL-R.

Figure 2:
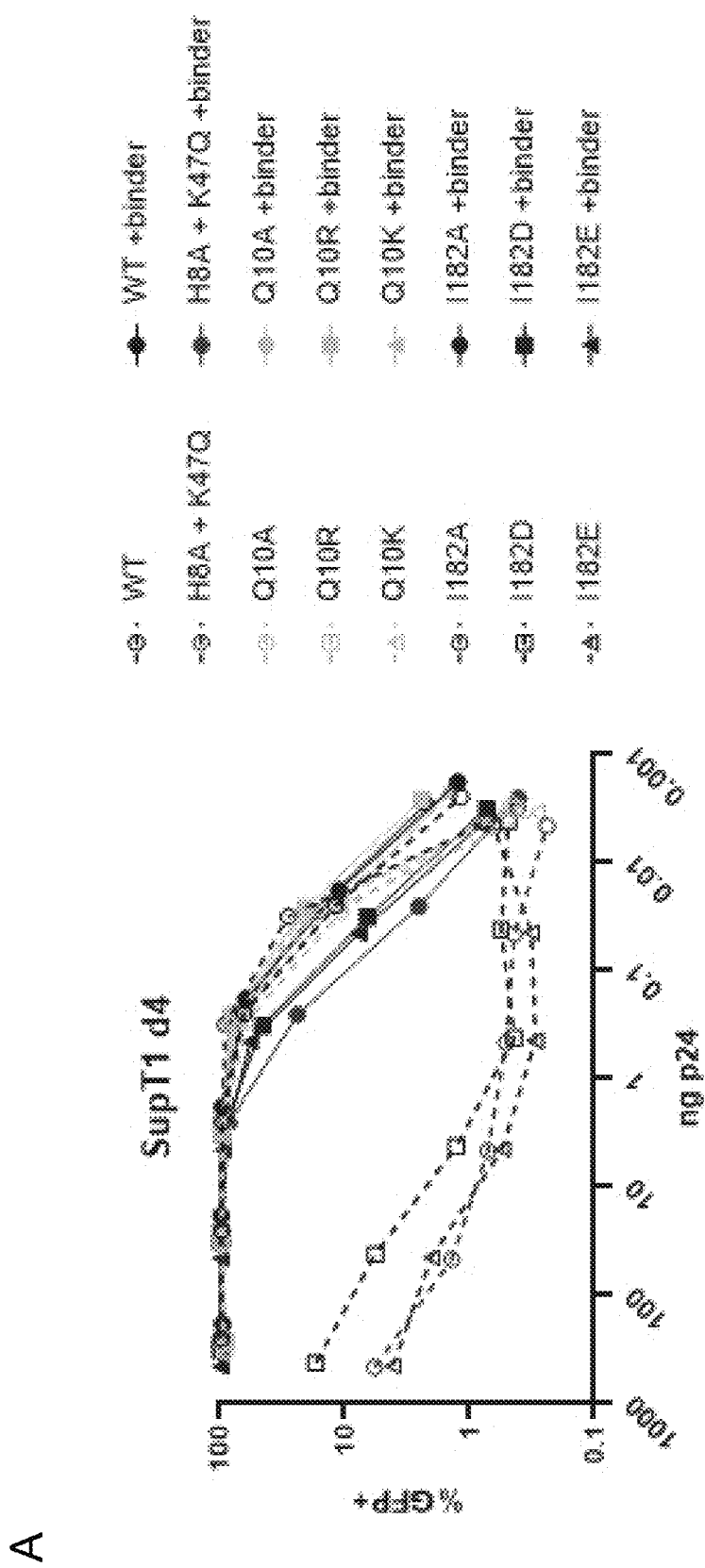
FIG. 2 Panels A and B illustrate the effect of adding negatively charged amino acids to the VSV-G:LDL-R binding interface on native tropism and fusogenicity.
Figure 2:
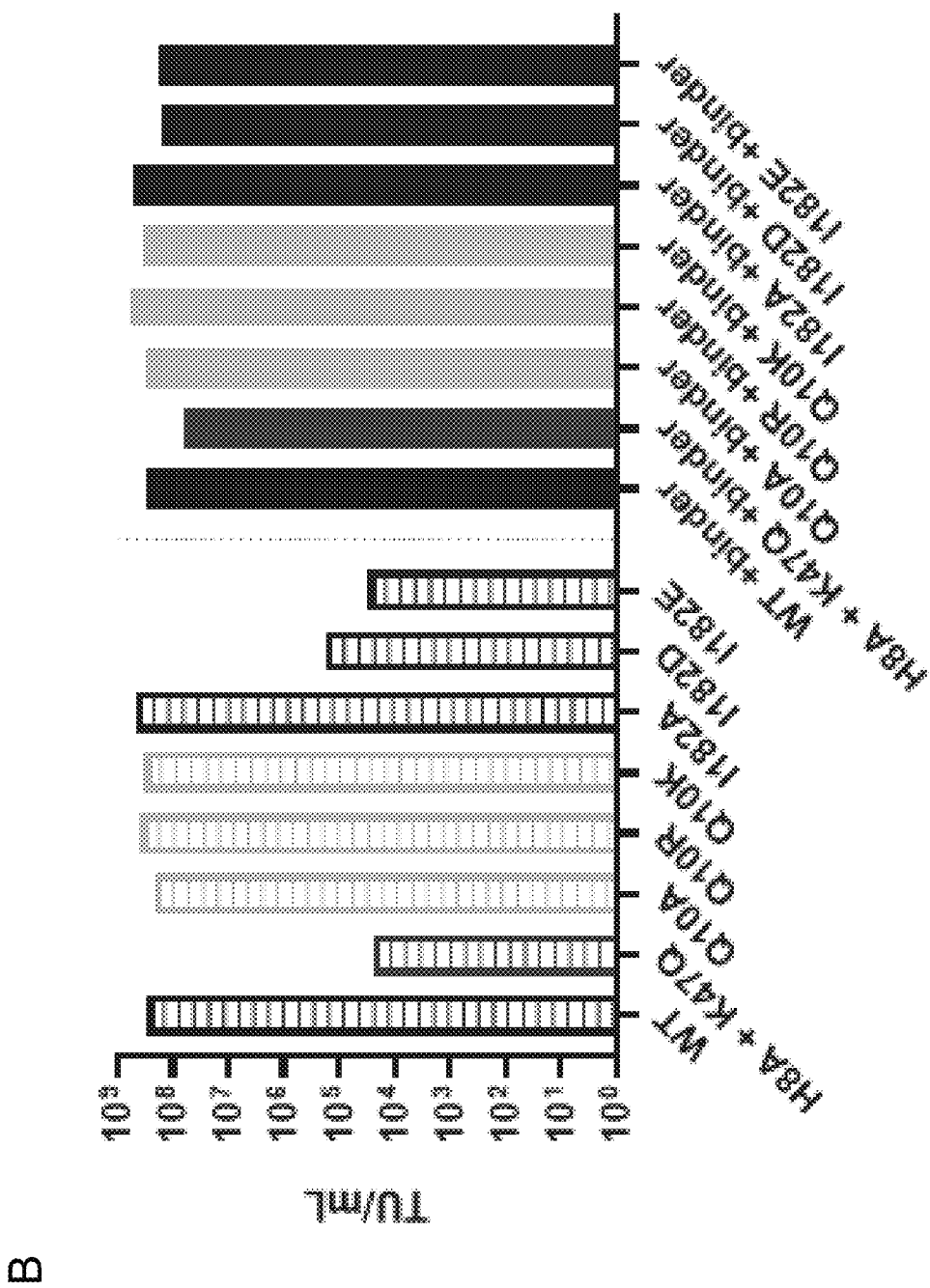

Addition of negative charges in the binding interface ablate native tropism without altering fusogenicity. Titration of viral supernatants on the CD7+ T cell line SupT1 validated the structural predictions for residue I182. In the absence of any compensatory binder molecule, WT VSV-G reached titers of 3.0e8 while both I182D and I182E were ~3 orders of magnitude lower (FIG. 2). Substitutions at residue I182 preserved fusogenicity, as titers were restored to 1e8 in the presence of a binder redirecting the virions to CD7.

The data is illustrated in FIG. 2, which shows that the addition of negative charges in the binding interface ablate native tropism without altering fusogenicity. FIG. 2 Panel A shows the titration of VSV-G constructs on SupT1 cells. Plotted is the percentage of SupT1 cells expressing GFP at each amount of viral input in terms of p24 antigen. Dashed lines/open circles indicate VSV-G constructs alone, solid lines/filled circles indicate the same construct with a CD7 targeting molecule expressed in trans. FIG. 2 Panel B illustrates Functional titer of each construct calculated from the titration in A, expressed as transducing units per mL of concentrated virus supernatant (TU/mL).

Thus these examples demonstrate that a mutation at position 182 is sufficient to abrogate the LDL-R interaction, but retain fusogenic properties when combining with a targeting moiety that binds to a target on the target cell.

Example 2: Serum Stable VSV-G Protein

WT VSV-G is reported to be sensitive to inactivation by naïve human serum, with inactivation ranging from minimal change to about 100-fold decrease depending on study parameters. Accordingly, it was assessed i) whether substitution at position I182 produced a variant VSV-G with similar sensitivity to serum and ii) whether incorporation of known serum stabilizing VSV-G mutations into the I182 substituted constructs had an effect on the serum stability of the constructs.

Figure 4:
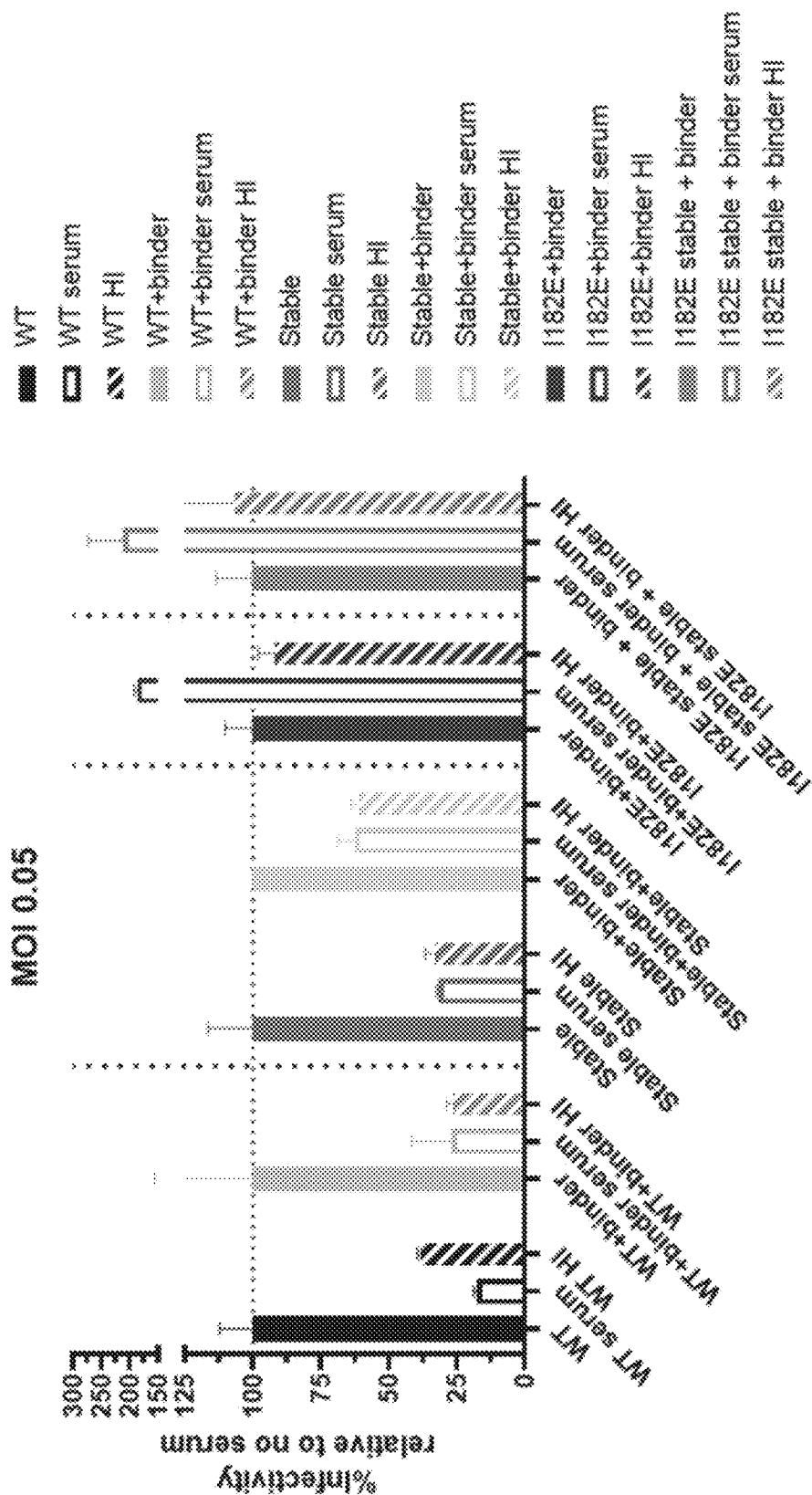
FIG. 4 illustrates the effect of various VSV-G mutations on the serum stability of viral constructs in combination with a CD7 binder.

WT VSV-G, Serum Stable VSV-G (T214N, T352A), LDL-R de-targeted VSV-G (I182E), and LDL-R de-targeted serum stable VSV-G (I182E, T214N, T352A) were tested for their ability to infect SupT1 cells in the presence or absence of naïve serum or heat inactivated serum (HI) (FIG. 4). As expected WT VSV-G had a dramatic decrease in percent infectivity when administered in the presence of serum with a mild rescue of infectivity if serum was heat inactivated (HI) (FIG. 4, columns 1-3). The inclusion of the CD7 targeting moiety on an IgG1 Fc stalk (WT) did not rescue the serum inactivation (FIG. 4, columns 4-6). The VSV-G constructs harboring the T214N and T352A mutations showed a similar reduction in infectivity in the presence of serum with no distinction between naïve or HI serum (FIG. 4, columns 7-9). However, the inclusion of the targeting moiety was able to partially rescue the inactivation in either serum condition (FIG. 4, columns 10-12). Surprisingly, the LDL-R de-targeted VSV-G (I182E) showed no reduction in infectivity percentage in the presence of either serum condition (FIG. 4, columns 13-15), but rather showed increased infectivity in the presence of naïve serum as compared to serum free or HI serum conditions. Further inclusion of the known serum stable mutations into VSV-G (I182E, T214N, T352A) also demonstrated increased infectivity in the presence of serum as compared to serum free conditions (FIG. 4, columns 16-18). Further, the I182E, T214N, T352A construct also demonstrates increased infectivity in the presence of HI serum (FIG. 4, column 18), which indicates that the triple mutant construct has a higher degree of serum stability than the other constructs examined.

Figure 5:
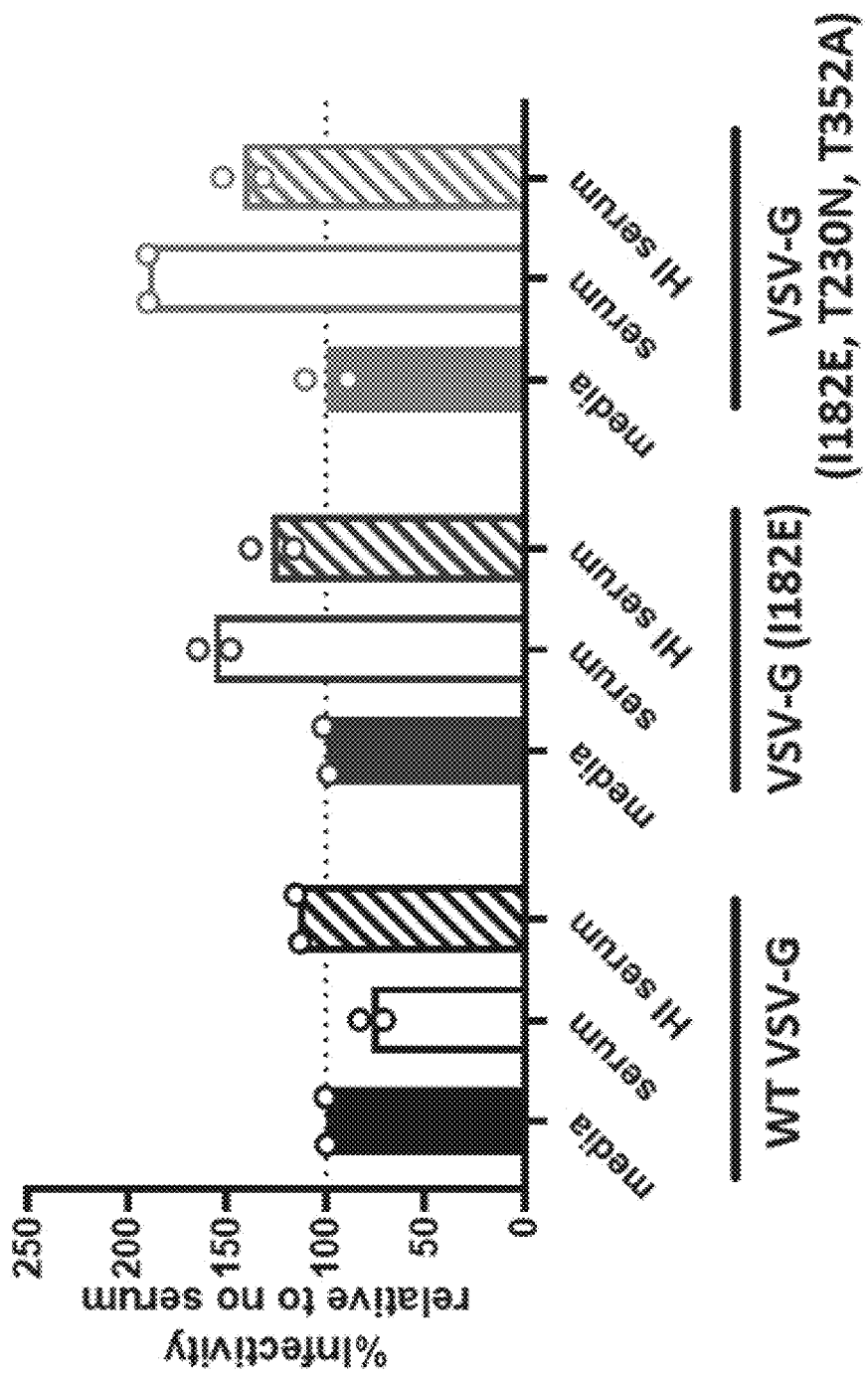
FIG. 5 illustrates the effect of various VSV-G mutations on the serum stability of viral constructs in combination with a CD7 binder.

To further characterize the effect of including serum stabilizing mutations in the viral constructs of the present application, WT VSV-G, VSV-G (I182E), and VSV-G (I182E, T230N, T352A) were assessed at a lower dose of vector (FIG. 5). In agreement with the previous assessment, WT VSV-G showed decreased infectivity in serum as compared to no-serum conditions (FIG. 5, columns 1 and 2). However, heat inactivation (HI) of serum did appear to have a rescuing effect on WT VSV-G infectivity (FIG. 5, column 3). In further agreement with the previous assessment, VSV-G (I182E) demonstrated enhanced infectivity in the presence of serum as compared to no serum conditions (FIG. 5, columns 4 and 5). The presence of HI serum also resulted in an increased infectivity compared to no serum, with a smaller effect than naïve serum (FIG. 5, column 6). VSV-G (I182E, T214N, T352A) also demonstrated increased infectivity in serum and HI serum conditions as compared to no serum conditions (FIG. 5, columns 7-9), in agreement with the previous assessment. Further, when compared to the respective no serum condition, VSV-G (I182E, T230N, T352A) results in a greater percent increased infectivity compared to VSV-G (I182E), suggesting that inclusion of all three mutations results in greater serum stability than just I182E alone.

Thus, these examples demonstrate that i) the LDL-R detargeting mutation I182E affords an unexpected level of protection against the serum inactivation observed for WT VSV-G, ii) the LDL-R detargeting mutation I182E does not abrogate the serum stabilizing effect of the T230N+T352A mutations, and iii) the combined mutation construct VSV-G (I182E, T230N, T352A) appears to have a greater serum stabilizing effect than either I182E alone or T230N+T352A alone. Thus, VSV-G (I182E, T230N, T352A) is able to ablate native tropism without alternating fusogenicity and additionally demonstrates a more stable profile and is not neutralized in serum.

Example 3: CD7 Targeting Moiety can be Linked to a Fc Stalk to Transduce PBMCs

Generation of Plasmids and Sequences.

The amino acid sequence including CDRs of the CD7 binder was determined via mass spectrometry (Rapid Novor). CD7 binder sequences were synthesized by IDT or GenScript (Piscataway, NJ) using codon optimization for human expression and inserted onto viral glycoprotein or IgG-based stalks and flanked by a G4S linker. An example viral glycoprotein is a Nipah-G protein with the CD7 binder attached to the extracellular region. An example IgG-based stalk was a human IgG1 Fc dimer with a CD8 or CD28 transmembrane region and an envelope incorporating motif with the CD7 binder attached to the extracellular region. The resulting binders were expressed under the direction of a CMV promoter.

Generation of Engineered Lentiviral Particles.

The recombinant lentiviral particles expressing the CD7 binder incorporated on the surface were generated by plasmid transection into HEK293T cells using Lipofectamine 3000 (ThermoFisher Scientific). In some embodiments, a total of 5 plasmids were transfected: (1) plasmid expressing the CD7 binder with the IgG stalk or a plasmid expressing the CD7 binder on a Nipah-G protein, (2) plasmid expressing a detargeted-VSV-G protein, (3) lentiviral genome expressing eGFP, (4) plasmid expressing gag-pol, (5) plasmid expressing rev. In some embodiments, a total of 5 plasmids were transfected: (1) plasmid expressing the CD7 binder with the Nipah-G protein, (2) plasmid expressing Nipah-F protein, (3) lentiviral genome expressing eGFP, (4) plasmid expressing gag-pol, (5) plasmid expressing rev. Media was changed 6 hours after transfection and cells were harvested 48 hours later. Virus in the media was concentrated by centrifugation through a sucrose cushion and resuspended in media. Lentiviral particle titer was determined using the Lenti-X p24 Rapid Titer Kit (Takara Bio, San Jose, CA)

CD7 binders attach to both human and non-human primate PBMCs, leading to CD7+ cell transduction.

Figure 6:
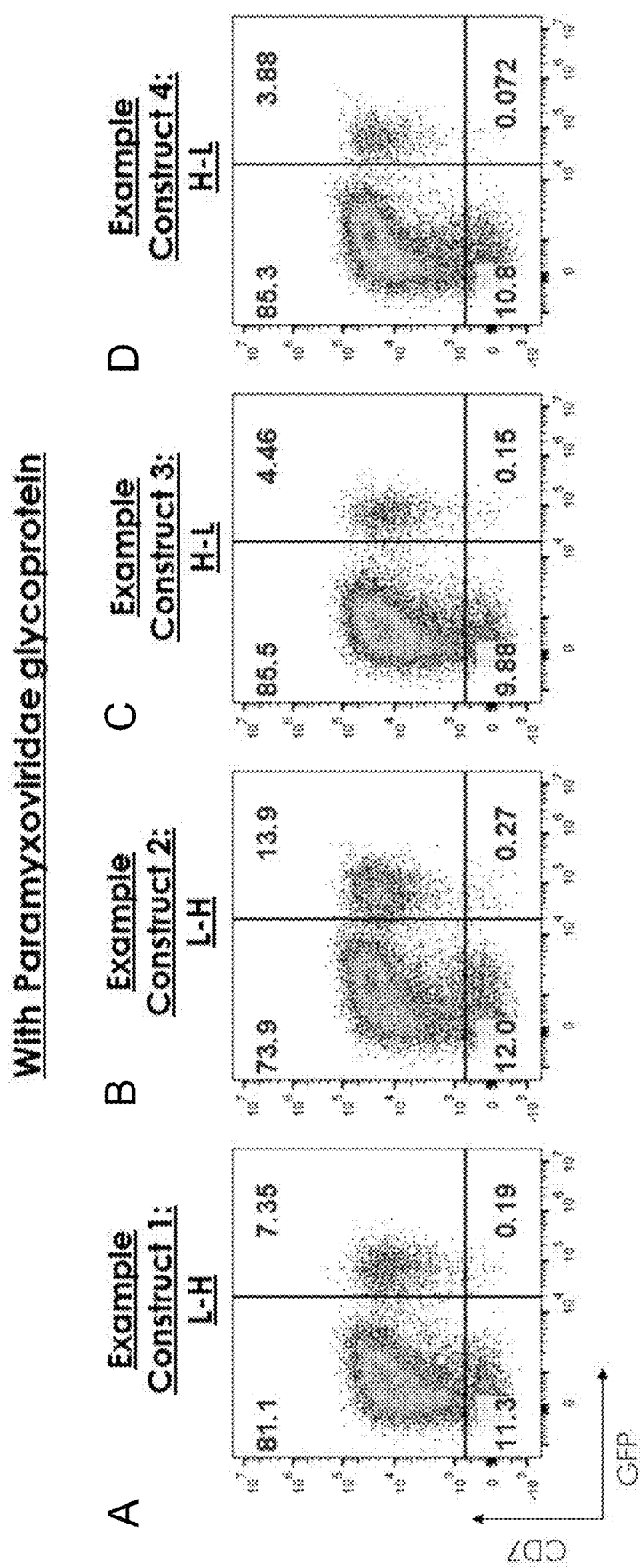
FIG. 6 Panels A-L show flow cytometry data of human PBMCs transduced with exemplary vectors comprising CD7 binders as disclosed herein.
Figure 6:
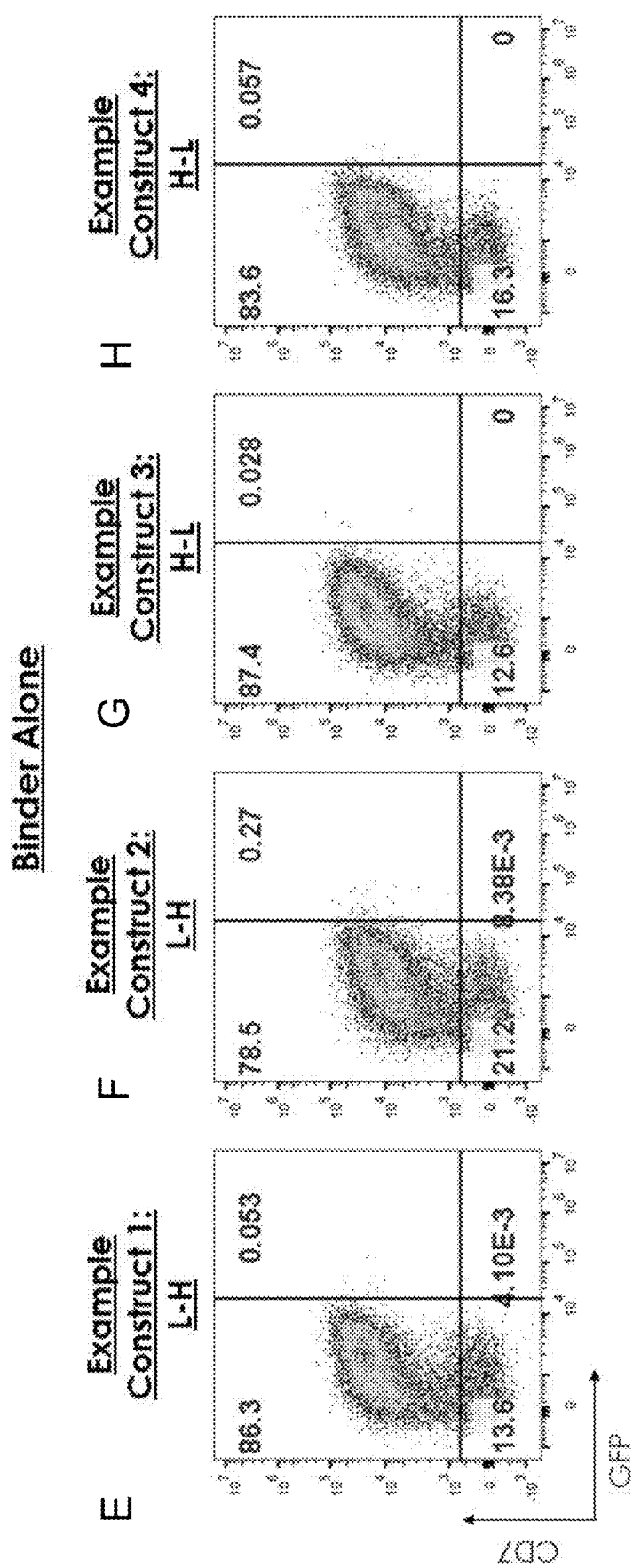
Figure 6:
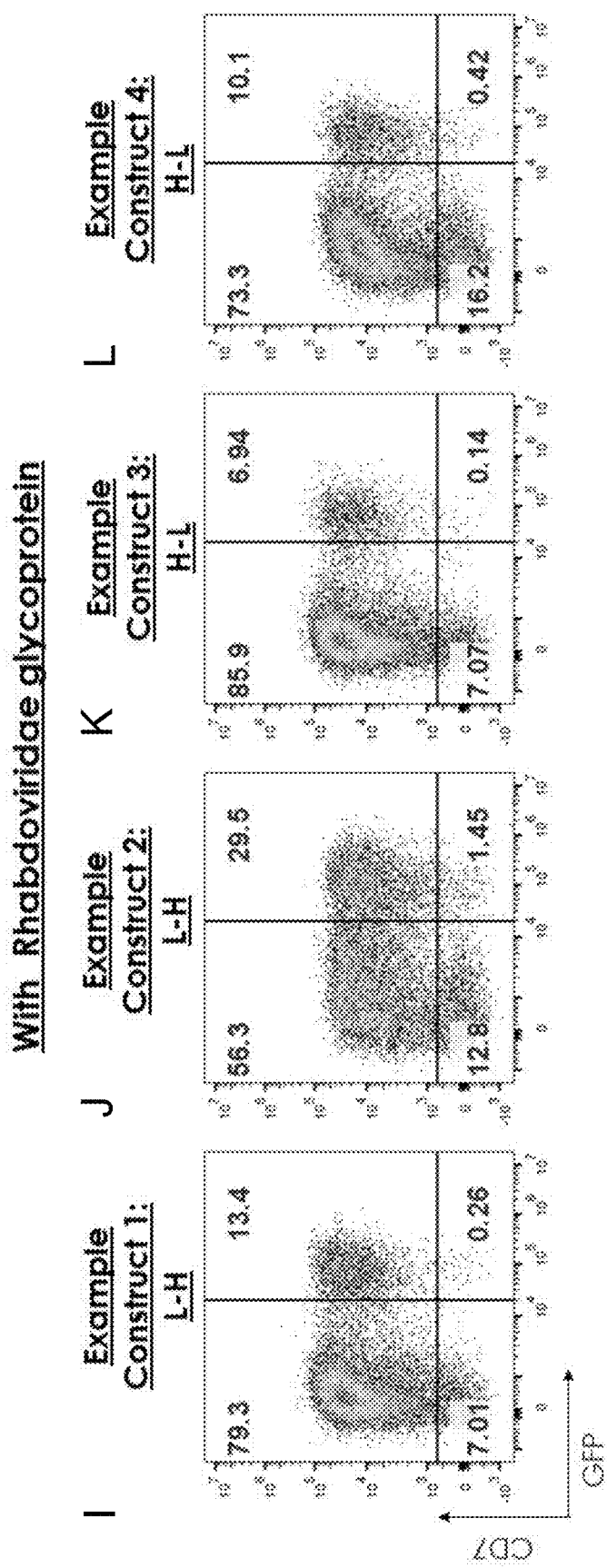
Figure 6:
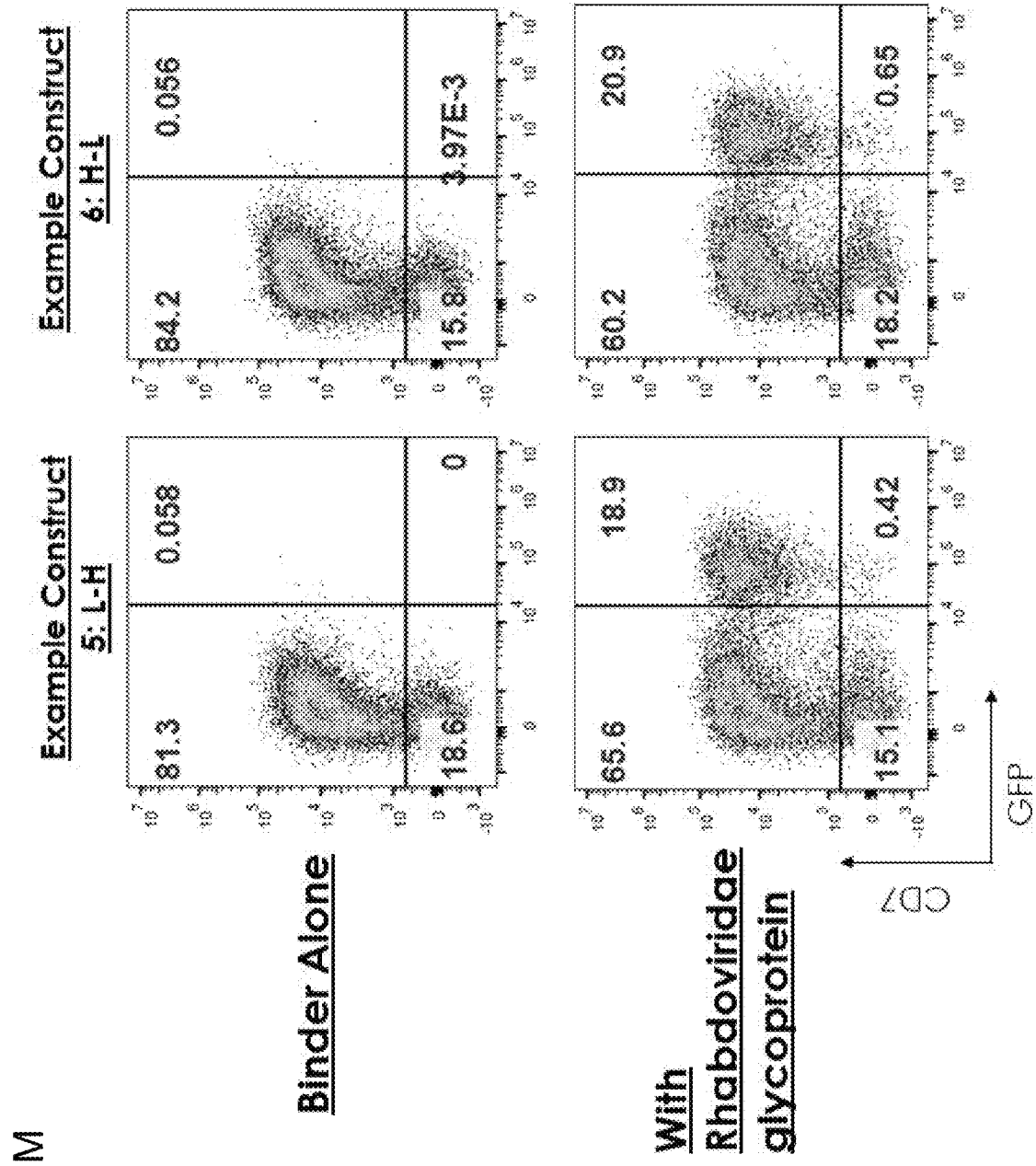
Figure 7:
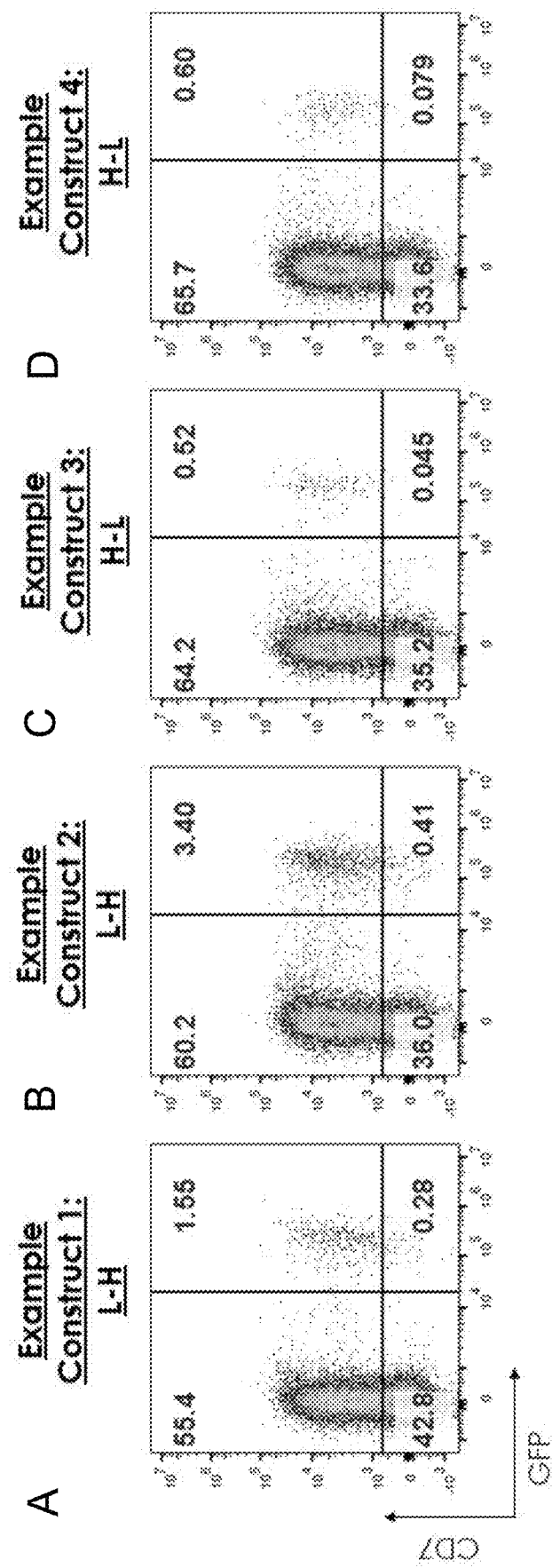
FIG. 7 Panels A-L shows flow cytometry data of non-human primate PBMCs transduced with exemplary vectors comprising CD7 binders as disclosed herein.
Figure 7:
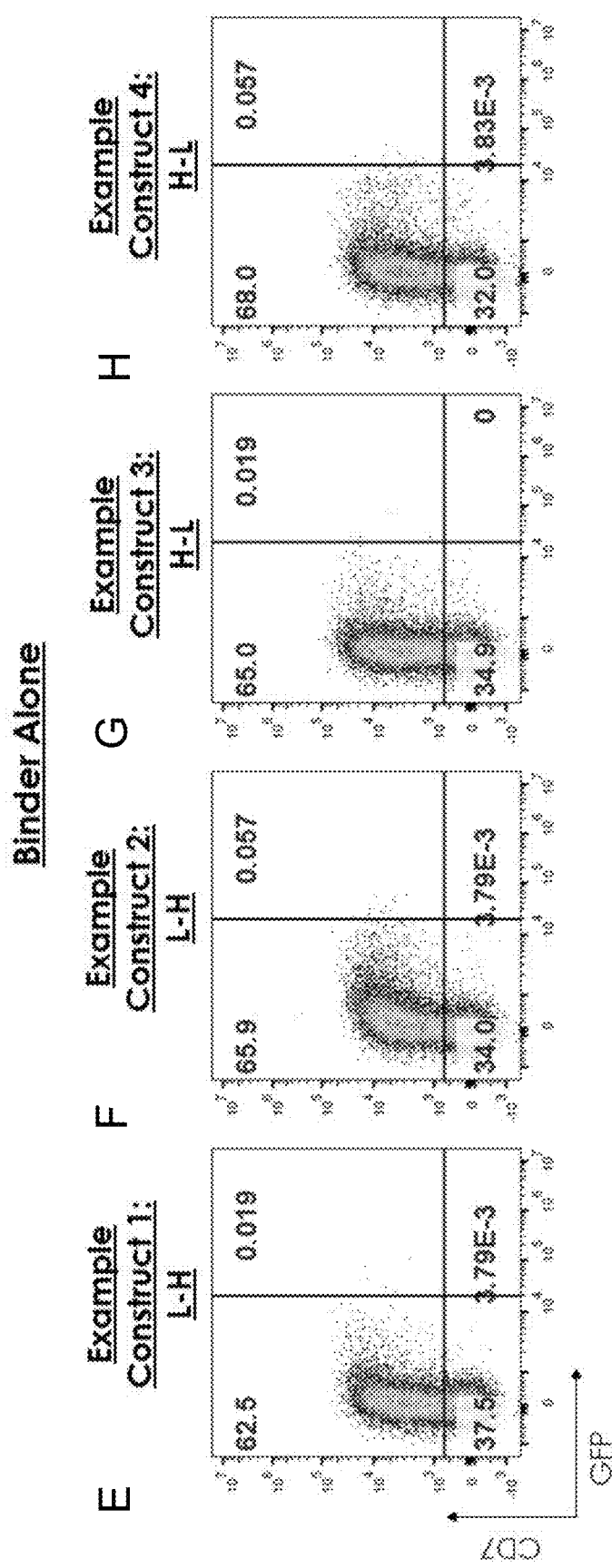
Figure 7:
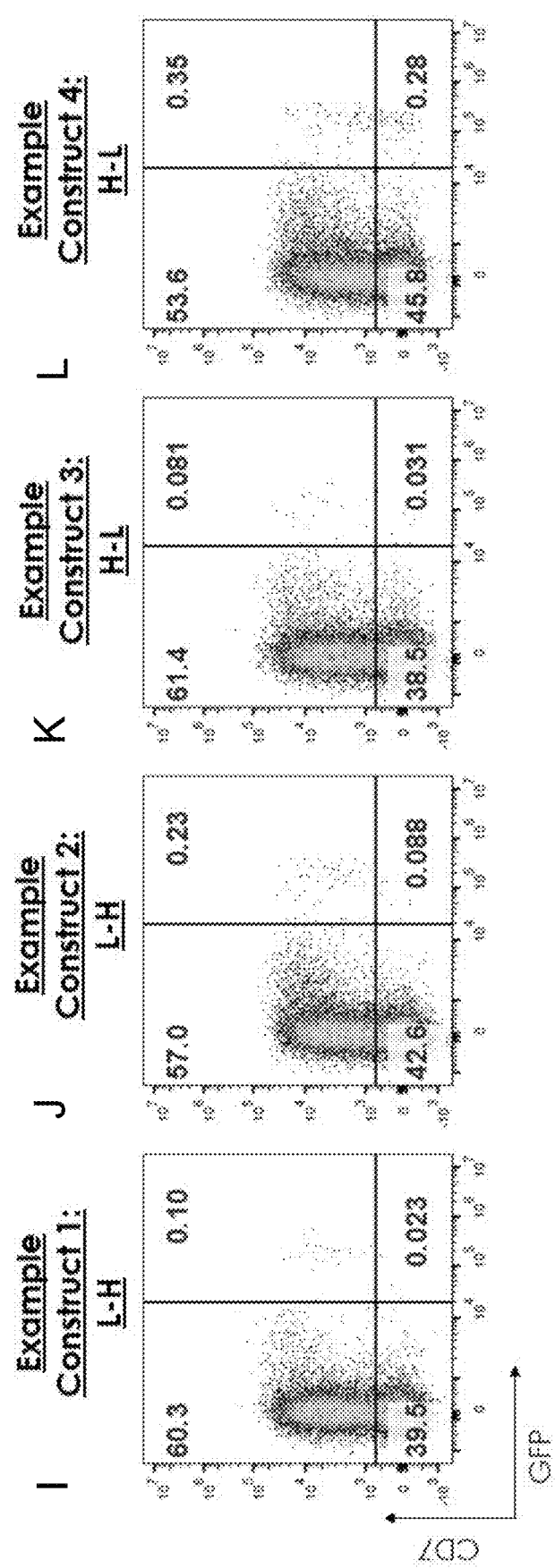
Figure 7:
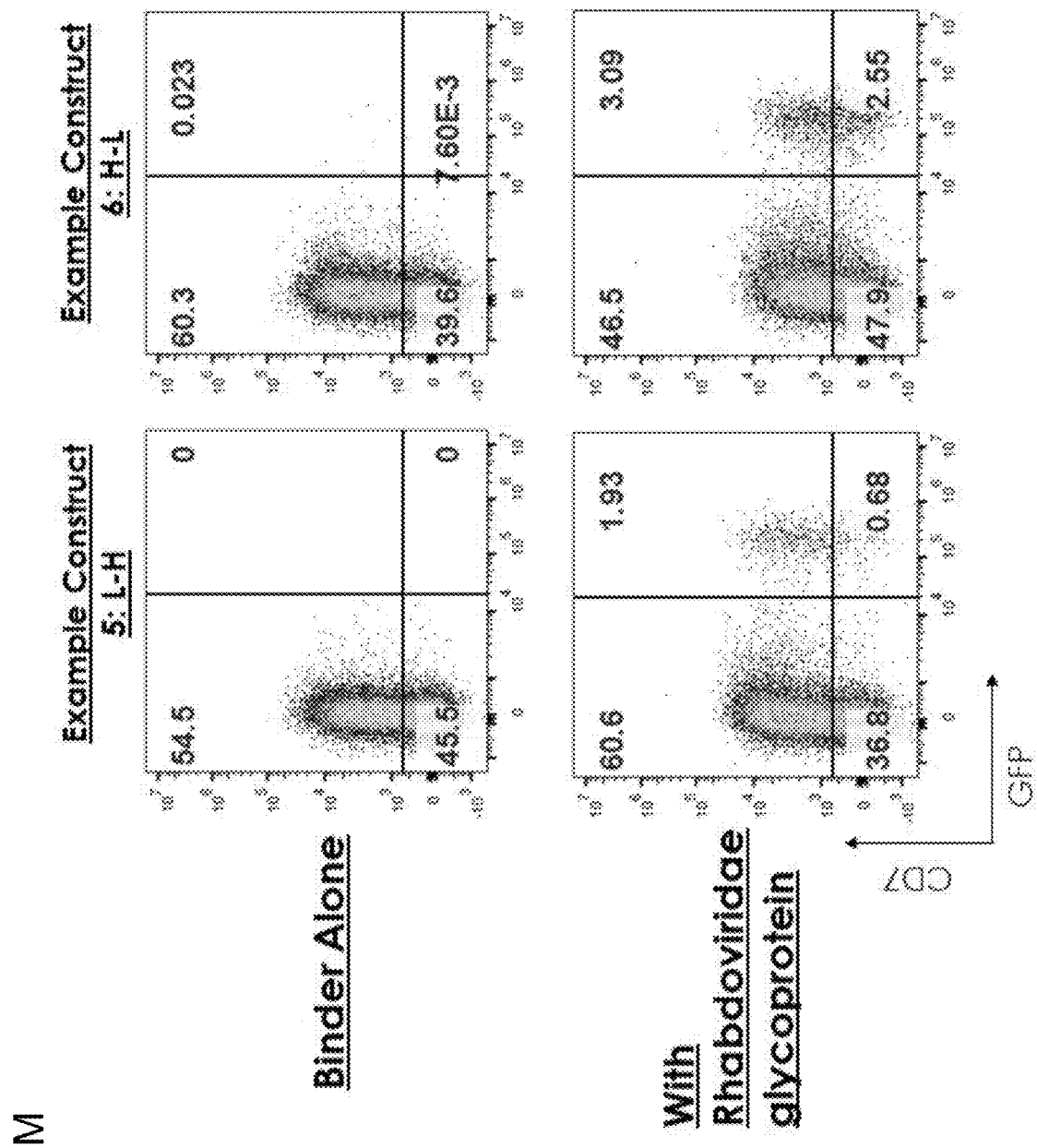
Figure 8:
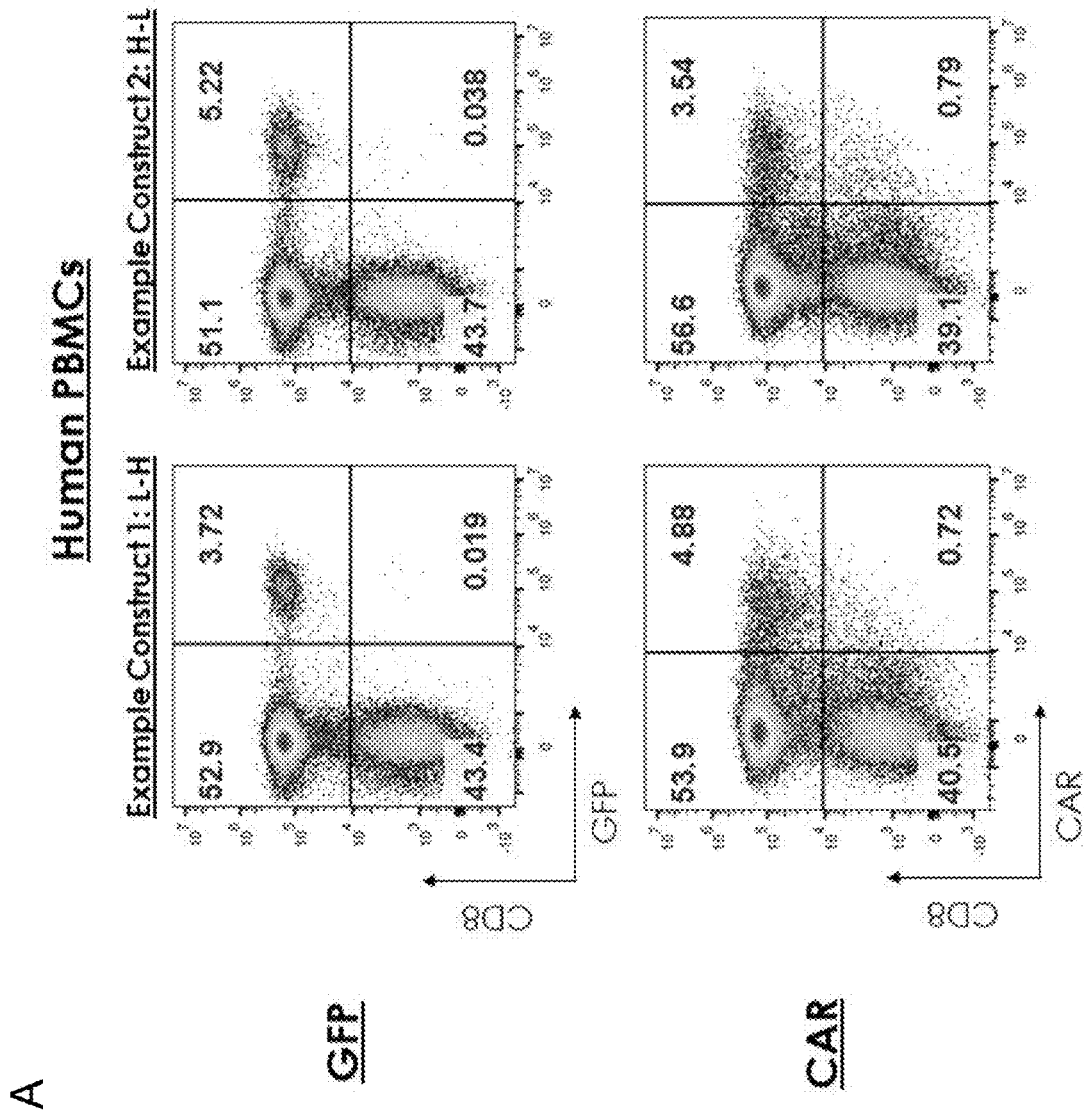
FIG. 8 Panel A shows flow cytometry data of human PBMCs transduced with exemplary vectors comprising CD8 binders as disclosed herein.
Figure 8:
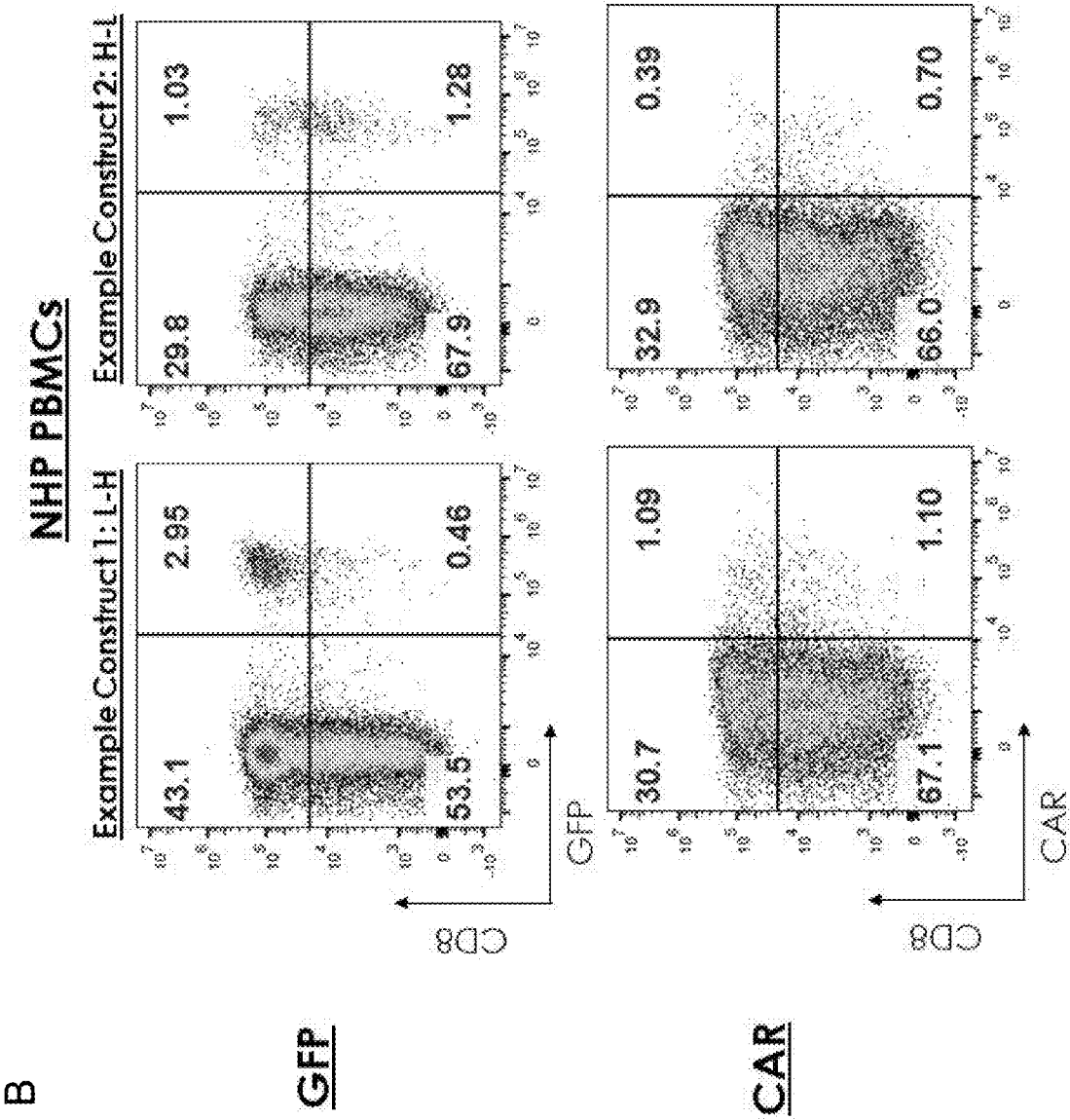
Figure 10:
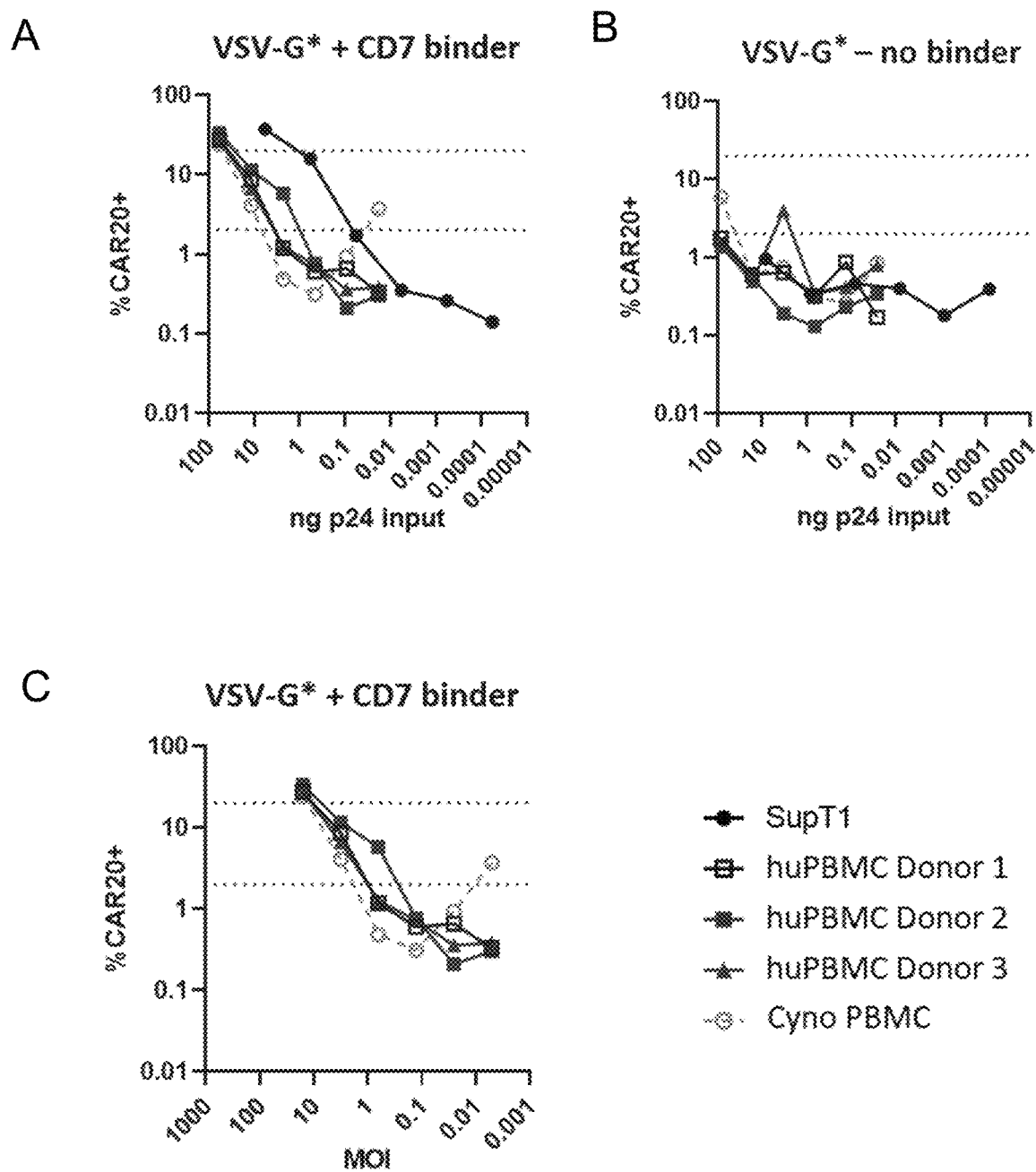
FIG. 10 Panel A illustrates the ability of VSV-G* pseudotyped lentiviral particles harboring a CD7 binder to transduce SupT1 cells as well as human and non-human primate PBMCs.

Human PBMC cells were maintained in X-Vivo10 media with 5% human serum and 20 ng/mL of human IL-2. Non-human primate cells were maintained in RPMI media with 10% FBS, 1% Pen/Strep with 1 mM Sodium Pyruvate and 100 units/mL hIL-2. Concentrated lentivirus was used to infect human and non-human primate cells. Media was replaced 24 hours later, and the transduced cells were analyzed by flow cytometry on days 4 and 7 after transduction. Cells were stained with an anti-CD7 antibody to detect CD7 positive cells (PE-Cy7 mouse-anti-human CD7, clone MT-701, Biolegend) as well as GFP expression. Cell viability was also determined. CD7 binders attached to Paramyxoviridae glycoproteins, such as Nipah-G (FIG. 6 Panels A-D and FIG. 7 Panels A-D) or with Rhabdoviridae glycoproteins, such as VSV-G (FIG. 6 Panels I-L and FIG. 7 Panels I-L) successfully transduced human PBMCs (FIG. 6 Panels A-L) or NHP PBMCs (FIG. 7 Panels A-L) compared to the binder alone (FIG. 6 Panels E-H and FIG. 7 Panels E-H) which shows no transduction. When CD7 with an IgG stalk was tested, the binder alone (top row) again did not transduce human (FIG. 6 Panel M) or NHP PBMCs (FIG. 7 Panel M) but when administered with detargeted VSV-G, transduction was seen in both human (FIG. 6 Panel M, bottom panel) and NHP PBMCs (FIG. 7 Panel M, bottom panel). GFP transduction experiments were repeated as described above for detargeted VSV-G pseudotyped lentiviral constructs with CD7 binders. Results of the repeat experiments were in agreement with the data of FIGS. 6 and 7 and are provided in Table 1 below.

TABLE 1

|  | WT VSVG | Detartgeted VSVG | CD7 Binder (SEQ ID NO. 51) | CD7 Binder (SEQ ID NO. 52) | CD8 Binder (SEQ ID NO. 69) | CD7 Binder (SEQ ID NO. 70) |
| --- | --- | --- | --- | --- | --- | --- |
| Human PBMC Transduction (% positive) | 52.76 | 0.00798 | 19.32 | 21.55 | 4.09 | 3.17 |
| NHP PBMC Transduction (% positive) | 48.4 | 0.026 | 2.61 | 5.64 | 1.8 | 0.76 |

These examples and embodiments demonstrate that the polypeptides can be used to bind to CD7 and target viral particles to cells expressing CD7 to transduce the cells expressing CD7.

Example 4: CD8 Targeting Moiety can be Linked to a Fc Stalk to Transduce PBMCs

Generation of Plasmids and Sequences.

The amino acid sequence including CDRs of the CD8 binder was determined via mass spectrometry (Rapid Novor). CD8 binder sequences were synthesized by IDT or GenScript (Piscataway, NJ) using codon optimization for human expression and inserted onto viral glycoprotein or IgG-based stalks and flanked by a G4S linker. An example viral glycoprotein is a Nipah-G protein with the CD8 binder attached to the extracellular region. An example IgG-based stalk was a human IgG1 Fc dimer with a CD8 or CD28 transmembrane region and an envelope incorporating motif with the CD8 binder attached to the extracellular region. The resulting binders were expressed under the direction of a CMV promoter.

Generation of Engineered Lentiviral Particles.

The recombinant lentiviral particles expressing the CD8 binder incorporated on the surface were generated by plasmid transection into HEK293T cells using Lipofectamine 3000 (ThermoFisher Scientific). In some embodiments, a total of 5 plasmids were transfected: (1) plasmid expressing the CD8 binder with the IgG stalk, (2) plasmid expressing a detargeted-VSV-G protein, (3) lentiviral genome expressing eGFP, (4) plasmid expressing gag-pol, (5) plasmid expressing rev. In some embodiments, the lentiviral genome expressing eGFP was replaced with a CAR molecule. Media was changed 6 hours after transfection and cells were harvested 48 hours later. Virus in the media was concentrated by centrifugation through a sucrose cushion and resuspended in media. Lentiviral particle titer was determined using the Lenti-X p24 Rapid Titer Kit (Takara Bio, San Jose, CA).

CD8 binders attach to both human and non-human primate PBMCs, leading to CD8+ cell transduction.

Human PBMC cells were maintained in X-Vivol0 media with 5% human serum and 20 ng/mL of human IL-2. Non-human primate cells were maintained in RPMI media with 10% FBS, 1% Pen/Strep with 1 mM Sodium Pyruvate and 100 units/mL hIL-2. Concentrated lentivirus was used to infect human and non-human primate cells. Media was replaced 24 hours later, and the transduced cells were analyzed by flow cytometry on day 6 after transduction. Cells were stained with an anti-CD8 antibody to detect CD8 positive cells (BV421 mouse-anti-human CD8, clone RPA-T8, Biolegend) as well as GFP or CAR20 expression. Cell viability was also determined. CD8 binders with detargeted VSV-G successfully transduced human PBMCs (FIG. 8 Panel A) or NHP PBMCs (FIG. 8 Panel B) with GFP (FIG. 8 Panel A-8 Panel B, top row) and CAR20 (FIG. 8 Panel A-8 Panel B, bottom row). GFP transduction experiments were repeated as described above for detargeted VSV-G pseudotyped lentiviral constructs with CD8 binders. Results of the repeat experiments were in agreement with the data of FIG. 8 and are provided in Table 1 above.

These examples and embodiments demonstrate that the polypeptides can be used to bind to CD8 and target viral particles to cells expressing CD8 to transduce the cells expressing CD8.

Example 5: Binder Construct Affects Transgene Expression

Concentrated lentivirus was used to transduce SupT1 cells. Media was replaced 24 hours later, and the transduced cells were analyzed by flow cytometry. Cells were stained with an anti-CD8 antibody to detect CD8 positive cells or an anti-CD7 antibody to detect CD7 positive cells as well as GFP or CAR20 expression.

Lentiviral constructs utilizing CD7 or CD8 binders as provided for herein exhibited comparable GFP transduction (FIG. 9 Panel A). Binder orientation (VH-VL vs VL-VH) had minimal effect on transgene expression. WT VSV-G was used as a positive control, and detargeted VSV-G was used as a negative control. With respect to a CD20-CAR transgene, lentiviral constructs utilizing CD7 binders as provided for herein provided superior transgene transduction as compared to lentiviral constructs utilizing CD8 binders (FIG. 9 Panel B). As with the GFP transgene, binder orientation had minimal effect on transgene expression. Lentiviral constructs utilizing CD7 or CD8 binders both demonstrated transgene expression levels near the level of WT VSV-G when greater amounts of virus were utilized.

These examples and embodiments demonstrate that the CD7 and CD8 binders of the present disclosure can be incorporated into a lentiviral particle to direct successful transgene expression in a target cell. Further, these examples and embodiments demonstrate that different binders result in differential transgene expression, and that both the identity of the binder and the identity of the transgene are important variable in the efficacy of the viral particle.

Example 6: VSV-G* Pseudotyped Lentiviruses Harboring CD7 Binder Transduce PBMCs Human PBMC cells were maintained in X-Vivol0 media with 5% human serum and 20 ng/mL of human IL-2. Non-human primate cells were maintained in RPMI media with 10% FBS, 1% Pen/Strep with 1 mM Sodium Pyruvate and 100 units/mL hIL-2. Concentrated lentivirus was used to infect human and non-human primate cells. The VSV-G protein utilized was a variant VSV-G protein harboring a mutation to prevent binding of VSV-G to the LDL-R. The variant VSV-G is denoted VSV-G* and corresponds to VSV-G (I182E, T214N, T352A) (e.g. SEQ ID NO: 23), as provided for herein. A CD7 binder construct was utilized in the present example. The CD7 binder was as provided for herein. Media was replaced 24 hours later, and the transduced cells were analyzed by flow cytometry on day 7 after transduction to determine CAR transduction. CAR expression was observed in all human and non-human primate PBMCs assessed (FIG. 10 Panel A) compared to the binder alone (FIG. 10 Panel B) which shows no transduction. Data are also presented as percent CAR expression vs multiplicity of infection (FIG. 10 Panel C).

These examples and embodiments demonstrate that the VSV-G* pseudotyped lentiviruses are able to successfully transduce a variety of human and non-human primate PMBCs.

Example 7: VSV-G* Pseudotyped Lentiviruses Harboring a CD7 Binder Exhibit Minimal Off Target Transduction The off target transduction of B-cells via VSV-G* pseudotyped lentiviral constructs utilizing CD7 binders as provided for herein was assessed in several B-cell populations. The VSV-G protein utilized was a variant VSV-G protein harboring a mutation to prevent binding of VSV-G to the LDL-R. The variant VSV-G is denoted VSV-G* and corresponds to VSV-G (I182E, T214N, T352A) (e.g. SEQ ID NO: 23), as provided for herein. B-cells cells were maintained in X-Vivo10 media with 5% human serum and 20 ng/mL of human 1L-2. Non-human primate cells were maintained in RPMI media with 10% FBS, 1% Pen/Strep with 1 mM Sodium Pyruvate and 100 units/mL hIL-2. Concentrated lentivirus was used to infect the various B-cell populations. A CD7 binder construct was utilized in the present example. The CD7 binder was as provided for herein. Media was replaced 24 hours later, and the transduced cells were analyzed by flow cytometry on day 5 after transduction to determine GFP transduction. As a control, SupT1 cells were also infected with the same lentiviral constructs. None of the B-cell populations assessed demonstrated any significant level of GFP expression (FIG. 11 Panel A).

Lentiviral constructs delivering a CAR20-T2A-GFP transgene were also assessed in a similar manner. VSV-G* pseudotyped lentiviruses utilizing the CD7 binder still exhibited minimal off target transduction of B-cells in all cell populations tested (FIG. 11 Panel B). The percent of CAR-T2A-GFP positive cells only exceeded 1% in line DB at the highest lentiviral concentrations utilized.

These examples and embodiments demonstrate that the i) VSV-G* pseudotyped lentiviruses utilizing the CD7 binders of the present disclosure have low off target transduction of B-cells and ii) delivery of a CAR20 transgene instead of a GFP transgene does not significantly increase off target transduction in B-cells.

Example 8: VSV-G* Pseudotyped Lentiviruses with CD20-CAR Transgene Payload Kills CD20 Positive Lymphoma Cells In Vitro The ability of VSV-G* pseudotyped lentiviral constructs with a CD20-CAR transgene to kill CD20 positive lymphoma cells in vitro was assessed. The VSV-G* pseudotyped lentiviral constructs utilized CD7 binders as provided for herein. The VSV-G protein utilized was a variant VSV-G protein harboring a mutation to prevent binding of VSV-G to the LDL-R. The variant VSV-G is denoted VSV-G* and corresponds to VSV-G (I182E, T214N, T352A) (e.g. SEQ ID NO: 23), as provided for herein. Human PBMCs were transduced with a lentiviral construct carrying a CD20-CAR (CAR20) transgene. The CAR20 transgenes comprised antigen binding domains of SEQ ID NO: 75 or SEQ ID NO: 76. CD20 positive lymphoma cells were then added to the CAR20 cells at a given effector to target ratio (E:T). All lentiviral constructs tested produced a dose dependent killing of CAR20 positive lymphoma cells (FIG. 12)

These examples and embodiments demonstrate that the VSV-G* pseudotyped lentiviruses utilizing the CD7 binders of the present disclosure not only transduce the appropriate target cells as demonstrated by the previous examples, but also produce robust and dose dependent killing of CD20 positive lymphoma cells in vivo.

Figure 13:
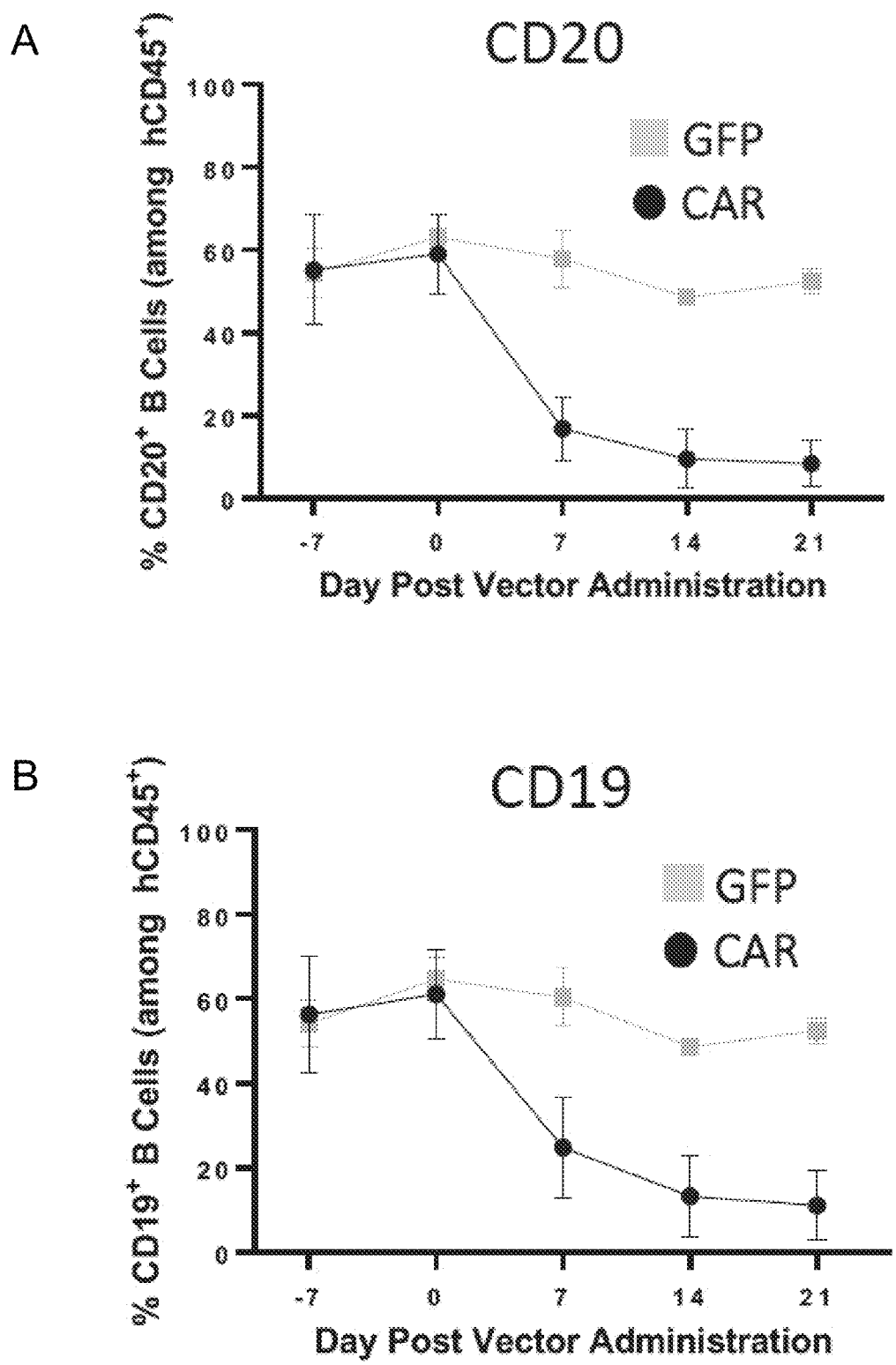
FIG. 13 Panels A and B illustrate the ability of VSV-G* pseudotyped lentiviral particles utilizing CD7 binders and a CD20-CAR transgene as provided for herein to deplete B-cells in vivo in huCD34 NSG mice. B-cells were detected via assessment for CD20 (FIG. 13 Panel A) or CD19 (FIG. 13 Panel B).

Example 9: VSV-G* Pseudotyped Lentiviruses Deplete B-Cells and Eliminate Established Tumors in Mice The ability of VSV-G* pseudotyped lentiviral constructs to deplete B-cell populations in vivo was assessed. The VSV-G* pseudotyped lentiviral constructs utilized CD7 binders as provided for herein. The VSV-G protein utilized was a variant VSV-G protein harboring a mutation to prevent binding of VSV-G to the LDL-R. The variant VSV-G is denoted VSV-G* and corresponds to VSV-G (I182E, T214N, T352A) (e.g. SEQ ID NO: 23, SEQ ID NO: 25), as provided for herein. Mice were injected with lentiviral particles expressing a GFP transgene, or a CD20-CAR transgene. The mice utilized were huCD34 NSG mice which have circulating human T and B cells. Mice receiving lentiviral constructs expressing GFP saw no loss of CD20 (FIG. 13 Panel A) or CD19 (FIG. 13 Panel B) B cells. Mice receiving the CD20-CAR transgene saw a dramatic and sustained loss of B cells over three weeks as exhibited by a dramatic loss of both CD20 positive B cells (FIG. 13 Panel A) and CD19 positive B cells (FIG. 13 Panel B).

Figure 14:
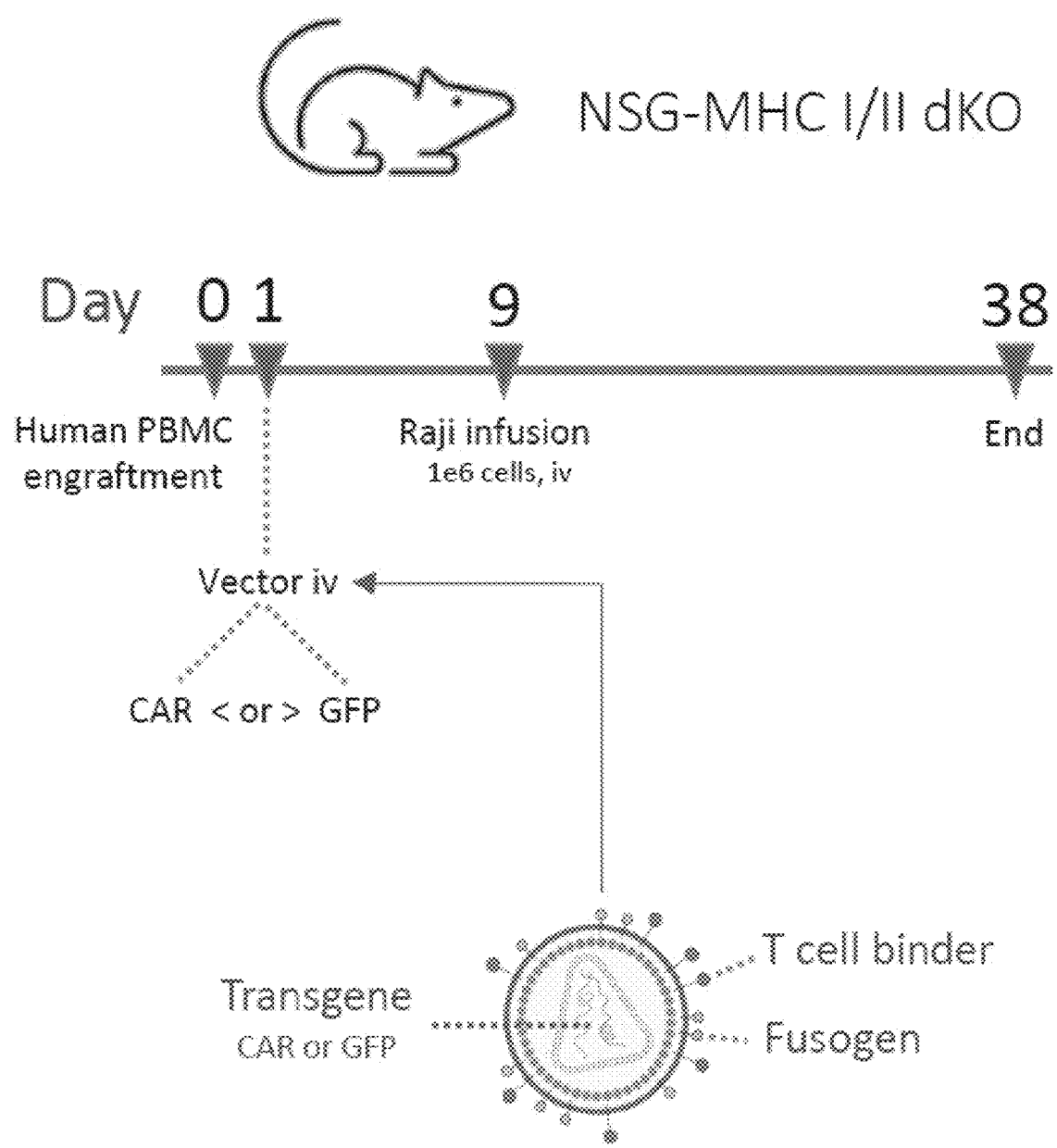
FIG. 14 Panels A and B illustrate the ability of VSV-G* pseudotyped lentiviral particles utilizing CD7 binders and a CD20-CAR transgene as provided for herein to prevent tumor formation in vivo.
Figure 14:
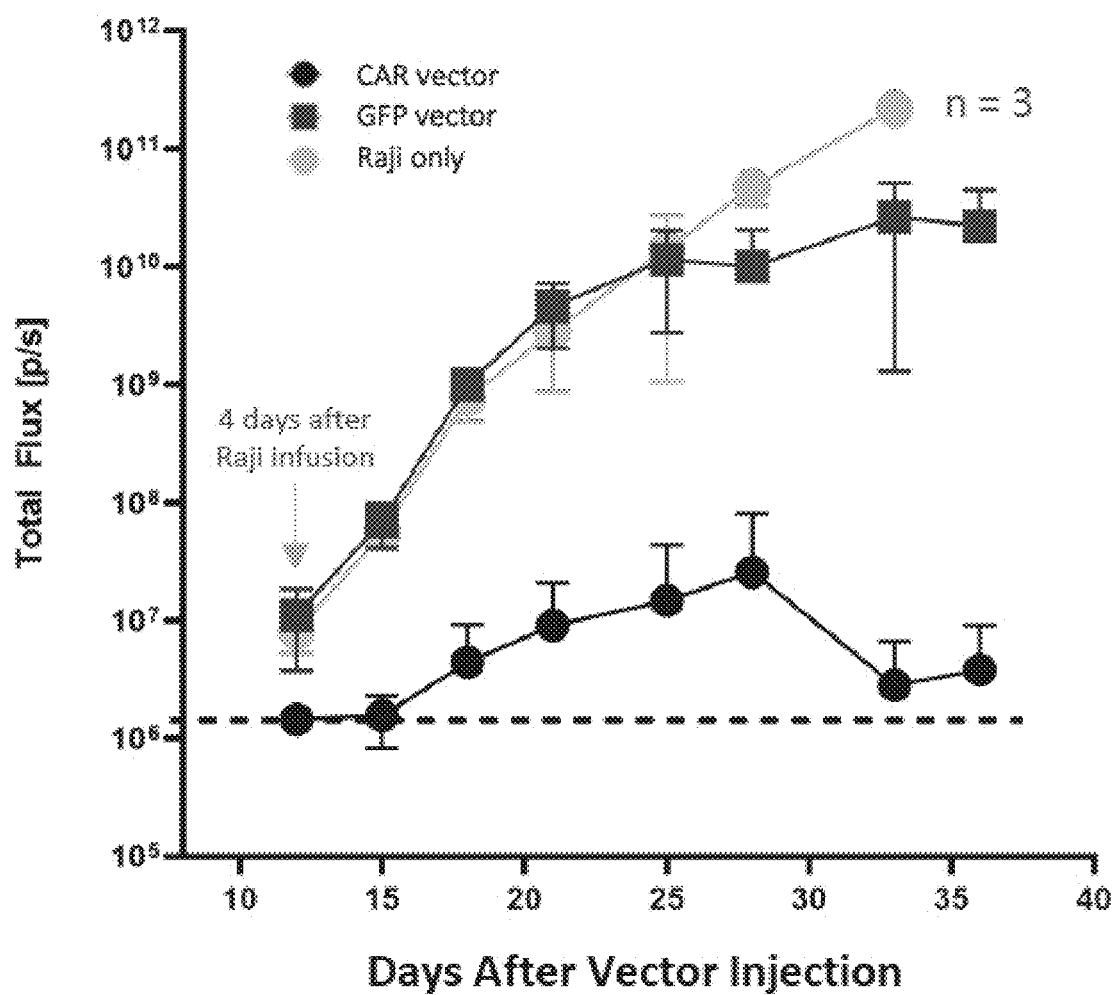

To further characterize the in vivo efficacy of the viral particles, the ability of VSV-G* pseudotyped lentiviral constructs to prevent tumor formation was assessed. Mice were injected with viral particles expressing a GFP transgene or a CD20-CAR transgene on protocol Day 1. On Day 9, mice were infused with Raji tumor cells and tumor progression was monitored. The experimental protocol illustrated in FIG. 14 Panel A. Mice receiving no treatment or lentiviral constructs expressing GFP demonstrated progressive tumor development and spread as determined by IVIS imaging. In contrast, mice receiving lentiviral constructs expressing the CD20-CAR transgene demonstrated no tumor development after Raji cell infusion (FIG. 14 Panel B).

Figure 15:
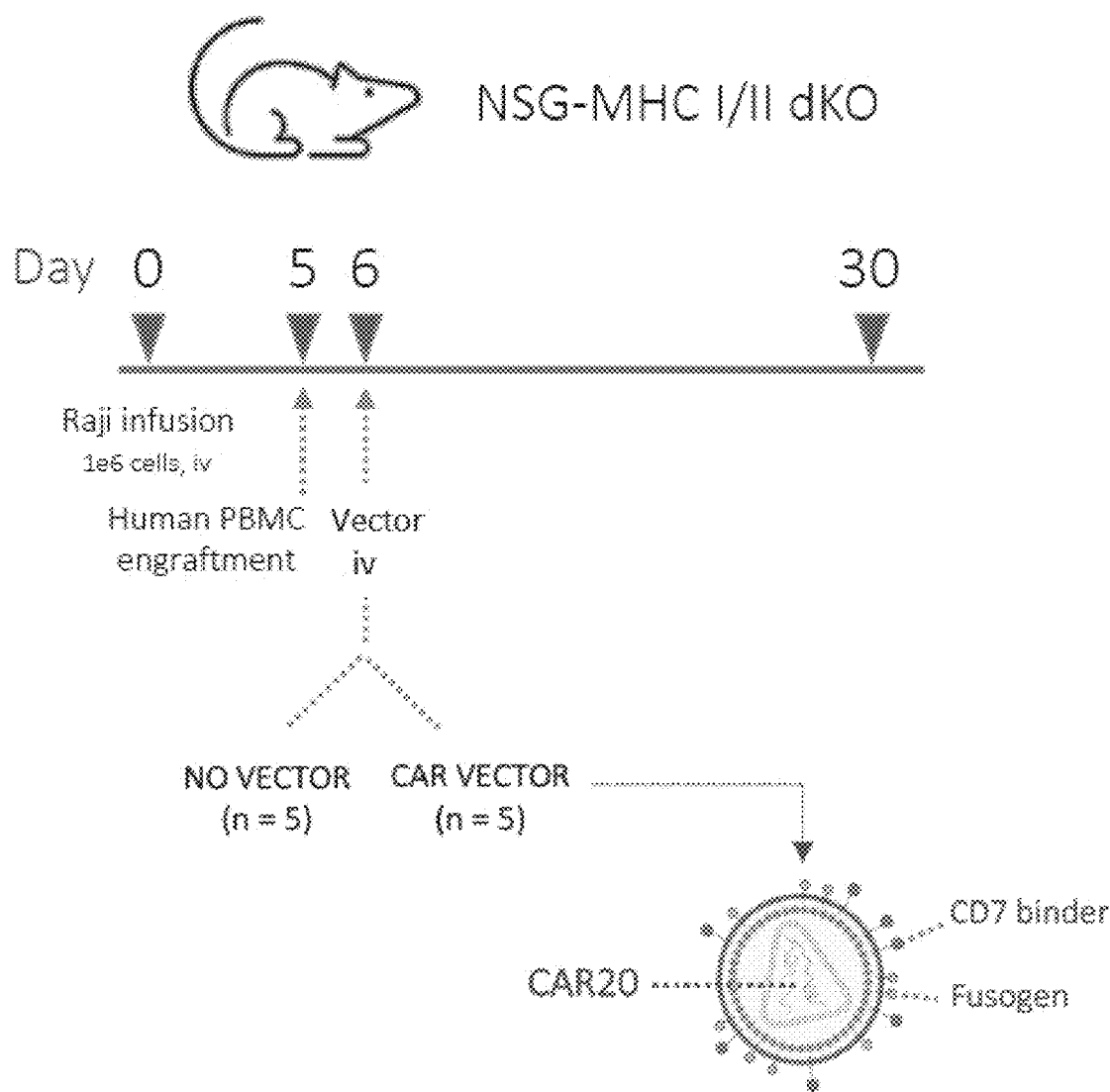
FIG. 15 Panels A and B illustrate the ability of VSV-G* pseudotyped lentiviral particles utilizing CD7 binders and a CD20-CAR transgene as provided for herein to eliminate established Raji tumors in vivo.
Figure 15:
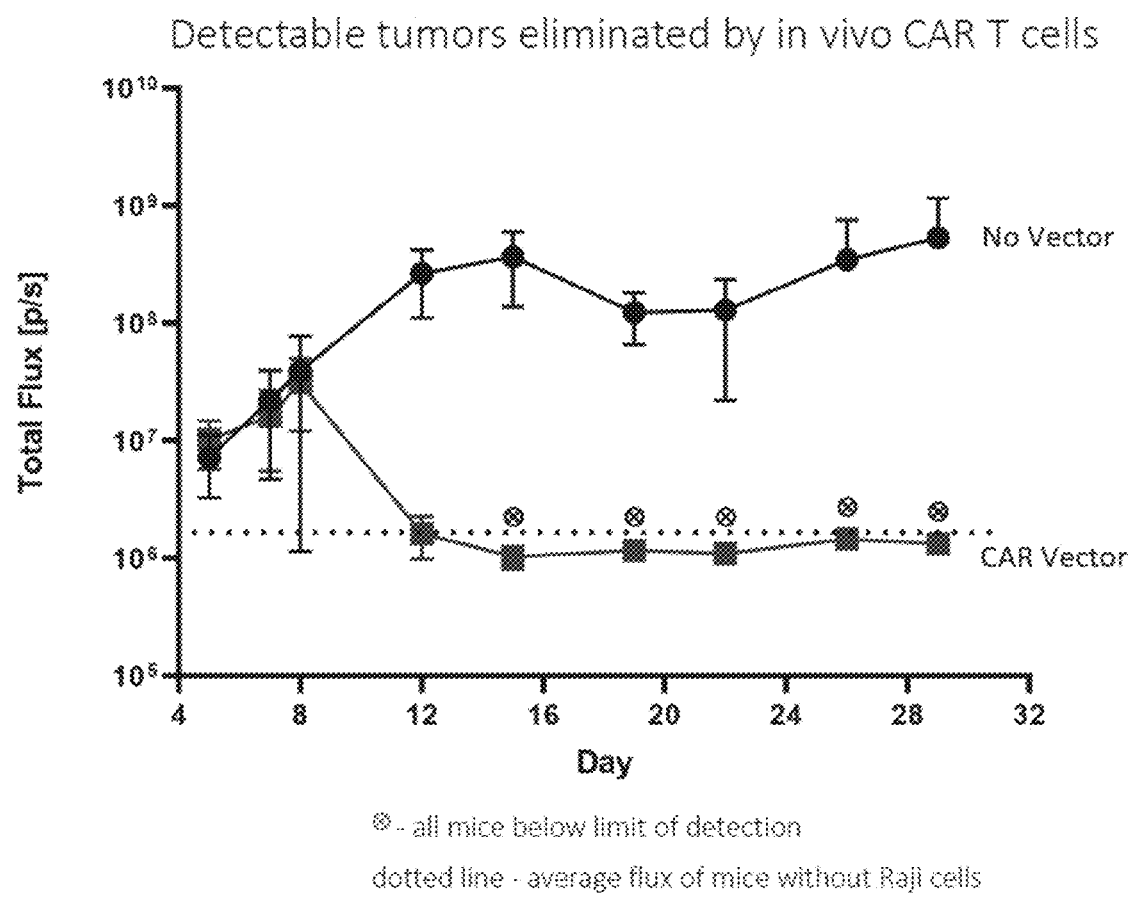

The ability of the viral particles to affect established tumors in vivo was also assessed. Mice were infused with Raji tumor cells on protocol Day 0. Mice were humanized via human PBMC engraftment on protocol Day 5, and mice were either not injected with viral particles (control) or injected with viral particles expressing a CD20-CAR transgene on protocol Day 6. Tumor progression was monitored through protocol Day 30. The experimental protocol is illustrated in FIG. 15 Panel A. Control and virus treated mice demonstrated comparable tumor load on Day 5 (prior to virus administration), Day 7, and Day 8 as determined by IVIS imaging, indicating that Raji tumors were established in both groups. At Day 12, control mice continued to exhibit increased tumor load, whereas virus treated mice exhibited a dramatic decrease in tumor load. The decreased tumor load was sustained throughout the duration of the experiment (FIG. 15 Panel B).

These examples and embodiments demonstrate that the VSV-G* pseudotyped lentiviral constructs of the present disclosure are able to properly target B-cells in vivo, prevent tumor formation in vivo, and eliminate established tumors in vivo.

Example 10: VSV-G* Pseudotyped Lentiviruses Deplete B-Cells in Non-Human Primates The ability of VSV-G* pseudotyped lentiviral constructs to deplete B-cell populations in vivo was also assessed in non-human primates (Macaques). The VSV-G* pseudotyped lentiviral constructs utilized CD7 binders as provided for herein. The VSV-G protein utilized was a variant VSV-G protein harboring a mutation to prevent binding of VSV-G to the LDL-R. The variant VSV-G is denoted VSV-G* and corresponds to VSV-G (I182E, T214N, T352A) (e.g. SEQ ID NO: 23), as provided for herein. Macaques were injected with lentiviral particles on protocol Day 0 and their CD20+ cells were monitored. Injection of the lentiviral particles results in B-cell depletion in 6/6 Macaques tested.

This specification contains numerous citations to patents, patent applications, and publications. Each is hereby incorporated by reference for all purposes.

The specification also makes reference to various sequences, such as those provided herein and below.

VSV-G Indiana Full length WT:
(SEQ ID NO: 1)
MKCLLYLAFLFIGVNCKFTIVFPHNQKGNWKNVPSNYHYCPSSSDLNWHNDLIGTALQVKMPKSHKAIQADGWMCHA

SKWVTTCDFRWYGPKYITHSIRSFTPSVEQCKESIEQTKQGTWLNPGFPPQSCGYATVTDAEAVIVQVTPHHVLVDE

YTGEWVDSQFINGKCSNYICPTVHNSTTWHSDYKVKGLCDSNLISMDITFFSEDGELSSLGKEGTGFRSNYFAYETG

GKACKMQYCKHWGVRLPSGVWFEMADKDLFAAARFPECPEGSSISAPSQTSVDVSLIQDVERILDYSLCQETWSKIR

AGLPISPVDLSYLAPKNPGTGPAFTIINGTLKYFETRYIRVDIAAPILSRMVGMISGTTTERELWDDWAPYEDVEIG

PNGVLRTSSGYKFPLYMIGHGMLDSDLHLSSKAQVFEHPHIQDAASQLPDDESLFFGDTGLSKNPIELVEGWFSSWK

SSIASFFFIIGLIIGLFLVLRVGIHLCIKLKHTKKRQIYTDIEMNRLGK

VSV-G Indiana Ectodomain WT:
(SEQ ID NO: 2)
KFTIVFPHNQKGNWKNVPSNYHYCPSSSDLNWHNDLIGTALQVKMPKSHKAIQADGWMCHASKWVTTCDFRWYGPKY

ITHSIRSFTPSVEQCKESIEQTKQGTWLNPGFPPQSCGYATVTDAEAVIVQVTPHHVLVDEYTGEWVDSQFINGKCS

NYICPTVHNSTTWHSDYKVKGLCDSNLISMDITFFSEDGELSSLGKEGTGFRSNYFAYETGGKACKMQYCKHWGVRL

PSGVWFEMADKDLFAAARFPECPEGSSISAPSQTSVDVSLIQDVERILDYSLCQETWSKIRAGLPISPVDLSYLAPK

NPGTGPAFTIINGTLKYFETRYIRVDIAAPILSRMVGMISGTTTERELWDDWAPYEDVEIGPNGVLRTSSGYKFPLY

MIGHGMLDSDLHLSSKAQVFEHPHIQDAASQLPDDESLFFGDTGLSKNPIELVEGWFSSWKSSIASFFFIIGLIIGL

FLVLRVGIHLCIKLKHTKKRQIYTDIEMNRLGK

VSV-G Indiana ectodomain I182A:
(SEQ ID NO: 3)
KFTIVFPHNQKGNWKNVPSNYHYCPSSSDLNWHNDLIGTALQVKMPKSHKAIQADGWMCHASKWVTTCDFRWYGPKY

ITHSIRSFTPSVEQCKESIEQTKQGTWLNPGFPPQSCGYATVTDAEAVIVQVTPHHVLVDEYTGEWVDSQFINGKCS

NYICPTVHNSTTWHSDYKVKGLCDSNLASMDITFFSEDGELSSLGKEGTGFRSNYFAYETGGKACKMQYCKHWGVRL

PSGVWFEMADKDLFAAARFPECPEGSSISAPSQTSVDVSLIQDVERILDYSLCQETWSKIRAGLPISPVDLSYLAPK

NPGTGPAFTIINGTLKYFETRYIRVDIAAPILSRMVGMISGTTTERELWDDWAPYEDVEIGPNGVLRTSSGYKFPLY

MIGHGMLDSDLHLSSKAQVFEHPHIQDAASQLPDDESLFFGDTGLSKNPIELVEGWFSSWKSSIASFFFIIGLIIGL

FLVLRVGIHLCIKLKHTKKRQIYTDIEMNRLGK

VSV-G Indiana ectodomain I182D:
(SEQ ID NO: 4)
KFTIVFPHNQKGNWKNVPSNYHYCPSSSDLNWHNDLIGTALQVKMPKSHKAIQADGWMCHASKWVTTCDFRWYGPKY

ITHSIRSFTPSVEQCKESIEQTKQGTWLNPGFPPQSCGYATVTDAEAVIVQVTPHHVLVDEYTGEWVDSQFINGKCS

NYICPTVHNSTTWHSDYKVKGLCDSNLDSMDITFFSEDGELSSLGKEGTGFRSNYFAYETGGKACKMQYCKHWGVRL

PSGVWFEMADKDLFAAARFPECPEGSSISAPSQTSVDVSLIQDVERILDYSLCQETWSKIRAGLPISPVDLSYLAPK

NPGTGPAFTIINGTLKYFETRYIRVDIAAPILSRMVGMISGTTTERELWDDWAPYEDVEIGPNGVLRTSSGYKFPLY

MIGHGMLDSDLHLSSKAQVFEHPHIQDAASQLPDDESLFFGDTGLSKNPIELVEGWFSSWKSSIASFFFIIGLIIGL

FLVLRVGIHLCIKLKHTKKRQIYTDIEMNRLGK

VSV-G Indiana ectodomain I182E:
(SEQ ID NO: 5)
KFTIVFPHNQKGNWKNVPSNYHYCPSSSDLNWHNDLIGTALQVKMPKSHKAIQADGWMCHASKWVTTCDFRWYGPKY

ITHSIRSFTPSVEQCKESIEQTKQGTWLNPGFPPQSCGYATVTDAEAVIVQVTPHHVLVDEYTGEWVDSQFINGKCS

NYICPTVHNSTTWHSDYKVKGLCDSNLESMDITFFSEDGELSSLGKEGTGFRSNYFAYETGGKACKMQYCKHWGVRL

PSGVWFEMADKDLFAAARFPECPEGSSISAPSQTSVDVSLIQDVERILDYSLCQETWSKIRAGLPISPVDLSYLAPK

NPGTGPAFTIINGTLKYFETRYIRVDIAAPILSRMVGMISGTTTERELWDDWAPYEDVEIGPNGVLRTSSGYKFPLY

-continued

MIGHGMLDSDLHLSSKAQVFEHPHIQDAASQLPDDESLFFGDTGLSKNPIELVEGWFSSWKSSIASFFFIIGLIIGL

FLVLRVGIHLCIKLKHTKKRQIYTDIEMNRLGK

VSV-G Indiana ectodomain H8A + K47Q:

(SEQ ID NO: 6)

KFTIVFPANQKGNWKNVPSNYHYCPSSSDLNWHNDLIGTALQVKMPQSHKAIQADGWMCHASKWVTTCDFRWYGPKY

ITHSIRSFTPSVEQCKESIEQTKQGTWLNPGFPPQSCGYATVTDAEAVIVQVTPHHVLVDEYTGEWVDSQFINGKCS

NYICPTVHNSTTWHSDYKVKGLCDSNLISMDITFFSEDGELSSLGKEGTGFRSNYFAYETGGKACKMQYCKHWGVRL

PSGVWFEMADKDLFAAARFPECPEGSSISAPSQTSVDVSLIQDVERILDYSLCQETWSKIRAGLPISPVDLSYLAPK

NPGTGPAFTIINGTLKYFETRYIRVDIAAPILSRMVGMISGTTTERELWDDWAPYEDVEIGPNGVLRTSSGYKFPLY

MIGHGMLDSDLHLSSKAQVFEHPHIQDAASQLPDDESLFFGDTGLSKNPIELVEGWFSSWKSSIASFFFIIGLIIGL

FLVLRVGIHLCIKLKHTKKRQIYTDIEMNRLGK

VSV-G Indiana ectodomain Q10A:

(SEQ ID NO: 7)

KFTIVFPHNAKGNWKNVPSNYHYCPSSSDLNWHNDLIGTALQVKMPKSHKAIQADGWMCHASKWVTTCDFRWYGPKY

ITHSIRSFTPSVEQCKESIEQTKQGTWLNPGFPPQSCGYATVTDAEAVIVQVTPHHVLVDEYTGEWVDSQFINGKCS

NYICPTVHNSTTWHSDYKVKGLCDSNLISMDITFFSEDGELSSLGKEGTGFRSNYFAYETGGKACKMQYCKHWGVRL

PSGVWFEMADKDLFAAARFPECPEGSSISAPSQTSVDVSLIQDVERILDYSLCQETWSKIRAGLPISPVDLSYLAPK

NPGTGPAFTIINGTLKYFETRYIRVDIAAPILSRMVGMISGTTTERELWDDWAPYEDVEIGPNGVLRTSSGYKFPLY

MIGHGMLDSDLHLSSKAQVFEHPHIQDAASQLPDDESLFFGDTGLSKNPIELVEGWFSSWKSSIASFFFIIGLIIGL

FLVLRVGIHLCIKLKHTKKRQIYTDIEMNRLGK

VSV-G Indiana ectodomain Q10R:

(SEQ ID NO: 8)

KFTIVFPHNRKGNWKNVPSNYHYCPSSSDLNWHNDLIGTALQVKMPKSHKAIQADGWMCHASKWVTTCDFRWYGPKY

ITHSIRSFTPSVEQCKESIEQTKQGTWLNPGFPPQSCGYATVTDAEAVIVQVTPHHVLVDEYTGEWVDSQFINGKCS

NYICPTVHNSTTWHSDYKVKGLCDSNLISMDITFFSEDGELSSLGKEGTGFRSNYFAYETGGKACKMQYCKHWGVRL

PSGVWFEMADKDLFAAARFPECPEGSSISAPSQTSVDVSLIQDVERILDYSLCQETWSKIRAGLPISPVDLSYLAPK

NPGTGPAFTIINGTLKYFETRYIRVDIAAPILSRMVGMISGTTTERELWDDWAPYEDVEIGPNGVLRTSSGYKFPLY

MIGHGMLDSDLHLSSKAQVFEHPHIQDAASQLPDDESLFFGDTGLSKNPIELVEGWFSSWKSSIASFFFIIGLIIGL

FLVLRVGIHLCIKLKHTKKRQIYTDIEMNRLGK

VSV-G Indiana ectodomain Q10K:

(SEQ ID NO: 9)

KFTIVFPHNKKGNWKNVPSNYHYCPSSSDLNWHNDLIGTALQVKMPKSHKAIQADGWMCHASKWVTTCDFRWYGPKY

ITHSIRSFTPSVEQCKESIEQTKQGTWLNPGFPPQSCGYATVTDAEAVIVQVTPHHVLVDEYTGEWVDSQFINGKCS

NYICPTVHNSTTWHSDYKVKGLCDSNLISMDITFFSEDGELSSLGKEGTGFRSNYFAYETGGKACKMQYCKHWGVRL

PSGVWFEMADKDLFAAARFPECPEGSSISAPSQTSVDVSLIQDVERILDYSLCQETWSKIRAGLPISPVDLSYLAPK

NPGTGPAFTIINGTLKYFETRYIRVDIAAPILSRMVGMISGTTTERELWDDWAPYEDVEIGPNGVLRTSSGYKFPLY

MIGHGMLDSDLHLSSKAQVFEHPHIQDAASQLPDDESLFFGDTGLSKNPIELVEGWFSSWKSSIASFFFIIGLIIGL

FLVLRVGIHLCIKLKHTKKRQIYTDIEMNRLGK

VSV-G New Jersey Full length WT:

(SEQ ID NO: 10)

MLSYLIFALVVSPILGKIEIVFPQHTTGDWKRVPHEYNYCPTSADKNSHGTQTGIPVELTMPKGLTTHQVDGFMCHS

ALWMTTCDFRWYGPKYITHSIHNEEPTDYQCLEAIKAYKDGVSFNPGFPPQSCGYGTVTDAEAHIVTVTPHSVKVDE

YTGEWIDPHFIGGRCKGQICETVHNSTKWFTSSDGESVCSQLFTLVGGTFFSDSEEITSMGLPETGIRSNYFPYVST

EGICKMPFCRKPGYKLKNDLWFQITDPDLDKTVRDLPHIKDCDLSSSIVTPGEHATDISLISDVERILDYALCQNTW

SKIEAGEPITPVDLSYLGPKNPGAGPVFTIINGSLHYFMSKYLRVELESPVIPRMEGKVAGTRIVRQLWDQWFPFGE

VEIGPNGVLKTKQGYKFPLHIIGTGEVDNDIKMERIVKHWEHPHIEAAQTFLKKDDTEEVLYYGDTGVSKNPVELVE
GWFSGWRSSIMGVLAVIIGFVILIFLIRLIGVLSSLFRQKRRPIYKSDVEMAHFR

VSV-G New Jersey ectodomain WT:
(SEQ ID NO: 11)
KIEIVFPQHTTGDWKRVPHEYNYCPTSADKNSHGTQTGIPVELTMPKGLTTHQVDGFMCHSALWMTTCDFRWYGPKY
ITHSIHNEEPTDYQCLEAIKAYKDGVSFNPGFPPQSCGYGTVTDAEAHIVTVTPHSVKVDEYTGEWIDPHFIGGRCK
GQICETVHNSTKWFTSSDGESVCSQLFTLVGGTFFSDSEEITSMGLPETGIRSNYFPYVSTEGICKMPFCRKPGYKL
KNDLWFQITDPDLDKTVRDLPHIKDCDLSSSIVTPGEHATDISLISDVERILDYALCQNTWSKIEAGEPITPVDLSY
LGPKNPGAGPVFTIINGSLHYFMSKYLRVELESPVIPRMEGKVAGTRIVRQLWDQWFPFGEVEIGPNGVLKTKQGYK
FPLHIIGTGEVDNDIKMERIVKHWEHPHIEAAQTFLKKDDTEEVLYYGDTGVSKNPVELVEGWFSGWRSSIMGVLAV
IIGFVILIFLIRLIGVLSSLFRQKRRPIYKSDVEMAHFR VSV-G Marraba Full length WT:
(SEQ ID NO: 12)
<u>MLRLFLFCFLALGAHSK</u>FTIVFPHHQKGNWKNVPSTYHYCPSSSDQNWHNDLTGVSLHVKIPKSHKAIQADGWMCHA
AKWVTTCDFRWYGPKYITHSIHSMSPTLEQCKTSIEQTKQGVWINPGFPPQSCGYATVTDAEVVVVQATPHHVLVDE
YTGEWIDSQLVGGKCSKEVCQTVHNSTVWHADYKITGLCESNLASVDITFFSEDGQKTSLGKPNTGFRSNHFAYESG
EKACRMQYCTQWGIRLPSGVWFELVDKDLFQAAKLPECPRGSSISAPSQTSVDVSLIQDVERILDYSLCQETWSKIR
AKLPVSPVDLSYLAPKNPGSGPAFTIINGTLKYFETRYIRVDISNPIIPHMVGTMSGTTTERELWNDWYPYEDVEIG
PNGVLKTPTGFKFPLYMIGHGMLDSDLHKSSQAQVFEHPHAKDAASQLPDDETLFFGDTGLSKNPVELVEGWFSSWK
STLASFFLIIGLGVALIFIIRIIVAIRYKYKGRKTQKIYNDVEMSRLGNK VSV-G Marraba ectodomain WT:
(SEQ ID NO: 13)
KFTIVFPHHQKGNWKNVPSTYHYCPSSSDQNWHNDLTGVSLHVKIPKSHKAIQADGWMCHAAKWVTTCDFRWYGPKY
ITHSIHSMSPTLEQCKTSIEQTKQGVWINPGFPPQSCGYATVTDAEVVVVQATPHHVLVDEYTGEWIDSQLVGGKCS
KEVCQTVHNSTVWHADYKITGLCESNLASVDITFFSEDGQKTSLGKPNTGFRSNHFAYESGEKACRMQYCTQWGIRL
PSGVWFELVDKDLFQAAKLPECPRGSSISAPSQTSVDVSLIQDVERILDYSLCQETWSKIRAKLPVSPVDLSYLAPK
NPGSGPAFTIINGTLKYFETRYIRVDISNPIIPHMVGTMSGTTTERELWNDWYPYEDVEIGPNGVLKTPTGFKFPLY
MIGHGMLDSDLHKSSQAQVFEHPHAKDAASQLPDDETLFFGDTGLSKNPVELVEGWFSSWKSTLASFFLIIGLGVAL
IFIIRIIVAIRYKYKGRKTQKIYNDVEMSRLGNK VSV-G Carajas Full length WT:
(SEQ ID NO: 14)
<u>MKMKMVIAGLILCIGILPAIGK</u>ITISFPQSLKGDWRPVPKGYNYCPTSADKNLHGDLIDIGLRLRAPKSFKGISADG
WMCHAARWITTCDFRWYGPKYITHSIHSFRPSNDQCKEAIRLTNEGNWINPGFPPQSCGYASVTDSESVVVTVTKHQ
VLVDEYSGSWIDSQFPGGSCTSPICDTVHNSTLWHADHTLDSICDQEFVAMDAVLFTESGKFEEFGKPNSGIRSNYF
PYESLKDVCQMDFCKRKGFKLPSGVWFEIEDAEKSHKAQVELKIKRCPHGAVISAPNQNAADINLIMDVERILDYSL
CQATWSKIQNKEALTPIDISYLGPKNPGPGPAFTIINGTLHYFNTRYIRVDIAGPVTKEITGFVSGTSTSRVLWDQW
FPYGENSIGPNGLLKTASGYKYPLFMVGTGVLDADIHKLGEATVIEHPHAKEAQKVVDDSEVIFFGDTGVSKNPVEV
VEGWFSGWRSSLMSIFGIILLIVCLVLIVRILIALKYCCVRHKKRTIYKEDLEMGRIPRRA VSV-G Carajas ectodomain WT:
(SEQ ID NO: 15)
KITISFPQSLKGDWRPVPKGYNYCPTSADKNLHGDLIDIGLRLRAPKSFKGISADGWMCHAARWITTCDFRWYGPKY
ITHSIHSFRPSNDQCKEAIRLTNEGNWINPGFPPQSCGYASVTDSESVVVTVTKHQVLVDEYSGSWIDSQFPGGSCT
SPICDTVHNSTLWHADHTLDSICDQEFVAMDAVLFTESGKFEEFGKPNSGIRSNYFPYESLKDVCQMDFCKRKGFKL
PSGVWFEIEDAEKSHKAQVELKIKRCPHGAVISAPNQNAADINLIMDVERILDYSLCQATWSKIQNKEALTPIDISY
LGPKNPGPGPAFTIINGTLHYFNTRYIRVDIAGPVTKEITGFVSGTSTSRVLWDQWFPYGENSIGPNGLLKTASGYK -continued

YPLFMVGTGVLDADIHKLGEATVIEHPHAKEAQKVVDDSEVIFFGDTGVSKNPVEVVEGWFSGWRSSLMSIFGIILL

IVCLVLIVRILIALKYCCVRHKKRTIYKEDLEMGRIPRRA

VSV-G Alagoa Full length WT:
(SEQ ID NO: 16)
MTPAFILCMLLAGSSWAKFTIVFPQSQKGDWKDVPPNYRYCPSSADQNWHGDLLGVNIRAKMPKVHKAIKADGWMCH

AAKWVTTCDYRWYGPQYITHSIHSFIPTKAQCEESIKQTKEGVWINPGFPPKNCGYASVSDAESIIVQATAHSVMID

EYSGDWLDSQFPTGRCTGSTCETIHNSTLWYADYQVTGLCDSALVSTEVTFYSEDGLMTSIGRQNTGYRSNYFPYEK

GAAACRMKYCTHEGIRLPSGVWFEMVDKELLESVQMPECPAGLTISAPTQTSVDVSLILDVERMLDYSLCQETWSKV

HSGLPISPVDLGYIAPKNPGAGPAFTIVNGTLKYFDTRYLRIDIEGPVLKKMTGKVSGTPTKRELWTEWFPYDDVEI

GPNGVLKTPEGYKFPLYMIGHGLLDSDLQKTSQAEVFHHPQIAEAVQKLPDDETLFFGDTGISKNPVEVIEGWFSNW

RSSVMAIVFAILLLVITVLMVRLCVAFRHFCCQKRHKIYNDLEMNQLRR

VSV-G Alagoa ectodomain WT:
(SEQ ID NO: 17)
KFTIVFPQSQKGDWKDVPPNYRYCPSSADQNWHGDLLGVNIRAKMPKVHKAIKADGWMCHAAKWVTTCDYRWYGPQY

ITHSIHSFIPTKAQCEESIKQTKEGVWINPGFPPKNCGYASVSDAESIIVQATAHSVMIDEYSGDWLDSQFPTGRCT

GSTCETIHNSTLWYADYQVTGLCDSALVSTEVTFYSEDGLMTSIGRQNTGYRSNYFPYEKGAAACRMKYCTHEGIRL

PSGVWFEMVDKELLESVQMPECPAGLTISAPTQTSVDVSLILDVERMLDYSLCQETWSKVHSGLPISPVDLGYIAPK

NPGAGPAFTIVNGTLKYFDTRYLRIDIEGPVLKKMTGKVSGTPTKRELWTEWFPYDDVEIGPNGVLKTPEGYKFPLY

MIGHGLLDSDLQKTSQAEVFHHPQIAEAVQKLPDDETLFFGDTGISKNPVEVIEGWFSNWRSSVMAIVFAILLLVIT

VLMVRLCVAFRHFCCQKRHKIYNDLEMNQLRR

VSV-G Cocal Full length WT:
(SEQ ID NO: 18)
MNFLLLTFIVLPLCSHAKFSIVFPQSQKGNWKNVPSSYHYCPSSSDQNWHNDLLGITMKVKMPKTHKAIQADGWMCH

AAKWITTCDFRWYGPKYITHSIHSIQPTSEQCKESIKQTKQGTWMSPGFPPQNCGYATVTDSVAVVVQATPHHVLVD

GDKVCKMNYCKHAGVRLPSGVWFEFVDQDVYAAAKLPECPVGATISAPTQTSVDVSLILDVERILDYSLCQETWSKI

RSKQPVSPVDLSYLAPKNPGTGPAFTIINGTLKYFETRYIRIDIDNPIISKMVGKISGSQTERELWTEWFPYEGVEI

GPNGILKTPTGYKFPLFMIGHGMLDSDLHKTSQAEVFEHPHLAEAPKQLPEEETLFFGDTGISKNPVELIEGWFSSW

KSTVVTFFFAIGVFILLYVVARIVIAVRYRYQGSNNKRIYNDIEMSRFRK

VSV-G Cocal ectodomain WT:
(SEQ ID NO: 19)
KFSIVFPQSQKGNWKNVPSSYHYCPSSSDQNWHNDLLGITMKVKMPKTHKAIQADGWMCHAAKWITTCDFRWYGPKY

ITHSIHSIQPTSEQCKESIKQTKQGTWMSPGFPPQNCGYATVTDSVAVVVQATPHHVLVDEYTGEWIDSQFPNGKCE

TEECETVHNSTVWYSDYKVTGLCDATLVDTEITFFSEDGKKESIGKPNTGYRSNYFAYEKGDKVCKMNYCKHAGVRL

PSGVWFEFVDQDVYAAAKLPECPVGATISAPTQTSVDVSLILDVERILDYSLCQETWSKIRSKQPVSPVDLSYLAPK

NPGTGPAFTIINGTLKYFETRYIRIDIDNPIISKMVGKISGSQTERELWTEWFPYEGVEIGPNGILKTPTGYKFPLF

MIGHGMLDSDLHKTSQAEVFEHPHLAEAPKQLPEEETLFFGDTGISKNPVELIEGWFSSWKSTVVTFFFAIGVFILL

YVVARIVIAVRYRYQGSNNKRIYNDIEMSRFRK

VSV-G Morreton Full length WT:
(SEQ ID NO: 20)
MLVLYLLLSLLALGAQCKFTIVFPHNQKGNWKNVPANYQYCPSSSDLNWHNGLIGTSLQVKMPKSHKAIQADGWMCH

AAKWVTTCDFRWYGPKYVTHSIKSMIPTVDQCKESIAQTKQGTWLNPGFPPQSCGYASVTDAEAVIVKATPHQVLVD

EYTGEWVDSQFPTGKCNKDICPTVHNSTTWHSDYKVTGLCDANLISMDITFFSEDGKLTSLGKEGTGFRSNYFAYEN

GDKACRMQYCKHWGVRLPSGVWFEMADKDIYNDAKFPDCPEGSSIAAPSQTSVDVSLIQDVERILDYSLCQETWSKI

RAHLPISPVDLSYLSPKNPGTGPAFTIINGTLKYFETRYIRVDIAGPIIPQMRGVISGTTTERELWTDWYPYEDVEI

GPNGVLKTATGYKFPLYMIGHGMLDSDLHISSKAQVFEHPHIQDAASQLPDDETLFFGDTGLSKNPIELVEGWFSGW

KSTIASFFFIIGLVIGLYLVLRIGIALCIKCRVQEKRPKIYTDVEMNRLDR

VSV-G Morreton ectodomain WT:
(SEQ ID NO: 21)
KFTIVFPHNQKGNWKNVPANYQYCPSSSDLNWHNGLIGTSLQVKMPKSHKAIQADGWMCHAAKWVTTCDFRWYGPKY

VTHSIKSMIPTVDQCKESIAQTKQGTWLNPGFPPQSCGYASVTDAEAVIVKATPHQVLVDEYTGEWVDSQFPTGKCN

KDICPTVHNSTTWHSDYKVTGLCDANLISMDITFFSEDGKLTSLGKEGTGFRSNYFAYENGDKACRMQYCKHWGVRL

PSGVWFEMADKDIYNDAKFPDCPEGSSIAAPSQTSVDVSLIQDVERILDYSLCQETWSKIRAHLPISPVDLSYLSPK

NPGTGPAFTIINGTLKYFETRYIRVDIAGPIIPQMRGVISGTTTERELWTDWYPYEDVEIGPNGVLKTATGYKFPLY

MIGHGMLDSDLHISSKAQVFEHPHIQDAASQLPDDETLFFGDTGLSKNPIELVEGWFSGWKSTIASFFFIIGLVIGL

YLVLRIGIALCIKCRVQEKRPKIYTDVEMNRLDR

Fc IgG1 (Accession No. P01857)
(SEQ ID NO: 26)
ASTKGPSVFPLAPSSKSTSGGTAALGCLVKDYFPEPVTVSWNSGALTSGVHTFPAVLQSSGLYSLSSVVTVPSSSLG

TQTYICNVNHKPSNTKVDKKVEPKSCDKTHTCPPCPAPELLGGPSVFLFPPKPKDTLMISRTPEVTCVVVDVSHEDP

EVKFNWYVDGVEVHNAKTKPREEQYNSTYRVVSVLTVLHQDWLNGKEYKCKVSNKALPAPIEKTISKAKGQPREPQV

YTLPPSRDELTKNQVSLTCLVKGFYPSDIAVEWESNGQPENNYKTTPPVLDSDGSFFLYSKLTVDKSRWQQGNVFSC

SVMHEALHNHYTQKSLSLSPGK

Fc IgG2 (Accession No. AAN76043)
(SEQ ID NO: 27)
STKGPSVFPLAPCSRSTSESTAALGCLVKDYFPEPVTVSWNSGALTSGVHTFPAVLQSSGLYSLSSVVTVPSSSLGT

QTYTCNVDHKPSNTKVDKTVERKCCVECPPCPAPPVAGPSVFLFPPKPKDTLMISRTPEVTCVVVDVSHEDPEVQFN

WYVDGVEVHNAKTKPREEQFNSTFRVVSVLTVVHQDWLNGKEYKCKVSNKGLPAPIEKTISKTKGQPREPQVYTLPP

SREEMTKNQVSLTCLVKGFYPSDIAVEWESNGQPENNYKTTPPMLDSDGSFFLYSKLTVDKSRWQQGNVFSCSVMHE

ALHNHYTQKSLSLSPGK

Fc IgG4 (Accession No. AAB59394)
(SEQ ID NO: 28)
STKGPSVFPLAPCSRSTSESTAALGCLVKDYFPEPVTVSWNSGALTSGVHTFPAVLQSSGLYSLSSVVTVPSSSLGT

KTYTCNVDHKPSNTKVDKRVESKYGPPCPSCPAPEFLGGPSVFLFPPKPKDTLMISRTPEVTCVVVDVSQEDPEVQF

NWYVDGVEVHNAKTKPREEQFNSTYRVVSVLTVLHQDWLNGKEYKCKVSNKGLPSSIEKTISKAKGQPREPQVYTLP

PSQEEMTKNQVSLTCLVKGFYPSDIAVEWESNGQPENNYKTTPPVLDSDGSFFLYSRLTVDKSRWQEGNVFSCSVMH

EALHNHYTQKSLSLSLGK

```
                           SEQUENCE LISTING

Sequence total quantity: 81
SEQ ID NO: 1            moltype = AA  length = 511
FEATURE                 Location/Qualifiers
source                  1..511
                        mol_type = protein
                        organism = synthetic construct
SEQUENCE: 1
MKCLLYLAFL FIGVNCKFTI VFPHNQKGNW KNVPSNYHYC PSSSDLNWHN DLIGTALQVK   60
MPKSHKAIQA DGWMCHASKW VTTCDFRWYG PKYITHSIRS FTPSVEQCKE SIEQTKQGTW  120
LNPGFPPQSC GYATVTDAEA VIVQVTPHHV LVDEYTGEWV DSQFINGKCS NYICPTVHNS  180
TTWHSDYKVK GLCDSNLISM DITFFSEDGE LSSLGKEGTG FRSNYFAYET GGKACKMQYC  240
KHWGVRLPSG VWFEMADKDL FAAARFPECP EGSSISAPSQ TSVDVSLIQD VERILDYSLC  300
QETWSKIRAG LPISPVDLSY LAPKNPGTGP AFTIINGTLK YFETRYIRVD IAAPILSRMV  360
GMISGTTTER ELWDDWAPYE DVEIGPNGVL RTSSGYKFPL YMIGHGMLDS DLHLSSKAQV  420
FEHPHIQDAA SQLPDDESLF FGDTGLSKNP IELVEGWFSS WKSSIASFFF IIGLIIGLFL  480
VLRVGIHLCI KLKHTKKRQI YTDIEMNRLG K                                 511

SEQ ID NO: 2            moltype = AA  length = 495
FEATURE                 Location/Qualifiers
source                  1..495
                        mol_type = protein
                        organism = synthetic construct
```

```
SEQUENCE: 2
KFTIVFPHNQ KGNWKNVPSN YHYCPSSSDL NWHNDLIGTA LQVKMPKSHK AIQADGWMCH  60
ASKWVTTCDF RWYGPKYITH SIRSFTPSVE QCKESIEQTK QGTWLNPGFP PQSCGYATVT  120
DAEAVIVQVT PHHVLVDEYT GEWVDSQFIN GKCSNYICPT VHNSTTWHSD YKVKGLCDSN  180
LISMDITFFS EDGELSSLGK EGTGFRSNYF AYETGGKACK MQYCKHWGVR LPSGVWFEMA  240
DKDLFAAARF PECPEGSSIS APSQTSVDVS LIQDVERILD YSLCQETWSK IRAGLPISPV  300
DLSYLAPKNP GTGPAFTIIN GTLKYFETRY IRVDIAAPIL SRMVGMISGT TTERELWDDW  360
APYEDVEIGP NGVLRTSSGY KFPLYMIGHG MLDSDLHLSS KAQVFEHPHI QDAASQLPDD  420
ESLFFGDTGL SKNPIELVEG WFSSWKSSIA SFFFIIGLII GLFLVLRVGI HLCIKLKHTK  480
KRQIYTDIEM NRLGK                                                  495

SEQ ID NO: 3              moltype = AA   length = 495
FEATURE                   Location/Qualifiers
source                    1..495
                          mol_type = protein
                          organism = synthetic construct
SEQUENCE: 3
KFTIVFPHNQ KGNWKNVPSN YHYCPSSSDL NWHNDLIGTA LQVKMPKSHK AIQADGWMCH  60
ASKWVTTCDF RWYGPKYITH SIRSFTPSVE QCKESIEQTK QGTWLNPGFP PQSCGYATVT  120
DAEAVIVQVT PHHVLVDEYT GEWVDSQFIN GKCSNYICPT VHNSTTWHSD YKVKGLCDSN  180
LASMDITFFS EDGELSSLGK EGTGFRSNYF AYETGGKACK MQYCKHWGVR LPSGVWFEMA  240
DKDLFAAARF PECPEGSSIS APSQTSVDVS LIQDVERILD YSLCQETWSK IRAGLPISPV  300
DLSYLAPKNP GTGPAFTIIN GTLKYFETRY IRVDIAAPIL SRMVGMISGT TTERELWDDW  360
APYEDVEIGP NGVLRTSSGY KFPLYMIGHG MLDSDLHLSS KAQVFEHPHI QDAASQLPDD  420
ESLFFGDTGL SKNPIELVEG WFSSWKSSIA SFFFIIGLII GLFLVLRVGI HLCIKLKHTK  480
KRQIYTDIEM NRLGK                                                  495

SEQ ID NO: 4              moltype = AA   length = 495
FEATURE                   Location/Qualifiers
source                    1..495
                          mol_type = protein
                          organism = synthetic construct
SEQUENCE: 4
KFTIVFPHNQ KGNWKNVPSN YHYCPSSSDL NWHNDLIGTA LQVKMPKSHK AIQADGWMCH  60
ASKWVTTCDF RWYGPKYITH SIRSFTPSVE QCKESIEQTK QGTWLNPGFP PQSCGYATVT  120
DAEAVIVQVT PHHVLVDEYT GEWVDSQFIN GKCSNYICPT VHNSTTWHSD YKVKGLCDSN  180
LDSMDITFFS EDGELSSLGK EGTGFRSNYF AYETGGKACK MQYCKHWGVR LPSGVWFEMA  240
DKDLFAAARF PECPEGSSIS APSQTSVDVS LIQDVERILD YSLCQETWSK IRAGLPISPV  300
DLSYLAPKNP GTGPAFTIIN GTLKYFETRY IRVDIAAPIL SRMVGMISGT TTERELWDDW  360
APYEDVEIGP NGVLRTSSGY KFPLYMIGHG MLDSDLHLSS KAQVFEHPHI QDAASQLPDD  420
ESLFFGDTGL SKNPIELVEG WFSSWKSSIA SFFFIIGLII GLFLVLRVGI HLCIKLKHTK  480
KRQIYTDIEM NRLGK                                                  495

SEQ ID NO: 5              moltype = AA   length = 495
FEATURE                   Location/Qualifiers
source                    1..495
                          mol_type = protein
                          organism = synthetic construct
SEQUENCE: 5
KFTIVFPHNQ KGNWKNVPSN YHYCPSSSDL NWHNDLIGTA LQVKMPKSHK AIQADGWMCH  60
ASKWVTTCDF RWYGPKYITH SIRSFTPSVE QCKESIEQTK QGTWLNPGFP PQSCGYATVT  120
DAEAVIVQVT PHHVLVDEYT GEWVDSQFIN GKCSNYICPT VHNSTTWHSD YKVKGLCDSN  180
LESMDITFFS EDGELSSLGK EGTGFRSNYF AYETGGKACK MQYCKHWGVR LPSGVWFEMA  240
DKDLFAAARF PECPEGSSIS APSQTSVDVS LIQDVERILD YSLCQETWSK IRAGLPISPV  300
DLSYLAPKNP GTGPAFTIIN GTLKYFETRY IRVDIAAPIL SRMVGMISGT TTERELWDDW  360
APYEDVEIGP NGVLRTSSGY KFPLYMIGHG MLDSDLHLSS KAQVFEHPHI QDAASQLPDD  420
ESLFFGDTGL SKNPIELVEG WFSSWKSSIA SFFFIIGLII GLFLVLRVGI HLCIKLKHTK  480
KRQIYTDIEM NRLGK                                                  495

SEQ ID NO: 6              moltype = AA   length = 495
FEATURE                   Location/Qualifiers
source                    1..495
                          mol_type = protein
                          organism = synthetic construct
SEQUENCE: 6
KFTIVFPANQ KGNWKNVPSN YHYCPSSSDL NWHNDLIGTA LQVKMPQSHK AIQADGWMCH  60
ASKWVTTCDF RWYGPKYITH SIRSFTPSVE QCKESIEQTK QGTWLNPGFP PQSCGYATVT  120
DAEAVIVQVT PHHVLVDEYT GEWVDSQFIN GKCSNYICPT VHNSTTWHSD YKVKGLCDSN  180
LISMDITFFS EDGELSSLGK EGTGFRSNYF AYETGGKACK MQYCKHWGVR LPSGVWFEMA  240
DKDLFAAARF PECPEGSSIS APSQTSVDVS LIQDVERILD YSLCQETWSK IRAGLPISPV  300
DLSYLAPKNP GTGPAFTIIN GTLKYFETRY IRVDIAAPIL SRMVGMISGT TTERELWDDW  360
APYEDVEIGP NGVLRTSSGY KFPLYMIGHG MLDSDLHLSS KAQVFEHPHI QDAASQLPDD  420
ESLFFGDTGL SKNPIELVEG WFSSWKSSIA SFFFIIGLII GLFLVLRVGI HLCIKLKHTK  480
KRQIYTDIEM NRLGK                                                  495

SEQ ID NO: 7              moltype = AA   length = 495
FEATURE                   Location/Qualifiers
```

```
                            -continued source                  1..495
                        mol_type = protein
                        organism = synthetic construct
SEQUENCE: 7
KFTIVFPHNA KGNWKNVPSN YHYCPSSSDL NWHNDLIGTA LQVKMPKSHK AIQADGWMCH    60
ASKWVTTCDF RWYGPKYITH SIRSFTPSVE QCKESIEQTK QGTWLNPGFP PQSCGYATVT   120
DAEAVIVQVT PHHVLVDEYT GEWVDSQFIN GKCSNYICPT VHNSTTWHSD YKVKGLCDSN   180
LISMDITFFS EDGELSSLGK EGTGFRSNYF AYETGGKACK MQYCKHWGVR LPSGVWFEMA   240
DKDLFAAARF PECPEGSSIS APSQTSVDVS LIQDVERILD YSLCQETWSK IRAGLPISPV   300
DLSYLAPKNP GTGPAFTIIN GTLKYFETRY IRVDIAAPIL SRMVGMISGT TTERELWDDW   360
APYEDVEIGP NGVLRTSSGY KFPLYMIGHG MLDSDLHLSS KAQVFEHPHI QDAASQLPDD   420
ESLFFGDTGL SKNPIELVEG WFSSWKSSIA SFFFIIGLII GLFLVLRVGI HLCIKLKHTK   480
KRQIYTDIEM NRLGK                                                   495

SEQ ID NO: 8            moltype = AA  length = 495
FEATURE                 Location/Qualifiers
source                  1..495
                        mol_type = protein
                        organism = synthetic construct
SEQUENCE: 8
KFTIVFPHNR KGNWKNVPSN YHYCPSSSDL NWHNDLIGTA LQVKMPKSHK AIQADGWMCH    60
ASKWVTTCDF RWYGPKYITH SIRSFTPSVE QCKESIEQTK QGTWLNPGFP PQSCGYATVT   120
DAEAVIVQVT PHHVLVDEYT GEWVDSQFIN GKCSNYICPT VHNSTTWHSD YKVKGLCDSN   180
LISMDITFFS EDGELSSLGK EGTGFRSNYF AYETGGKACK MQYCKHWGVR LPSGVWFEMA   240
DKDLFAAARF PECPEGSSIS APSQTSVDVS LIQDVERILD YSLCQETWSK IRAGLPISPV   300
DLSYLAPKNP GTGPAFTIIN GTLKYFETRY IRVDIAAPIL SRMVGMISGT TTERELWDDW   360
APYEDVEIGP NGVLRTSSGY KFPLYMIGHG MLDSDLHLSS KAQVFEHPHI QDAASQLPDD   420
ESLFFGDTGL SKNPIELVEG WFSSWKSSIA SFFFIIGLII GLFLVLRVGI HLCIKLKHTK   480
KRQIYTDIEM NRLGK                                                   495

SEQ ID NO: 9            moltype = AA  length = 495
FEATURE                 Location/Qualifiers
source                  1..495
                        mol_type = protein
                        organism = synthetic construct
SEQUENCE: 9
KFTIVFPHNK KGNWKNVPSN YHYCPSSSDL NWHNDLIGTA LQVKMPKSHK AIQADGWMCH    60
ASKWVTTCDF RWYGPKYITH SIRSFTPSVE QCKESIEQTK QGTWLNPGFP PQSCGYATVT   120
DAEAVIVQVT PHHVLVDEYT GEWVDSQFIN GKCSNYICPT VHNSTTWHSD YKVKGLCDSN   180
LISMDITFFS EDGELSSLGK EGTGFRSNYF AYETGGKACK MQYCKHWGVR LPSGVWFEMA   240
DKDLFAAARF PECPEGSSIS APSQTSVDVS LIQDVERILD YSLCQETWSK IRAGLPISPV   300
DLSYLAPKNP GTGPAFTIIN GTLKYFETRY IRVDIAAPIL SRMVGMISGT TTERELWDDW   360
APYEDVEIGP NGVLRTSSGY KFPLYMIGHG MLDSDLHLSS KAQVFEHPHI QDAASQLPDD   420
ESLFFGDTGL SKNPIELVEG WFSSWKSSIA SFFFIIGLII GLFLVLRVGI HLCIKLKHTK   480
KRQIYTDIEM NRLGK                                                   495

SEQ ID NO: 10           moltype = AA  length = 517
FEATURE                 Location/Qualifiers
source                  1..517
                        mol_type = protein
                        organism = synthetic construct
SEQUENCE: 10
MLSYLIFALV VSPILGKIEI VFPQHTTGDW KRVPHEYNYC PTSADKNSHG TQTGIPVELT    60
MPKGLTTHQV DGFMCHSALW MTTCDFRWYG PKYITHSIHN EEPTDYQCLE AIKAYKDGVS   120
FNPGFPPPQS CGYGTVTDAEA HIVTVTPHSV KVDEYTGEWI DPHFIGGRCK GQICETVHNS   180
TKWFTSSDGE SVCSQLFTLV GGTFFSDSEE ITSMGLPETG IRSNYFPYVS TEGICKMPFC   240
RKPGYKLKND LWFQITDPDL DKTVRDLPHI KDCDLSSSIV TPGEHATDIS LISDVERILD   300
YALCQNTWSK IEAGEPITPV DLSYLGPKNP GAGPVFTIIN GSLHYFMSKY LRVELESPVI   360
PRMEGKVAGT RIVRQLWDQW FPFGEVEIGP NGVLKTKQGY KFPLHIIGTG EVDNDIKMER   420
IVKHWEHPHI EAAQTFLKKD DTEEVLYYGD TGVSKNPVEL VEGWFSGWRS SIMGVLAVII   480
GFVILIFLIR LIGVLSSLFR QKRRPIYKSD VEMAHFR                            517

SEQ ID NO: 11           moltype = AA  length = 501
FEATURE                 Location/Qualifiers
source                  1..501
                        mol_type = protein
                        organism = synthetic construct
SEQUENCE: 11
KIEIVFPQHT TGDWKRVPHE YNYCPTSADK NSHGTQTGIP VELTMPKGLT THQVDGFMCH    60
SALWMTTCDF RWYGPKYITH SIHNEEPTDY QCLEAIKAYK DGVSFNPGFP PQSCGYGTVT   120
DAEAHIVTVT PHSVKVDEYT GEWIDPHFIG GRCKGQICET VHNSTKWFTS SDGESVCSQL   180
FTLVGGTFFS DSEEITSMGL PETGIRSNYF PYVSTEGICK MPFCRKPGYK LKNDLWFQIT   240
DPDLDKTVRD LPHIKDCDLS SSIVTPGEHA TDISLISDVE RILDYALCQN TWSKIEAGEP   300
ITPVDLSYLG PKNPGAGPVF TIINGSLHYF MSKYLRVELE SPVIPRMEGK VAGTRIVRQL   360
WDQWFPFGEV EIGPNGVLKT KQGYKFPLHI IGTGEVDNDI KMERIVKHWE HPHIEAAQTF   420
LKKDDTEEVL YYGDTGVSKN PVELVEGWFS GWRSSIMGVL AVIIGFVILI FLIRLIGVLS   480
SLFRQKRRPI YKSDVEMAHF R                                            501

SEQ ID NO: 12           moltype = AA  length = 512
```

```
FEATURE                 Location/Qualifiers
source                  1..512
                        mol_type = protein
                        organism = synthetic construct
SEQUENCE: 12
MLRLFLFCFL ALGAHSKFTI VFPHHQKGNW KNVPSTYHYC PSSSDQNWHN DLTGVSLHVK    60
IPKSHKAIQA DGWMCHAAKW VTTCDFRWYG PKYITHSIHS MSPTLEQCKT SIEQTKQGVW   120
INPGFPPQSC GYATVTDAEV VVVQATPHHV LVDEYTGEWI DSQLVGGKCS KEVCQTVHNS   180
TVWHADYKIT GLCESNLASV DITFFSEDGQ KTSLGKPNTG FRSNHFAYES GEKACRMQYC   240
TQWGIRLPSG VWFELVDKDL FQAAKLPECP RGSSISAPSQ TSVDVSLIQD VERILDYSLC   300
QETWSKIRAK LPVSPVDLSY LAPKNPGSGP AFTIINGTLK YFETRYIRVD ISNPIIPHMV   360
GTMSGTTTER ELWNDWYPYE DVEIGPNGVL KTPTGFKFPL YMIGHGMLDS DLHKSSQAQV   420
FEHPHAKDAA SQLPDDETLF FGDTGLSKNP VELVEGWFSS WKSTLASFFL IIGLGVALIF   480
IIRIIVAIRY KYKGRKTQKI YNDVEMSRLG NK                                 512

SEQ ID NO: 13           moltype = AA  length = 496
FEATURE                 Location/Qualifiers
source                  1..496
                        mol_type = protein
                        organism = synthetic construct
SEQUENCE: 13
KFTIVFPHHQ KGNWKNVPST YHYCPSSSDQ NWHNDLTGVS LHVKIPKSHK AIQADGWMCH    60
AAKWVTTCDF RWYGPKYITH SIHSMSPTLE QCKTSIEQTK QGVWINPGFP PQSCGYATVT   120
DAEVVVVQAT PHHVLVDEYT GEWIDSQLVG GKCSKEVCQT VHNSTVWHAD YKITGLCESN   180
LASVDITFFS EDGQKTSLGK PNTGFRSNHF AYESGEKACR MQYCTQWGIR LPSGVWFELV   240
DKDLFQAAKL PECPRGSSIS APSQTSVDVS LIQDVERILD YSLCQETWSK IRAKLPVSPV   300
DLSYLAPKNP GSGPAFTIIN GTLKYFETRY IRVDISNPII PHMVGTMSGT TTERELWNDW   360
YPYEDVEIGP NGVLKTPTGF KFPLYMIGHG MLDSDLHKSS QAQVFEHPHA KDAASQLPDD   420
ETLFFGDTGL SKNPVELVEG WFSSWKSTLA SFFLIIGLGV ALIFIIRIIV AIRYKYKGRK   480
TQKIYNDVEM SRLGNK                                                   496

SEQ ID NO: 14           moltype = AA  length = 523
FEATURE                 Location/Qualifiers
source                  1..523
                        mol_type = protein
                        organism = synthetic construct
SEQUENCE: 14
MKMKMVIAGL ILCIGILPAI GKITISFPQS LKGDWRPVPK GYNYCPTSAD KNLHGDLIDI    60
GLRLRAPKSF KGISADGWMC HAARWITTCD FRWYGPKYIT HSIHSFRPSN DQCKEAIRLT   120
NEGNWINPGF PPQSCGYASV TDSESVVVTV TKHQVLVDEY SGSWIDSQFP GGSCTSPICD   180
TVHNSTLWHA DHTLDSICDQ EFVAMDAVLF TESGKFEEFG KPNSGIRSNY FPYESLKDVC   240
QMDFCKRKGF KLPSGVWFEI EDAEKSHKAQ VELKIKRCPH GAVISAPNQN AADINLIMDV   300
ERILDYSLCQ ATWSKIQNEK ALTPIDISYL GPKNPGPGPA FTIINGTLHY FNTRYIRVDI   360
AGPVTKEITG FVSGTSTSRV LWDQWFPYGE NSIGPNGLLK TASGYKYPLF MVGTGVLDAD   420
IHKLGEATVI EHPHAKEAQK VVDDSEVIFF GDTGVSKNPV EVVEGWFSGW RSSLMSIFGI   480
ILLIVCLVLI VRILIALKYC CVRHKKRTIY KEDLEMGRIP RRA                     523

SEQ ID NO: 15           moltype = AA  length = 502
FEATURE                 Location/Qualifiers
source                  1..502
                        mol_type = protein
                        organism = synthetic construct
SEQUENCE: 15
KITISFPQSL KGDWRPVPKG YNYCPTSADK NLHGDLIDIG LRLRAPKSFK GISADGWMCH    60
AARWITTCDF RWYGPKYITH SIHSFRPSND QCKEAIRLTN EGNWINPGFP PQSCGYASVT   120
DSESVVVTVT KHQVLVDEYS GSWIDSQFPG GSCTSPICDT VHNSTLWHAD HTLDSICDQE   180
FVAMDAVLFT ESGKFEEFGK PNSGIRSNYF PYESLKDVCQ MDFCKRKGFK LPSGVWFEIE   240
DAEKSHKAQV ELKIKRCPHG AVISAPNQNA ADINLIMDVE RILDYSLCQA TWSKIQNKEA   300
LTPIDISYLG PKNPGPGPAF TIINGTLHYF NTRYIRVDIA GPVTKEITGF VSGTSTSRVL   360
WDQWFPYGEN SIGPNGLLKT ASGYKYPLFM VGTGVLDADI HKLGEATVIE HPHAKEAQKV   420
VDDSEVIFFG DTGVSKNPVE VVEGWFSGWR SSLMSIFGII LLIVCLVLIV RILIALKYCC   480
VRHKKRTIYK EDLEMGRIPR RA                                            502

SEQ ID NO: 16           moltype = AA  length = 511
FEATURE                 Location/Qualifiers
source                  1..511
                        mol_type = protein
                        organism = synthetic construct
SEQUENCE: 16
MTPAFILCML LAGSSWAKFT IVFPQSQKGD WKDVPPNYRY CPSSDQNWH GDLLGVNIRA    60
KMPKVHKAIK ADGWMCHAAK WVTTCDYRWY GPQYITHSIH SFIPTKAQCE ESIKQTKEGV   120
WINPGFPPKN CGYASVSDAE SIIVQATAHS VMIDEYSGDW LDSQFPTGRC TGSTCETIHN   180
STLWYADYQV TGLCDSALVS TEVTFYSEDG LMTSIGRQNT GYRSNYFPYE KGAAACRMKY   240
CTHEGIRLPS GVWFEMVDKE LLESVQMPEC PAGLTISAPT QTSVDVSLIL DVERMLDYSL   300
CQETWSKVHS GLPISPVDLG YIAPKNPGAG PAFTIVNGTL KYFDTRYLRI DIEGPVLKKM   360
TGKVSGTPTK RELWTEWFPY DDVEIGPNGV LKTPEGYKFP LYMIGHGLLD SDLQKTSQAE   420
VFHHPQIAEA VQKLPDDETL FFGDTGISKN PVEVIEGWFS NWRSSVMAIV FAILLLVITV   480
LMVRLCVAFR HFCCQKRHKI YNDLEMNQLR R                                  511
```

```
SEQ ID NO: 17          moltype = AA  length = 494
FEATURE                Location/Qualifiers
source                 1..494
                       mol_type = protein
                       organism = synthetic construct
SEQUENCE: 17
KFTIVFPQSQ KGDWKDVPPN YRYCPSSADQ NWHGDLLGVN IRAKMPKVHK AIKADGWMCH    60
AAKWVTTCDY RWYGPQYITH SIHSFIPTKA QCEESIKQTK EGVWINPGFP PKNCGYASVS   120
DAESIIVQAT AHSVMIDEYS GDWLDSQFPT GRCTGSTCET IHNSTLWYAD YQVTGLCDSA   180
LVSTEVTFYS EDGLMTSIGR QNTGYRSNYF PYEKGAAACR MKYCTHEGIR LPSGVWFEMV   240
DKELLESVQM PECPAGLTIS APTQTSVDVS LILDVERMLD YSLCQETWSK VHSGLPISPV   300
DLGYIAPKNP GAGPAFTIVN GTLKYFDTRY LRIDIEGPVL KKMTGKVSGT PTKRELWTEW   360
FPYDDVEIGP NGVLKTPEGY KFPLYMIGHG LLDSDLQKTS QAEVFHHPQI AEAVQKLPDD   420
ETLFFGDTGI SKNPVEVIEG WFSNWRSSVM AIVFAILLLV ITVLMVRLCV AFRHFCCQKR   480
HKIYNDLEMN QLRR                                                    494

SEQ ID NO: 18          moltype = AA  length = 512
FEATURE                Location/Qualifiers
source                 1..512
                       mol_type = protein
                       organism = synthetic construct
SEQUENCE: 18
MNFLLLTFIV LPLCSHAKFS IVFPQSQKGN WKNVPSSYHY CPSSSDQNWH NDLLGITMKV    60
KMPKTHKAIQ ADGWMCHAAK WITTCDFRWY GPKYITHSIH SIQPTSEQCK ESIKQTKQGT   120
WMSPGFPPQN CGYATVTDSV AVVVQATPHH VLVDEYTGEW IDSQFPNGKC ETEECETVHN   180
STVWYSDYKV TGLCDATLVD TEITFFSEDG KKESIGKPNT GYRSNYFAYE KGDKVCKMNY   240
CKHAGVRLPS GVWFEFVDQD VYAAAKLPEC PVGATISAPT QTSVDVSLIL DVERILDYSL   300
CQETWSKIRS KQPVSPVDLS YLAPKNPGTG PAFTIINGTL KYFETRYIRI DIDNPIISKM   360
VGKISGSQTE RELWTEWFPY EGVEIGPNGI LKTPTGYKFP LFMIGHGMLD SDLHKTSQAE   420
VFEHPHLAEA PKQLPEEETL FFGDTGISKN PVELIEGWFS SWKSTVVTFF FAIGVFILLY   480
VVARIVIAVR YRQGSNNKR IYNDIEMSRF RK                                 512

SEQ ID NO: 19          moltype = AA  length = 495
FEATURE                Location/Qualifiers
source                 1..495
                       mol_type = protein
                       organism = synthetic construct
SEQUENCE: 19
KFSIVFPQSQ KGNWKNVPSS YHYCPSSSDQ NWHNDLLGIT MKVKMPKTHK AIQADGWMCH    60
AAKWITTCDF RWYGPKYITH SIHSIQPTSE QCKESIKQTK QGTWMSPGFP PQNCGYATVT   120
DSVAVVVQAT PHHVLVDEYT GEWIDSQFPN GKCETEECET VHNSTVWYSD YKVTGLCDAT   180
LVDTEITFFS EDGKKESIGK PNTGYRSNYF AYEKGDKVCK MNYCKHAGVR LPSGVWFEFV   240
DQDVYAAAKL PECPVGATIS APTQTSVDVS LILDVERILD YSLCQETWSK IRSKQPVSPV   300
DLSYLAPKNP GTGPAFTIIN GTLKYFETRY IRIDIDNPII SKMVGKISGS QTERELWTEW   360
FPYEGVEIGP NGILKTPTGY KFPLFMIGHG MLDSDLHKTS QAEVFEHPHL AEAPKQLPEE   420
ETLFFGDTGI SKNPVELIEG WFSSWKSTVV TFFFAIGVFI LLYVVARIVI AVRYRQGSN   480
NKRIYNDIEM SRFRK                                                   495

SEQ ID NO: 20          moltype = AA  length = 513
FEATURE                Location/Qualifiers
source                 1..513
                       mol_type = protein
                       organism = synthetic construct
SEQUENCE: 20
MLVLYLLLSL LALGAQCKFT IVFPHNQKGN WKNVPANYQY CPSSSDLNWH NGLIGTSLQV    60
KMPKSHKAIQ ADGWMCHAAK WVTTCDFRWY GPKYVTHSIK SMIPTVDQCK ESIAQTKQGT   120
WLNPGFPPQS CGYASVTDAE AVIVKATPHQ VLVDEYTGEW VDSQFPTGKC NKDICPTVHN   180
STTWHSDYKV TGLCDANLIS MDITFFSEDG KLTSLGKEGT GFRSNYFAYE NGDKACRMQY   240
CKHWGVRLPS GVWFEMADKD IYNDAKFPDC PEGSSIAAPS QTSVDVSLIQ DVERILDYSL   300
CQETWSKIRA HLPISPVDLS YLSPKNPGTG PAFTIINGTL KYFETRYIRV DIAGPIIPQM   360
RGVISGTTTE RELWTDWYPY EDVEIGPNGV LKTATGYKFP LYMIGHGMLD SDLHISSKAQ   420
VFEHPHIQDA ASQLPDDETL FFGDTGLSKN PIELVEGWFS GWKSTIASFF FIIGLVIGLY   480
LVLRIGIALC IKCRVQEKRP KIYTDVEMNR LDR                                513

SEQ ID NO: 21          moltype = AA  length = 496
FEATURE                Location/Qualifiers
source                 1..496
                       mol_type = protein
                       organism = synthetic construct
SEQUENCE: 21
KFTIVFPHNQ KGNWKNVPAN YQYCPSSSDL NWHNGLIGTS LQVKMPKSHK AIQADGWMCH    60
AAKWVTTCDF RWYGPKYVTH SIKSMIPTVD QCKESIAQTK QGTWLNPGFP PQSCGYASVT   120
DAEAVIVKAT PHQVLVDEYT GEWVDSQFPT GKCNKDICPT VHNSTTWHSD YKVTGLCDAN   180
LISMDITFFS EDGKLTSLGK EGTGFRSNYF AYENGDKACR MQYCKHWGVR LPSGVWFEMA   240
DKDIYNDAKF PDCPEGSSIA APSQTSVDVS LIQDVERILD YSLCQETWSK IRAHLPISPV   300
DLSYLSPKNP GTGPAFTIIN GTLKYFETRY IRVDIAGPII PQMRGVISGT TTERELWTDW   360
YPYEDVEIGP NGVLKTATGY KFPLYMIGHG MLDSDLHISS KAQVFEHPHI QDAASQLPDD   420
ETLFFGDTGL SKNPIELVEG WFSGWKSTIA SFFFIIGLVI GLYLVLRIGI ALCIKCRVQE   480
KRPKIYTDVE MNRLDR                                                  496
```

```
SEQ ID NO: 22            moltype = AA  length = 495
FEATURE                  Location/Qualifiers
source                   1..495
                         mol_type = protein
                         organism = synthetic construct
SEQUENCE: 22
KFTIVFPHNQ KGNWKNVPSN YHYCPSSSDL NWHNDLIGTA LQVKMPKSHK AIQADGWMCH   60
ASKWVTTCDF RWYGPKYITH SIRSFTPSVE QCKESIEQTK QGTWLNPGFP PQSCGYATVT  120
DAEAVIVQVT PHHVLVDEYT GEWVDSQFIN GKCSNYICPT VHNSTTWHSD YKVKGLCDSN  180
LDSMDITFFS EDGELSSLGK EGTGFRSNYF AYENGGKACK MQYCKHWGVR LPSGVWFEMA  240
DKDLFAAARF PECPEGSSIS APSQTSVDVS LIQDVERILD YSLCQETWSK IRAGLPISPV  300
DLSYLAPKNP GTGPAFTIIN GTLKYFETRY IRVDIAAPIL SRMVGMISGT TAERELWDDW  360
APYEDVEIGP NGVLRTSSGY KFPLYMIGHG MLDSDLHLSS KAQVFEHPHI QDAASQLPDD  420
ESLFFGDTGL SKNPIELVEG WFSSWKSSIA SFFFIIGLII GLFLVLRVGI HLCIKLKHTK  480
KRQIYTDIEM NRLGK                                                  495

SEQ ID NO: 23            moltype = AA  length = 495
FEATURE                  Location/Qualifiers
source                   1..495
                         mol_type = protein
                         organism = synthetic construct
SEQUENCE: 23
KFTIVFPHNQ KGNWKNVPSN YHYCPSSSDL NWHNDLIGTA LQVKMPKSHK AIQADGWMCH   60
ASKWVTTCDF RWYGPKYITH SIRSFTPSVE QCKESIEQTK QGTWLNPGFP PQSCGYATVT  120
DAEAVIVQVT PHHVLVDEYT GEWVDSQFIN GKCSNYICPT VHNSTTWHSD YKVKGLCDSN  180
LESMDITFFS EDGELSSLGK EGTGFRSNYF AYENGGKACK MQYCKHWGVR LPSGVWFEMA  240
DKDLFAAARF PECPEGSSIS APSQTSVDVS LIQDVERILD YSLCQETWSK IRAGLPISPV  300
DLSYLAPKNP GTGPAFTIIN GTLKYFETRY IRVDIAAPIL SRMVGMISGT TAERELWDDW  360
APYEDVEIGP NGVLRTSSGY KFPLYMIGHG MLDSDLHLSS KAQVFEHPHI QDAASQLPDD  420
ESLFFGDTGL SKNPIELVEG WFSSWKSSIA SFFFIIGLII GLFLVLRVGI HLCIKLKHTK  480
KRQIYTDIEM NRLGK                                                  495

SEQ ID NO: 24            moltype = AA  length = 511
FEATURE                  Location/Qualifiers
source                   1..511
                         mol_type = protein
                         organism = synthetic construct
SEQUENCE: 24
MKCLLYLAFL FIGVNCKFTI VFPHNQKGNW KNVPSNYHYC PSSSDLNWHN DLIGTALQVK   60
MPKSHKAIQA DGWMCHASKW VTTCDFRWYG PKYITHSIRS FTPSVEQCKE SIEQTKQGTW  120
LNPGFPPQSC GYATVTDAEA VIVQVTPHHV LVDEYTGEWV DSQFINGKCS NYICPTVHNS  180
TTWHSDYKVK GLCDSNLDSM DITFFSEDGE LSSLGKEGTG FRSNYFAYEN GGKACKMQYC  240
KHWGVRLPSG VWFEMADKDL FAAARFPECP EGSSISAPSQ TSVDVSLIQD VERILDYSLC  300
QETWSKIRAG LPISPVDLSY LAPKNPGTGP AFTIINGTLK YFETRYIRVD IAAPILSRMV  360
GMISGTTAER ELWDDWAPYE DVEIGPNGVL RTSSGYKFPL YMIGHGMLDS DLHLSSKAQV  420
FEHPHIQDAA SQLPDDESLF FGDTGLSKNP IELVEGWFSS WKSSIASFFF IIGLIIGLFL  480
VLRVGIHLCI KLKHTKKRQI YTDIEMNRLG K                                 511

SEQ ID NO: 25            moltype = AA  length = 511
FEATURE                  Location/Qualifiers
source                   1..511
                         mol_type = protein
                         organism = synthetic construct
SEQUENCE: 25
MKCLLYLAFL FIGVNCKFTI VFPHNQKGNW KNVPSNYHYC PSSSDLNWHN DLIGTALQVK   60
MPKSHKAIQA DGWMCHASKW VTTCDFRWYG PKYITHSIRS FTPSVEQCKE SIEQTKQGTW  120
LNPGFPPQSC GYATVTDAEA VIVQVTPHHV LVDEYTGEWV DSQFINGKCS NYICPTVHNS  180
TTWHSDYKVK GLCDSNLESM DITFFSEDGE LSSLGKEGTG FRSNYFAYEN GGKACKMQYC  240
KHWGVRLPSG VWFEMADKDL FAAARFPECP EGSSISAPSQ TSVDVSLIQD VERILDYSLC  300
QETWSKIRAG LPISPVDLSY LAPKNPGTGP AFTIINGTLK YFETRYIRVD IAAPILSRMV  360
GMISGTTAER ELWDDWAPYE DVEIGPNGVL RTSSGYKFPL YMIGHGMLDS DLHLSSKAQV  420
FEHPHIQDAA SQLPDDESLF FGDTGLSKNP IELVEGWFSS WKSSIASFFF IIGLIIGLFL  480
VLRVGIHLCI KLKHTKKRQI YTDIEMNRLG K                                 511

SEQ ID NO: 26            moltype = AA  length = 16
FEATURE                  Location/Qualifiers
source                   1..16
                         mol_type = protein
                         organism = synthetic construct
SEQUENCE: 26
MKCLLYLAFL FIGVNC                                                   16

SEQ ID NO: 27            moltype = AA  length = 16
FEATURE                  Location/Qualifiers
source                   1..16
                         mol_type = protein
                         organism = synthetic construct
```

```
SEQUENCE: 27
MLSYLIFALV VSPILG                                                        16

SEQ ID NO: 28           moltype = AA  length = 16
FEATURE                 Location/Qualifiers
source                  1..16
                        mol_type = protein
                        organism = synthetic construct
SEQUENCE: 28
MLRLFLFCFL ALGAHS                                                        16

SEQ ID NO: 29           moltype = AA  length = 21
FEATURE                 Location/Qualifiers
source                  1..21
                        mol_type = protein
                        organism = synthetic construct
SEQUENCE: 29
MKMKMVIAGL ILCIGILPAI G                                                  21

SEQ ID NO: 30           moltype = AA  length = 17
FEATURE                 Location/Qualifiers
source                  1..17
                        mol_type = protein
                        organism = synthetic construct
SEQUENCE: 30
MTPAFILCML LAGSSWA                                                       17

SEQ ID NO: 31           moltype = AA  length = 17
FEATURE                 Location/Qualifiers
source                  1..17
                        mol_type = protein
                        organism = synthetic construct
SEQUENCE: 31
MNFLLLTFIV LPLCSHA                                                       17

SEQ ID NO: 32           moltype = AA  length = 17
FEATURE                 Location/Qualifiers
source                  1..17
                        mol_type = protein
                        organism = synthetic construct
SEQUENCE: 32
MLVLYLLLSL LALGAQC                                                       17

SEQ ID NO: 33           moltype = AA  length = 240
FEATURE                 Location/Qualifiers
source                  1..240
                        mol_type = protein
                        organism = Homo sapiens
SEQUENCE: 33
MAGPPRLLLL PLLLALARGL PGALAAQEVQ QSPHCTTVPV GASVNITCST SGGLRGIYLR         60
QLGPQPQDII YYEDGVVPTT DRRFRGRIDF SGSQDNLTIT MHRLQLSDTG TYTCQAITEV        120
NVYGSGTLVL VTEEQSQGWH RCSDAPPRAS ALPAPPTGSA LPDPQTASAL PDPPAASALP        180
AALAVISFLL GLGLGVACVL ARTQIKKLCS WRDKNSAACV VYEDMSHSRC NTLSSPNQYQ        240

SEQ ID NO: 34           moltype = AA  length = 330
FEATURE                 Location/Qualifiers
source                  1..330
                        mol_type = protein
                        organism = Homo sapiens
SEQUENCE: 34
ASTKGPSVFP LAPSSKSTSG GTAALGCLVK DYFPEPVTVS WNSGALTSGV HTFPAVLQSS         60
GLYSLSSVVT VPSSSLGTQT YICNVNHKPS NTKVDKKVEP KSCDKTHTCP PCPAPELLGG        120
PSVFLFPPKP KDTLMISRTP EVTCVVVDVS HEDPEVKFNW YVDGVEVHNA KTKPREEQYN        180
STYRVVSVLT VLHQDWLNGK EYKCKVSNKA LPAPIEKTIS KAKGQPREPQ VYTLPPSRDE        240
LTKNQVSLTC LVKGFYPSDI AVEWESNGQP ENNYKTTPPV LDSDGSFFLY SKLTVDKSRW        300
QQGNVFSCSV MHEALHNHYT QKSLSLSPGK                                        330

SEQ ID NO: 35           moltype = AA  length = 7
FEATURE                 Location/Qualifiers
source                  1..7
                        mol_type = protein
                        organism = synthetic construct
SEQUENCE: 35
GYPFTSY                                                                   7

SEQ ID NO: 36           moltype = AA  length = 6
FEATURE                 Location/Qualifiers
```

```
source                    1..6
                          mol_type = protein
                          organism = synthetic construct
SEQUENCE: 36
DPNSGD                                                              6

SEQ ID NO: 37             moltype = AA   length = 12
FEATURE                   Location/Qualifiers
source                    1..12
                          mol_type = protein
                          organism = synthetic construct
SEQUENCE: 37
SPYYSNDNSM DY                                                      12

SEQ ID NO: 38             moltype = AA   length = 11
FEATURE                   Location/Qualifiers
source                    1..11
                          mol_type = protein
                          organism = synthetic construct
SEQUENCE: 38
RASQSIGTSI H                                                       11

SEQ ID NO: 39             moltype = AA   length = 7
FEATURE                   Location/Qualifiers
source                    1..7
                          mol_type = protein
                          organism = synthetic construct
SEQUENCE: 39
YASESIS                                                             7

SEQ ID NO: 40             moltype = AA   length = 9
FEATURE                   Location/Qualifiers
source                    1..9
                          mol_type = protein
                          organism = synthetic construct
SEQUENCE: 40
QQSNSWPTT                                                           9

SEQ ID NO: 41             moltype = AA   length = 5
FEATURE                   Location/Qualifiers
source                    1..5
                          mol_type = protein
                          organism = synthetic construct
SEQUENCE: 41
SYWIH                                                               5

SEQ ID NO: 42             moltype = AA   length = 17
FEATURE                   Location/Qualifiers
source                    1..17
                          mol_type = protein
                          organism = synthetic construct
SEQUENCE: 42
RIDPNSGDTK YNEKFKN                                                 17

SEQ ID NO: 43             moltype = AA   length = 8
FEATURE                   Location/Qualifiers
source                    1..8
                          mol_type = protein
                          organism = synthetic construct
SEQUENCE: 43
GYPFTSYW                                                            8

SEQ ID NO: 44             moltype = AA   length = 8
FEATURE                   Location/Qualifiers
source                    1..8
                          mol_type = protein
                          organism = synthetic construct
SEQUENCE: 44
IDPNSGDT                                                            8

SEQ ID NO: 45             moltype = AA   length = 14
FEATURE                   Location/Qualifiers
source                    1..14
                          mol_type = protein
                          organism = synthetic construct
SEQUENCE: 45
ARSPYYSNDN SMDY                                                    14

SEQ ID NO: 46             moltype = AA   length = 6
```

```
FEATURE                 Location/Qualifiers
source                  1..6
                        mol_type = protein
                        organism = synthetic construct
SEQUENCE: 46
QSIGTS                                                                      6

SEQ ID NO: 47           moltype = AA   length = 121
FEATURE                 Location/Qualifiers
source                  1..121
                        mol_type = protein
                        organism = synthetic construct
SEQUENCE: 47
QVQLQQPGAE LVKPGASVKL SCKASGYPFT SYWIHWVKQR PGRGLEWLGR IDPNSGDTKY           60
NEKFKNKATL TVDKSSTTAY MQLSSLTSED SAVYYCARSP YYSNDNSMDY WGQGTSVTVS          120
S                                                                         121

SEQ ID NO: 48           moltype = AA   length = 108
FEATURE                 Location/Qualifiers
source                  1..108
                        mol_type = protein
                        organism = synthetic construct
SEQUENCE: 48
DILLTQSPAI LSVSPGERVS FSCRASQSIG TSIHWYQQRT NDSPRLLIKY ASESISGIPS           60
RFSGSGSGTD FTLSINSVES EDIADYYCQQ SNSWPTTFGG GTKLEIKR                       108

SEQ ID NO: 49           moltype = AA   length = 5
FEATURE                 Location/Qualifiers
source                  1..5
                        mol_type = protein
                        organism = synthetic construct
REPEAT                  1..5
                        note = Linker sequence may be repeated 1, 2, 3, 4, or 5
                         times
SEQUENCE: 49
GGGGS                                                                       5

SEQ ID NO: 50           moltype = AA   length = 20
FEATURE                 Location/Qualifiers
source                  1..20
                        mol_type = protein
                        organism = synthetic construct
SEQUENCE: 50
GGGGSGGGGS GGGGSGGGGS                                                       20

SEQ ID NO: 51           moltype = AA   length = 249
FEATURE                 Location/Qualifiers
source                  1..249
                        mol_type = protein
                        organism = synthetic construct
SEQUENCE: 51
DILLTQSPAI LSVSPGERVS FSCRASQSIG TSIHWYQQRT NDSPRLLIKY ASESISGIPS           60
RFSGSGSGTD FTLSINSVES EDIADYYCQQ SNSWPTTFGG GTKLEIKRGG GGSGGGGSGG          120
GGSGGGGSQV QLQQPGAELV KPGASVKLSC KASGYPFTSY WIHWVKQRPG RGLEWLGRID          180
PNSGDTKYNE KFKNKATLTV DKSSTTAYMQ LSSLTSEDSA VYYCARSPYY SNDNSMDYWG          240
QGTSVTVSS                                                                 249

SEQ ID NO: 52           moltype = AA   length = 249
FEATURE                 Location/Qualifiers
source                  1..249
                        mol_type = protein
                        organism = synthetic construct
SEQUENCE: 52
QVQLQQPGAE LVKPGASVKL SCKASGYPFT SYWIHWVKQR PGRGLEWLGR IDPNSGDTKY           60
NEKFKNKATL TVDKSSTTAY MQLSSLTSED SAVYYCARSP YYSNDNSMDY WGQGTSVTVS          120
SGGGGSGGGG SGGGGSGGGG SDILLTQSPA ILSVSPGERV SFSCRASQSI GTSIHWYQQR          180
TNDSPRLLIK YASESISGIP SRFSGSGSGT DFTLSINSVE SEDIADYYCQ QSNSWPTTFG          240
GGTKLEIKR                                                                 249

SEQ ID NO: 53           moltype = AA   length = 235
FEATURE                 Location/Qualifiers
source                  1..235
                        mol_type = protein
                        organism = Homo sapiens
SEQUENCE: 53
MALPVTALLL PLALLLHAAR PSQFRVSPLD RTWNLGETVE LKCQVLLSNP TSGCSWLFQP           60
RGAAASPTFL LYLSQNKPKA AEGLDTQRFS GKRLGDTFVL TLSDFRRENE GCYFCSALSN          120
SIMYFSHFVP VFLPAKPTTT PAPRPPTPAP TIASQPLSLR PEACRPAAGG AVHTRGLDFA          180
CDIYIWAPLA GTCGVLLLSL VITLYCNHRN RRRVCKCPRP VVKSGDKPSL SARYV              235
```

| | | |
|---|---|---|
| SEQ ID NO: 54 | moltype = AA length = 210 | |
| FEATURE | Location/Qualifiers | |
| source | 1..210 | |
| | mol_type = protein | |
| | organism = Homo sapiens | |

SEQUENCE: 54
```
MRPRLWLLLA AQLTVLHGNS VLQQTPAYIK VQTNKMVMLS CEAKISLSNM RIYWLRQRQA    60
PSSDSHHEFL ALWDSAKGTI HGEEVEQEKI AVFRDASRFI LNLTSVKPED SGIYFCMIVG   120
SPELTFGKGT QLSVVDFLPT TAQPTKKSTL KKRVCRLPRP ETQKGPLCSP ITLGLLVAGV   180
LVLLVSLGVA IHLCCRRRRA RLRFMKQLYK                                   210
```

| | | |
|---|---|---|
| SEQ ID NO: 55 | moltype = AA length = 7 | |
| FEATURE | Location/Qualifiers | |
| source | 1..7 | |
| | mol_type = protein | |
| | organism = synthetic construct | |

SEQUENCE: 55
RYTFTDY 7

| | | |
|---|---|---|
| SEQ ID NO: 56 | moltype = AA length = 6 | |
| FEATURE | Location/Qualifiers | |
| source | 1..6 | |
| | mol_type = protein | |
| | organism = synthetic construct | |

SEQUENCE: 56
YPYNGG 6

| | | |
|---|---|---|
| SEQ ID NO: 57 | moltype = AA length = 12 | |
| FEATURE | Location/Qualifiers | |
| source | 1..12 | |
| | mol_type = protein | |
| | organism = synthetic construct | |

SEQUENCE: 57
DHRYNEGVSF DY 12

| | | |
|---|---|---|
| SEQ ID NO: 58 | moltype = AA length = 15 | |
| FEATURE | Location/Qualifiers | |
| source | 1..15 | |
| | mol_type = protein | |
| | organism = synthetic construct | |

SEQUENCE: 58
RASESVDGFG NSFMN 15

| | | |
|---|---|---|
| SEQ ID NO: 59 | moltype = AA length = 7 | |
| FEATURE | Location/Qualifiers | |
| source | 1..7 | |
| | mol_type = protein | |
| | organism = synthetic construct | |

SEQUENCE: 59
LASNLES 7

| | | |
|---|---|---|
| SEQ ID NO: 60 | moltype = AA length = 9 | |
| FEATURE | Location/Qualifiers | |
| source | 1..9 | |
| | mol_type = protein | |
| | organism = synthetic construct | |

SEQUENCE: 60
QQNNEDPYT 9

| | | |
|---|---|---|
| SEQ ID NO: 61 | moltype = AA length = 5 | |
| FEATURE | Location/Qualifiers | |
| source | 1..5 | |
| | mol_type = protein | |
| | organism = synthetic construct | |

SEQUENCE: 61
DYNLH 5

| | | |
|---|---|---|
| SEQ ID NO: 62 | moltype = AA length = 17 | |
| FEATURE | Location/Qualifiers | |
| source | 1..17 | |
| | mol_type = protein | |
| | organism = synthetic construct | |

SEQUENCE: 62
FIYPYNGGTG YNQKFKN 17

| | | |
|---|---|---|
| SEQ ID NO: 63 | moltype = AA length = 8 | |
| FEATURE | Location/Qualifiers | |

```
source                      1..8
                            mol_type = protein
                            organism = synthetic construct
SEQUENCE: 63
RYTFTDYN                                                                         8

SEQ ID NO: 64               moltype = AA   length = 8
FEATURE                     Location/Qualifiers
source                      1..8
                            mol_type = protein
                            organism = synthetic construct
SEQUENCE: 64
IYPYNGGT                                                                         8

SEQ ID NO: 65               moltype = AA   length = 14
FEATURE                     Location/Qualifiers
source                      1..14
                            mol_type = protein
                            organism = synthetic construct
SEQUENCE: 65
ARDHRYNEGV SFDY                                                                 14

SEQ ID NO: 66               moltype = AA   length = 10
FEATURE                     Location/Qualifiers
source                      1..10
                            mol_type = protein
                            organism = synthetic construct
SEQUENCE: 66
ESVDGFGNSF                                                                      10

SEQ ID NO: 67               moltype = AA   length = 121
FEATURE                     Location/Qualifiers
source                      1..121
                            mol_type = protein
                            organism = synthetic construct
SEQUENCE: 67
EVQLQQSGPE LVKPGASVKI SCKASRYTFT DYNLHWVKLS HEKSLEWIGF IYPYNGGTGY               60
NQKFKNKAKL TVDYSSSTAY MELRSLTSVD AAVYYCARDH RYNEGVSFDY WGQGTTLTVS              120
S                                                                              121

SEQ ID NO: 68               moltype = AA   length = 112
FEATURE                     Location/Qualifiers
source                      1..112
                            mol_type = protein
                            organism = synthetic construct
SEQUENCE: 68
NIVLTQSPAS LAVSLGQRAT ISCRASESVD GFGNSFMNWY QQKPGQSPKL LIYLASNLES               60
GVPARFSGSG SRTDFTLTID PVEADDAATY YCQQNNEDPY TFGGGTKLEI KR                      112

SEQ ID NO: 69               moltype = AA   length = 253
FEATURE                     Location/Qualifiers
source                      1..253
                            mol_type = protein
                            organism = synthetic construct
SEQUENCE: 69
NIVLTQSPAS LAVSLGQRAT ISCRASESVD GFGNSFMNWY QQKPGQSPKL LIYLASNLES               60
GVPARFSGSG SRTDFTLTID PVEADDAATY YCQQNNEDPY TFGGGTKLEI KRGGGGSGGG              120
GSGGGGSGGG GSEVQLQQSG PELVKPGASV KISCKASRYT FTDYNLHWVK LSHEKSLEWI              180
GFIYPYNGGT GYNQKFKNKA KLTVDYSSST AYMELRSLTS VDAAVYYCAR DHRYNEGVSF              240
DYWGQGTTLT VSS                                                                 253

SEQ ID NO: 70               moltype = AA   length = 253
FEATURE                     Location/Qualifiers
source                      1..253
                            mol_type = protein
                            organism = synthetic construct
SEQUENCE: 70
EVQLQQSGPE LVKPGASVKI SCKASRYTFT DYNLHWVKLS HEKSLEWIGF IYPYNGGTGY               60
NQKFKNKAKL TVDYSSSTAY MELRSLTSVD AAVYYCARDH RYNEGVSFDY WGQGTTLTVS              120
SGGGGSGGGG SGGGGSGGGG SNIVLTQSPA SLAVSLGQRA TISCRASESV DGFGNSFMNW              180
YQQKPGQSPK LLIYLASNLE SGVPARFSGS GSRTDFTLTI DPVEADDAAT YYCQQNNEDP              240
YTFGGGTKLE IKR                                                                 253

SEQ ID NO: 71               moltype = AA   length = 325
FEATURE                     Location/Qualifiers
source                      1..325
                            mol_type = protein
                            organism = Homo sapiens
```

```
SEQUENCE: 71
STKGPSVFPL APCSRSTSES TAALGCLVKD YFPEPVTVSW NSGALTSGVH TFPAVLQSSG    60
LYSLSSVVTV PSSSLGTQTY TCNVDHKPSN TKVDKTVERK CCVECPPCPA PPVAGPSVFL   120
FPPKPKDTLM ISRTPEVTCV VVDVSHEDPE VQFNWYVDGV EVHNAKTKPR EEQFNSTFRV   180
VSVLTVVHQD WLNGKEYKCK VSNKGLPAPI EKTISKTKGQ PREPQVYTLP PSREEMTKNQ   240
VSLTCLVKGF YPSDIAVEWE SNGQPENNYK TTPPMLDSDG SFFLYSKLTV DKSRWQQGNV   300
FSCSVMHEAL HNHYTQKSLS LSPGK                                        325

SEQ ID NO: 72          moltype = AA  length = 326
FEATURE                Location/Qualifiers
source                 1..326
                       mol_type = protein
                       organism = Homo sapiens
SEQUENCE: 72
STKGPSVFPL APCSRSTSES TAALGCLVKD YFPEPVTVSW NSGALTSGVH TFPAVLQSSG    60
LYSLSSVVTV PSSSLGTKTY TCNVDHKPSN TKVDKRVESK YGPPCPSCPA PEFLGGPSVF   120
LPPKPKDTL MISRTPEVTC VVVDVSQEDP EVQFNWYVDG VEVHNAKTKP REEQFNSTYR    180
VVSVLTVLHQ DWLNGKEYKC KVSNKGLPSS IEKTISKAKG QPREPQVYTL PPSQEEMTKN   240
QVSLTCLVKG FYPSDIAVEW ESNGQPENNY KTTPPVLDSD GSFFLYSRLT VDKSRWQEGN   300
VFSCSVMHEA LHNHYTQKSL SLSLGK                                       326

SEQ ID NO: 73          moltype = AA  length = 122
FEATURE                Location/Qualifiers
source                 1..122
                       mol_type = protein
                       organism = synthetic construct
SEQUENCE: 73
EVQLVESGGG LVQPGRSLRL SCAASGFTFN DYAMHWVRQA PGKGLEWVST ISWNSGSIGY    60
ADSVKGRFTI SRDNAKKSLY LQMNSLRAED TALYYCAKDI QYGNYYYGMD VWGQGTTVTV   120
SS                                                                 122

SEQ ID NO: 74          moltype = AA  length = 107
FEATURE                Location/Qualifiers
source                 1..107
                       mol_type = protein
                       organism = synthetic construct
SEQUENCE: 74
EIVLTQSPAT LSLSPGERAT LSCRASQSVS SYLAWYQQKP GQAPRLLIYD ASNRATGIPA    60
RFSGSGSGTD FTLTISSLEP EDFAVYYCQQ RSNWPITFGQ GTRLEIK                107

SEQ ID NO: 75          moltype = AA  length = 244
FEATURE                Location/Qualifiers
source                 1..244
                       mol_type = protein
                       organism = synthetic construct
SEQUENCE: 75
EVQLVESGGG LVQPGRSLRL SCAASGFTFN DYAMHWVRQA PGKGLEWVST ISWNSGSIGY    60
ADSVKGRFTI SRDNAKKSLY LQMNSLRAED TALYYCAKDI QYGNYYYGMD VWGQGTTVTV   120
SSGGGGSGGG GSGGGGSEIV LTQSPATLSL SPGERATLSC RASQSVSSYL AWYQQKPGQA   180
PRLLIYDASN RATGIPARFS GSGSGTDFTL TISSLEPEDF AVYYCQQRSN WPITFGQGTR   240
LEIK                                                               244

SEQ ID NO: 76          moltype = AA  length = 244
FEATURE                Location/Qualifiers
source                 1..244
                       mol_type = protein
                       organism = synthetic construct
SEQUENCE: 76
EIVLTQSPAT LSLSPGERAT LSCRASQSVS SYLAWYQQKP GQAPRLLIYD ASNRATGIPA    60
RFSGSGSGTD FTLTISSLEP EDFAVYYCQQ RSNWPITFGQ GTRLEIKGGG GSGGGGSGGG   120
GSEVQLVESG GGLVQPGRSL RLSCAASGFT FNDYAMHWVR QAPGKGLEWV STISWNSGSI   180
GYADSVKGRF TISRDNAKKS LYLQMNSLRA EDTALYYCAK DIQYGNYYYG MDVWGQGTTV   240
TVSS                                                               244

SEQ ID NO: 77          moltype = AA  length = 15
FEATURE                Location/Qualifiers
source                 1..15
                       mol_type = protein
                       organism = synthetic construct
SEQUENCE: 77
GGGGSGGGGS GGGGS                                                    15

SEQ ID NO: 78          moltype = AA  length = 110
FEATURE                Location/Qualifiers
source                 1..110
                       mol_type = protein
                       organism = synthetic construct
```

```
SEQUENCE: 78
DIVLTQSPAI LSASPGEKVT MTCRASSSVN YMDWYQKKPG SSPKPWIYAT SNLASGVPAR    60
FSGSGSGTSY SLTISRVEAE DAATYYCQQW SFNPPTFGGG TKLEIKGSTS              110

SEQ ID NO: 79           moltype = AA  length = 122
FEATURE                 Location/Qualifiers
source                  1..122
                        mol_type = protein
                        organism = synthetic construct
SEQUENCE: 79
EVQLQQSGAE LVKPGASVKM SCKASGYTFT SYNMHWVKQT PGQGLEWIGA IYPGNGDTSY    60
NQKFKGKATL TADKSSSTAY MQLSSLTSED SADYYCARSN YYGSSYWFFD VWGAGTTVTV    120
SS                                                                  122

SEQ ID NO: 80           moltype = AA  length = 248
FEATURE                 Location/Qualifiers
source                  1..248
                        mol_type = protein
                        organism = synthetic construct
SEQUENCE: 80
DIVLTQSPAI LSASPGEKVT MTCRASSSVN YMDWYQKKPG SSPKPWIYAT SNLASGVPAR    60
FSGSGSGTSY SLTISRVEAE DAATYYCQQW SFNPPTFGGG TKLEIKGSTS GGGGSGGGGS    120
GGGGSSEVQL QQSGAELVKP GASVKMSCKA SGYTFTSYNM HWVKQTPGQG LEWIGAIYPG    180
NGDTSYNQKF KGKATLTADK SSSTAYMQLS SLTSEDSADY YCARSNYYGS SYWFFDVWGA    240
GTTVTVSS                                                            248

SEQ ID NO: 81           moltype = AA  length = 248
FEATURE                 Location/Qualifiers
source                  1..248
                        mol_type = protein
                        organism = synthetic construct
SEQUENCE: 81
SEVQLQQSGA ELVKPGASVK MSCKASGYTF TSYNMHWVKQ TPGQGLEWIG AIYPGNGDTS    60
YNQKFKGKAT LTADKSSSTA YMQLSSLTSE DSADYYCARS NYYGSSYWFF DVWGAGTTVT    120
VSSGGGGSGG GGSGGGGSDI VLTQSPAILS ASPGEKVTMT CRASSSVNYM DWYQKKPGSS    180
PKPWIYATSN LASGVPARFS GSGSGTSYSL TISRVEAEDA ATYYCQQWSF NPPTFGGGTK    240
LEIKGSTS                                                            248
```

What is claimed:

1. A pseudotyped lentivirus comprising:
    i) a mutant VSV-G polypeptide comprising an amino acid sequence that is at least 95% identical to the amino acid sequence of SEQ ID NO: 2;
    ii) a targeting moiety on the surface of the pseudotyped lentivirus comprising an antibody that binds to CD7; and
    iii) a nucleic acid molecule encoding a heterologous molecule of interest;
    wherein the mutant VSV-G polypeptide is not linked or conjugated to the targeting moiety.

2. The pseudotyped lentivirus of claim 1, wherein the mutant VSV-G polypeptide is at least 97% identical to the amino acid sequence of SEQ ID NO: 2.

3. The pseudotyped lentivirus of claim 1, wherein the mutant VSV-G polypeptide is at least 99% identical to the amino acid sequence of SEQ ID NO: 2.

4. The pseudotyped lentivirus of claim 1, wherein the VSV-G polypeptide comprises a T214N mutation or a T352A mutation.

5. The pseudotyped lentivirus of claim 2, wherein the VSV-G polypeptide comprises a T214N mutation or a T352A mutation.

6. The pseudotyped lentivirus of claim 3, wherein the VSV-G polypeptide comprises a T214N mutation or a T352A mutation.

7. The pseudotyped lentivirus of claim 1, wherein the VSV-G polypeptide comprises a T214N mutation and a T352A mutation.

8. The pseudotyped lentivirus of claim 2, wherein the VSV-G polypeptide comprises a T214N mutation and a T352A mutation.

9. The pseudotyped lentivirus of claim 3, wherein the VSV-G polypeptide comprises a T214N mutation and a T352A mutation.

10. The pseudotyped lentivirus of claim 1, wherein the antibody is an scFv antibody, a VHH domain antibody, or a single domain antibody.

11. The pseudotyped lentivirus of claim 1, wherein the lentivirus does not comprise a targeting moiety that binds to CD3.

12. The pseudotyped lentivirus of claim 1, wherein the heterologous molecule of interest is a chimeric antigen receptor ("CAR").

13. The pseudotyped lentivirus of claim 1, wherein the heterologous molecule of interest is an siRNA, an shRNA, a non-coding RNA, a peptide, a polypeptide, a viral payload, a viral genome, or a combination thereof.

14. A pharmaceutical composition comprising the pseudotyped lentivirus of claim 1.

15. A pharmaceutical composition comprising the pseudotyped lentivirus of claim 4.

16. A pharmaceutical composition comprising the pseudotyped lentivirus of claim 5.

17. A pharmaceutical composition comprising the pseudotyped lentivirus of claim 6.

18. A pharmaceutical composition comprising the pseudotyped lentivirus of claim 8.

19. The pseudotyped lentivirus of claim 1, wherein the targeting moiety is attached to the viral surface through an IgG Fc stalk.

20. The pseudotyped lentivirus of claim 19, wherein the stalk comprises a transmembrane domain.

* * * * *